US011702480B2

(12) United States Patent
Liu et al.

(10) Patent No.: US 11,702,480 B2
(45) Date of Patent: Jul. 18, 2023

(54) ENGINEERED ANTIBODIES AND USES THEREOF

(71) Applicant: The Regents of the University of California, Oakland, CA (US)

(72) Inventors: Bin Liu, San Francisco, CA (US); Namkyung Lee, San Francisco, CA (US); Yang Su, San Francisco, CA (US); Scott Bidlingmaier, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 512 days.

(21) Appl. No.: 16/349,958

(22) PCT Filed: Nov. 17, 2017

(86) PCT No.: PCT/US2017/062418
§ 371 (c)(1),
(2) Date: May 14, 2019

(87) PCT Pub. No.: WO2018/094282
PCT Pub. Date: May 24, 2018

(65) Prior Publication Data
US 2019/0330365 A1 Oct. 31, 2019

Related U.S. Application Data

(60) Provisional application No. 62/424,337, filed on Nov. 18, 2016.

(51) Int. Cl.
*C07K 16/30* (2006.01)
*C07K 16/28* (2006.01)
*A61K 31/713* (2006.01)
*C07K 16/46* (2006.01)

(52) U.S. Cl.
CPC ............ *C07K 16/30* (2013.01); *A61K 31/713* (2013.01); *C07K 16/2821* (2013.01); *C07K 16/2866* (2013.01); *C07K 16/468* (2013.01); *C07K 2317/31* (2013.01); *C07K 2317/622* (2013.01); *C07K 2317/64* (2013.01); *C07K 2317/76* (2013.01); *C07K 2317/77* (2013.01); *C07K 2317/92* (2013.01)

(58) Field of Classification Search
CPC .. C07K 16/30; C07K 16/2821; C07K 16/468; C07K 2317/31; C07K 2317/622; C07K 2317/92
See application file for complete search history.

(56) References Cited

U.S. PATENT DOCUMENTS

| 8,865,873 B2 * | 10/2014 | Liu | C07K 16/18 530/388.8 |
|---|---|---|---|
| 2005/0186214 A1 | 8/2005 | Liu et al. | |
| 2011/0123532 A1 * | 5/2011 | Gurney | A61K 39/3955 424/136.1 |
| 2014/0080766 A1 | 3/2014 | Pirie et al. | |
| 2014/0141000 A1 | 5/2014 | Chiu et al. | |
| 2014/0220040 A1 * | 8/2014 | Abo | A61P 19/00 424/172.1 |
| 2014/0234317 A1 * | 8/2014 | Onsum | A61P 43/00 424/136.1 |
| 2015/0010567 A1 * | 1/2015 | Bourquin | A61P 35/02 424/136.1 |
| 2016/0251440 A1 * | 9/2016 | Roobrouck | C07K 16/2863 424/138.1 |

FOREIGN PATENT DOCUMENTS

| WO | WO-2011/103426 A2 | 8/2011 |
| WO | WO-2011/103426 A3 | 8/2011 |
| WO | WO-2011/138391 A1 | 11/2011 |

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Rhoden et al, The Journal of Biological chemistry, vol. 291, No. 21, 11337-11347, May 20, 2016. (Year: 2016).*
Conrad, F. et al. (May 2009, e-published Feb. 14, 2009). "Human antibodies targeting cell surface antigens overexpressed by the hormone refractory metastatic prostate cancer cells: ICAM-1 is a tumor antigen that mediates prostate cancer cell invasion," *Journal of Molecular Medicine* 87(5):507-514.
Extended European Search Report dated Sep. 4, 2020 for EP Patent Application No. 17872047.0, 10 pages.
International Search Report dated Apr. 13, 2018, for PCT Application No. PCT/US2017/062418, filed Nov. 17, 2017, 7 pages.

(Continued)

*Primary Examiner* — Julie Wu
*Assistant Examiner* — Cheom-Gil Cheong
(74) *Attorney, Agent, or Firm* — Mintz, Levin, Cohn, Ferris, Glovsky & Popeo, P.C.

(57) ABSTRACT

The present disclosure relates to an engineered antibody that co-engages a cell type-selective (or specific) antigen (guide) and a signaling receptor (effector) on a target cell. In some instances, the engineered antibody is capable of modulating a signaling pathway on a target cell. In other embodiments, an engineered antibody of the present disclosure is administered to a subject for the treatment of a disease or condition.

17 Claims, 38 Drawing Sheets

Specification includes a Sequence Listing.

(56) References Cited

OTHER PUBLICATIONS

Jarantow, S.W. et al. (Oct. 9, 2015, e-published Aug. 10, 2015). "Impact of Cell-surface Antigen Expression on Target Engagement and Function of an Epidermal Growth Factor Receptor – c-MET Bispecific Antibody," *The Journal of Biological Chemistry* 290(41):24689-24704.

Partial Supplementary European Search Report dated May 26, 2020 for EP Patent Application No. 17872047.0, 7 pages.

Rhoden, J.J. et al. (May 20, 2016, e-published Mar. 28, 2016). "A Modeling and Experimental Investigation of the Effects of Antigen Density, Binding Affinity, and Antigen Expression Ratio on Bispecific Antibody Binding to Cell Surface Targets," *The Journal of Biological Chemistry* 291(21):11337-11347.

Stone, A. et al. (2014). "EGFR and c-Met Inhibitors are Effective in Reducing Tumorigenicity in Cancer," *Journal of Carcinogenesis and Mutagenesis* 5:3, 9 pages.

Written Opinion dated Apr. 13, 2018, for PCT Application No. PCT/US2017/062418, filed Nov. 17, 2017, 12 pages.

Zheng, S. et al. (2016, e-published Jan. 13, 2016). "Cross-arm binding efficiency of an EGFR – c-Met bispecific antibody," *MAbs* 8(3):551-561.

Gong, Y. et al. (Sep. 13, 2010). "Wnt Isoform-Specific Interactions with Coreceptor Specify Inhibition or Potentiation of Signaling by LRP6 Antibodies," *PLoS One* 5(9):e12682.

Kuroki, M. et al. (2014). "Novel treatment strategies for cancer and their tumor-targeting approaches using antibodies against tumor-associated antigens," *Anticancer Research* 34(8):4481-4488.

\* cited by examiner

FIG. 16C

ENGINEERED ANTIBODIES AND USES THEREOF

CROSS-REFERENCE TO RELATED APPLICATIONS

This application is a U.S. National Phase Application of PCT International Application No. PCT/US2017/062418, filed on Nov. 17, 2017, designating the United States of America, which is an International Application of and claims the benefit of priority to U.S. Provisional Application No. 62/424,337, filed on Nov. 18, 2016. The disclosures of the above-referenced applications are hereby expressly incorporated by reference in their entireties and for all purposes.

STATEMENT REGARDING FEDERALLY SPONSORED RESEARCH OR DEVELOPMENT

This invention was made with government support under grant nos. R01 CA118919, R01 CA129491, and R01 CA171315, awarded by the National Institutes of Health. The government has certain rights in this invention.

REFERENCE TO A "SEQUENCE LISTING," A TABLE, OR A COMPUTER PROGRAM LISTING APPENDIX SUBMITTED AS AN ASCII FILE

The present application contains a Sequence Listing, which is being submitted via EFS-Web on even date herewith. The Sequence Listing is submitted in a file entitled "Sequence Listing 048536-594N01US.txt," which was created on May 10, 2019, and is approximately 177 kb in size. This Sequence Listing is hereby incorporated by reference.

BACKGROUND

Cell signaling pathways are important for maintaining homeostasis and regulating cell growth and survival. Normal and disease cells often use overlapping pathways, creating a roadblock to therapeutic targeting. Selective sensitivity of disease cells to pathway modulation may allow certain pathways to be targeted for treatment, thereby demonstrating clinical applicability. In this regard, monoclonal antibodies have emerged a cancer therapeutic, due in part to its high specificity and affinity in target binding, as well as ease of chemical and molecular modifications that enable the development of more complex antibody-based therapeutics. Bispecific antibodies have emerged as a possible therapeutic. For example, the bispecific T-cell engager (BiTE) Blinatumomab has an anti-CD19 and an anti-CD3 single-chain variable-fragment (scFv) for tumor-targeted T cell recruitment and activation. Other examples include IgG-scFv containing anti-ErbB3 scFv fused to the heavy chain C-termini of an anti-IGF-1R IgG, and CrossMAb having heterodimeric pairs of two heavy and light chains against VEGF-A and angiopoietin-2. The bispecificity in the foregoing antibodies is designed to either introduce a new activity (in the case of BiTE) or to block two pathways critical for cell growth and survival without cell type selectivity. In these co-targeting strategies, however, toxicity is a concern as both antibodies bind to signaling receptors critical for cell growth and survival. Various embodiments in accordance with the present disclosures overcome the foregoing disadvantages and provide a novel and effective approach which allows modular development of bispecific antibody with a goal of achieving maximum effect on a target cell (e.g. tumor) but no or minimum effect on normal cells. Furthermore, the system and platform disclosed herein is not limited to a certain pathway and/or a cell type but can be generally applicable to a variety of signaling pathways and target cell types. In some instances, selective sensitivity of disease cells to pathway modulation allows certain pathways to be targeted for treatment.

SUMMARY OF THE INVENTION

In one aspect, the disclosure provided herewith relates to an engineered antibody, having a first antigen binding region and a second antigen binding region, wherein the first antigen binding region binds to a guide antigen expressed on the surface of a cell and the second antigen binding region binds to an effector antigen expressed on the surface of the same cell, and wherein the guide antigen is characterized by a density that is at least four-fold higher than the density of the effector antigen.

In some embodiments, the guide antigen is characterized by a density that is at least five-fold higher than the density of the effector antigen.

In some embodiments, the guide antigen is characterized by a density that is at least ten-fold higher than the density of the effector antigen.

In some embodiments, the guide antigen is further characterized by an expression of at least 15,000 copies on the cell surface.

In some embodiments, the guide antigen is further characterized by an expression of at least 20,000 copies on the cell surface.

In another aspect, the disclosure provided herewith relates to an engineered antibody, having a first antigen binding region and a second antigen binding region, wherein the first antigen binding region binds to a guide antigen expressed on the surface of a cell and the second antigen binding region binds to an effector antigen expressed on the surface of the same cell, and wherein the guide antigen is characterized by an expression of at least 15,000 copies on the cell surface.

In some embodiments, the guide antigen is characterized by an expression of at least 20,000 copies on the cell surface.

In some embodiments, the guide antigen is further characterized by a density that is at least four-fold higher than the density of the effector antigen.

In some embodiments, the guide antigen is further characterized by a density that is at least five-fold higher than the density of the effector antigen.

In some embodiments, the guide antigen is further characterized by a density that is at least ten-fold higher than the density of the effector antigen.

In some embodiments, binding of the engineered antibody to the effector antigen results in modulation of a signaling pathway in the cell.

In some embodiments, the signaling pathway is selected from AKT pathway, c-MET pathway, NF-kB pathway, Notch signaling pathway, p53 pathway, Ras-Raf-MEK-ERK pathway, STAT signaling pathway, Wnt signaling pathway, YAP/Wnt signaling pathway, Receptor tyrosine kinase (RTK) signaling pathway families including but are not limited to the epidermal growth factor receptor (EGFR) family, the fibroblast growth factor receptor (FGFR) family, the insulin-like growth factor receptor (IGFR) family, the vascular endothelial growth factor receptor (VEGFR) family, and the platelet-derived growth factor receptors (PDGFR) family, NK (natural killer) activating pathway, NK inhibitory pathway, macrophage regulatory pathway, dendritic cell signaling pathway, T cell regulatory pathway and checkpoint inhibitory pathway.

In some embodiments, the signaling pathway is Wnt signaling pathway.

In some embodiments, the effector antigen is a tumor antigen.

In some embodiments, the effector antigen is a tumor-associated antigen.

In still another aspect, the disclosure provided herewith relates to an engineered antibody first antigen binding region and a second antigen binding region, wherein the first antigen binding region binds to an effector antigen on a surface of a target cell, wherein the effector antigen is associated with a signaling pathway and the second antigen binding region binds to a guide antigen on the surface of the target cell, wherein the density of the guide antigen is substantially higher than the density of the effector antigen from the target cell, and wherein binding of the bispecific antibody to the target cell results in modulation of the signaling pathway in the target cell.

In some embodiments, the engineered antibody is a bispecific antibody.

In some embodiments, the level of occupancy of the effector antigen is higher using the bispecific antibody as compared to the level of occupancy using an antibody monospecific for the effector antigen.

In some embodiments, the antibody is selected from the group consisting of: M10A12, RYR, H3 and PD32.

In some embodiments, the second antigen binding region has a sequence listed in Table 5 and/or any fragment thereof.

In some embodiments, the ratio of the density of the guide antigen to the effector antigen in the target cell is about 5:1, 6:1. 7:1, 8:1. 9:1, or 10:1.

In some embodiments, a threshold level of expression of the guide antigen present on the surface of the target cell ranges between about 15,000 and about 20,000 copies per cell.

In some embodiments, the first antigen binding region has a single chain variable fragment (scFv) binding to a tumor-specific antigen.

In some embodiments, the effector antigen is LRP6.

In some embodiments, the first antigen binding region has a heavy chain variable region having three complementarity determining regions (CDRs), wherein the CDRs from the heavy chain variable region are selected from Tables 3 or 4.

In some embodiments, the first antigen binding region has a light chain variable region having three complementarity determining regions (CDRs), wherein the CDRs from the light chain variable region are selected from Tables 3 or 4.

In some embodiments, the first antigen binding region has a heavy chain variable region having three complementarity determining regions (CDRs) and a light chain variable region having three complementarity determining regions (CDRs), wherein the CDRs from the heavy chain variable region and the CDRs from light chain variable region are selected from Tables 3 or 4.

In some embodiments, the first antigen binding region has a heavy chain variable region having at least 80%, 85%, 90%, 95%, or 99% sequence identity to a heavy chain variable sequence selected from Tables 3 or 4.

In some embodiments, the first antigen binding region has a light chain variable region having at least 80%, 85%, 90%, 95%, or 99% sequence identity to a light chain variable sequence selected from Tables 3 or 4.

In some embodiments, the first antigen binding region has a heavy chain variable region having at least 80%, 85%, 90%, 95%, or 99% sequence identity to a heavy chain variable sequence selected from Tables 3 or 4 and a light chain variable region having at least 80%, 85%, 90%, 95%, or 99% sequence identity to a light chain variable sequence selected from Tables 3 or 4.

In some embodiments, the first antigen binding region has a heavy chain variable region having a sequence selected from Tables 3 or 4 and a light chain variable region having a sequence selected from Tables 3 or 4.

In some embodiments, the guide antigen is a cell type-selective cell surface antigen.

In some embodiments, the guide antigen is a tumor-associated antigen.

In some embodiments, the guide antigen is a tumor specific antigen.

In some embodiments, the second antigen binding region has a heavy chain variable region having three complementarity determining regions (CDRs), wherein the CDRs from the heavy chain variable region are selected from Table 5.

In some embodiments, the second antigen binding region has a light chain variable region having three complementarity determining regions (CDRs), wherein the CDRs from the light chain variable region are selected from Table 5.

In some embodiments, the second antigen binding region has a heavy chain variable region having three complementarity determining regions (CDRs) and a light chain variable region having three complementarity determining regions (CDRs), wherein the CDRs from the heavy chain variable region and the CDRs from light chain variable region are selected from Table 5.

In some embodiments, the second antigen binding region has a heavy chain variable region having at least 80%, 85%, 90%, 95%, or 99% sequence identity to a heavy chain variable sequence selected from Table 5.

In some embodiments, the second antigen binding region has a light chain variable region having at least 80%, 85%, 90%, 95%, or 99% sequence identity to a light chain variable sequence selected from Table 5.

In some embodiments, the second antigen binding region has a heavy chain variable region having at least 80%, 85%, 90%, 95%, or 99% sequence identity to a heavy chain variable sequence selected from Table 5 and a light chain variable region having at least 80%, 85%, 90%, 95%, or 99% sequence identity to a light chain variable sequence selected from Table 5.

In some embodiments, the second antigen binding region has a heavy chain variable region having a sequence selected from Table 5 and a light chain variable region having a sequence selected from Table 5.

In some embodiments, binding of the bispecific antibody to the target cell results in downregulation of the signaling pathway.

In some embodiments, an IC50 value of the bispecific antibody is decreased at least 100-fold as compared to an IC50 value of an antibody monospecific to the effector antigen.

In some embodiments, binding of the bispecific antibody to the target cell results in upregulation of the signaling pathway.

In some embodiments, activity of the signaling pathway is increased at least 10-fold using the bispecific antibody as compared to using an antibody monospecific to the effector antigen, wherein the activity of the signaling pathway is measured by a reporter assay that is responsive to the signaling pathway In still another aspect, the disclosure provided herewith relates to a pharmaceutical composition including an engineered antibody and an excipient.

In some embodiments, the engineered antibody is formulated for parenteral administration.

In still another aspect, the disclosure provided herewith relates to a method of treating a disease or condition in a subject in need thereof, having administering to the subject a therapeutically effective amount of an engineered or bispecific antibody.

In some embodiments, the disease or condition is associated with a dysregulation of a signaling pathway in the cell.

In some embodiments, the signaling pathway is selected from AKT pathway, c-MET pathway, NF-kB pathway, Notch signaling pathway, p53 pathway, Ras-Raf-MEK-ERK pathway, STAT signaling pathway, Wnt signaling pathway, YAP/Wnt signaling pathway, NK (natural killer) activating pathway, NK inhibitory pathway, and checkpoint inhibitory pathway, Receptor tyrosine kinase (RTK) signaling pathway families including but are not limited to the epidermal growth factor receptor (EGFR) family, the fibroblast growth factor receptor (FGFR) family, the insulin-like growth factor receptor (IGFR) family, the vascular endothelial growth factor receptor (VEGFR) family, and the platelet-derived growth factor receptors (PDGFR) family, NK (natural killer) activating pathway, NK inhibitory pathway, macrophage regulatory pathway, dendritic cell signaling pathway, T cell regulatory pathway and checkpoint inhibitory pathway.

In still another aspect, the disclosure provided herewith relates to a method of generating an engineered antibody. The method includes a) selecting a cell expressing a plurality of guide antigens and effector antigens on the cell surface; b) determining a density ratio of the plurality of guide antigens and effector antigens; and c) preparing an engineered antibody having a first antigen binding region that binds to the guide antigen and a second antigen binding region that binds to the effector antigen on the cell if the density ratio of the guide antigen to effector antigen is at least 4:1.

In some embodiments, the density ratio of the guide antigen to effector antigen is at least 5:1.

In some embodiments, the density ratio of the guide antigen to effector antigen is at least 10:1.

In some embodiments, the cell expresses at least 15,000 or more copies of the guide antigen on the cell surface.

In some embodiments, the cell expresses at least 20,000 or more copies of the guide antigen on the cell surface.

In still another aspect, the disclosure provided herewith relates to a method of generating an engineered antibody. The method includes a) selecting a cell expressing a plurality of guide antigens and effector antigens on the cell surface; b) determining a copy number of the guide antigen expressed on the cell surface; and c) preparing an engineered antibody having a first antigen binding region that binds to the guide antigen and a second antigen binding region that binds to the effector antigen on the cell if the cell expresses at least 15,000 copies of the guide antigen.

In some embodiments, the cell expresses at least 20,000 or more copies of the guide antigen on the cell surface.

In some embodiments, the method further includes determining a density ratio of guide antigens to effector antigens.

In some embodiments, the density ratio of the guide antigen to effector antigen is at least 4:1.

In some embodiments, the density ratio of the guide antigen to effector antigen is at least 5:1.

In some embodiments, the density ratio of the guide antigen to effector antigen is at least 10:1.

In still another aspect, the disclosure provided herewith relates to an engineered antibody produced by the process of: a) selecting a cell expressing a plurality of guide antigens and effector antigens on the cell surface; b) determining a density ratio of the plurality of guide antigens and effector antigens; and c) preparing an engineered antibody having a first antigen binding region that binds to the guide antigen and a second antigen binding region that binds to the effector antigen on the cell if the density ratio of the guide antigen to effector antigen is at least 4:1.

In some embodiments, the density ratio of the guide antigen to effector antigen is at least 5:1.

In some embodiments, the density ratio of the guide antigen to effector antigen is at least 10:1.

In some embodiments, the cell expresses at least 15,000 or more copies of the guide antigen on the cell surface.

In some embodiments, the cell expresses at least 20,000 or more copies of the guide antigen on the cell surface.

In still another aspect, the disclosure provided herewith relates to an engineered antibody produced by the process of: a) selecting a cell expressing a plurality of guide antigens and effector antigens on the cell surface; b) determining a copy number of the guide antigen expressed on the cell surface; and c) preparing an engineered antibody having a first antigen binding region that binds to the guide antigen and a second antigen binding region that binds to the effector antigen on the cell if the cell expresses at least 15,000 copies of the guide antigen.

In some embodiments, the cell expresses at least 20,000 or more copies of the guide antigen on the cell surface.

In some embodiments, the process further includes determining a density ratio of guide antigens to effector antigens.

In some embodiments, the density ratio of the guide antigen to effector antigen is at least 4:1.

In some embodiments, the density ratio of the guide antigen to effector antigen is at least 5:1.

In some embodiments, the density ratio of the guide antigen to effector antigen is at least 10:1.

In still another aspect, the disclosure provided herewith relates to an antibody-cell complex including an engineered antibody wherein the engineered antibody has a first antigen binding region that binds to a guide antigen on a cell, and a second antigen binding region that binds to an effector antigen on the cell, wherein the cell is characterized by a density ratio of about 4:1 guide antigen to effector antigen.

In some embodiments, the cell is characterized by a density ratio of about 5:1 guide antigen to effector antigen.

In some embodiments, the cell is characterized by a density ratio of about 10:1 guide antigen to effector antigen.

In some embodiments, the cell has about 15,000 or more copies of the guide antigen, expressed on the surface of the cell.

In some embodiments, the cell has about 20,000 or more copies of the guide antigen, expressed on the surface of the cell.

In still another aspect, the disclosure provided herewith relates to an antibody-cell complex including an engineered antibody wherein the engineered antibody has a first antigen binding region that binds to a guide antigen on a cell, and a second antigen binding region that binds to an effector antigen on the cell, wherein the cell has about 15,000 or more copies of the guide antigen expressed on the cell surface.

In some embodiments, the cancer cell has about 20,000 or more copies of the guide antigen, expressed on the surface of the cell.

In some embodiments, the cell is further characterized by a density ratio of about 4:1 guide antigen to effector antigen.

In some embodiments, the cell is further characterized by a density ratio of about 5:1 guide antigen to effector antigen.

In some embodiments, the cell is further characterized by a density ratio of about 10:1 guide antigen to effector antigen.

BRIEF DESCRIPTION OF THE DRAWINGS

An understanding of certain features and advantages of the present disclosure will be obtained by reference to the following detailed description that sets forth illustrative embodiments, in which the principles of the disclosure are utilized, and the accompanying drawings of which:

FIG. 1A depicts a schematic diagram of the extracellular E1E2 and E3E4 domains of LRP6, including two β-propeller (BP) and EGF-like domains, separately. Each Fc fusion was purified and used for following scFv phage display selections. FIG. 1B depicts the results of STF reporter assays screening antagonistic scFv phage antibodies against LRP6E1E2 or LRP6E3E4 domain. HEK293 cells transfected with STF reporter and Wnt3a- or Wnt1-expression constructs were treated with individually amplified phage antibodies. Agonistic (blue or B) or antagonistic (red or R) effect against Wnt/β-catenin reporter activity was determined by phage antibody treatment. Relative luciferase activity was described by dividing Firefly luciferase (FL) reporter activity by co-transfected *Renilla* Luciferase (RL) activity. FIG. 1C depicts the results of STF reporter assays with scFv-Fc fusions. Purified E34N19 or E12N21 scFv-Fc (100 nM) was tested for Wnt3a- or Wnt1-specific reporter inhibition, respectively. Error bars represent SD (standard deviation) for n=3. FIG. 1D depicts the results illustrating evaluation of β-catenin reporter inhibition potency of E34N19 or E12N21 scFv-Fc. HEK293 cells were transfected with STF reporter and Wnt3a- or Wnt1-expression constructs and treated with various concentrations of E34N19 or E12N21 scFv-Fc, respectively. Each value represents mean±SD for n=3.

FIG. 2A depicts a schematic design of bispecific tandem scFv-Fc constructs. Purified E34N19 scFv-Fc (~60 kDa) and TaFv-Fc (~90 kDa) fusions were analyzed by SDS-PAGE under reducing conditions. FIG. 2B depicts a schematic design of an IgG-based bispecific antibody (bsIgG) harboring a guide scFv antibody. The heavy chain of E34N19 IgG is preserved and the light chain is modified with the anti-ALCAM H3 scFv to the C-termini. Under reducing conditions, SDS-PAGE analysis of E34N19 IgG shows two separate heavy (~50 kDa) and light (~25 kDa) chains, while E34N19/H3 bsIgG displays two bands, both at around 50 kDa. FIG. 2C depicts the results of STF reporter assays to compare the potency of mono- or bi-specific anti-LRP6E3E4 antibodies. Reporter activity was assessed by incubating varying concentrations of each antibody with Wnt3a-transfected HEK293 cells. Values represent mean±SD. FIG. 2D the results of depicts STF reporter assays to test the potency of antibodies against LRP6E1E2 domain. Each antibody was titrated in HEK293 cells transfected with Wnt1-expression plasmid and reporter constructs. Relative luciferase reporter activities were separately analyzed. Values represent mean±SD in duplicate determinations.

FIG. 3A depicts the results of EphA2-selective Wnt3a/β-catenin signaling inhibition of RYR/E34N19. STF reporter assays were conducted using parent HEK293 cells or HEk293-EphA2 cells. Cells were transfected with reporter and Wnt3a-expression constructs, followed by treatment with varying concentrations of RYR/E34N19. IC50 values were calculated based on the curve fitting. CM; Cell membrane. FIG. 3B depicts the results illustrating potent anti-Wnt3a/β-catenin signaling activity of RYR/E34N19. HEK293 cells were transiently transfected with reporter plasmids, Wnt3a-, and EphA2-expression constructs and used to compare STF reporter inhibition potencies of indicated antibodies. IC50 values were estimated based on the curve fitting. FIG. 3C depicts the results illustrating ICAM-1-selective Wnt3a/β-catenin signaling blockade of M10A12/E34N19. STF reporter assays were performed with parent HEK293 cells or transiently ICAM-1-overexpressing HEK293 cells (HEK293-ICAM-1high). Reporter inhibition potency of M10A12/E34N19 was assessed after antibody treatment and IC50 was calculated based on the curve fitting. FIG. 3D depicts the results of potent Wnt3a/β-catenin signaling blockade of M10A12/E34N19. STF reporter assays were conducted with HEK293 cells transiently expressing high level of ICAM-1. Transfected HEK293 cells were treated with varying concentrations of indicated antibodies. IC50 values were estimated from each non-linear curve fitting. FIG. 3E depicts correlation analysis between EphA2 copy numbers and corresponding Wnt/β-catenin reporter inhibition efficacies of RYR/E34N19. HEK293 cells with varying copy numbers of EphA2 were prepared by transient transfection and treated with RYR/E34N19 (10 nM). STF reporter activities were analyzed after incubating cells with the antibody and EphA2 copy numbers were simultaneously detected by flow cytometry. FIG. 3F depicts the results of correlation analysis between ICAM-1 copy numbers and corresponding Wnt/β-catenin reporter inhibition efficacies of M10A12/E34N19. Similarly as described in E, HEK293 cells transiently transfected with ICAM-1 were utilized for STF reporter assay and ICAM-1 copy number determination. 10 nM of M10A12/E34N19 was treated to transfected cells, and then Wnt/β-catenin reporter activities and ICAM-1 copy numbers were analyzed at the same time. Each relative reporter activity in E and F was plotted and Pearson's correlation coefficient (r) was calculated from the graph. Error bars represent SD of a duplicate.

FIG. 4A depicts the results demonstrating LRP6 co-localization with internalizing or non-internalizing bsAbs. Parent HEK293 cells and HEK293-EphA2 cells were separately incubated with H3/E34N19 or RYR/E34N19. Membrane-bound or internalizing antibodies were stained with secondary anti-human IgG-FITC (green), and then LRP6 was detected by Alexa® 647-labeled E12N21 IgG (Red). Stained cells were visualized under confocal microscope. Scale bar, 10 μm. FIG. 4B depicts cell surface guide- and effector-antigen densities after inducing bsAb-mediated internalization. HEK293-EphA2 cells were incubated with RYR/E34N19, H3/E34N19, or C10/E34N19 and washed to remove unbound antibodies. Copy numbers of EphA2, ALCAM, or LRP6 on cell surface were determined using separate Alexa® 647-labeled antibodies, recognizing another epitope on each antigen. Calculated copy number (ABC) was normalized against an ABC value of each antigen measured from the cells treated without any antibody. Data represent mean±SD of a duplicate. *P<0.05. FIG.

4C depicts inhibition of Wnt1-induced signaling by LRP6 turnover. HEK293-EphA2 cells were transfected with reporter and Wnt1-expression constructs, followed by treatment with varying concentrations of each indicated TaFv-Fc. Values represent mean±SD for a duplicate. *P<0.05.

Figure 5A:
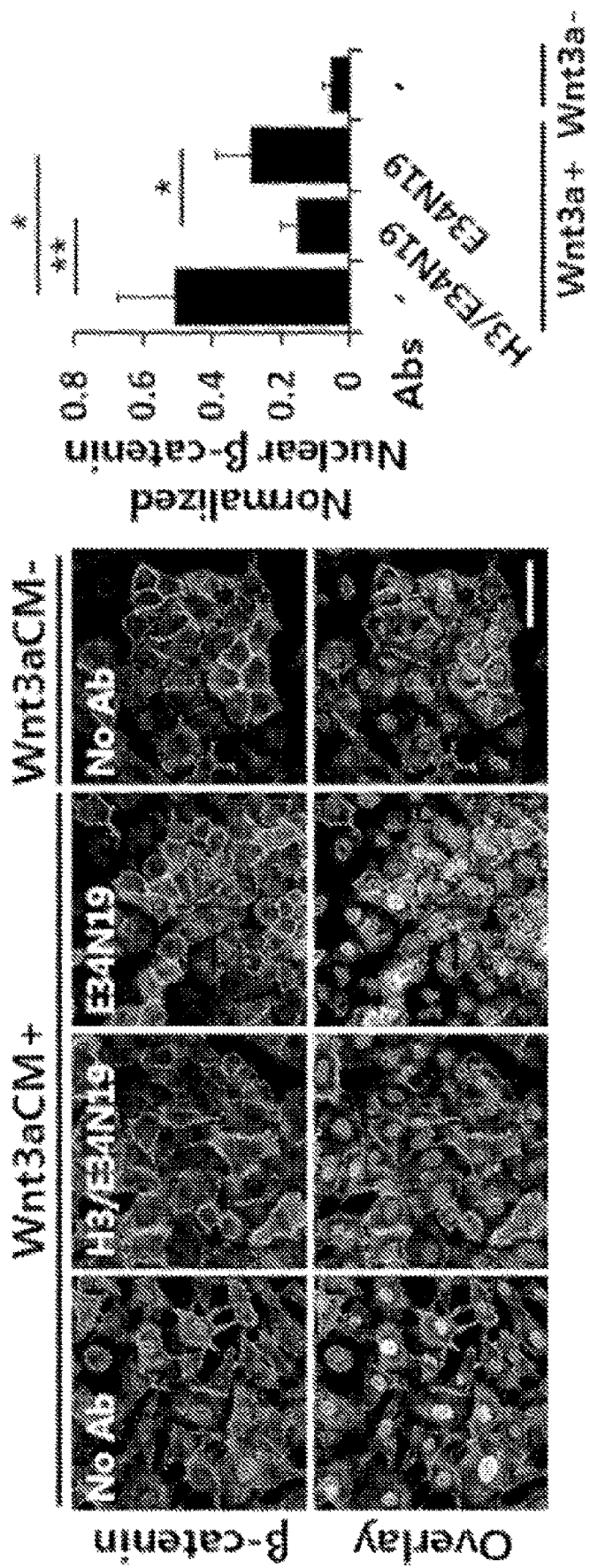
Figure 5B:
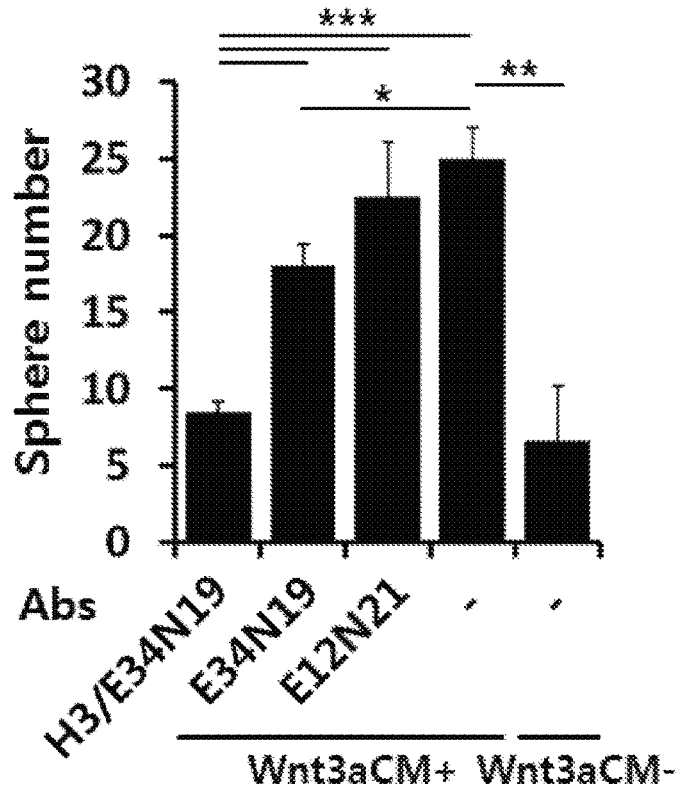
Figure 5C:
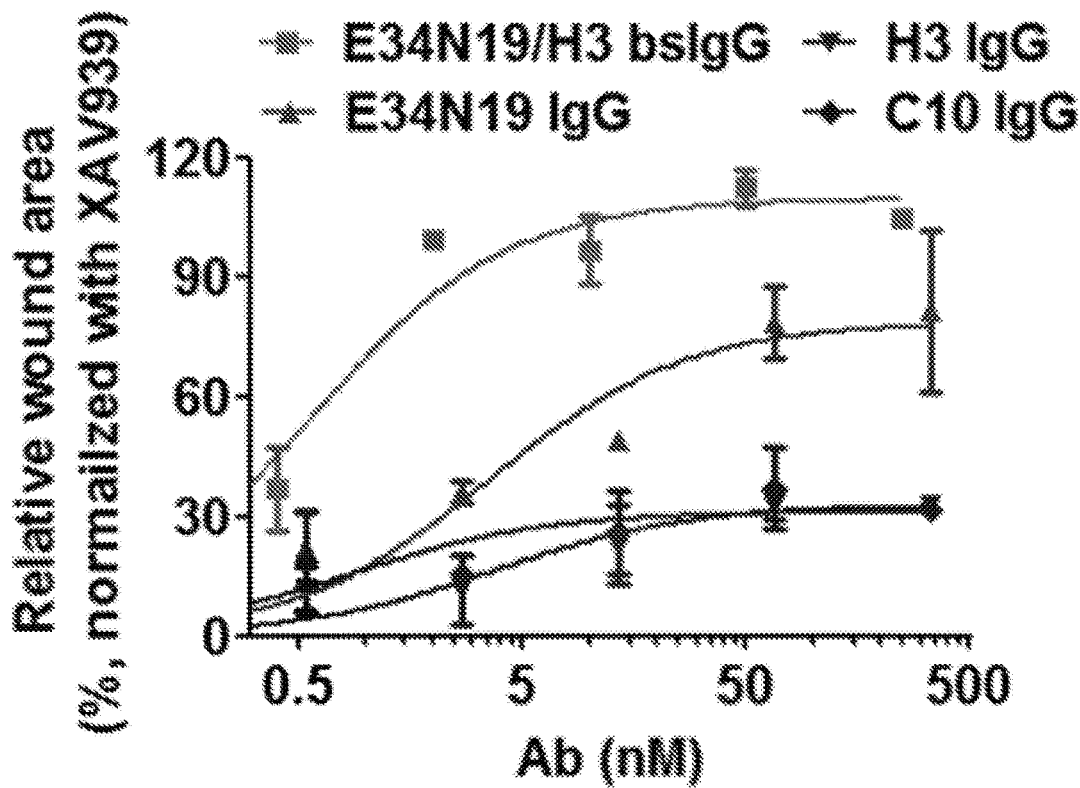
Figure 5D:
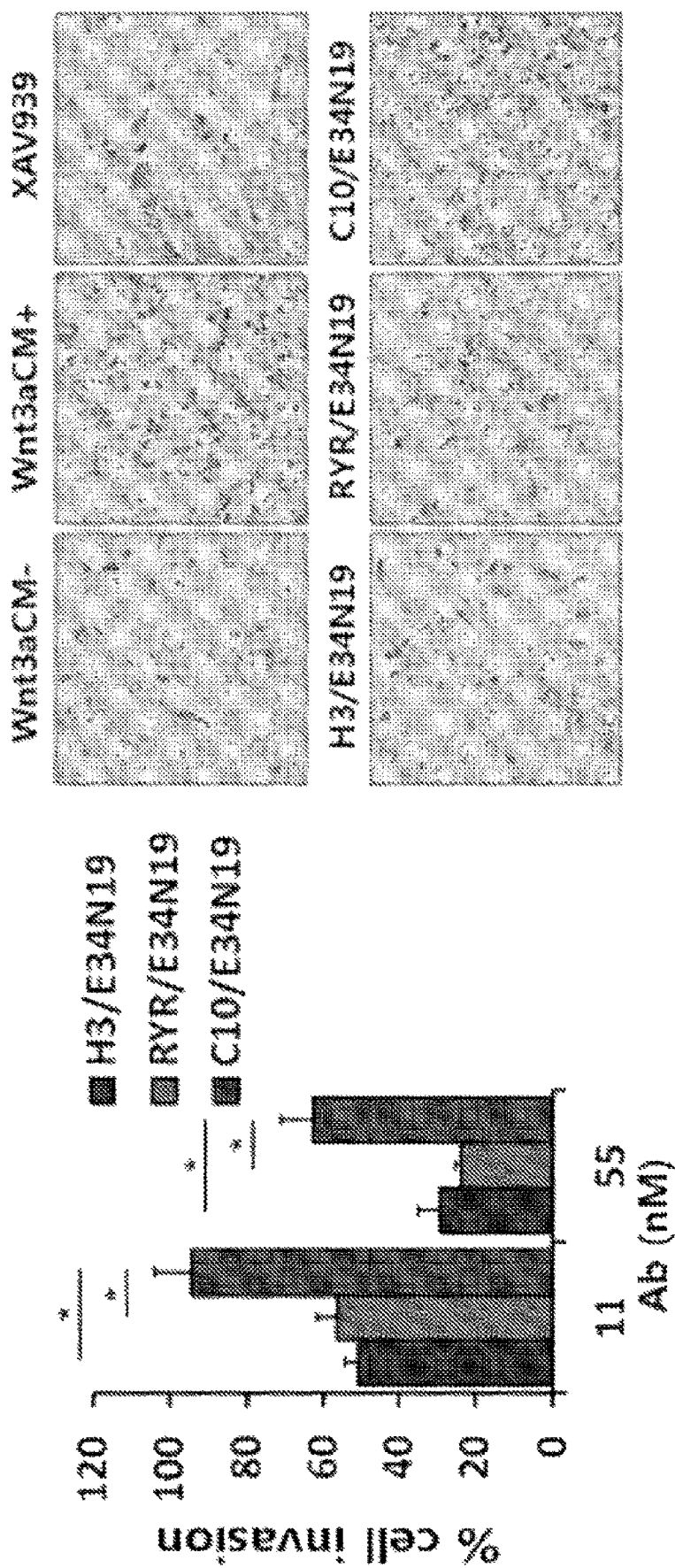

FIGS. 5A-5D depict the results illustrating that guided anti-LRP6 bsAbs maximize anti-tumorigenic activities in vitro. FIG. 5A depicts the results of immunostaining analysis to assess nuclear translocation of β-catenin. A549 cells were treated with 20% Wnt3a-CM and/or each antibody (100 nM). Cells incubated without Wnt3a-CM and/or antibodies were used as controls. Cellular β-catenin (red) and nuclei (blue) were stained after antibody incubation and merged to determine nuclear localization of β-catenin. Nuclear β-catenin signals were quantified using ImageJ and normalized with background fluorescence (right). Scale bar denotes 100 μm. *P<0.05 and **P<0.01. FIG. 5B depicts the results illustrating potent tumor sphere-forming inhibition by H3/E34N19. Single cell population of A549 cells was incubated in sphere-forming media supplemented with or without 10% Wnt3a-CM and each antibody (50 μg/ml) for 2 weeks. The number of tumor spheres with >100 μm in diameter was quantified from each well. Data represent mean±SD of a duplicate.*P<0.05, P<0.01, and *P<0.001. FIG. 5C depicts the results of wound healing assays to assess migration inhibition activities of bsAbs. A549 monolayer was scratched and treated with 20% Wnt3a-CM and different concentrations of each IgG or bsIgG. Wound areas were quantified using ImageJ and normalized against a positive control (XAV939, 50 μM). Data represent mean±SD of a duplicate. FIG. 5D depicts the results of transwell assays to validate inhibition efficacies of bsAbs in cell invasion. PC3 cells seeded on the upper compartment of transwell chambers were incubated with each TaFv-Fc and 20% Wnt3a-CM was supplemented in the lower compartment. Invaded cells were stained with crystal violet after 24 hrs incubation and microscopic images were taken at 10× magnification. The number of cells was evaluated in five fields from each experimental group and normalized against a control group without antibody treatment (left). Representative images of stained transwells are shown (right). *P<0.05.

Figure 6A:
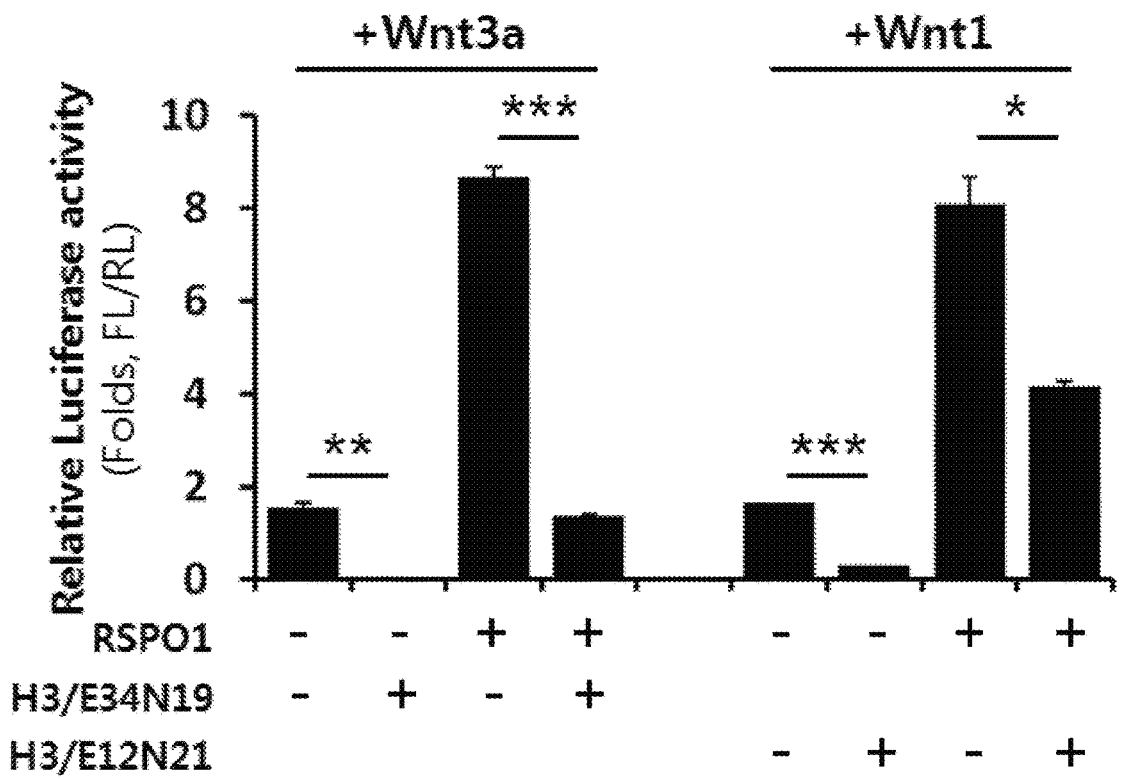
Figure 6B:
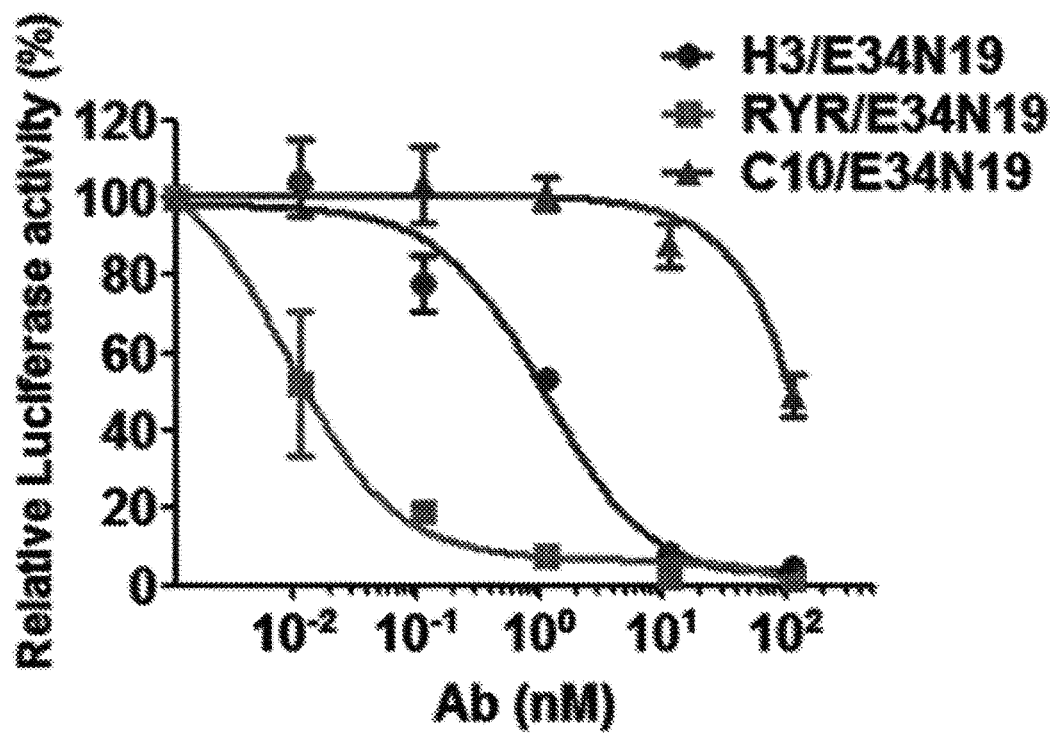
Figure 6C:
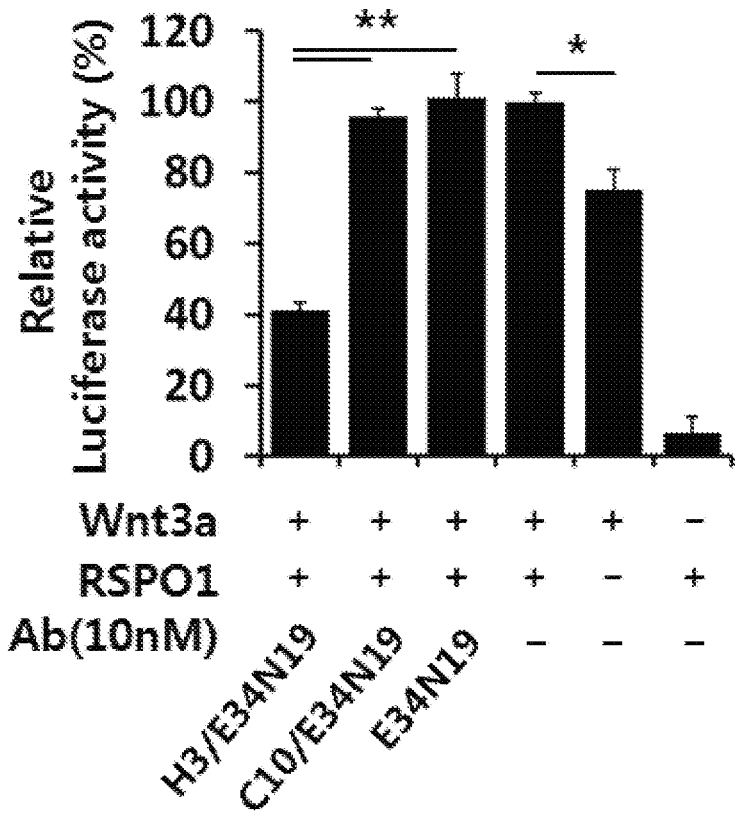
Figure 6D:
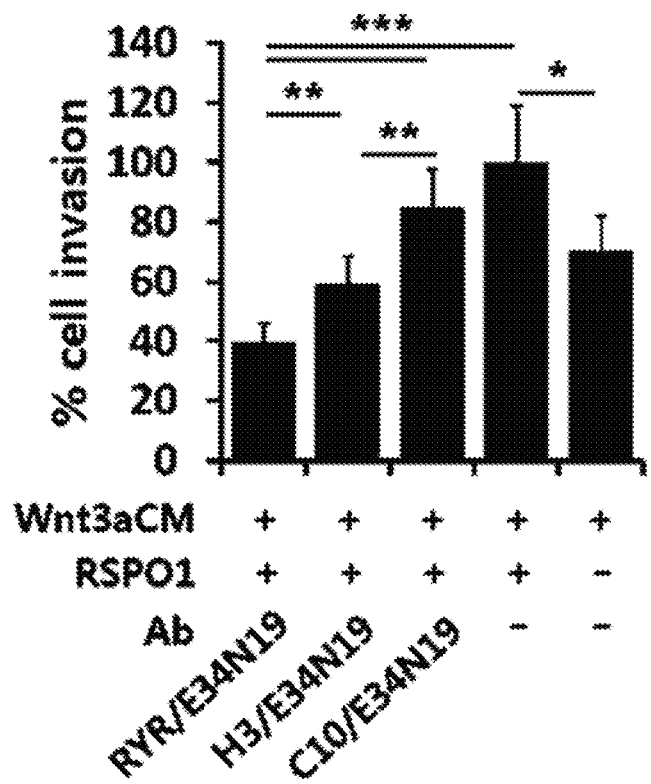

FIGS. 6A-6D depict the results illustrating that guided anti-LRP6 bsAbs suppress β-catenin activity stimulated by RSPO1. FIG. 6A depicts the results of STF reporter assays to determine RSPO1-stimulated β-catenin activation and the signaling inhibition by bsAbs. HEK293 cells transfected with STF reporter and Wnt3a- or Wnt1-expression constructs were treated with or without recombinant RSPO1 (100 ng/ml) and/or each TaFv-Fc (10 μg/ml). Values represent mean±SD of a duplicate. FIG. 6B depicts the results illustrating antigen copy number dependency in inhibiting RSPO1-induced Wnt3a/β-catenin signaling by bsAbs. HEK293-EphA2 cells that express different levels of guide antigen EphA2 or ALCAM were transfected with STF reporter and Wnt3a-expression constructs, followed by treatment with recombinant RSPO1 (100 ng/ml) and varying concentrations of each b2scFv-Fc. Values represent mean±SD for n=3. FIG. 6C depicts potent inhibition of RSPO1-induced Wnt3a/β-catenin signaling by H3/E34N19 in A549 cancer cells. Cells were transfected with STF reporter and Wnt3a-expression constructs, followed by treatment with recombinant RSPO1 (100 ng/ml) and each antibody (10 nM). Error bars represent SD of duplicate determinations. FIG. 6D depicts the results illustrating anti-invasive effects of bsAbs under Wnt3a/RSPO1-induced signaling stimulation. PC3 cells seeded on the upper compartment of transwell with each antibody and the lower compartment was provided with 20% Wnt3a-CM and recombinant RSPO1 (100 ng/ml). Invaded cells were visualized by crystal violet staining after 24 hrs incubation. The number of stained cells was quantified from five fields of each experimental group and normalized against a control group with no antibody treatment. *, , and * in graphs denote P-values of <0.05, <0.01, and <0.001, respectively.

Figure 7A:
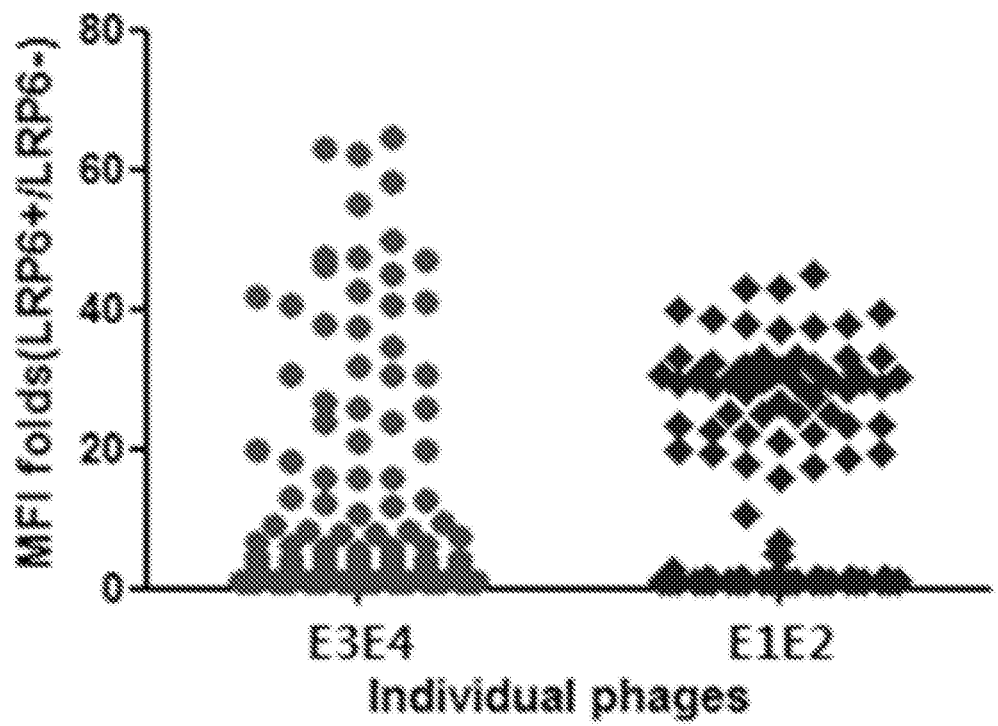
Figure 7B:
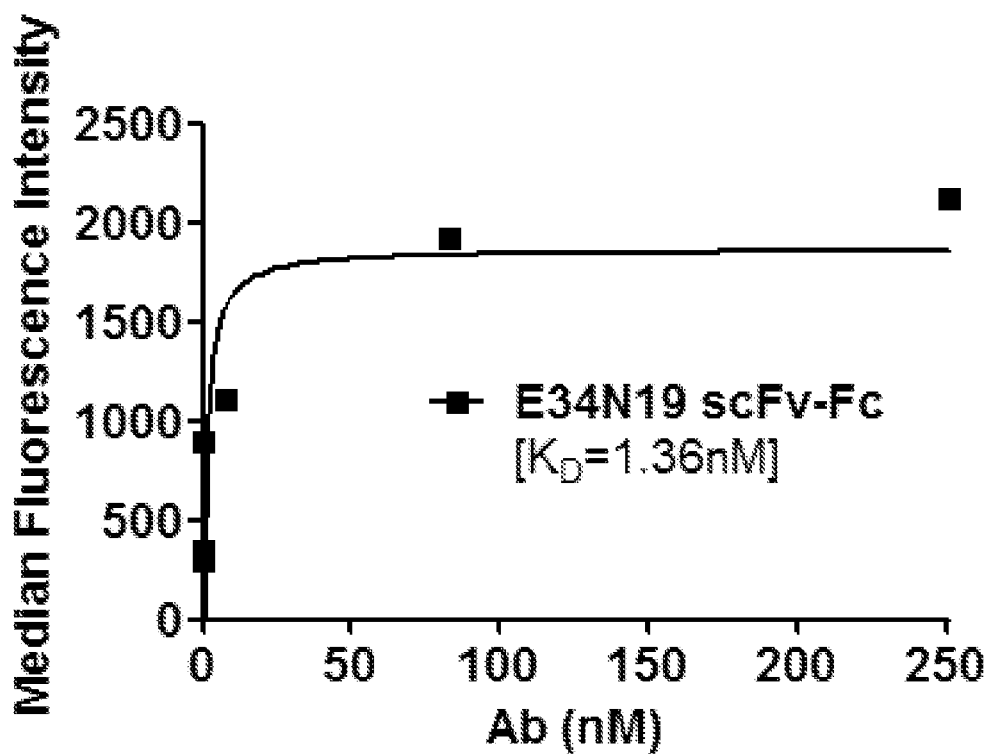
Figure 7C:
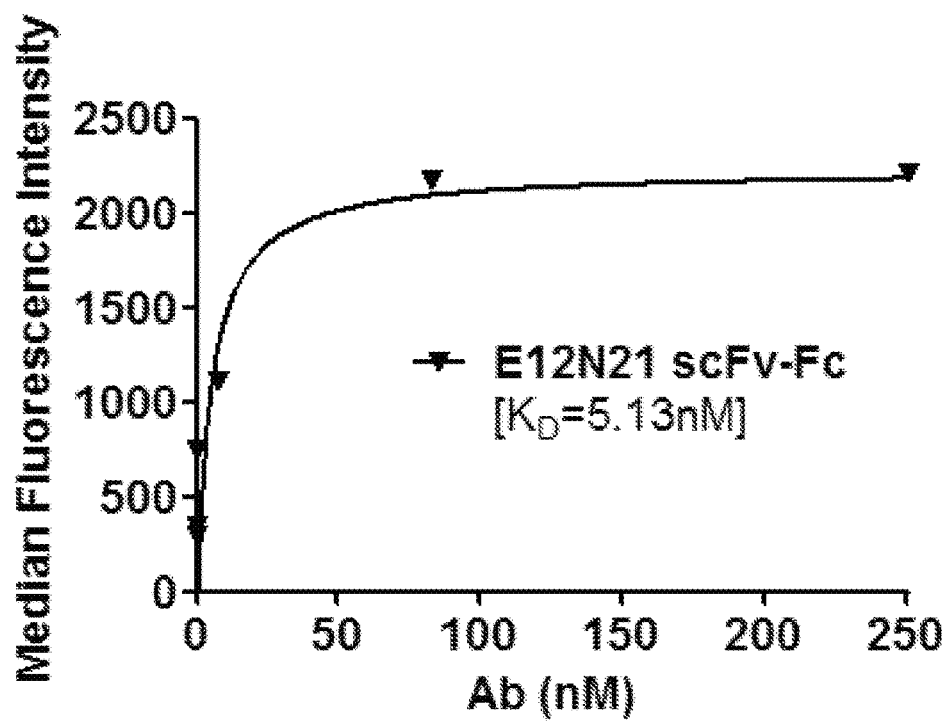
Figure 7D:
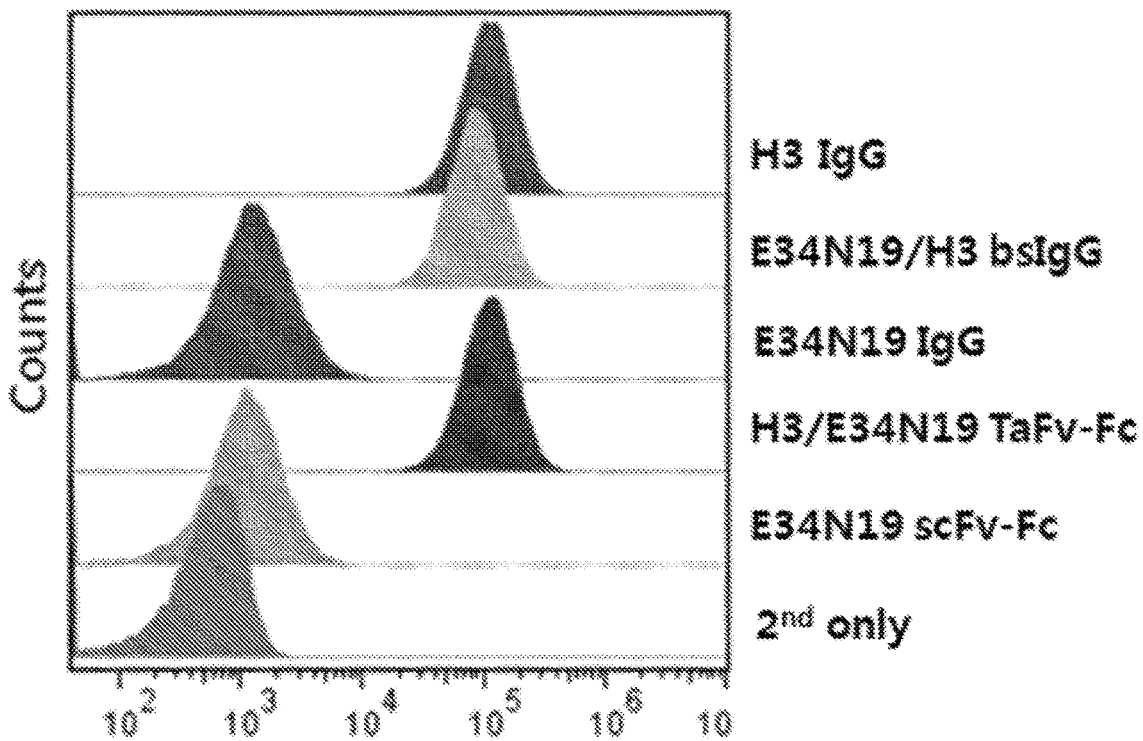
Figure 7E:
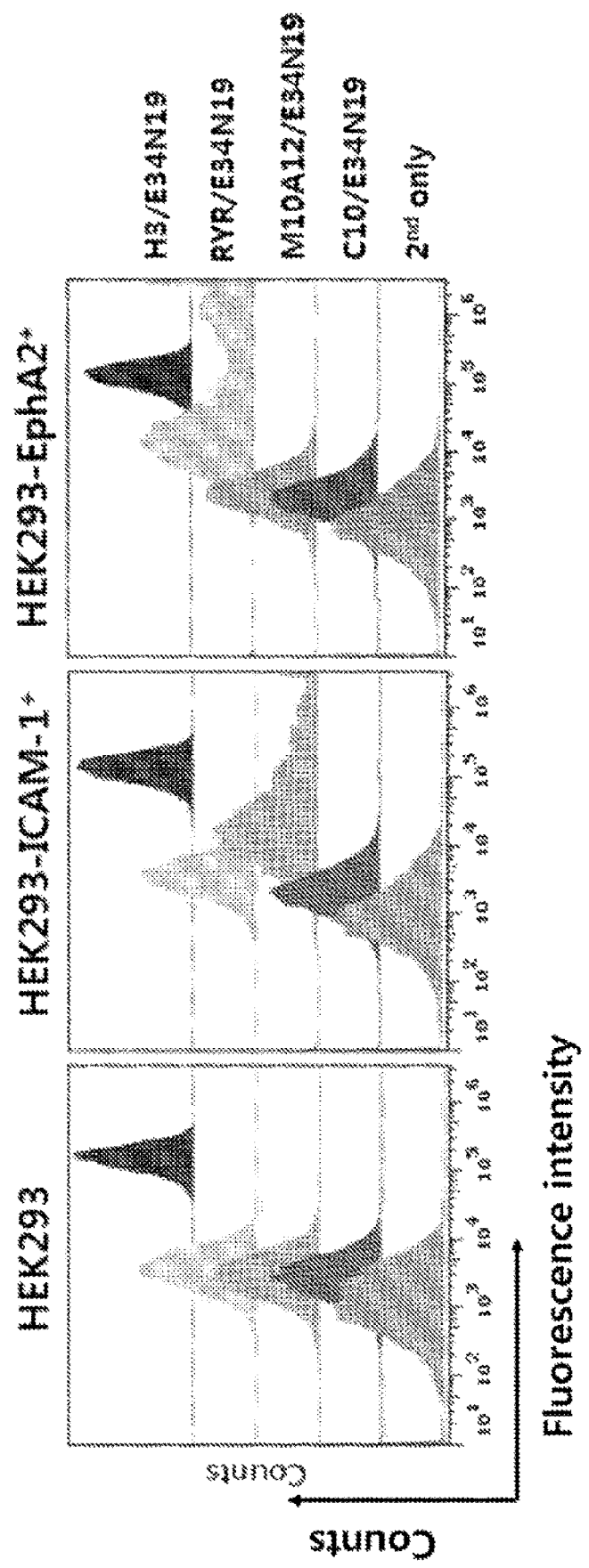

FIGS. 7A-7E depict the results illustrating characterization of anti-LRP6 scFvs and derived bsAbs. FIG. 7A depicts the results of anti-LRP6 scFv-phage screening by flow cytometry analysis. Individual scFv-phage clones were separately amplified from the $3^{rd}$ round panning output against LRP6E1E2 or LRP6E3E4 domain. scFv-phage particles were incubated with parental HEK293 or LRP6-transfected HEK293 cells and detected by biotinylated anti-M13 IgG and PE-labeled streptavidin. Relative MFI values (folds of phage binding to LRP6+ cells against LRP6− cells) were plotted on a graph. FIGS. 7B and 7C depict the results of flow cytometry analysis for binding kinetics of E34N19 (B) or E12N21 (C) scFv-Fc to HEK293 cells. The apparent $K_D$ was calculated based on the non-linear curve fittings by Prism 5 program. FIG. 7D depicts the results of cell-binding analysis of mono- or bi-specific anti-LRP6 antibodies. Binding of E34N19 scFv-Fc, E34N19 IgG, H/6 TaFv-Fc, 6/H bsIgG, or H3 IgG (each 100 nM) to HEK293 cells originally expressing ALCAM was analyzed by flow cytometry. FIG. 7E depicts the results of binding specificity of TaFv-Fcs with different guide antibodies. HEK293 cells were transiently transfected with ICAM-1- or EphA2-expression construct, followed by incubation with each guided anti-LRP6 bsAb. Parental HEK293 cells highly express guide antigen ALCAM only and were used as a control cell line for RYR/E34N19 or M10A12/E34N19 TaFv-Fc.

Figure 8A:
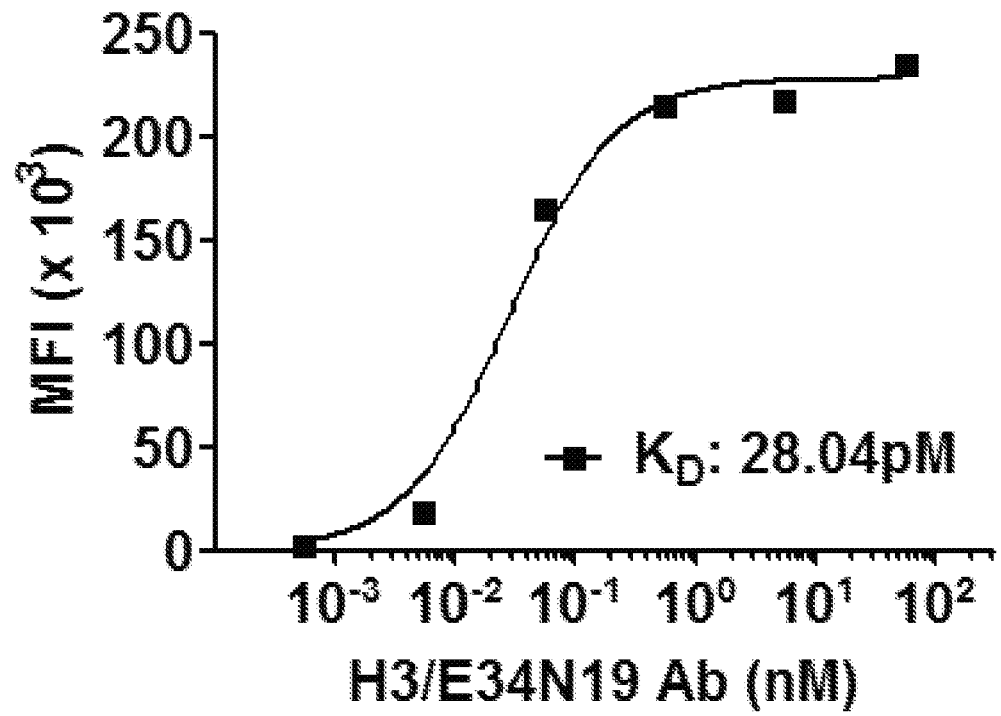
Figure 8B:
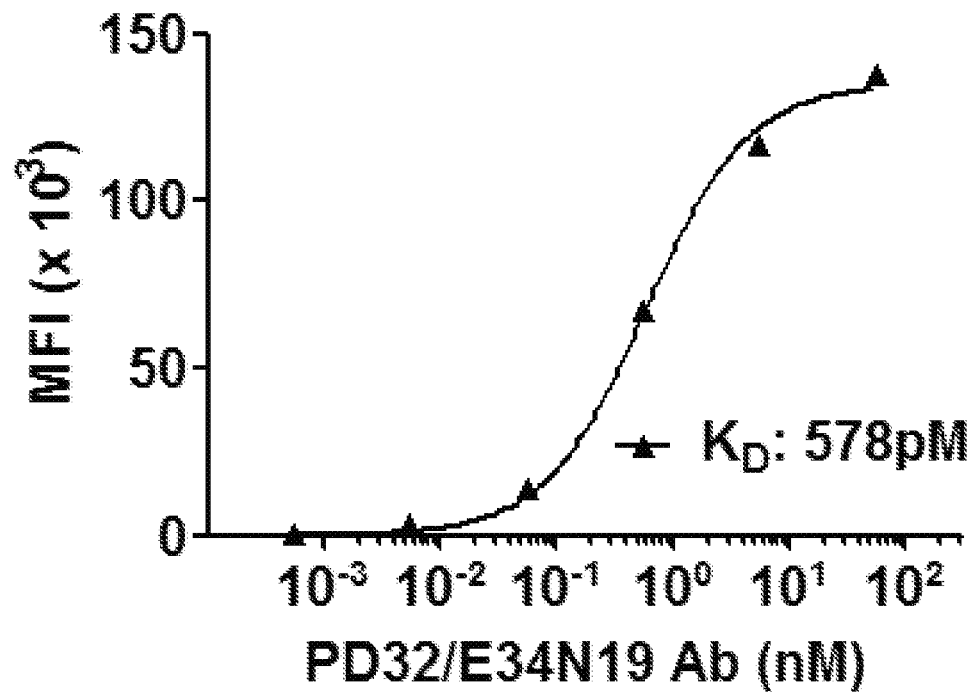
Figure 8C:
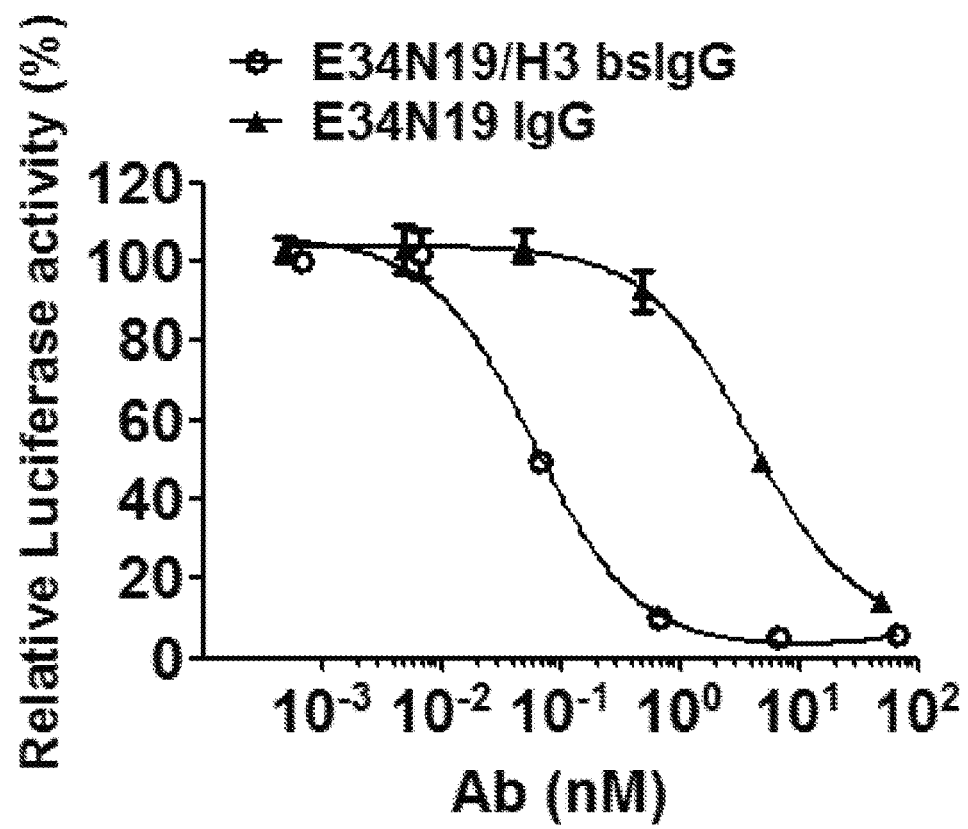
Figure 8D:
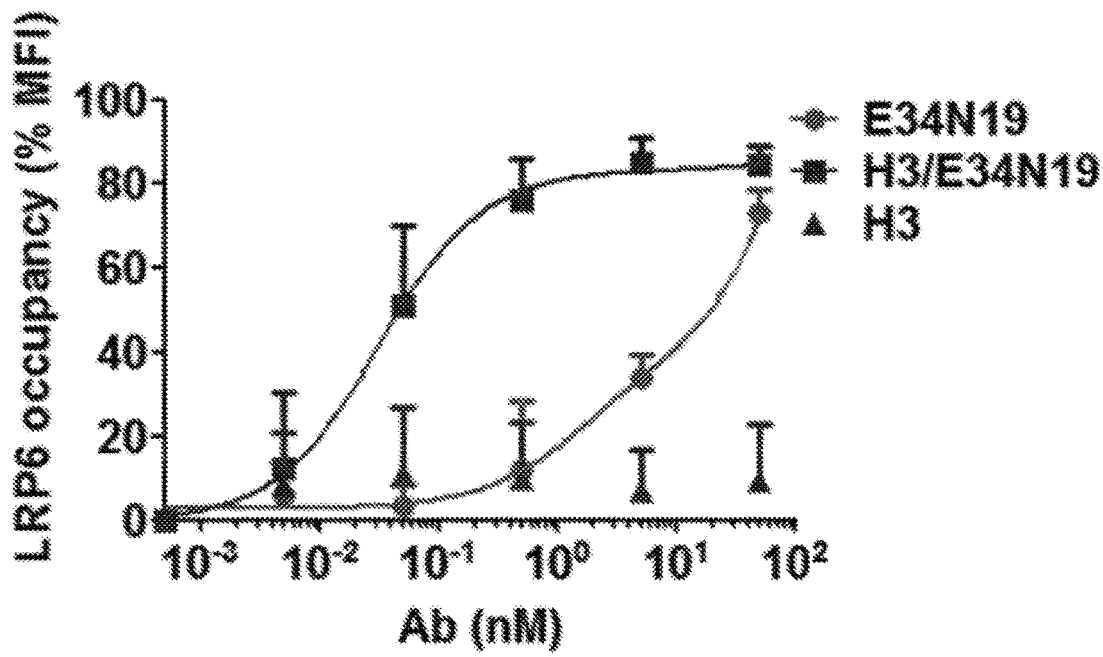

FIGS. 8A-8D depict the results illustrating improved binding and Wnt signaling blockade of guided anti-LRP6 bsAbs. FIGS. 8A and 8B depict the results illustrating affinity measurement of bispecific anti-LRP6 TaFv-Fcs. HEK293 cells were incubated with varying concentration of H3/E34N19 (A) or PD32/E34N19 (B) TaFv-Fc and analyzed by flow cytometry. Apparent $K_D$ values were calculated based on the non-linear curve fittings. FIG. 8C depicts STF reporter assays on HEK293 cells. E34N19 IgG and E34N19/H3 bsIgG were evaluated for their β-catenin reporter inhibition efficacies on Wnt3a-transfected HEK293 cells. IC50 was estimated from the curve fitting (E34N19 IgG: 5.2 nM, E34N19/H3 bsIgG: 44.6 pM). Values represent mean±SD for n=3. FIG. 8D depicts LRP6 occupancy when bound by bispecific vs, monospecific antibodies. HEK293 cells were incubated with the either the bispecific H3/E34N19 or the monospecific E34N19, and unoccupied LRP6 binding sites were detected by biotin-labeled E34N19 scFv-Fc. Normalized MFI from unoccupied sites over total is used to calculate the percent of the unoccupied effector antigen LRP6, from which the occupancy was calculated (100%−% unoccupied). Incubation with the anti-guide antibody only (H3) has no effect on the occupancy of the effector antigen (LRP6). Data points represent mean±SD of a duplicate.

Figure 9A:
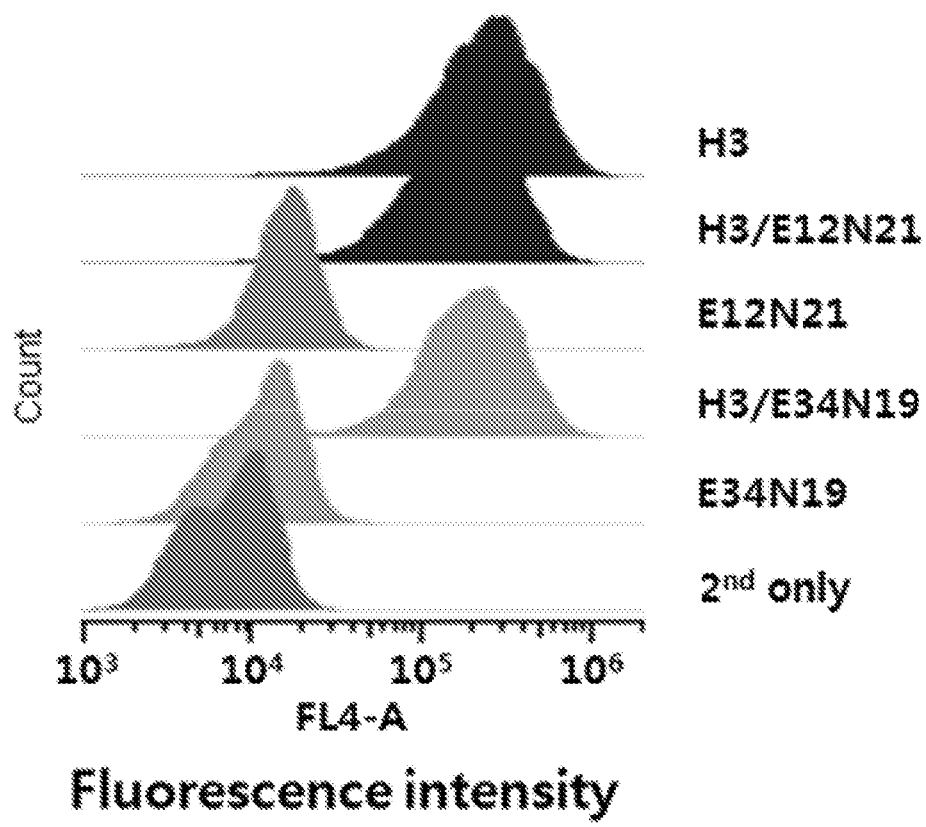
Figure 9B:
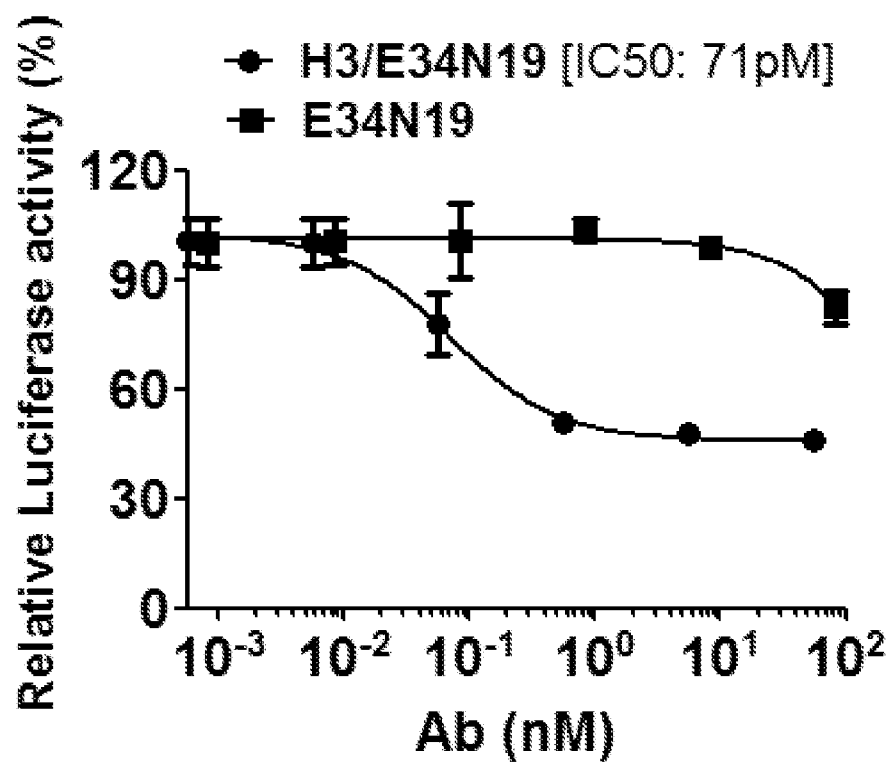
Figure 9C:
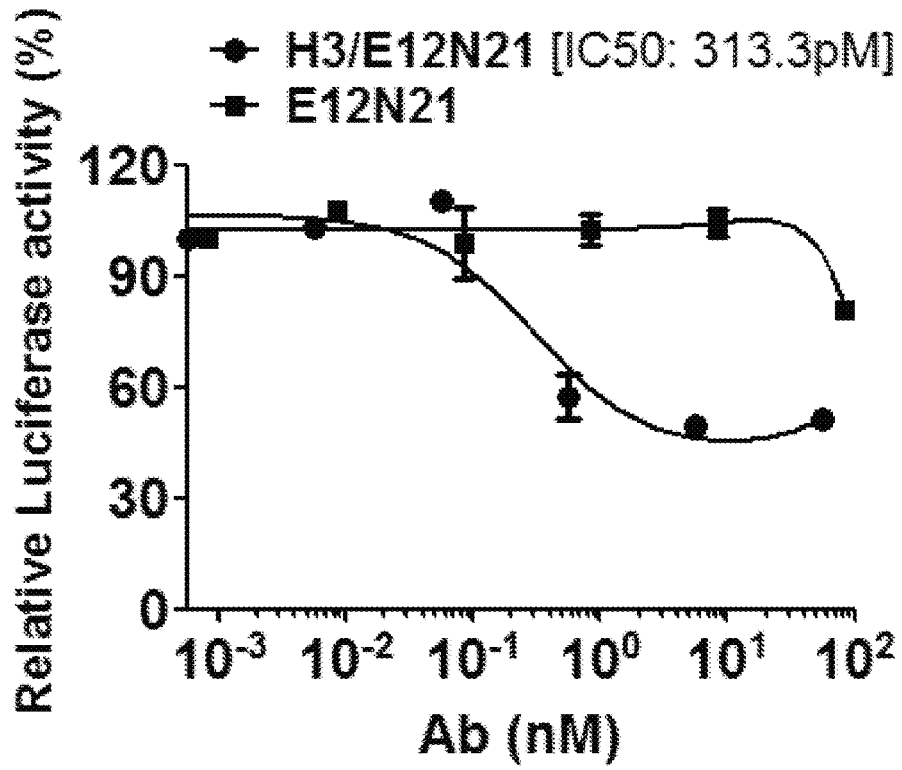
Figure 9D:
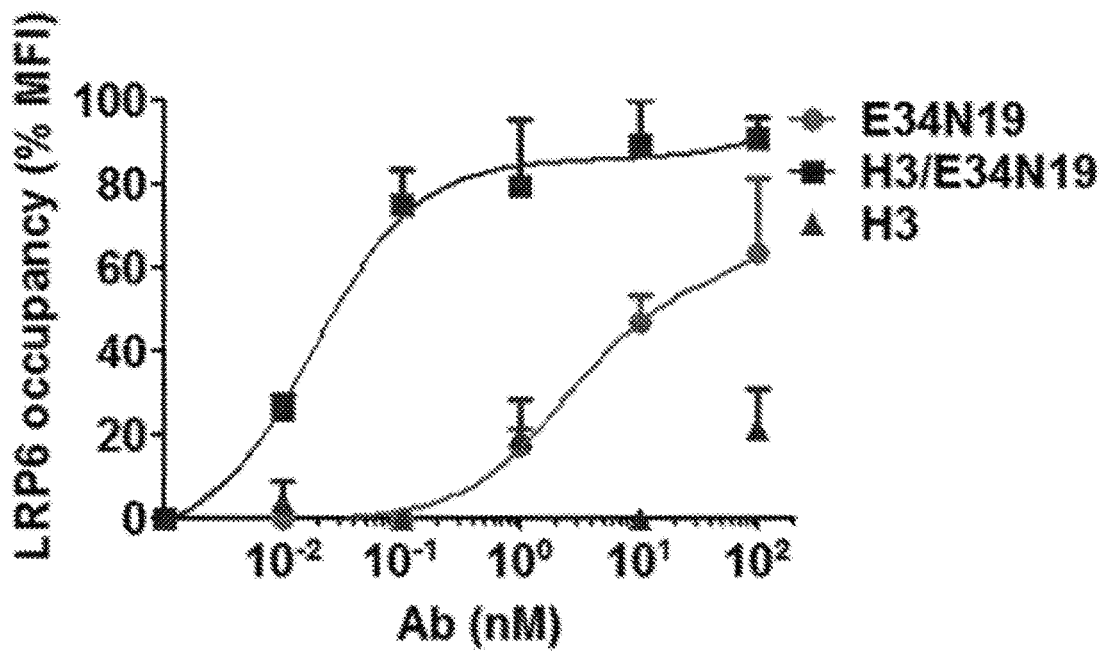

FIGS. 9A-9D depict the results illustrating improved binding and Wnt signaling blockade of guided anti-LRP6 bsAbs. FIG. 9A depicts the results illustrating binding activities of H3 IgG, H3/E12N21 or H3/E34N19 TaFv-Fc, and E12N21 or E34N19 scFv-Fc (each 100 nM) to A549 cells originally expressing ALCAM. FIGS. 9B and C depict STF reporter assays on A549 cells. Cells were transfected with STF reporter and Wnt3a- (B) or Wnt1-expression (C)

constructs, followed by treatment with varying concentrations of H3/E34N19 and E34N19 (B) or H3/E12N21 or E12N21 (C), respectively. IC50 values were estimated from the curve fitting. FIG. 9D depicts the results illustrating receptor occupancy of effector antigen LRP6 by incubating with antibodies. A549 cells were incubated with varying concentrations of each scFv-Fc or TaFv-Fc for 16 hr. Cells were collected and washed using chilled PBS three times to remove remaining antibodies. The amount of unoccupied LRP6 epitopes were determined by FACS using Alexa Fluor® 647-labeled E34N19 IgG. MFI values were normalized against a control group without antibody incubation to generate the rate of unoccupied effector antigen LRP6, from which the occupancy was derived (100%–% of unoccupied). Values represent mean±SD of a duplicate.

Figure 10A:
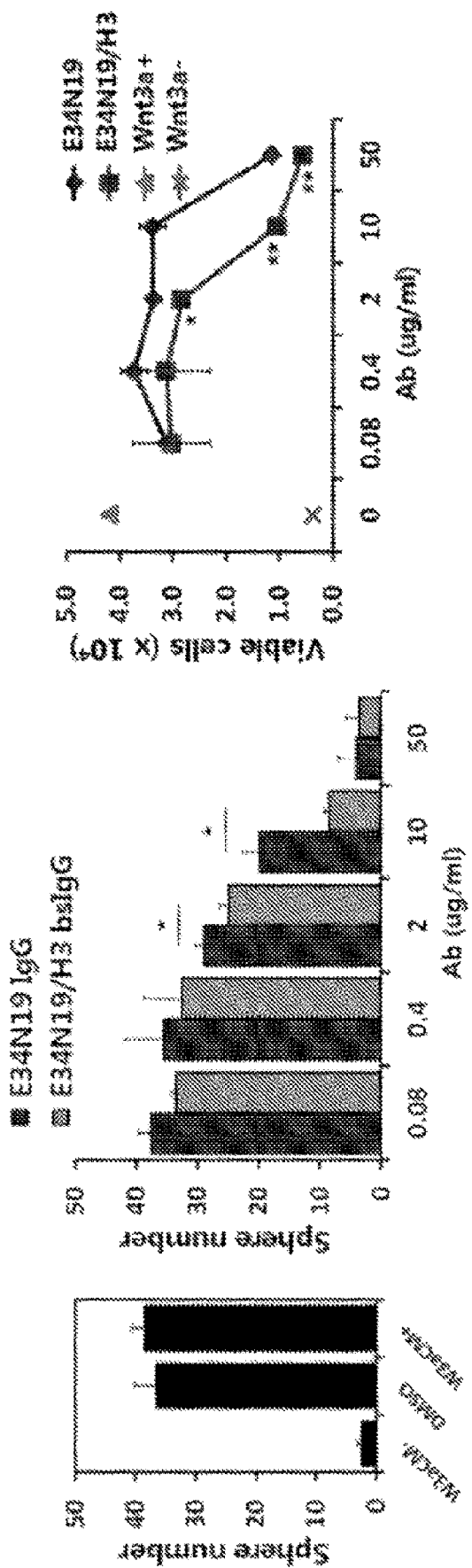
Figure 10B:
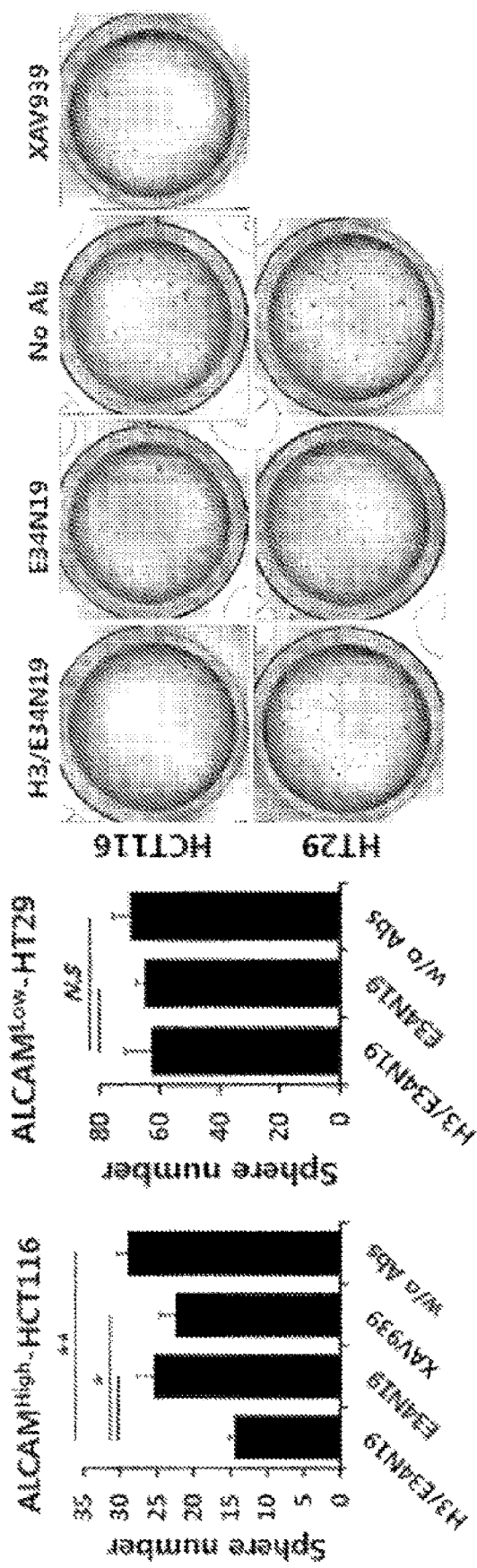

FIGS. 10A and 10B depict the results illustrating that antagonizing Wnt3a with bsAbs potently inhibits in vitro clonogenic activity in a guide antigen-dependent manner. In FIG. 10A, sphere-cultured HEK293 cells were dissociated into single cells and seeded at a density of 200 cells per well in 24-well low attachment plates. Sphere cells were treated with 10% Wnt3a-CM including each indicated antibody (50 µg/ml) and incubated for 2 weeks. The number of spheres (>100 µm) was counted from each well (left and middle), and then spheres were dissociated and stained with Calcein-AM (2 µM) for 1 hr. Viable cells from spheres were gated on FACS plot and the number was quantified for each experimental group. FIG. 10B depicts the results of tumor-sphere formation assays to determine guide antigen-specific anti-Wnt signaling potency of bsAbs. Secondary spheres generated from ALCAM$^{high}$ HCT116 or ALCAM$^{low}$ HT29 colon cancer cell line were dissociated into single cells and seeded as described in A, then the cells were incubated in sphere-forming medium supplemented with 10% Wnt3a-CM with each antibody (50 µg/ml) or XAV939 (50 µM). The number of spheres (>100 µm) in each well was separately counted (left) and representative whole-well images are shown (right). N.S, not significant. Values in A and B represent the average proportion of counted sphere numbers or viable cell numbers. Error bars denote SD of n=3. *P<0.05 and **P<0.01.

Figure 11:
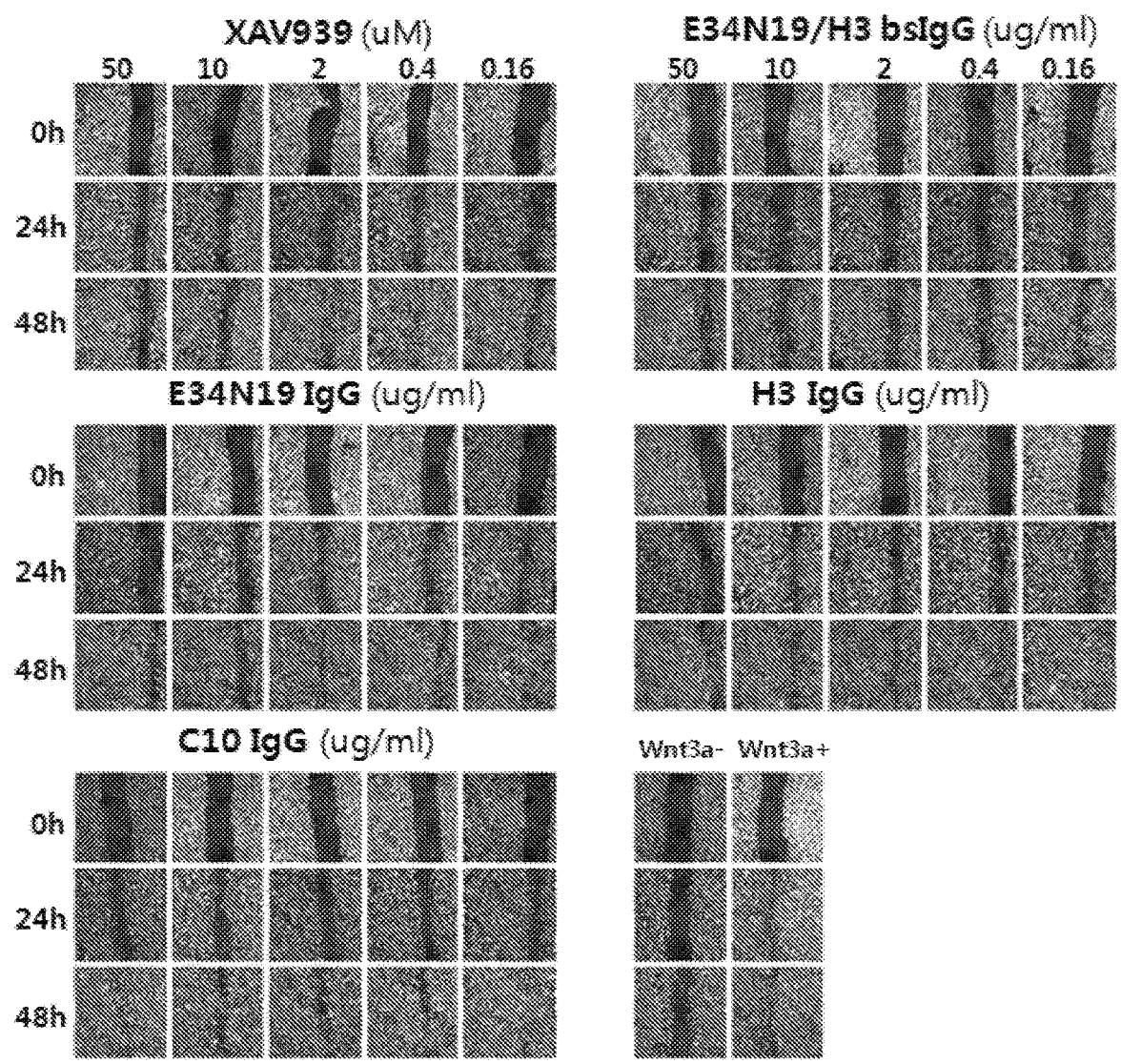

FIG. 11 depicts the results illustrating that E34N19/H3 bsIgG effectively inhibits cancer cell migration. FIG. 11 depicts representative images from wound-healing migration assays. Confluent A549 cells seeded on a 96-well plate were scratched and treated with varying concentrations of indicated antibodies or XAV939 for 48 hrs within 20% Wnt3a-CM. Cell images were taken at each time point and wound area was quantified by ImageJ.

Figure 12A:
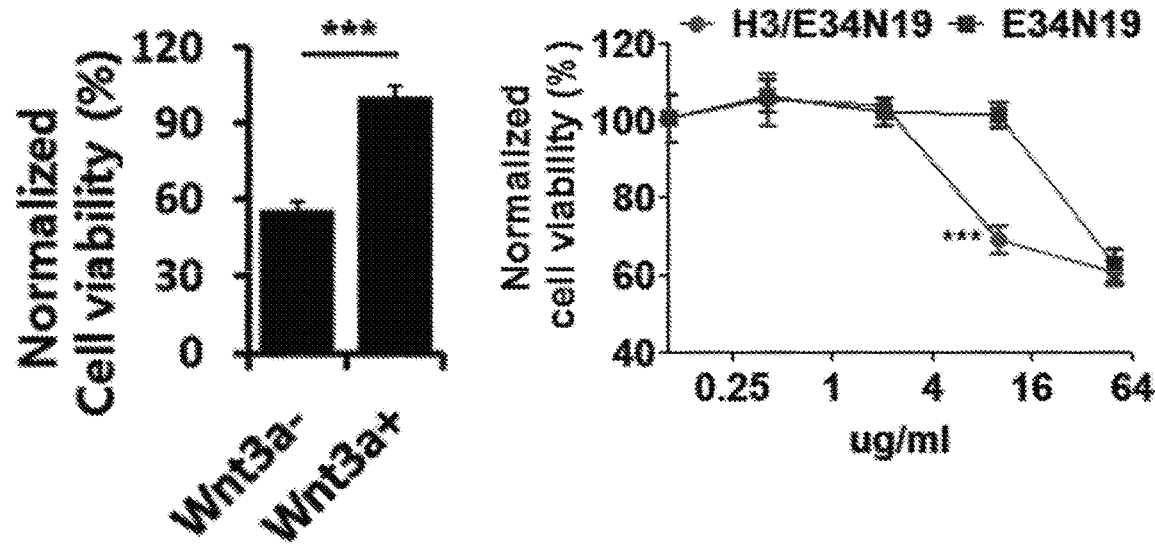
Figure 12B:
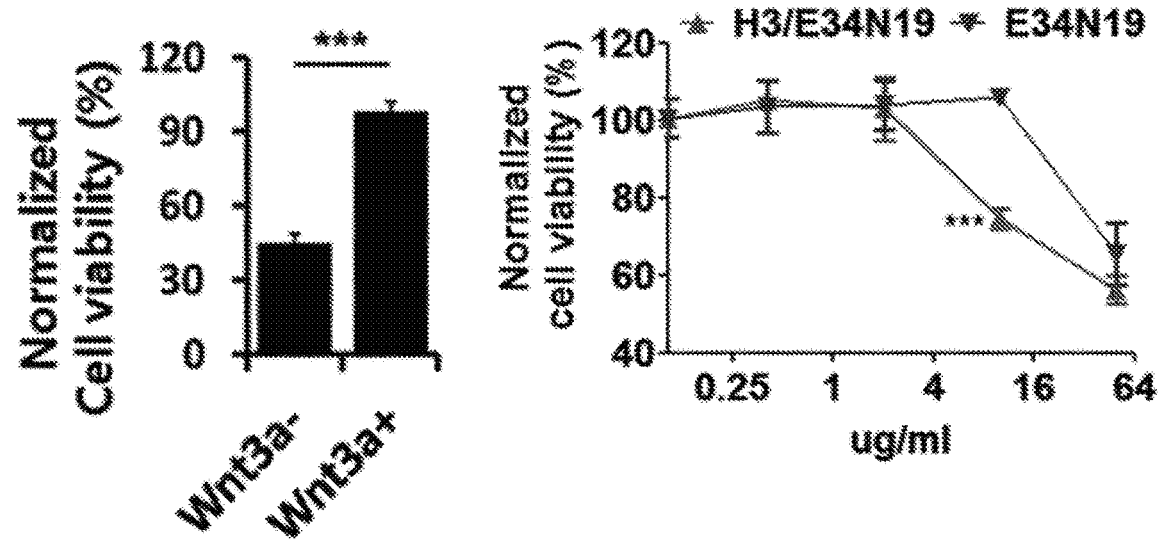
Figure 12C:
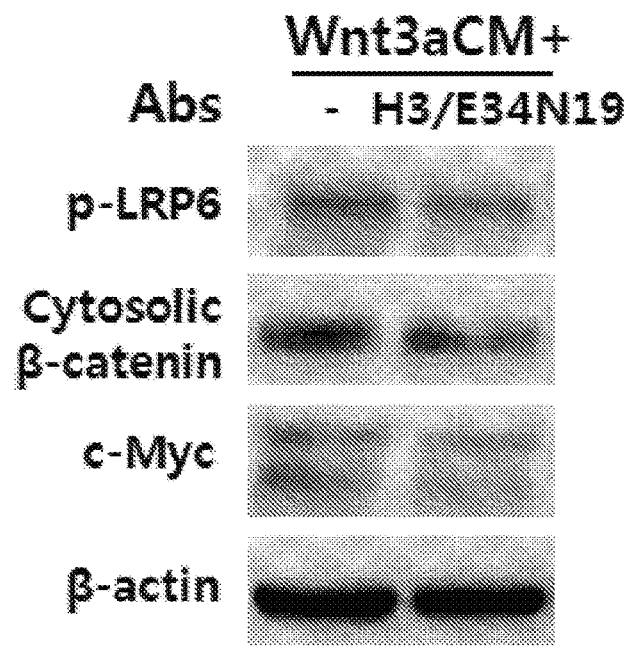

FIGS. 12A-12C depict the results illustrating that H3/E34N19 shows a potent anti-proliferation activity by destabilizing β-catenin. Guide antigen ALCAM-expressing A549 (A) or HCT116 cells (B) were seeded on a 96-well plate and treated with 10% Wnt3a-CM and indicated concentrations of H3/E34N19 TaFv-Fc or E34N19 scFv-Fc, respectively. Cells were incubated for 4 days and stained with Calcein-AM. Cell viabilities were measured and normalized with a control group without antibody treatment. FIG. 12C depicts the results illustrating inhibition of β-catenin and c-Myc levels by H3/E34N19 treatment. A549 cells were incubated with 10% Wnt3a-CM and/or H3/E34N19. After 24 hrs incubation, phosphorylated LRP6 (p-LRP6) or cytosolic β-catenin and c-Myc levels were analyzed from a membrane or cytosolic fraction, respectively.

Figure 13A:
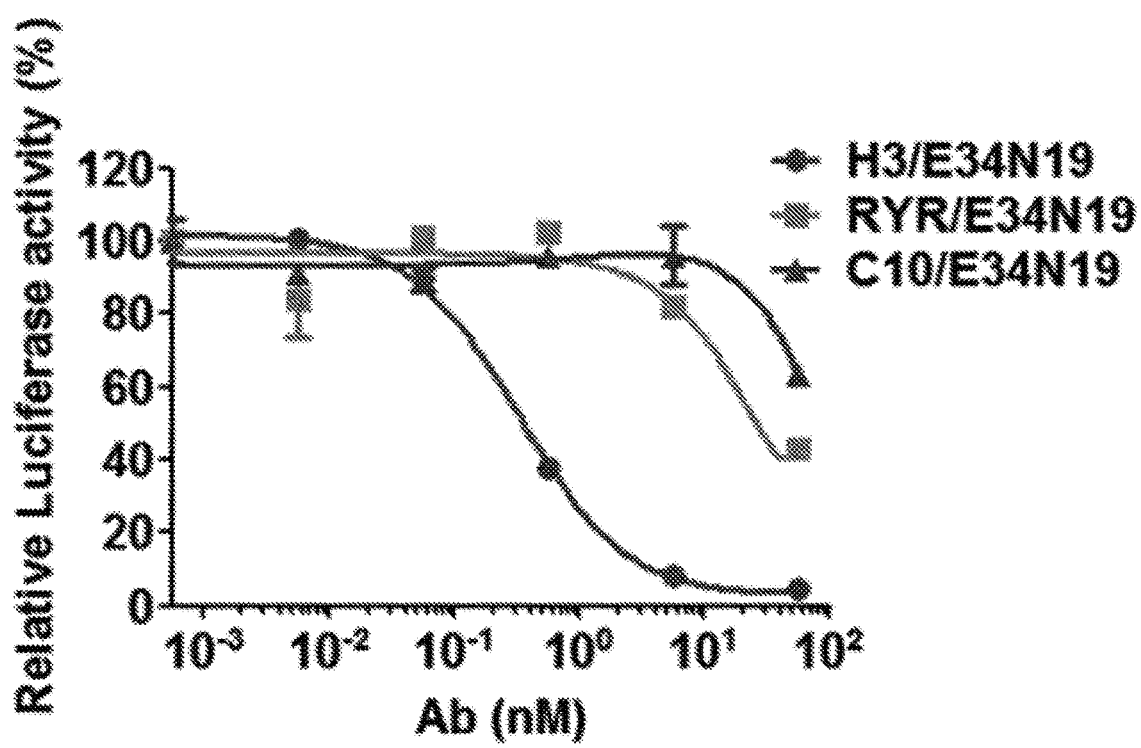
Figure 13B:
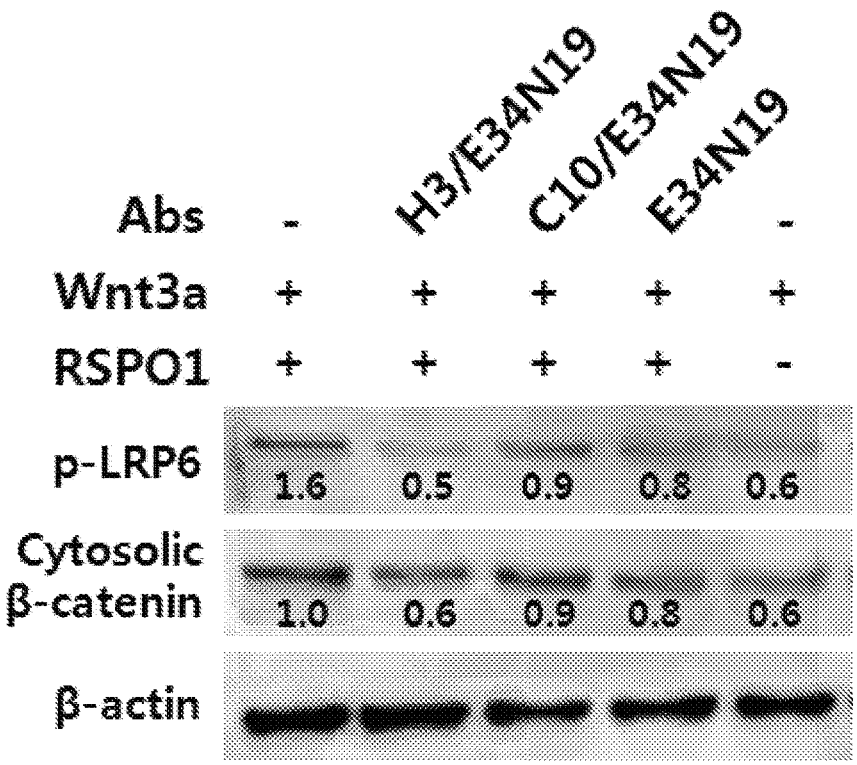
Figure 13C:
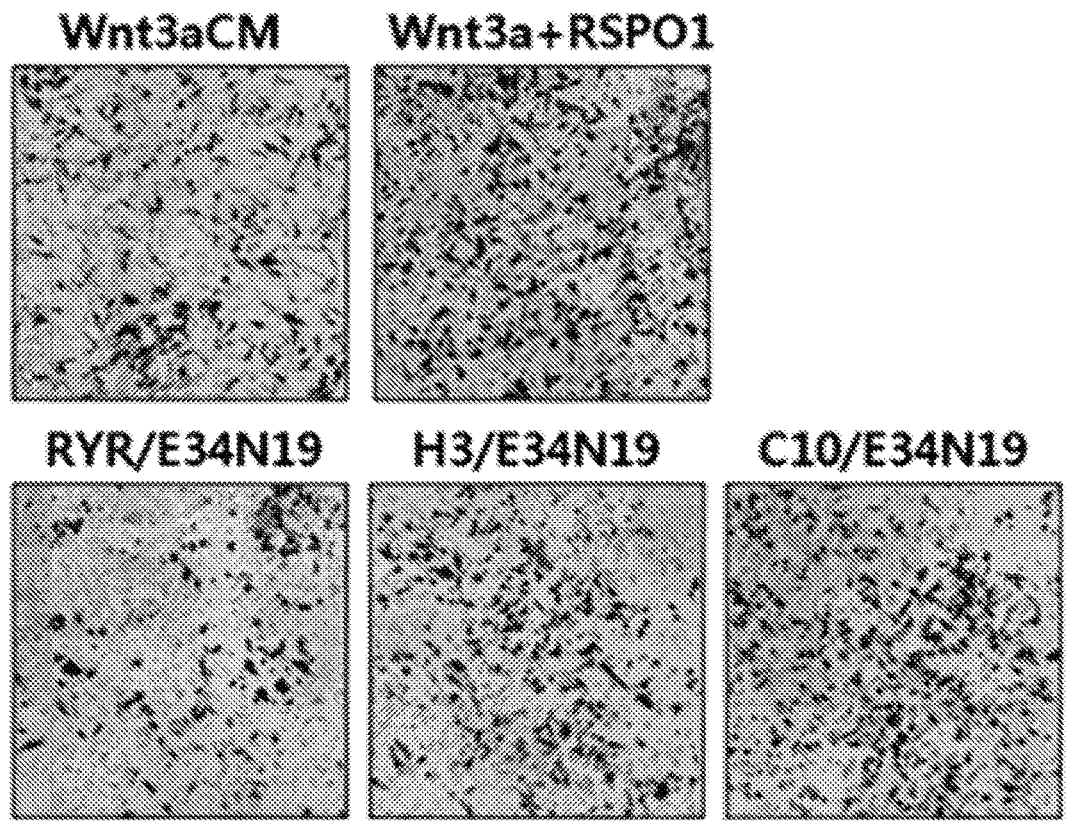

FIGS. 13A-13C depict the results illustrating that guided bsAbs are potent in inhibiting Wnt3a/RSPO1-induced Wnt signaling stimulation. FIG. 13A depicts the results of STF reporter assays to determine anti-Wnt signaling potency of H3/E34N19 under a Wnt3a/RSPO1-provided condition. HEK293 cells were transfected with STF reporter and Wnt3a-expression constructs, followed by treatment with recombinant RSPO1 (100 ng/ml) and varying concentrations of each TaFv-Fc. IC50 measured for H3/E34N19 was 327 pM, and IC50 value for RYR/E34N19 or C10/E34N19 was estimated about 50 nM or more than 100 nM, respectively. Values represent mean±SD for n=3. FIG. 13B depicts the results of western blot analysis to determine anti-Wnt signaling activity of bsAbs on Wnt3a/RSPO1-provided condition. A549 cells were incubated with Wnt3a-CM, recombinant RSPO1 (100 ng/ml), and each indicated antibody (20 µg/ml) for 24 hrs. Cells were fractionated into a membrane (for p-LRP6) and cytosolic (for β-catenin and (3-actin) fraction. Band intensities of p-LRP6 and β-catenin in each determination were normalized against each β-actin level and described under each band. FIG. 13C depicts the results of transwell invasion assays on PC3 cells. Representative images from each duplicate, corresponding to FIG. 6D. Cells were seeded on the upper compartment of transwell chambers and treated with RYR/E34N19, H3/E34N19, and C10/E34N19 (50 µg/ml), respectively. 20% Wnt3a-CM was provided in the lower compartment, followed by incubation for 24 hrs to induce cell invasion. Invaded cells were stained with crystal violet and microscopic images were taken at 10× magnification.

Figure 14:
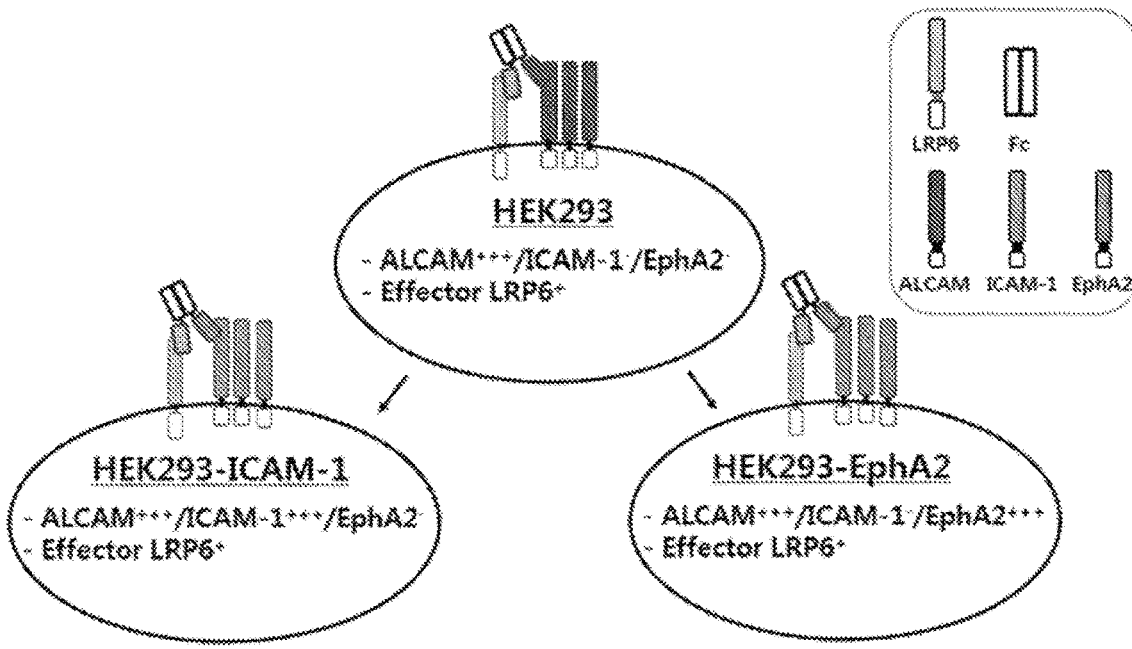

FIG. 14 depicts a schematic view of guide/effector cell model.

FIGS. 15A-15F depict the results illustrating that the guided bispecific does not inhibit Wnt signaling on normal cells and normal stem cells that express a low level of the guide antigen. A) The anti-LRP6E3E4 antibody E34N19 found to bind to both human and murine LRP6. Recombinant human LRP6E3E4-Fc (hLRP6E3E4), LRP6E1E2-Fc (hLRP6E1E2, as a control) and the mouse full-length LRP6-Fc (mLRP6, R&D systems) were diluted to 5 µg/ml in PBS and coated on a 96 well Maxisorp ELISA plate (Nunc) at 4° C. overnight. The plate was blocked by 2% skim milk in PBS at RT for 1 h, further incubated with biotinylated E34N19 and an isotype control non-binding antibody (Ctrl Ab), both at 5 µg/ml, at RT for 1 h, washed three times with 0.1% PBS-Tween20 and incubated with HRP-conjugated streptavidin (Sigma Aldrich) at RT for 1 h. TMB substrate (Thermo Scientific) was used for colorimetric reaction and 1 N HCl (100 µl/well) was added to stop the reaction after 3 min. O.D. values at 450 nm were determined by plate reader Synergy HT (BioTek). B) The anti-guide antibody RYR binds to both human and murine antigen. FACS analysis was performed on murine colon cancer cell line CT26 that express EphA2. Panels (C) and (D) show assessment of guide antigen expression on MC3T3-E1 and C3H/10T1/2, respectively. Binding of RYR (anti-EphA2) and E34N19 (anti-LRP6) (each at 100 nM) was analyzed by FACS. MFI values (after background subtraction) were used to calculate the guide to effector ratio as indicated under the histogram. Panels (E) and (F) show results of STF reporter assay on MC3T3-E1 and C3H/10T1/2, respectively. Both cell lines were transfected with the STF reporter plasmid, and treated with antibodies at indicated concentrations in Wnt3a-CM. Data in duplicates were analyzed by One-Way ANOVA using the Tukey's method, which showed no significant difference between any of the study groups.

Figure 16C:
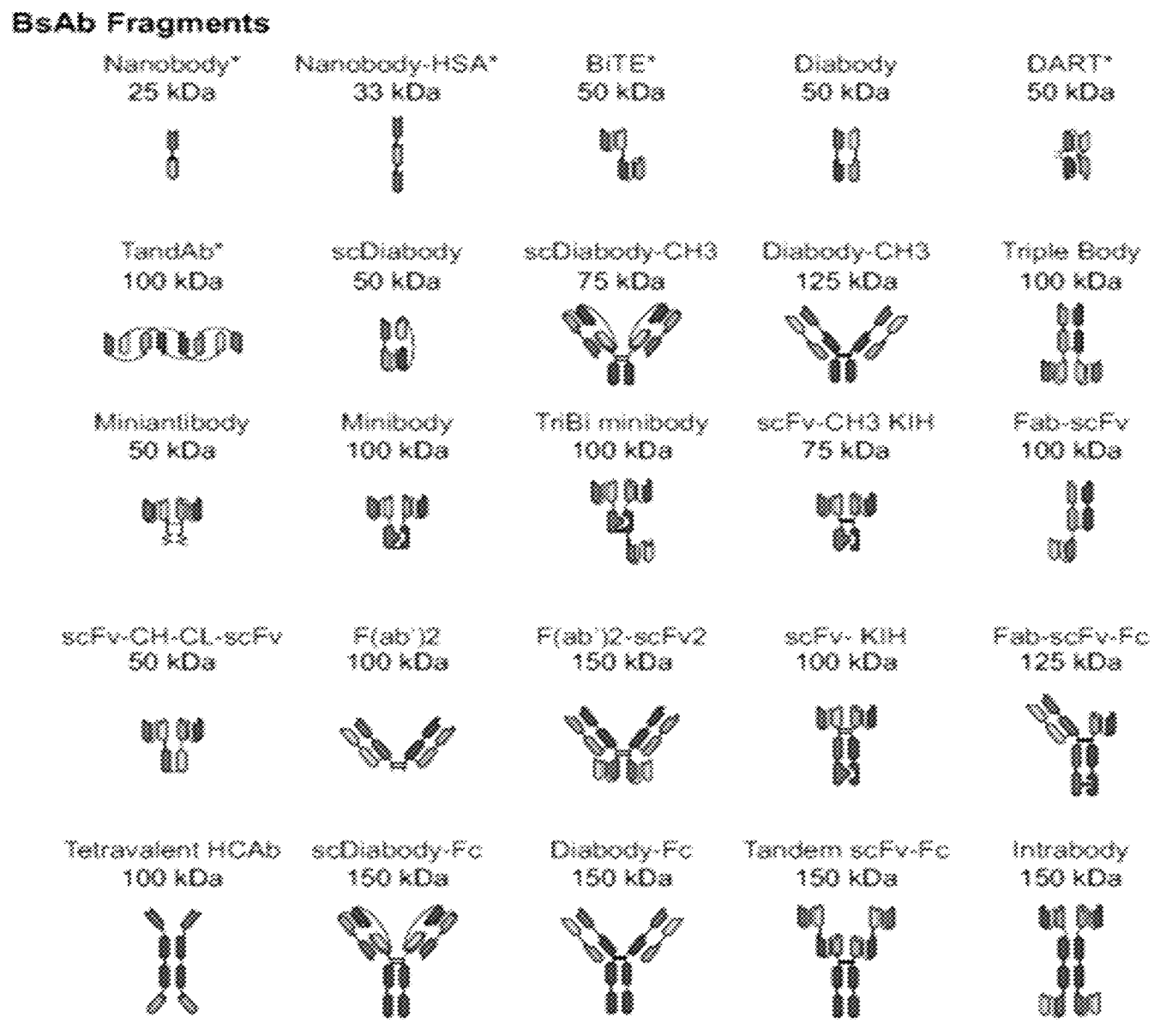

FIGS. 16A-16D illustrate exemplary bispecific antibodies of the present disclosure.

DETAILED DESCRIPTION

Antibody-based therapeutics have emerged as effective cancer treatment options, due to the specificity and affinity of the antibody to target binding and ease of chemical and molecular modifications. For example, approved antibody-based therapy has monoclonal antibodies such as rituximab, tositumomab, and trastuzumab; and bispecific T-cell engager such as Blinatumomab.

In some instances, low receptor copy numbers on a target cell, or low affinity toward an antigen has hindered the therapeutic effect of an antibody-based therapy. In some cases, non-specificity of an antibody toward a target antigen, or the presence of a target in both cancer and non-cancer cells have further limited the use of an antibody-based therapy.

In certain embodiments, described herein relate to platform technology for bispecific antibodies, compositions, engineered antibodies that recognize two different cell surface antigens and design methods of generating such antibodies. In some cases, the engineered antibodies co-engage cell type-selective antigens (guides) and a signaling receptors (effectors) on target cells. In some cases, the engineered antibodies utilize a guide/effector bispecific system to modulate, e.g., a signaling pathway in a cell-specific or cell-selective manner.

In some embodiments, described herein are engineered antibodies having the guide/effector bispecific system with enhanced binding affinity and/or potency relative to a monospecific antibody. In other embodiments, described herein are engineered antibodies having the guide/effector bispecific system that exhibit a synergistic interaction with a target cell.

In additional embodiments, also described herein include pharmaceutical compositions having an engineered antibody, methods of using the same, engineered antibody-cell complexes, and kits having an engineered antibody.

Definitions

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the disclosure.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The terms "polypeptide", "peptide", and "protein" are used interchangeably herein to designate a linear series of amino acid residues connected one to the other by peptide bonds, which includes proteins, polypeptides, oligopeptides, peptides, and fragments thereof. The protein may be made up of naturally occurring amino acids and/or synthetic (e.g. modified or non-naturally occurring) amino acids. Thus "amino acid", or "peptide residue", as used herein means both naturally occurring and synthetic amino acids. The terms "polypeptide", "peptide", and "protein" includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Furthermore, it should be noted that a dash at the beginning or end of an amino acid residue sequence indicates either a peptide bond to a further sequence of one or more amino acid residues or a covalent bond to a carboxyl or hydroxyl end group. However, the absence of a dash should not be taken to mean that such peptide bonds or covalent bond to a carboxyl or hydroxyl end group is not present, as it is conventional in representation of amino acid sequences to omit such.

By "nucleic acid" herein is meant either DNA or RNA, or molecules which contain deoxy- and/or ribonucleotides. Nucleic acid may be naturally occurring or synthetically made, and as such, includes analogs of naturally occurring polynucleotides in which one or more nucleotides are modified over naturally occurring nucleotides.

The terms "conjugated" and "joining" generally refer to a chemical linkage, either covalent or non-covalent that proximally associates one molecule with second molecule.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "purified" is intended to mean a compound of interest has been separated from components that accompany it in nature or during manufacture and provided in an enriched form.

The "potent" or "potency" used in the context of a compound herein refers to ability or capacity of the compound to exhibit a desired activity.

The term "density" used in the context of a molecule such as peptide fragment refers to a number of the molecule that is measured and/or estimated on a given area. For example, a density of antigen present on a cell surface can be presented as about 10,000 copies per cell, meaning the measured and/or estimated number of the molecules present on the cell surface is about 10,000.

The term "concentration" used in the context of a molecule such as peptide fragment refers to an amount of molecule present in a given volume. In some embodiments, a concentration of a molecule is given in a molar concentration where the number of moles of the molecules present in a given volume of solution is indicated.

The terms "antigen" and "epitope" interchangeably refer to the portion of a molecule (e.g., a polypeptide) which is specifically recognized by a component of the immune system, e.g., an antibody. As used herein, the term "antigen" encompasses antigenic epitopes, e.g., fragments of an antigen which are antigenic epitopes.

The term "antibody" encompasses polyclonal and monoclonal antibody where the antibody may be of any class of interest (e.g., IgG, IgM, and subclasses thereof), as well as hybrid antibodies, altered antibodies, F(ab')2 fragments, F(ab) molecules, Fv fragments, single chain fragment variable displayed on phage (scFv), single chain antibodies, single domain antibodies, diabodies, chimeric antibodies, humanized antibodies, and a fragment thereof. In some embodiments, the fragments of an antibody may be functional fragments which exhibit immunological binding properties of the parent antibody molecule. The antibodies described herein can be detectably labeled, e.g., with a radioisotope, an enzyme which generates a detectable product, a fluorescent protein, and the like. Detectable labels that find use in in vivo imaging are of interest. The antibodies may be further conjugated to other moieties, such as a cytotoxic molecule or other molecule, members of specific binding pairs, and the like.

A typical antibody structural unit, especially when it is in full length, is known to include a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

An "antigen-binding site" or "binding portion" refers to the part of an antibody molecule or fragment thereof that participates in antigen binding. The antigen binding site is formed by amino acid residues of the N-terminal variable heavy chain ($V_H$) and variable light chain ($V_L$). Three highly divergent stretches within the variable regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs". The CDRs are primarily responsible for binding to an epitope of an antigen.

Antibody and fragments thereof according to the present disclosure encompass bispecific antibodies and fragments thereof. Bispecific antibodies may resemble single antibodies (or antibody fragments) but have two different antigen binding sites. Bispecific antibodies may have binding specificities for at least two different epitopes. Bispecific antibodies and fragments can also be in form of heteroantibodies. Heteroantibodies are two or more antibodies, or antibody binding fragments (e.g., Fab) linked together, each antibody or fragment having a different specificity.

Antibody conjugates are also provided. The conjugates include any antibody of the present disclosure and an agent. The agent may be selected from a therapeutic agent, an imaging agent, a labeling agent, or an agent useful for therapeutic and/or labeling purposes.

The strength or affinity of immunological binding interactions between an antibody (or fragment thereof) and the specific antigen (or epitope) can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity and is thus equal to the equilibrium dissociation constant $K_D$ (see, generally, Davies et al. Ann. Rev. Biochem. 1990, 59: 439-15 473).

The term "specific binding of an antibody" or "antigen-specific antibody" in the context of a characteristic of an antibody refers to the ability of an antibody to preferentially bind to a particular antigen that is present in a mixture of different antigens. In certain embodiments, a specific binding interaction will discriminate between desirable and undesirable antigens (or "target" and "non-target" antigens) in a sample, in some embodiments more than about 10 to 100-fold or more (e.g., more than about 1000- or 10,000-fold). In certain embodiments, the affinity between an antibody and antigen when they are specifically bound in an antibody-antigen complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$M, or less than about $10^{-12}$M or less.

The term "monoclonal antibody" refers to an antibody composition having a homogeneous antibody population. The term encompasses whole antibody molecules, as well as Fab molecules, F(ab')2 fragments, Fv fragments, single chain fragment variable displayed on phage (scFv), fusion proteins having an antigen-binding portion of an antibody and a non-antibody protein, and other molecules that exhibit immunological binding properties of the parent monoclonal antibody molecule. Methods of making and screening polyclonal and monoclonal antibodies are known in the art.

The terms "derivative" and "variant" refer to without limitation any compound or antibody which has a structure or sequence derived from the compounds and antibodies of the present disclosure and whose structure/sequence is sufficiently similar to those disclosed herein and based upon that similarity, would be expected, by one skilled in the art, to exhibit the same or similar activities and utilities as the claimed and/or referenced compounds or antibody, thereby also interchangeably referred to "functional equivalent". Modifications to obtain "derivative" or "variant" includes, for example, by addition, deletion and/or substitution of one or more of the amino acid residues. The functional equivalent or fragment of the functional equivalent may have one or more conservative amino acid substitutions. The term "conservative amino acid substitution" refers to substitution of an amino acid to another amino acid that has similar properties to the original amino acid. The groups of conservative amino acids are as follows:

| Group | Name of the amino acids |
| --- | --- |
| Aliphatic | Gly, Ala, Val, Leu, Ile |
| Hydroxyl or Sulfur/Selenium-containing | Ser, Cys, Thr, Met |
| Cyclic | Pro |
| Aromatic | Phe, Tyr, Trp |
| Basic | His, Lys, Arg |
| Acidic and their Amide | Asp, Glu, Asn, Gln |

Conservative substitutions may be introduced in any position of a preferred predetermined peptide or fragment thereof. It may however also be desirable to introduce non-conservative substitutions, particularly, but not limited to, a non-conservative substitution in any one or more positions. A non-conservative substitution leading to the formation of a functionally equivalent fragment of the peptide would for example differ substantially in polarity, in electric charge, and/or in steric bulk while maintaining the functionality of the derivative or variant fragment.

"Percentage of sequence identity" is determined by comparing two optimally aligned sequences over a comparison window, wherein the portion of the polynucleotide or polypeptide sequence in the comparison window may have additions or deletions (i.e., gaps) as compared to the reference sequence (which does not have additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity" in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences or individual domains of the polypeptides), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 5 to 50 nucleotides or polypeptide sequences in length, or more preferably over a region that is 100 to 500 or 1000 or more nucleotides or polypeptide sequences in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (www.ncbi.nlm.nih.gov/).

"Cell(s) of interest" or "target cell(s)" used herein interchangeably refers to a cell or cells where one or more signaling pathways are intended to modulated. In some embodiments, the target cell(s) includes, but not limited to, a cancer cell(s). In some other embodiments, the target cell(s) includes immune effector cells such as natural killer cell(s), T cell(s), dendritic cell(s) and macrophage(s).

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell" or "cancerous cell", and encompasses cancer cells of a solid tumor, a semi-solid tumor, a primary tumor, a metastatic tumor, and the like.

By "treatment" in the context of disease or condition is meant that at least an amelioration of the symptoms associated with the condition afflicting an individual is achieved, where amelioration is used in a broad sense to refer to at least a reduction in the magnitude of a parameter, e.g. symptom, associated with the condition (e.g., cancer) being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells, or so as to protect against disease caused by bacterial infection, which protection can include elimination of detectable bacterial cells; and/or (iii) relief, that is, causing the regression of clinical symptoms.

The term "effective amount" of a composition as provided herein is intended to mean a non-lethal but sufficient amount of the composition to provide the desired utility. For instance, for eliciting a favorable response in a cell(s) of interest ("target cell(s)") such as modulating a signaling pathway, the effective amount of an (active, effective, potent or functional) antibody is the amount which results in notable and substantial change in the level of the activity of the signaling pathway, including downregulation and upregulation of the signaling pathway, when compared to use of no antibody or a control (inactive, ineffective, or non-functional) antibody. The measurement of changes in the level of the activity of the signaling pathway can be done by a variety of methods known in the art. In another example, for eliciting a favorable response in a subject to treat a disease (e.g., cancer), the effective amount is the amount which reduces, eliminates or diminishes the symptoms associated with the disorder, e.g., so as to provide for control of cancer metastasis, to eliminate cancer cells, and/or the like. As well be understood by a person having ordinary skill in the art, the exact amount required will vary from subject to subject, depending on the species, age, and general condition of the subject, the severity of the condition or disease that is being treated, the particular composition used, its mode of administration, and the like. Thus, it is not possible to specify an exact "effective amount." However, an appropriate effective amount may be determined by one of ordinary skill in the art using only routine experimentation.

The term "pharmaceutically acceptable excipient" as used herein refers to any suitable substance which provides a pharmaceutically acceptable compound for administration of a compound(s) of interest to a subject. "Pharmaceutically acceptable excipient" can encompass substances referred to as pharmaceutically acceptable diluents, pharmaceutically acceptable additives and pharmaceutically acceptable carrier s.

The terms "individual" or "subject" are intended to cover humans, mammals and other animals. The terms "individual" or "subject" are used interchangeably herein to refer to any mammalian subject to whom antibodies or fragments thereof in the present disclosure is subjected.

As used herein, the terms "cell signaling pathway", "signaling pathway", "cellular signaling" and "signal transduction" interchangeably refers to transmission of a molecular signal in the form of a chemical modification by recruitment of protein complexes along a signaling pathway that ultimately triggers a biochemical event in the cell. Signal transduction occurs when an extracellular signaling molecule activates a specific receptor located on the cell surface or inside the cell. In turn, this receptor triggers a biochemical chain of events inside the cell—known as a signaling cascade—that eventually elicits a response. Depending on the cell, the response alters cell's metabolism, shape, gene expression, or ability to divide. The signal can be amplified at any step; thus, one signaling molecule can generate a response involving hundreds to millions of molecules. Some examples of signaling pathways concerned in the present disclosure include, but not limited to, AKT pathway, c-MET pathway, NF-kB pathway, Notch signaling pathway, p53 pathway, Ras-Raf-MEK-ERK pathway, STAT signaling pathway, Wnt signaling pathway, YAP/Wnt signaling pathway, Receptor tyrosine kinase (RTK) signaling pathway families including but are not limited to the epidermal growth factor receptor (EGFR) family, the fibroblast growth factor receptor (FGFR) family, the insulin-like growth factor receptor (IGFR) family, the vascular endothelial growth factor receptor (VEGFR) family, and the platelet-derived growth factor receptors (PDGFR) family, NK (natural killer) activating pathway, NK inhibitory pathway, macrophage regulatory pathway, dendritic cell signaling pathway, T cell regulatory pathway and checkpoint inhibitory pathway.

As used herein, the term "modulation" of a signaling pathway (i.e. cell signaling pathway or signal transduction) is meant that an antibody, an antigen binding fragment, or recombinant protein thereof, is capable of upregulating (enhancing, stimulating, promoting, activating or increasing) or downregulating (suppressing, inhibiting, reducing, decreasing or diminishing) the activity of the signaling pathway in a cell or cells of interest (i.e. "target cell(s)"). In some embodiments, modulation of a signaling pathway using a bispecific antibody includes a change in the signaling pathway activity by at least 10%, 20%, 30%, 40%, 50%, 60%, 70%, 80%, 90%, 99% or 99.9% as compared to no antibody or using a monospecific antibody. In some embodiments, upregulation of a signaling pathway includes turning on or initiating the pathway that was off or substantially not active. In some embodiments, downregulation of a target signaling pathway can include turning off or substantially blocking the pathway that was on or substantially active.

Certain embodiments feature a bispecific antibody, antigen binding fragment, or recombinant protein thereof, which is capable of modulating of the activity of one or more signaling pathway in a cell or cells of interest. The modulation of the one or more signaling pathway may lead to certain changes in target cell(s)'s behavior, such as stimulating or reducing cell proliferation, cell growth, cell differentiation, cell survival, cell secretion, modulation of adhesion and/or motility of cells.

ABBREVIATIONS

LRP6—Low-density lipoprotein receptor-related protein 6
RSPO1—R-spondin 1
GSK—Glycogen synthase kinase
FZD—Frizzled
TCF/LEF—T-cell factor/Lymphoid enhancer factor
STF—SuperTopFlash
BiTE—Bispecific T cell engager
TaFv—Tandem scFv
ICAM-1—Intercellular cell adhesion molecule-1
Wnt—Wingless-type MMTV integration site family
ALCAM—Activated leukocyte cell adhesion molecule
EphA2—Ephrin type-A receptor 2
EC50—Half maximal effective concentration
IC50—Half maximal inhibitory concentration
ErbB3—Epidermal growth factor receptor 3
IGF-1R—Insulin-like growth factor 1 receptor
VEGF-A—Vascular endothelial growth factor A
MESF—Molecules of equivalent soluble fluorochrome
ABC—Antibody binding capacity
Engineered Antibodies The disclosures provided herewith relate to an engineered antibody (e.g. bispecific antibody) having a specificity to two separate antigens, a first antigen ("guide antigen") and a second antigen ("effector antigen"). In some instances, the engineered antibody utilizes a guide/effector bispecific system which can selectively enhance signal pathway modulation in a target cell(s) expressing the guide antigen. The potency of enhancement relying on the guide/effector system is striking for the bispecific antibody. In other instances, the engineered antibody utilizes a guide/effector bispecific system to enhance affinity of the engineered antibody to a target cell, to enhance potency of the antibody, and/or to enhance specificity of the antibody.

In some embodiments, an engineered antibody described herein has a first antigen binding region and a second antigen binding region, wherein the first antigen binding region binds to a guide antigen expressed on the surface of a cell and the second antigen binding region binds to an effector antigen expressed on the surface of the same cell, and wherein the guide antigen is characterized by a density that is at least four-fold higher than the density of the effector antigen. In other embodiments, an engineered antibody described herein has a first antigen binding region and a second antigen binding region, wherein the first antigen binding region binds to a guide antigen expressed on the surface of a cell and the second antigen binding region binds to an effector antigen expressed on the surface of the same cell, and wherein the guide antigen is characterized by an expression of at least 15,000 copies on the cell surface. In some instances, the guide antigen is characterized by a density that is at least five-fold higher than the density of the effector antigen. In some instances, the guide antigen is characterized by a density that is at least ten-fold higher than the density of the effector antigen. In some cases, the guide antigen is characterized by an expression of at least 15,000 copies on the cell surface. In some cases, the guide antigen is characterized by an expression of at least 20,000 copies on the cell surface.

In some cases, an engineered antibody described herein modulates a signaling pathway in a target cell expressing a guide antigen. In some instances, the engineered antibody directly modulates the signaling pathway, by interacting with the effector antigen present on the target cell, which participates within the signaling pathway. In other instances, the engineered antibody indirectly modulates the signaling pathway by interacting with an effector antigen which then triggers a signaling event. For example, an engineered antibody can interact with a tumor cell surface antigen such as CD38 which can then engage a natural killer (NK) cell and initiate subsequent signaling events in the NK cell to initiate antibody-dependent cell-mediated cytotoxicity (ADCC). In some instances, the engineered antibody upregulates a signaling pathway in a target cell expressing the guide antigen. In other instances, the engineered antibody downregulates a signaling pathway in a target cell expressing the guide antigen.

Upregulation of Signaling Pathway—Agonist

In some aspects, an engineered antibody functions as an agonist and activate a signaling pathway of interest (or a target signaling pathway). In certain embodiments, the engineered antibody functioning as an agonist of the target signaling pathway upregulates (e.g., stimulates, enhances, promotes or increases) the activity of the target signaling pathway by at least 10-, 20-, 30-, 40-, 50-, 60-, 70-, 80-, 90-, 100-, 150-, 200-, 250-, 300-, 400-, 500-, 600-, 700-, 800-, 900-, 1,000-, or more folds, or any values of folds therebetween as compared to using an antibody specific to either one of first and second antigens. The activity of the target signaling, in some embodiments, is measured via a report assay that is responsive to the activation of the signaling pathway. For example, when Wnt signaling pathway is concerned, a Wnt-responsive report, e.g. a Top Flash (TF) or Super Top Flash (STF) assay can be used as described in the field. See e.g. Chen Zhao, "Wnt Reporter Activity Assay", Bio-protocol, vol. 4, issue 14, 4 pages (Jul. 20, 2014)

Downregulation of Signaling Pathway—Antagonist

In another example, an engineered antibody can function as an antagonist and downregulates (e.g., suppresses, reduces, inhibits, diminishes or decreases) a signaling pathway of interest ("target signaling pathway"). In certain embodiments, the engineered antibody functioning as an antagonist of the target signaling pathway reduces the activity of the target signaling pathway by at least 10-, 20-, 30-, 40-, 50-, 60-, 70-, 80-, 90-, 100-, 150-, 200-, 250-, 300-, 400-, 500-, 600-, 700-, 800-, 900-, 1,000-, or more folds, or any values of folds therebetween as compared to using an antibody specific to either one of first and second antigens. In some embodiments, the downregulation of the target signaling pathway is determined via measurement of IC50 value. Half maximal inhibitory concentration (IC50) is a measure of the effectiveness of a substance in inhibiting a specific biological or biochemical function. This quantitative measure indicates how much of a particular substance (inhibitor such as an engineered antibody) is needed to inhibit a given biological process such as signaling transduction by half. The values are typically expressed as molar concentration. In certain embodiments, an IC50 value of an engineered antibody measured in downregulating a target signaling pathway quantified may be reduced at least by at least 10-, 20-, 30-, 40-, 50-, 60-, 70-, 80-, 90-, 100-, 150-, 200-, 250-, 300-, 400-, 500-, 600-, 700-, 800-, 900-, 1,000-, or more folds, or any values of folds therebetween as compared to an IC50 value of an antibody specific to either one of first and second antigens. Alternatively or in combination with the measurement of IC50, a report assay that is responsive to the inhibition of the signaling pathway, e.g. Top Flash (TF) or Super Top Flash (STF) assay in Wnt-signaling, can be used to determine the downregulation of the signaling pathway and the level thereof.

Exemplary Signaling Pathways

Engineered antibodies disclosed herein can be an antibody that modulates a signaling pathway. Various target signaling pathways can be modulated with engineered antibodies described herein. In some embodiments, a target signaling pathways includes a cellular process that involves transmission of a molecular signal in the form of a chemical modification by recruitment of protein complexes along a signaling pathway that ultimately triggers a biochemical event in the cell. Exemplary signaling pathways include, but are not limited to, AKT pathway, c-MET pathway, NF-kB pathway, Notch signaling pathway, p53 pathway, Ras-Raf-MEK-ERK pathway, STAT signaling pathway, Wnt signaling pathway, YAP/Wnt signaling pathway, Receptor tyrosine kinase (RTK) signaling pathway families including but are not limited to the epidermal growth factor receptor (EGFR) family, the fibroblast growth factor receptor (FGFR) family, the insulin-like growth factor receptor (IGFR) family, the vascular endothelial growth factor receptor (VEGFR) family, and the platelet-derived growth factor receptors (PDGFR) family, NK (natural killer) activating pathway, NK inhibitory pathway, macrophage regulatory pathway, dendritic cell signaling pathway, T cell regulatory pathway and checkpoint inhibitory pathway.

Antigens

Engineered antibodies, such as bispecific antibodies, can have specificity to two separate antigens. A bispecific antibodies can include at least two components, a first component and a second component, each of which binds to their respective antigen (or epitope), i.e. a first antigen ("effector antigen") and a second antigen ("guide antigen"), respectively. The first component can include a binding site (i.e.

antigen binding site) for the first antigen and the second component can include a second binding site for the second antigen.

In some embodiments, an engineered antibody described herein modulates a signaling pathway having AKT pathway, c-MET pathway, NF-kB pathway, Notch signaling pathway, p53 pathway, Ras-Raf-MEK-ERK pathway, STAT signaling pathway, Wnt signaling pathway, YAP/Wnt signaling pathway, Receptor tyrosine kinase (RTK) signaling pathway families including but are not limited to the epidermal growth factor receptor (EGFR) family, the fibroblast growth factor receptor (FGFR) family, the insulin-like growth factor receptor (IGFR) family, the vascular endothelial growth factor receptor (VEGFR) family, and the platelet-derived growth factor receptors (PDGFR) family, NK (natural killer) activating pathway, NK inhibitory pathway, macrophage regulatory pathway, dendritic cell signaling pathway, T cell regulatory pathway and checkpoint inhibitory pathway. In some instances, an engineered antibody described herein modulates the AKT pathway. In some instances, an engineered antibody described herein modulates the c-MET pathway. In some cases, an engineered antibody described herein modulates the NF-KB pathway. In some cases, an engineered antibody described herein modulates the p53 pathway. In some cases, an engineered antibody described herein modulates the Ras-Raf-MEK-ERK pathway. In some cases, an engineered antibody described herein modulates the Wnt signaling pathway. In some cases, an engineered antibody described herein modulates the YAP/Wnt signaling pathway. In some cases, an engineered antibody described herein modulates receptor tyrosine kinase (RTK) signaling pathway families including but are not limited to the epidermal growth factor receptor (EGFR) family, the fibroblast growth factor receptor (FGFR) family, the insulin-like growth factor receptor (IGFR) family, the vascular endothelial growth factor receptor (VEGFR) family, and the platelet-derived growth factor receptors (PDGFR) family. In some cases, an engineered antibody described herein modulates the NK activating pathway. In some cases, an engineered antibody described herein modulates the NK inhibitory pathway. In some cases, an engineered antibody described herein modulates macrophage regulatory pathway. In some cases, an engineered antibody described herein modulates dendritic cell regulatory pathway. In some cases, an engineered antibody described herein modulates the T cell regulatory pathway and checkpoint inhibitory pathway.

Effector Antigen

In some embodiments, an effector antigen that is recognized by an engineered antibody described herein is a molecule expressed on the surface of a cell of interest. In some embodiments, an effector antigen that is recognized by an engineered antibody described herein is a molecule associated with a signaling pathway of interest (e.g., a target signaling pathway). In some cases, the effector antigen has a tumor antigen (e.g., a tumor-associated antigen or a tumor-specific antigen). In some instances, the effector antigen has a cell surface antigen in which its density (or expression on the cell surface) is at least 4-fold, 5-fold, 10-fold lower than the density of a guide antigen on the same cell. In some instances, the effector antigen has a cell surface antigen which has less than 50,000, 40,000, 30,000, 20,000, 10,000, 5,000 or lower copies on the cell surface.

In some embodiments, an effector antigen has a receptor and/or co-receptor of a target signaling pathway. For example, when the target signaling is Wnt signaling, the effector antigen can be LRP6, R-spondin, ROR1, ROR2, or any member of Frizzled receptor family. In another example, when the target signaling is YAP/Wnt signaling, the effector antigen can be ROR1, ROR2, Erb3 or IGFR1R, EGFR, TRAIL receptors, PDL1, PDL2, CD38 or CD47. In still another example, when the target pathway is NK cell activating or inhibiting pathway, the effector antigen can be CD16, CD38, NKG2D, NKG2A, NKp46 or Killer-cell immunoglobulin-like receptors (KIRs). In still another example where the target signaling pathway is the checkpoint inhibitory pathway (which can be active in T cell), the effector antigen can be PD1, CTLA4 or Tim3.

In another example, when the target signaling is YAP/Wnt signaling, the effector antigen can be ROR1, ROR2, and the Frizzled family members. In still another example, when the target pathway regulates cell growth, the effector antigen can be Erb3, insulin-like growth factor receptor family members (e.g., IGF1R), and EGFR. In still another example, when the target pathway regulates cell death, the effector antigen can be TRAIL receptors. In still another example, when the target pathway is checkpoint inhibition (initiated at the tumor cell surface), the effector antigen can be PD-L1 and/or PD-L2. In still another example, when the target pathway is innate immune regulation (antibody-dependent cell-mediated cytotoxicity (ADCC) or antibody dependent cellular phagocytosis (ADCP)), the effector antigen can be CD38 or CD47.

Guide Antigen

In some embodiments, guide antigen that is recognized by an engineered antibody is a molecule serving as a cell-type associated antigen. The cell-type associated antigen generally refers to a molecule in which the expression level is substantially higher in a certain type of cell(s) of interest ("target cell(s)") as compared to a non-target cell(s). In some cases, the guide antigen can be any cell surface antigen that is overexpressed on the target cell. For example, there are molecules that are overexpressed in cancer cells such as intercellular adhesion molecule 1 (ICAM-1), ephrin type-A receptor 2 (EphA2), and activated leukocyte In some cases, the guide antigen is a cell adhesion molecule (ALCAM) and these molecules may be considered as cancer- or tumor-associated antigens. Some other examples of cancer- or tumor-associated guide antigens include CD30, CD33, PSMA, mesothelin, CD44, CD73, CD38, Muc1 and Muc16. In another example, when the target cell is NK cell, the guide antigen is a cell surface antigen in which its density (or expression on the cell surface) is at least 4-fold, 5-fold, 10-fold higher than the density of the effector antigen on the same cell.

In some embodiments, the guide antigen is a tumor antigen, which is overexpressed on the tumor cell surface relative to a non-tumor cell. In some embodiments, the guide antigen is a tumor-associated antigen overexpressed on the tumor cell surface relative to a non-tumor cell. In other embodiments, the guide antigen is a tumor-specific antigen overexpressed in a tumor cell relative to a non-tumor cell.

In some embodiments, exemplary guide antigens that are overexpressed in cancer cells include intercellular adhesion molecule 1 (ICAM-1), ephrin type-A receptor 2 (EphA2), ephrin type-A receptor 3 (EphA3), ephrin type-A receptor 4 (EphA4), or activated leukocyte cell adhesion molecule (ALCAM). In other examples, exemplary guide antigens, e.g., cancer- or tumor-associated guide antigens, include CD30, CD33, PSMA, mesothelin, CD44, CD73, CD38, Mucin 1 cell surface associated (MUC1), Mucin 2 oligomeric mucus gel-forming (MUC2), and MUC16 (CA-125). In some embodiments, a guide antigen has CD30, CD33, carcinoembroyonic antigen (CEA), mesothelin, cathepsin G, CD44, CD73, CD38, Muc1, Muc2, Muc16, preferentially expressed antigen of melanoma (PRAME), CD52, EpCAM, CEA, gpA33, Mucins, tumor associated glycoprotein 72 (TAG-72), carbonic anhydrase IX, PSMA, folate binding protein, gangliosides, Lewis-Y, immature laminin receptor, BING-4, calcium-activated chloride channel 2 (CaCC), gp100, synovial sarcoma X breakpoint 2 (SSX-2), or SAP-1. In some embodiments, a guide antigen has CD30, CD33, carcinoembroyonic antigen (CEA), mesothelin, cathepsin G, CD44, CD73, CD38, Muc1, Muc16, preferentially expressed antigen of melanoma (PRAMS), CD52, EpCAM, CEA, gpA33, Mucins, TAG-72, carbonic anhydrase IX, PSMA, folate binding protein, gangliosides or Lewis-Y. In some instances, a guide antigen is ICAM-1. In some instances, a guide antigen is EphA2. In some cases, a guide antigen is ALCAM.

In some embodiments, by specifically recognizing and binding to the cell-type associated guide antigen, an engineered antibody can be recruited to a target cell that is associated with the guide antigen, resulting in, e.g., a modulation of a signaling pathway in the target cell.

In some embodiments, the guide antigen of an engineered antibody of the present disclosure not only serves as a cell-type selector but also as a potency enhancer, resulting in, e.g., a potent and selective inhibition of a target signaling pathway. In certain embodiments, there is a threshold level of the expression for the guide antigen on the surface of a target cell, which results in enhancement in (1) the binding affinity of the engineered antibody to the target cell and (2) the occupancy of the effector antigen by the engineered antibody.

Effector/Guide System

In some embodiments, an engineered antibody described herein utilizes an effector/guide system to enhance the binding of the antibody to the effector antigen. In other embodiments, an engineered antibody described herein utilizes an effector/guide system to synergize the binding of the antibody to the effector antigen. In some instances, the binding of a first antigen binding region to the guide antigen on the surface of a target cell enhances binding of the second antigen binding region to the effector antigen present on the surface of the same target cell. In other instances, the binding of a first antigen binding region to the guide antigen on the surface of a target cell synergizes binding of the second antigen binding region to the effector antigen present on the surface of the same target cell.

In some embodiments, an engineered antibody of the present disclosure should not be considered a mere combination of two monospecific antibodies, each of which is specific to the guide antigen and the effector antigen, respectively. As disclosed above and elsewhere herein, in some instances a synergy is observed between the two antigen binding regions, e.g., the binding of the first antigen binding region to the guide antigen enhances binding of the second antigen binding region to the effector antigen, and this synergy is not observed under a monospecific antibody setting. In additional instances, the occupancy of the effector antigen by the bispecific antibodies is increased as compared to that of the monospecific antibody. These non-linear and striking enhancement on the binding affinity of the bispecific antibody as well as its effectiveness in modulating a target signaling pathway provide superior and unexpected advantages when such a modulation is in need.

For example, in some cases, binding of the second antigen binding region to the effector antigen is enhances by about 10-fold, about 50-fold, about 100-fold, about 200-fold, about 300-fold, about 400-fold, about 500-fold, about 1000-fold, or more relative to the binding of the second antigen binding region to the effector antigen in the absence of the first antigen binding region. In some embodiments, the binding is measured as a binding affinity. In some cases, the binding affinity of the engineered antibody is enhanced by about 10-fold, about 50-fold, about 100-fold, about 200-fold, about 300-fold, about 400-fold, about 500-fold, about 1000-fold, or more by the interaction of the second antigen binding region to the effector antigen relative to an antibody that is monospecific. In some cases, the binding is further measured as an IC50 value. In some cases, the IC50 value of the engineered antibody is decreased by about 10-fold, about 50-fold, about 100-fold, about 200-fold, about 300-fold, about 400-fold, about 500-fold, about 1000-fold, or more by the interaction of the second antigen binding region to the effector antigen relative to an antibody that is monospecific.

In some embodiments, a threshold level of a guide antigen expression on the surface of a target cell that is capable of exhibiting synergistic activity on a bispecific antibody of the present disclosure may vary depending on the nature of target signaling as well as the nature of target cell and its surrounding environment. The suitable threshold level of the guide in each occasion can be determined in view of the disclosure provided herewith as well as knowledge available in the art. Therefore, any level of expression of the guide, while not expressly indicated herewith, should still be considered within the scope of the present disclosure as long as such a threshold is capable of providing improvement (e.g. at least 10-fold or more) in the activity of a bispecific antibody in modulating a target signaling pathway as compared to that of monospecific antibody. Some examples of a threshold expression level of a guide antigen on the surface of target cell ranges about 100, 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 13,000, 14,000, 15,000, 16,000, 17,000, 18,000, 19,000, 20,000, 25,000, 30,000, 40,000, 50,000, 100,000, 200,000 or more copies or any intervening number of copies per cell. In some embodiments, a threshold expression level of a guide antigen on the surface of target cell ranges about 1,000 to 5,000 copies per cell, 5,000 to 10,000 copies per cell, 10,000 to 15,000 copies per cell or 15,000 to 20,000 copies per cell. In some embodiments, a threshold expression level of a guide antigen in the surface of target cell is more than about 10,000 copies per cell. In some embodiments, a threshold expression level of a guide antigen in the surface of target cell is more than about 15,000 copies per cell. In some embodiments, a threshold expression level of a guide antigen in the surface of target cell is more than about 20,000 copies per cell.

In some cases, a ratio of guide to effector antigen density on the surface of target cell that is capable of exhibiting synergistic activity on an engineered antibody of the present disclosure varies depending on the nature of target signaling as well as the nature of target cell and its surrounding environment. The suitable guide to effector density ratio in each occasion can be determined in view of the disclosure provided herewith as well as knowledge available in the art. Therefore, any ratio between the guide to effector antigen density, while not expressly indicated herewith, should still be considered within the scope of the present disclosure as long as such a ratio is capable of providing improvement (e.g. at least 10-fold or more) in the activity of an engineered bispecific antibody in modulating a target signaling pathway as compared to that of a monospecific antibody. Some examples of a ratio between guide to effector density on the surface of target cell ranges about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1 or more. In some embodiments, the density of a guide density is substantially higher than the density of an effector such that a ratio between the guide to effector density on the surface of target cell ranges about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1 or more, and in some particular embodiments the ratio ranges about 5:1 to 10:1. In some other embodiments where the density of a guide density is substantially higher than the density of an effector, a ratio between the guide to effector density on the surface of target cell ranges more than 10:1.

In some embodiments, a guide antigen density impacts the occupancy of the effector antigen of an engineered antibody. For example, when the ratio of the guide to effector antigen density reaches a suitable range that is capable of exhibiting an increased potency of an engineered antibody as compared to a monospecific antibody, the level of occupancy of the effector antigen by the engineered antibody may increase. Such an increase can be demonstrated, for example, via the difference of antibody concentrations necessary to occupy, e.g. 50% or 85% of the effector antigen on the surface of target cell. In some example, the concentration of an engineered antibody that is capable of achieving about 50% or about 85% occupancy of the effector antigen may be reduced at least 10-, 20-, 30-, 40-, 50-, 60-, 70-, 80-, 90-, 100-, 150-, 200-, 250-, 300-, 400-, 500-, 600-, 700-, 800-, 900-, 1,000-, or more folds, or any intervening values of folds as compared to the concentration of a monospecific antibody showing the same or similar occupancy. In certain examples, the concentration of an engineered antibody that is capable of achieving about 50% or about 85% occupancy of the effector antigen may be in anywhere between about 1 pM to 1000 pM, about 1 nM to 100 nM, about 100 nM to 1000 nM or higher than about 1000 nM in concentration.

In certain aspects, an engineered antibody of the present disclosure binds to its specific effector antigen with an affinity ($K_d$) of $10^{-6}$M, $10^{-7}$ M, $10^{-8}$ M, $10^{-9}$M, $10^{-10}$ M, $10^{-11}$ M, or $10^{-12}$M or less (lower meaning higher binding affinity). In certain aspects, an engineered antibody of the present disclosure binds to its specific guide antigen with an affinity ($K_d$) of $10^{-6}$M, $10^{-7}$ M, $10^{-8}$ M, $10^{-9}$ M, $10^{-10}$ M, $10^{-11}$ M, or $10^{-12}$M or less (lower meaning higher binding affinity).

As described elsewhere herein, the effector/guide system according to the present disclosure is not limited to a certain signaling pathway in a certain type of cell but can be applicable to any signaling pathway in any type of cell. In some embodiments, the effector/guide system is applied to an environment where certain conditions, e.g. a guide to effector density ratio as well as a threshold level of the guide expression reach at a certain desired level as described elsewhere in the present disclosure, are met, the engineered antibody can exhibit potency in modulating the target signaling pathway regardless of the molecular identifies of the antigens or target cell types. Therefore, an engineered antibody and its use according to the present disclosure are not limited by certain signaling pathway and/or cell types but should be considered generally applicable to any signaling pathway and to any types of cell.

Antibody Format

In some embodiments, an engineered antibody described herein has a humanized antibody or binding fragment thereof, a chimeric antibody or binding fragment thereof, a monoclonal antibody or binding fragment thereof, an Fab, an Fab', an F(ab')2, an F(ab')$_3$, an scFv, an sc(Fv)$_2$, a dsFv, a diabody, a minibody, and a nanobody or binding fragments thereof. In some instances, an engineered antibody described herein has a full-length immunoglobulin. In some instances, an engineered antibody described herein has an Fab, an Fab', an F(ab')2, an F(ab')3, an scFv, an sc(Fv)$_2$, a dsFv and a diabody or binding fragments thereof.

In some embodiments, an engineered antibody described herein is a bispecific IgG (BsIgG), an IgG appended with an additional antigen-binding moiety, a bispecific antibody (BsAb) fragment, a bispecific fusion protein, or a BsAb conjugate. In some embodiments, an engineered antibody described herein is a BsIgG. In some embodiments, BsIgG is produced by co-expression of two light and two heavy chains in a single host cell. In some embodiments, BsIgG is produced by expression of a first light chain and a first heavy chain in a first host cell and expression of a second light chain and a second heavy chain in a second host cell, wherein the expressed first light chain/first heavy chain and the expressed second light chain/second heavy chain are purified and assembled into BsIgG in vitro. In some embodiments, an engineered antibody described herein is an IgG appended with an additional antigen-binding moiety. In some embodiments, the additional antigen-binding moiety is a single domain antibody (e.g. unpaired variable light ($V_L$) or variable heavy ($V_H$) chains), paired antibody variable domains (e.g. Fv or scFv), or engineered protein scaffolds. In some embodiments, the IgG appended with an additional antigen-binding moiety is a dual variable domain IgG (DVD-Ig). In some embodiments, an engineered antibody described herein is a BsAb fragment. In some embodiments, the BsAb fragment has a heavy chain, a light chain, and a short peptide linker sequence. In some embodiments, the BsAb fragment is a scFv, tandem scFv, a diabody, a tetravalent tandem diabody (TandAb), a bispecific T cell engage (BiTE), a single domain antibody fragment (dAbs), or a nanobody. In some embodiments, the BsAb fragment does not have an Fc region. In some embodiments, an engineered antibody described herein is a bispecific fusion protein. In some embodiments, the Dock-and-Lock method (DNL) is used to create a bispecific antibody. In some embodiments, the Bs an engineered antibody described herein Ab is fused to a human serum albumin or a albumin binding protein. In some embodiments, an engineered antibody described herein is a BsAb conjugate.

In some embodiments, an engineered antibody described herein has a bispecific antibody disclosed in Spiess et al. Molecular Immunology 67 (2015) 95-106.

In some embodiments, an engineered antibody described herein has a bispecific antibody illustrated in FIGS. 16A-16D.

Exemplary Engineered Antibodies

In one aspect, the present disclosure provides, as non-limiting examples, antibodies that target Wnt signaling pathway. In some embodiments, the antibodies targeting Wnt signaling pathway have cell-type specificity or selectivity to cancer cells. This bi-specificity of the antibodies is achieved by having two components, a first component and a second component each of which specifically recognizes and binds to their respective antigen. The first antigen (an "effector" antigen) is associated with Wnt signaling pathway and the second antigen (a "guide" antigen) is associated with cancer cells.

In certain embodiments, the effector antigen of bispecific antibodies targeting Wnt signaling pathway is any one of Wnt receptors or co-receptors. In some embodiments, such an effector antigen is LRP6, a Wnt receptor LRP6 or fragment(s) thereof. In some embodiments, bispecific antibodies binding to LRP6 or fragment(s) thereof can also bind to a cancer- or tumor-associated, guide antigen, thereby referring to anti-LRP6/anti-cancer-(or tumor-) associated guide antigen. Some examples of such cancer- or tumor-associated guide antigens include intercellular adhesion molecule 1 (ICAM-1), ephrin type-A receptor 2 (EphA2), and activated leukocyte cell adhesion molecule (ALCAM) that are overexpressed in cancer cells and a fragment thereof. Thus, in certain embodiments, bispecific antibodies presented herewith include anti-LRP6/anti-ICAM-1 antibody, anti-LRP6/anti-EphA2 antibody and anti-LRP6/anti-ALCAM antibody.

In one aspect, as non-limiting examples, anti-LRP6 antibodies of the present disclosure including monospecific and bispecific antibodies bind to E1 and/or E2 region of LRP6. In certain embodiments, an anti-LRP6 antibody specific to E1 and/or E2 regions of LRP6, i.e. "anti-LRP6E1E2 antibody" can include at least one, two, three, four, five, or six CDRs selected from the CDR sequences those identified in Table 3.

In one aspect, an anti-LRP6E1E2 antibody can have a heavy chain variable domain ($V_H$) sequence having at least 50%, 60%, 70%, 80%, 90%, 91%, 92%, 93%, 94%, 95%, 96%, 97%, 98%, 99%, or 100% sequence identity to any one of $V_H$ sequence identified in Table 3. In certain embodiments, a $V_H$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-LRP6 antibody having that sequence retains the ability to bind to LRP6 E1 and/or E2 regions. In certain embodiments, a total of 1 to 10 amino acids have been substituted, inserted and/or deleted in a heavy chain variable domain ($V_H$) sequence having at least 50%, 60%, 70%, 80%, 90%, 91%, 92%, 93%, 94%, 95%, 96%, 97%, 98%, 99%, or 100% sequence identity to any one of $V_H$ sequence identified in Table 3 In certain embodiments, substitutions, insertions, or deletions occur in regions outside the CDRs (i.e., in the FRs).

In one aspect, an anti-LRP6E1E2 antibody can include a light chain variable domain ($V_L$) sequence having at least 50%, 60%, 70%, 80%, 90%, 91%, 92%, 93%, 94%, 95%, 96%, 97%, 98%, 99%, or 100% sequence identity to any one of $V_L$ sequence identified in Table 3. In certain embodiments, a $V_L$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-LRP6 antibody having that sequence retains the ability to bind to LRP6 E1 and/or E2 regions. In certain embodiments, a total of 1 to 10 amino acids have been substituted, inserted and/or deleted in a light chain variable domain ($V_L$) sequence having at least 50%, 60%, 70%, 80%, 90%, 91%, 92%, 93%, 94%, 95%, 96%, 97%, 98%, 99%, or 100% sequence identity to any one of $V_L$ sequence identified in Table 3 In certain embodiments, substitutions, insertions, or deletions occur in regions outside the CDRs (i.e., in the FRs).

In one aspect, as non-limiting examples, anti-LRP6 antibodies of the present disclosure including monospecific and bispecific antibodies bind to E3 and/or E4 region of LRP6. In certain embodiments, an anti-LRP6 antibody specific to E3 and/or E4 regions of LRP6, i.e. "anti-LRP6E3E4 antibody" can include at least one, two, three, four, five, or six CDRs selected from the CDR sequences those identified in Table 4.

In one aspect, an anti-LRP6E3E4 antibody can include a heavy chain variable domain ($V_H$) sequence having at least 50%, 60%, 70%, 80%, 90%, 91%, 92%, 93%, 94%, 95%, 96%, 97%, 98%, 99%, or 100% sequence identity to any one of $V_H$ sequence identified in Table 4. In certain embodiments, a $V_H$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-LRP6 antibody having that sequence retains the ability to bind to LRP6 E3 and/or E4 regions. In certain embodiments, a total of 1 to 10 amino acids have been substituted, inserted and/or deleted in a heavy chain variable domain ($V_H$) sequence having at least 50%, 60%, 70%, 80%, 90%, 91%, 92%, 93%, 94%, 95%, 96%, 97%, 98%, 99%, or 100% sequence identity to any one of $V_H$ sequence identified in Table 4 In certain embodiments, substitutions, insertions, or deletions occur in regions outside the CDRs (i.e., in the FRs).

In one aspect, an anti-LRP6E3E4 antibody can include a light chain variable domain ($V_L$) sequence having at least 50%, 60%, 70%, 80%, 90%, 91%, 92%, 93%, 94%, 95%, 96%, 97%, 98%, 99%, or 100% sequence identity to any one of $V_L$ sequence identified in Table 4. In certain embodiments, a $V_L$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-LRP6 antibody having that sequence retains the ability to bind to LRP6 E3 and/or E4 regions. In certain embodiments, a total of 1 to 10 amino acids have been substituted, inserted and/or deleted in a light chain variable domain ($V_L$) sequence having at least 50%, 60%, 70%, 80%, 90%, 91%, 92%, 93%, 94%, 95%, 96%, 97%, 98%, 99%, or 100% sequence identity to any one of $V_L$ sequence identified in Table 4 In certain embodiments, substitutions, insertions, or deletions occur in regions outside the CDRs (i.e., in the FRs).

In one aspect, as a non-limiting example, an anti-LRP6 antibody (e.g. anti-LRP6E1F2 antibody and anti-LRP6E3E4 antibody) can have a $V_H$ as in any of the embodiments provided above, and a $V_L$ as in any of the embodiments provided above.

In certain embodiments, antibodies of the present disclosure including monospecific and bispecific antibodies are specific or selective to a certain type of cell such as cancer cell. In such embodiments, the antibodies specifically bind to an antigen ("guide" antigen) that is associated with cancer or tumor, thereby being a cancer- or tumor-associated, guide antigen.

In some embodiments, the cancer- or tumor-associated guide antigen, disclosed as a non-limiting example, is intercellular adhesion molecule 1 (ICAM-1) or a fragment thereof. Therefore, the antibodies in such embodiments are anti-ICAM-1. In certain embodiments, an anti-ICAM-1 antibody can include at least one, two, three, four, five, or six CDRs selected from the CDR sequences identified in Table 5 for M10A12.

The present disclosure further provides, as a non-limiting example, an anti-ICAM-1 antibody that can include a heavy chain variable domain ($V_H$) sequence having at least 50%, 60%, 70%, 80%, 90%, 91%, 92%, 93%, 94%, 95%, 96%, 97%, 98%, 99%, or 100% sequence identity to the $V_H$ sequence identified in Table 5 for M10A12. In certain embodiments, a $V_H$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-ICAM-1 antibody having that sequence retains the ability to bind to ICAM-1 or a fragment thereof. In certain embodiments, a total of 1 to 10 amino acids have been substituted, inserted and/or deleted in a heavy chain variable domain ($V_H$) sequence having at least 50%, 60%, 70%, 80%, 90%, 91%, 92%, 93%, 94%, 95%, 96%, 97%, 98%, 99%, or 100% sequence identity to the $V_H$ sequence identified in Table 5 for M10A12 In certain embodiments, substitutions, insertions, or deletions occur in regions outside the CDRs (i.e., in the FRs).

The present disclosure further provides, as a non-limiting example, an anti-ICAM-1 that can include a light chain variable domain ($V_L$) sequence having at least 50%, 60%, 70%, 80%, 90%, 91%, 92%, 93%, 94%, 95%, 96%, 97%, 98%, 99%, or 100% sequence identity to the $V_L$ sequence identified in Table 5 for M10A12. In certain embodiments, a $V_L$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-ICAM-1 antibody having that sequence retains the ability to bind to ICAM-1 or a fragment thereof. In certain embodiments, a total of 1 to 10 amino acids have been substituted, inserted and/or deleted in a light chain variable domain ($V_L$) sequence having at least 50%, 60%, 70%, 80%, 90%, 91%, 92%, 93%, 94%, 95%, 96%, 97%, 98%, 99%, or 100% sequence identity to the $V_L$ sequence identified in Table 5 for M10A12 In certain embodiments, substitutions, insertions, or deletions occur in regions outside the CDRs (i.e., in the FRs).

The present disclosure further provides, as a non-limiting example, an anti-ICAM-1 antibody, wherein the antibody can include a $V_H$ as in any of the embodiments provided above, and a $V_L$ as in any of the embodiments provided above.

In certain embodiments, as a non-limiting example, an anti-ICAM-1 antibody can include a scFV fragment that specifically binds to ICAM-1 or a fragment thereof. Some examples of the scFV fragment that is anti-ICAM-1 include M10A12, which is known in the field. See, U.S. patent application Ser. No. 11/972,130, which is issued to U.S. Pat. No. 7,582,736, which is incorporated by reference. An anti-ALCAM antibody of the present disclosure can have a fragment having at least 50%, 60%, 70%, 80%, 90%, 91%, 92%, 93%, 94%, 95%, 96%, 97%, 98%, 99%, or 100% sequence identity to the scFV fragment of M10A12 that is identified in Table 5.

In some embodiments, the cancer- or tumor-associated guide antigen is ephrin type-A receptor 2 (EphA2) or a fragment thereof. Therefore, the antibodies in such embodiments, disclosed as non-limiting examples, are anti-EphA2. In certain embodiments, an anti-EphA2 antibody can include at least one, two, three, four, five, or six CDRs selected from the CDR sequences identified in Table 5 for RYR.

The present disclosure further provides, as a non-limiting example, an anti-EphA2 antibody that can include a heavy chain variable domain ($V_H$) sequence having at least 50%, 60%, 70%, 80%, 90%, 91%, 92%, 93%, 94%, 95%, 96%, 97%, 98%, 99%, or 100% sequence identity to the $V_H$ sequence identified in Table 5 for RYR. In certain embodiments, a $V_H$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-EphA2 antibody having that sequence retains the ability to bind to EphA2 or a fragment thereof. In certain embodiments, a total of 1 to 10 amino acids have been substituted, inserted and/or deleted in a heavy chain variable domain ($V_H$) sequence having at least 50%, 60%, 70%, 80%, 90%, 91%, 92%, 93%, 94%, 95%, 96%, 97%, 98%, 99%, or 100% sequence identity to the $V_H$ sequence identified in Table 5 for RYR In certain embodiments, substitutions, insertions, or deletions occur in regions outside the CDRs (i.e., in the FRs).

The present disclosure further provides, as a non-limiting example, an anti-EphA2 that can include a light chain variable domain ($V_L$) sequence having at least 50%, 60%, 70%, 80%, 90%, 91%, 92%, 93%, 94%, 95%, 96%, 97%, 98%, 99%, or 100% sequence identity to the $V_L$ sequence identified in Table 5 for RYR. In certain embodiments, a $V_L$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-EphA2 antibody having that sequence retains the ability to bind to EphA2 or a fragment thereof. In certain embodiments, a total of 1 to 10 amino acids have been substituted, inserted and/or deleted in a light chain variable domain ($V_L$) sequence having at least 50%, 60%, 70%, 80%, 90%, 91%, 92%, 93%, 94%, 95%, 96%, 97%, 98%, 99%, or 100% sequence identity to the $V_L$ sequence identified in Table 5 for RYR In certain embodiments, substitutions, insertions, or deletions occur in regions outside the CDRs (i.e., in the FRs).

The present disclosure further provides, as a non-limiting example, an anti-EphA2 antibody, wherein the antibody can include a $V_H$ as in any of the embodiments provided above, and a $V_L$ as in any of the embodiments provided above.

In certain embodiments, an anti-EphA2 antibody, disclosed as a non-limiting example, can include a scFV fragment that specifically binds to EphA2 or a fragment thereof. Some examples of the scFV fragment that is anti-EphA2 include RYR which is known in the field. See, U.S. Provisional Application No. 62/023,689; and PCT publication No. WO201600774, each of which is incorporated by reference. RYR is identified as HCA-F1 in the foregoing references. An anti-EphA2 antibody of the present disclosure can have a fragment having at least 50%, 60%, 70%, 80%, 90%, 91%, 92%, 93%, 94%, 95%, 96%, 97%, 98%, 99%, or 100% sequence identity to the scFV fragment of RYR that is identified in Table 5.

In some embodiments, the cancer- or tumor-associated guide antigen, disclosed as, as a non-limiting example, is activated leukocyte cell adhesion molecule (ALCAM) or a fragment thereof. Therefore, the antibodies in such embodiments are anti-ALCAM. In certain embodiments, an anti-ALCAM antibody can include at least one, two, three, four, five, or six CDRs selected from the CDR sequences identified in Table 5 for H3 (585I141) and variant thereof (e.g. 585I141.1), and PD32.

The present disclosure further provides, as a non-limiting example, an anti-ALCAM antibody that can include a heavy chain variable domain ($V_H$) sequence having at least 50%, 60%, 70%, 80%, 90%, 91%, 92%, 93%, 94%, 95%, 96%, 97%, 98%, 99%, or 100% sequence identity to any of the $V_H$ sequences identified in Table 5 for H3 (585I141) and variant thereof (e.g. 585I141.1), and PD32. In certain embodiments, a $V_H$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-ALCAM antibody having that sequence retains the ability to bind to ALCAM or a fragment thereof. In certain embodiments, a total of 1 to 10 amino acids have been substituted, inserted and/or deleted in a heavy chain variable domain ($V_H$) sequence having at least 50%, 60%, 70%, 80%, 90%, 91%, 92%, 93%, 94%, 95%, 96%, 97%, 98%, 99%, or 100% sequence identity to any of the $V_H$ sequences identified in Table 5 for H3 (585I141) and variant thereof (e.g. 585I141.1), and PD32 In certain embodiments, substitutions, insertions, or deletions occur in regions outside the HVRs (i.e., in the FRs).

The present disclosure further provides, as a non-limiting example, an anti-ALCAM that can include a light chain variable domain ($V_L$) sequence having at least 50%, 60%, 70%, 80%, 90%, 91%, 92%, 93%, 94%, 95%, 96%, 97%, 98%, 99%, or 100% sequence identity to any of the $V_L$ sequences identified in Table 5 for H3 (585I141) and variant thereof (e.g. 585I141.1), and PD32. In certain embodiments, a $V_L$ sequence having at least 50%, 60%, 70%, 80%, 90%, 91%, 92%, 93%, 94%, 95%, 96%, 97%, 98%, or 99% identity contains substitutions (e.g., conservative substitutions as disclosed below), insertions, or deletions relative to the reference sequence, but an anti-ALCAM antibody having that sequence retains the ability to bind to ALCAM or a fragment thereof. In certain embodiments, a total of 1 to 10 amino acids have been substituted, inserted and/or deleted in a light chain variable domain ($V_L$) sequence having at least 50%, 60%, 70%, 80%, 90%, 91%, 92%, 93%, 94%, 95%, 96%, 97%, 98%, 99%, or 100% sequence identity to any of the $V_L$ sequences identified in Table 5 for H3 (585I141) and variant thereof (e.g. 585I141.1), and PD32 In certain embodiments, substitutions, insertions, or deletions occur in regions outside the CDRs (i.e., in the FRs).

The present disclosure further provides, as a non-limiting example, an anti-ALCAM antibody, wherein the antibody can include a $V_H$ as in any of the embodiments provided above, and a $V_L$ as in any of the embodiments provided above.

In certain embodiments, an anti-ALCAM antibody, disclosed as a non-limiting example, can include a scFV fragment that specifically binds to ALCAM or a fragment thereof. Some examples of the scFV fragment that is anti-ICAM-1 include H3 (585I141) and variant thereof (e.g. 585I141.1), and PD32 which are known in the field. See, e.g. Ruan et al. *Molecular & Cellular Proteomics* 5. 12: 2364-2373 (2006); Liu et al., *J. Mol Med.* 85:1113-1123 (2007); U.S. patent application Ser. No. 14/486,943, which is published to U.S. 20150071937; and U.S. patent application Ser. No. 13/172,759, which is issued to U.S. Pat. No. 9,145,462 in which PD32 is identified as GPD32, each of which is incorporated by reference. An anti-ALCAM antibody of the present disclosure can have a fragment having at least 50%, 60%, 70%, 80%, 90%, 91%, 92%, 93%, 94%, 95%, 96%, 97%, 98%, 99%, or 100% sequence identity to the scFV fragment of H3, any variant H3 (e.g. 585I141.1) or PD32 that are identified in Table 5.

The present disclosure further provides bispecific antibodies, as non-limiting examples, that bind to both LRP6 (or any fragment(s) thereof) and a cancer- or tumor-associated antigen such as ICAM-1, EphA2 and ALCAM (or a fragment thereof) (i.e., anti-LRP6/anti-ICAM-1, EphA2 or ALCAM bispecific antibodies). In some embodiments, depending on the fragment recognized by the antibody, anti-LRP6 can be further defined anti-LRP6E1E2 or antiLRP6E3E4 as described above. Therefore, in certain embodiments, the scope of the term "anti-LRP6A" encompasses "anti-LRP6E1E2" and "antiLRP6E3E4". A bispecific antibody has two different components each of which has two different binding specificities. For example, and not by way of limitation, the presently disclosed subject matter provides bispecific antibodies having a first component having a binding site (e.g., antigen binding site) for a first antigen present on LRP6 or a fragment thereof and a second component having another binding site for a second antigen present on ICAM-1, EphA2 or ALCAM (or a fragment thereof).

The present disclosure further provides, as a non-limiting example, a bispecific antibody that is an anti-LRP6/anti-ICAM-1.

In some embodiments, an anti-LRP6/anti-ICAM-1 bispecific antibody, disclosed as a non-limiting example, can include at least one, two, three, four, five, or six CDRs that are responsible for binding to LRP6 or a fragment thereof. Each of the at least one, two, three, four, five, or six CDRs specific for LRP6 or a fragment thereof can be selected from any of the embodiments provided above in the context of the CDRs of anti-LRP6 antibody. In some embodiments, in addition to the one to six CDRs specific for LRP6 or a fragment thereof, an anti-LRP6/anti-ICAM-1 bispecific antibody can include at least one, two, three, four, five, or six CDRs that are responsible for binding to ICAM-1 or a fragment thereof. Each of the at least one, two, three, four, five, or six CDRs specific for ICAM-1 or a fragment thereof can be selected from any of the embodiments provided above in the context of the CDRs of anti-ICAM-1 antibody.

The present disclosure further provides, as a non-limiting example, an anti-LRP6/anti-ICAM-1 bispecific antibody that can include a heavy chain variable domain ($V_H$) sequence responsible for binding to LRP6 or a fragment thereof. The $V_H$ sequence specific for LRP6 or a fragment thereof can be selected from any of the embodiments provided above in the context of the $V_H$ sequences of anti-LRP6 antibody. In some embodiments, in addition to the $V_H$ sequence specific for LRP6 or a fragment thereof, an anti-LRP6/anti-ICAM-1 bispecific antibody can include a $V_H$ sequence that is responsible for binding to ICAM-1 or a fragment thereof. Each of the $V_H$ sequence specific for ICAM-1 or a fragment thereof can be selected from any of the embodiments provided above in the context of the $V_H$ sequences of anti-ICAM-1 antibody.

The present disclosure further provides, as a non-limiting example, an anti-LRP6/anti-ICAM-1 bispecific antibody that can include a light chain variable domain ($V_L$) sequence responsible for binding to LRP6 or a fragment thereof. The $V_L$ sequence specific for LRP6 or a fragment thereof can be selected from any of the embodiments provided above in the context of the $V_L$ sequences of anti-LRP6 antibody. In some embodiments, in addition to the $V_L$ sequence specific for LRP6 or a fragment thereof, an anti-LRP6/anti-ICAM-1 bispecific antibody can include a $V_L$ sequence that is responsible for binding to ICAM-1 or a fragment thereof. Each of the $V_L$ sequence specific for ICAM-1 or a fragment thereof can be selected from any of the embodiments provided above in the context of the $V_L$ sequences of anti-ICAM-1 antibody.

In one aspect, as a non-limiting example, a bispecific antibody can be an anti-LRP6/anti-ICAM-1 bispecific antibody, wherein the bispecific antibody can include a $V_H$ as in any of the embodiments provided above, and a $V_L$ as in any of the embodiments provided above.

The present disclosure further provides, as a non-limiting example, a bispecific antibody that is an anti-LRP6/anti-EphA2.

In some embodiments, an anti-LRP6/anti-EphA2 bispecific antibody, disclosed, as a non-limiting example, can include at least one, two, three, four, five, or six CDRs that are responsible for binding to LRP6 or a fragment thereof. Each of the at least one, two, three, four, five, or six CDRs specific for LRP6 or a fragment thereof can be selected from any of the embodiments provided above in the context of the CDRs of anti-LRP6 antibody. In some embodiments, in addition to the one to six CDRs specific for LRP6 or a fragment thereof, an anti-LRP6/anti-EphA2 bispecific antibody can include at least one, two, three, four, five, or six CDRs that are responsible for binding to EphA2 or a fragment thereof. Each of the at least one, two, three, four, five, or six CDRs specific for EphA2 or a fragment thereof can be selected from any of the embodiments provided above in the context of the CDRs of anti-EphA2 antibody.

The present disclosure further provides, as a non-limiting example, an anti-LRP6/anti-EphA2 bispecific antibody that can include a heavy chain variable domain ($V_H$) sequence responsible for binding to LRP6 or a fragment thereof. The $V_H$ sequence specific for LRP6 or a fragment thereof can be selected from any of the embodiments provided above in the context of the $V_H$ sequences of anti-LRP6 antibody. In some embodiments, in addition to the $V_H$ sequence specific for LRP6 or a fragment thereof, an anti-LRP6/anti-EphA2 bispecific antibody can include a $V_H$ sequence that is responsible for binding to EphA2 or a fragment thereof. Each of the $V_H$ sequence specific for EphA2 or a fragment thereof can be selected from any of the embodiments provided above in the context of the $V_H$ sequences of anti-EphA2 antibody.

The present disclosure further provides, as a non-limiting example, an anti-LRP6/anti-EphA2 bispecific antibody that can include a light chain variable domain ($V_L$) sequence responsible for binding to LRP6 or a fragment thereof. The $V_L$ sequence specific for LRP6 or a fragment thereof can be selected from any of the embodiments provided above in the context of the $V_L$ sequences of anti-LRP6 antibody. In some embodiments, in addition to the $V_L$ sequence specific for LRP6 or a fragment thereof, an anti-LRP6/anti-EphA2 bispecific antibody can include a $V_L$ sequence that is responsible for binding to EphA2 or a fragment thereof. Each of the $V_L$ sequence specific for EphA2 or a fragment thereof can be selected from any of the embodiments provided above in the context of the $V_L$ sequences of anti-EphA2 antibody.

The present disclosure further provides, as a non-limiting example, an anti-LRP6/anti-EphA2 bispecific antibody, wherein the bispecific antibody can include a $V_H$ as in any of the embodiments provided above, and a $V_L$ as in any of the embodiments provided above.

The present disclosure further provides a bispecific antibody that is an anti-LRP6/anti-ALCAM.

In some embodiments, an anti-LRP6/anti-ALCAM bispecific antibody, disclosed, as a non-limiting example, can include at least one, two, three, four, five, or six CDRs that are responsible for binding to LRP6 or a fragment thereof. Each of the at least one, two, three, four, five, or six CDRs specific for LRP6 or a fragment thereof can be selected from any of the embodiments provided above in the context of the CDRs of anti-LRP6 antibody. In some embodiments, in addition to the one to six CDRs specific for LRP6 or a fragment thereof, an anti-LRP6/anti-ALCAM bispecific antibody can include at least one, two, three, four, five, or six CDRs that are responsible for binding to ALCAM or a fragment thereof. Each of the at least one, two, three, four, five, or six CDRs specific for ALCAM or a fragment thereof can be selected from any of the embodiments provided above in the context of the CDRs of anti-ALCAM antibody.

The present disclosure further provides, as a non-limiting example, an anti-LRP6/anti-ALCAM bispecific antibody that can include a heavy chain variable domain ($V_H$) sequence responsible for binding to LRP6 or a fragment thereof. The $V_H$ sequence specific for LRP6 or a fragment thereof can be selected from any of the embodiments provided above in the context of the $V_H$ sequences of anti-LRP6 antibody. In some embodiments, in addition to the $V_H$ sequence specific for LRP6 or a fragment thereof, an anti-LRP6/anti-ALCAM bispecific antibody can include a $V_H$ sequence that is responsible for binding to ALCAM or a fragment thereof. Each of the $V_H$ sequence specific for ALCAM or a fragment thereof can be selected from any of the embodiments provided above in the context of the $V_H$ sequences of anti-ALCAM antibody.

The present disclosure further provides, as a non-limiting example, an anti-LRP6/anti-ALCAM bispecific antibody that can include a light chain variable domain ($V_L$) sequence responsible for binding to LRP6 or a fragment thereof. The $V_L$ sequence specific for LRP6 or a fragment thereof can be selected from any of the embodiments provided above in the context of the $V_L$ sequences of anti-LRP6 antibody. In some embodiments, in addition to the $V_L$ sequence specific for LRP6 or a fragment thereof, an anti-LRP6/anti-ALCAM bispecific antibody can include a $V_L$ sequence that is responsible for binding to ALCAM or a fragment thereof. Each of the $V_L$ sequence specific for ALCAM or a fragment thereof can be selected from any of the embodiments provided above in the context of the $V_L$ sequences of anti-ALCAM antibody.

The present disclosure further provides, as a non-limiting example, an anti-LRP6/anti-ALCAM bispecific antibody, wherein the bispecific antibody can include a $V_H$ as in any of the embodiments provided above, and a $V_L$ as in any of the embodiments provided above.

In certain aspects, a bispecific antibody of the present disclosure that is anti-LRP6 and anti-cancer- (or -tumor) associated antigen (e.g. anti-LRP6/anti-ICAM-1, anti-LRP6/anti-EphA2, and anti-LRP6/anti-ALCAM) binds to LRP6 or a fragment thereof with an affinity (KO of $10^{-6}$M, $10^{-7}$ M, $10^{-8}$ M, $10^{-9}$ M, $10^{-10}$ M, $10^{-11}$ M, or $10^{-12}$M or less (lower meaning higher binding affinity). In certain aspects, a bispecific antibody of the present disclosure that is anti-LRP6 and anti-cancer- (or tumor-) associated antigen (e.g. anti-LRP6/anti-ICAM-1m anti-LRP6/anti-EphA2, and anti-LRP6/anti-ALCAM) binds to the cancer- (or tumor-associated) antigen or a fragment thereof with an affinity ($K_d$) of $10^{-6}$M, $10^{-7}$ M, $10^{-8}$ M, $10^{-9}$ M, $10^{-10}$ M, $10^{-11}$M, or $10^{-12}$ M or less.

According to certain embodiments, a bispecific antibody of the present disclosure, such as anti-LRP6/anti-ICAM-1, anti-LRP6/anti-EphA2 and anti-LRP6/anti-ALCAM antibodies binds to its effector antigen (e.g. LRP6 or a fragment thereof) and/or its guide antigen (e.g. ICAM-1, EphA2, ALCAM or a fragment thereof) with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% or more higher affinity (e.g., preferentially binds) compared to the binding affinity of an antibody that is monospecific to only one of antigen.

Methods of Designing a Guide/Effector Bispecific System

Disclosed herein, in certain embodiments, are methods of designing a guide/effector bispecific system. In some embodiments, designing a guide/effector bispecific system has: (1) determining a density ratio of a guide antigen to an effector antigen (2) determining a threshold density of the guide antigen, and (3) determining whether the guide antigen and the effector antigen are expressed on a target cell.

In some embodiments, a method disclosed herein for generating an engineered antibody has (a) selecting a cell expressing a plurality of guide antigens and effector antigens on the cell surface; (b) determining a density ratio of the plurality of guide antigens and effector antigens; and (c) preparing an engineered antibody having a first antigen binding region that binds to the guide antigen and a second antigen binding region that binds to the effector antigen on the cell if the density ratio of the guide antigen to effector antigen is at least 4:1.

In some embodiments, a method of generating an engineered antibody has (a) selecting a cell expressing a plurality of guide antigens and effector antigens on the cell surface; (b) determining a copy number of the guide antigen expressed on the cell surface; and (c) preparing an engineered antibody having a first antigen binding region that binds to the guide antigen and a second antigen binding region that binds to the effector antigen on the cell if the cell expresses at least 15,000 copies of the guide antigen.

In some embodiments, producing an engineered antibody has determining a density ratio of a guide antigen to an effector antigen on a target cell. In some embodiments, the potency of signal pathway modulation may increase with increasing the density of the guide antigen to the density of the effector antigen (the density ratio). In some embodiments, the density of the guide antigen is substantially higher than the density of the effector antigen such that the density ratio between the guide antigen to effector antigen on the surface of target cell ranges about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1 or more, and in some particular embodiments the ratio ranges about 5:1 to 10:1. In some embodiments, the density ratio between the guide antigen to effector antigen on the surface of a target cell is 4:1. In some embodiments, the density ratio between the guide antigen to effector antigen on the surface of a target cell is 5:1. In some embodiments, the density ratio between the guide antigen to effector antigen on the surface of a target cell is 10:1. In some other embodiments where the density of a guide antigen is substantially higher than the density of an effector antigen, a density ratio between the guide antigen to effector antigen on the surface of target cell ranges more than 10:1. In some examples, when the density ratio is greater than 10:1, about a thousand-fold potency enhancement can be achieved in a target cell-specific manner.

In some embodiments, producing an engineered antibody has determining a threshold density of the guide antigen. In some instances, a certain (e.g. high) level of threshold of cell surface guide antigen density enhances cell-type selective potency. In some embodiments, a threshold of cell surface guide antigen density ranges about 100, 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 13,000, 14,000, 15,000, 16,000, 17,000, 18,000, 19,000, 20,000, 25,000, 30,000, 40,000, 50,000, 100,000, 200,000 or more copies or any intervening number of copies per cell. In some embodiments, a threshold of cell surface guide antigen density ranges about 1,000 to 5,000 copies per cell, 5,000 to 10,000 copies per cell, 10,000 to 15,000 copies per cell or 15,000 to 20,000 copies per cell. In some embodiments, a threshold expression level of a guide antigen in the surface of target cell is more than about 10,000 copies per cell. In some embodiments, a threshold expression level of a guide antigen in the surface of target cell is more than about 15,000 copies per cell. In some embodiments, a threshold expression level of a guide antigen in the surface of target cell is more than about 20,000 copies per cell. The exact threshold of the guide antigen density may vary depending on the nature of the signaling pathway and/or the nature of target cell and such a threshold can be determined in view of the guidance provided in the present disclosure. As illustrated in the Examples of the present disclosure, when the guide antigen is expressed at a high level (e.g. about 100, 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 13,000, 14,000, 15,000, 16,000, 17,000, 18,000, 19,000, 20,000, 25,000, 30,000, 40,000, 50,000, 100,000, 200,000 or more copies per cell, in particular, 15,000 to 20,000 copies or more per cell), the effect of the guide in the bispecific antibody is apparent.

In some embodiments, designing a guide/effector bispecific system has determining whether the guide antigen and the effector antigen are expressed on a target cell. In some embodiments, the target cell is a T cell or an NK cell. In other instances, the target cell is a cancer cell.

Method of Modulating a Signaling Pathway

In some embodiments, an engineered antibody described herein modulates a signaling pathway including upregulation and downregulation thereof. In some embodiments, an engineered antibody can function as an agonist and upregulates (enhances, stimulates, promotes, activates or increases) a signaling pathway of interest, i.e. a target pathway. In certain embodiments, a bispecific antibody is an antibody that increases the activity of the target pathway by at least 10%, 20%, 30%, 40%, 50%, 60%, 70%, 80%, 90%, 99% or 99.9% as compared to no antibody or a monospecific antibody. In some other embodiments, upregulation of a target signaling pathway includes turning on or initiating the pathway that was off or substantially not active. In another example, an engineered antibody can function as an antagonist and downregulates (suppresses, inhibits, reduces, decreases or diminishes) the target pathway. In certain embodiments, an engineered antibody is an antibody that decreases the activity of the target pathway by at least 10%, 20%, 30%, 40%, 50%, 60%, 70%, 80%, 90%, 99% or 99.9% as compared to no antibody or a monospecific antibody. In some embodiments, downregulation of a target signaling pathway includes turning off or substantially blocking the pathway that was on or substantially active.

The specificity to a target pathway of an engineered antibody of the present disclosure is determined by the binding affinity of the antibody to its first antigen or effector antigen. The effector antigen is associated with the target pathway, e.g. by being a component of the signaling cascade of the target pathway. Upon binding of an engineered antibody to its specific effector antigen that is present on a target cell, the activity of the target pathway is modulated, i.e. upregulated or downregulated. In some embodiments, a target signaling pathway is associated with one or more of cellular behaviors such as cell growth, survival, proliferation, differentiation, migration, extracellular matrix remodeling, fibrosis, metastasis, inflammation and angiogenesis. Therefore, use of an engineered antibody of the present disclosure can lead to at least one or more of the following as a result of modulating a target signaling pathway:
  i) stimulating or suppressing cell growth,
  ii) stimulating or suppressing cell survival,
  iii) stimulating or suppressing cell proliferation,
  iv) stimulating or suppressing cell differentiation,
  v) stimulating or suppressing cell migration, vi) stimulating or suppressing extracellular matrix remodeling, vii) stimulating or suppressing development of organ fibrosis, viii) stimulating or suppressing development of tissue fibrosis, ix) stimulating or suppressing development of metastasis, x) stimulating or suppressing angiogenesis, xi) stimulating or suppressing inflammation, and/or xii) stimulating or suppressing cell secretion.

In some embodiments, an engineered antibody of the present disclosure modulates a target signaling pathway in a cell-selective or cell-specific manner. In other words, the modulation of a target signaling pathway by a bispecific antibody is performed only or highly preferentially on a certain cell of interest, i.e. a target cell. This cell-specificity or cell-selectivity a bispecific antibody of the present disclosure is determined by the binding affinity of the antibody to its second antigen or guide antigen. The guide antigen is associated with a specific cell type, e.g. cancer call, by being overexpressed thereon. Therefore, an engineered antibody can be substantially enriched to the surface of the target cell that overexpresses a guide antigen on its surface as compared to a non-target cell where the expression level of the guide antigen is less.

In some embodiments, an engineered antibody is not equivalent to a mere mixture of monospecific antibodies, one specific to an effector antigen and the other specific to a guide antigen but shows synergistic improvements in the potency of the antibody to modulate a target signaling in a cell-specific or -selective manner. In some embodiments, a guide/effector design according to the present disclosure selectively enhances signal pathway modulation in target cells expressing the guide antigen. In some cases, the potency is enhanced under the effector/guide bispecific system, which in some instances is several hundreds to a thousand-fold more potent than a monospecific antibody. As exemplified in the non-limiting examples section herein, this phenomenon was observed using three different guide antigens (ALCAM, ICAM-1 and EphA2) in the examples presented in the present disclosure and multiple types of effector-ligand interaction, i.e., Wnt3a and Wnt1 binding to LRP6E3E4 and E1E2 domains, respectively, as well as RSPO1-mediated Wnt signaling amplification.

As disclosed supra, a parameter for the guide/effector design of the present disclosure has (1) co-presentation of the guide and effector on the same cell (target cell), and a certain (e.g. high) ratio of the guide to effector antigen density. In some embodiments, the potency of signal pathway modulation increases with increasing guide to effector ratio. In some embodiments, the density of a guide density is substantially higher than the density of an effector such that a ratio between the guide to effector density on the surface of target cell ranges about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1 or more, and in some particular embodiments the ratio ranges about 5:1 to 10:1. In some other embodiments where the density of a guide density is substantially higher than the density of an effector, a ratio between the guide to effector density on the surface of target cell ranges more than 10:1. In some examples, when the ratio is greater than 10:1, about a thousand-fold potency enhancement can be achieved in a target cell-specific manner.

One parameter for the guide/effector design capable of the synergistic results is a certain (e.g. high) level of threshold of cell surface guide antigen density is required to achieve the cell-type selective potency enhancement. Some examples of a threshold of cell surface guide antigen density ranges about 100, 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 13,000, 14,000, 15,000, 16,000, 17,000, 18,000, 19,000, or 20,000 or more copies or any intervening number of copies per cell. In some embodiments, a threshold of cell surface guide antigen density ranges about 1,000 to 5,000 copies per cell, 5,000 to 10,000 copies per cell, 10,000 to 15,000 copies per cell or 15,000 to 20,000 copies per cell. In some embodiments, a threshold expression level of a guide antigen in the surface of target cell is more than about or 20,000 or more copies per cell, in particular, 15,000 to 20,000 copies or more per cell), the effect of the guide in the bispecific antibody is apparent. This fits well with tumor targeting as many cell surface molecules have found to be overexpressed by tumor cells, thus can serve as the guide antigens to redirect and enhance the activity of a bispecific antibody, e.g. anti-LPR6 antibodies in Wnt signaling inhibition.

Methods of Treating a Disease or Condition

The present disclosure provides methods of treating a disease or condition (e.g., cancer) using an engineered antibody. In some embodiments, the treatment is performed via modulation of a signaling pathway using an engineered activity of the present disclosure. In some instances, the methods include administering to a subject in need thereof a therapeutically effective amount of an engineered antibody or a pharmaceutical composition having the engineered antibody described herein, alone (e.g., as a monotherapy) or in combination (e.g., as a combination therapy) with one or more additional agents, e.g. a pharmaceutically acceptable excipient. In certain aspects, a bispecific antibody or a pharmaceutical composition that is administered to a subject specifically targets a cell wherein a signaling pathway is modulated as a result of the treatment.

In some embodiments, engineered antibody and conjugate compositions/formulations described herein are administered to a subject (e.g., a human patient) for the treatment of a disease or condition associated with a dysregulation of a signaling pathway. In some instances, a signaling pathway is selected from AKT pathway, c-MET pathway, NF-kB pathway, Notch signaling pathway, p53 pathway, Ras-Raf-MEK-ERK pathway, STAT signaling pathway, Wnt signaling pathway, YAP/Wnt signaling pathway, NK (natural killer) activating pathway, NK inhibitory pathway, and checkpoint inhibitory pathway. In some cases, the disease or condition is associated with a dysregulation of the YAP/Wnt-signaling pathway, Receptor tyrosine kinase (RTK) signaling pathway families, NK (natural killer) activating pathway, NK inhibitory pathway, macrophage regulatory pathway, dendritic cell regulatory pathway, T cell regulatory pathway and checkpoint inhibitory pathway. In some cases, the disease or condition is associated with a dysregulation of the YAP/Wnt-signaling pathway. In some cases, the disease or condition is associated with a dysregulation of the Wnt-signaling pathway.

In some embodiments, engineered antibody and conjugate compositions/formulations described herein are administered to an individual (e.g. a human patient) to, for example, reduce the viability and/or invasiveness of cancerous cells, e.g., to reduce tumor size or metastasis, reduce tumor load, and/or improve the clinical outcome in patients. In certain aspects, antibody compositions can be used to disrupt the cell cycle of the cancer cell, and facilitate entry of the cell into apoptosis, e.g., by inducing cancerous cells to enter the pre-G0 cell cycle phase. The methods relating to cancer contemplated herein include, for example, use of antibody therapy alone or in combination with anti-cancer vaccine or therapy, as well as use of antibodies generated using an effector and/or guide antigens in anti-cancer vaccines (e.g., by passive immunization) or therapies. The methods are useful in the context of treating or preventing a wide variety of cancers. In one aspect, cancer refers to a general term encompassing primary cancer and metastatic cancer. In some embodiments, primary cancer may be meant a group of tumor cells, which have acquired at least one characteristic feature of cancer cells, however have not yet invaded the neighboring tissues and hold together in a tumor localized at the place of primary origin. In some other embodiments, metastatic cancer may be meant a group of tumor cells, which originate from the cells of a primary cancer, which have invaded the tissue surrounding said primary cancer, disseminated through the body, adhered at a new distant place and grown to a new tumor. Examples of cancers include, but is not limited by, carcinoma of the breast, esophageal cancer, colorectal, pancreas, stomach, GIST, hepatocellular, liver, lung, small cell lung, ovarian, uterine, cervix, bladder, renal, colon, small intestine, large intestine, gastric cancer, prostate, testis, thyroid carcinoma, malignant melanoma, uveal melanoma, multiple myeloma, mesothelioma, osteosarcoma, chondrosarcoma, myosarcoma, glioblastoma, sarcoma, glioma, or other brain tumors, head/neck other gastrointestinal and germ cell tumors, and haematologic malignancies. In some cases, the haematologic malignancies include leukemia, lymphoma, myeloma or B-cell malignancies. In some embodiments, cancer contemplated herein is not limited to prostate cancer, ovarian cancer, breast cancer, lung cancer, cervical cancer, epidermoid carcinoma, brain cancer, glioblastoma multiforme and Ras-transformed cancer.

In certain embodiments, the antibody compositions are used in an anti-cancer therapy, where the cancerous cells present a cell-specific marker, which can serve as a guide antigen for a bispecific antibody of the present disclosure on an extracellularly accessible cell surface. Cancers particularly amenable to therapy using bispecific antibody of the present disclosure include those targeted by the antibody through biding to the guide antigen. In some embodiments, the presence or expression level of such a guide antigen in normal human tissue or cells can be transient and low abundance as compared to cancer cells that overexpress the guide antigen. The guide antigen can be prevalent primarily in abnormal cells, such as cancer cells. Since expression of high levels of the guide antigen may exist predominantly in cancer cells, treatment with bispecific antibody of the present disclosure or the composition having the antibody can be used to treat the cancer cells with high specificity or selectivity, minimizing non-specific, cytotoxicity to non-cancerous or healthy cells.

In some embodiments, a mode of treatment is to modulate a signaling pathway using an engineered antibody of the present disclosure. Dysregulation of a signaling pathway is often associated with occurrence and/or advancement of a disease or condition in that modulation of such signaling pathway can result in effective treatment of the disease or condition. In some examples, a disease or condition may be related to dysregulation of one or more signaling pathway and such dysregulation may be ameliorated or diminished by modulation of another signaling pathway. In such an occasion, up- or downregulation of a signaling pathway using the engineered antibody of the present disclosure that can counteract or reduce the activity of the dysregulated signaling pathway can provide an effective treatment means.

In some embodiments, the cells subjected to the treatment using an engineered antibody of the present disclosure or a composition having the antibody are not limited to cancer cells but encompass any cells where a signaling modulation may be desired. Such cells include, but not limited, to immune effector cells such as natural killer cell(s), T cell(s), dendritic cell(s) and macrophage(s).

In some embodiments, an engineered antibody of the present disclosure or a pharmaceutical composition having thereof can successfully be used for the treating any primary cancer and/or metastatic cancer selected from breast-, colorectal-, pancreas-, stomach-, hepatocellular-, other gastrointestinal-, lung-, small cell lung-, ovarian-, uterine-, cervix-, testis-, prostate, bladder-, renal-, thyroid- and head/neck carcinoma, malignant melanoma and other skin cancers, osteosarcoma, chondrosarcoma, myosarcoma, glioblastoma or other brain tumors, germ cell tumors and haematopoietic malignancies.

Dosage

In the methods of the present disclosure, an effective amount of an engineered antibody of the present disclosure or the composition having the antibody is administered to an individual in need thereof. For example, in some embodiments, the bispecific antibody inhibits growth, metastasis and/or invasiveness of a cancer cell(s) in an individual when the antibody or the composition thereof is administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of the bispecific antibody or composition, the treating clinician's assessment of the medical situation, and other relevant factors. It is expected that the amount will fall in a relatively broad range that can be determined through routine trials. For example, the amount of the bispecific antibody or composition thereof employed to inhibit cancer cell growth, metastasis and/or invasiveness is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the individual, and may be determined based on the pharmacokinetics and pharmacology for absorption, distribution, metabolism, and excretion ("ADME") of the antibody, and thus based on the disposition of the composition within the individual. This includes consideration of the route of administration as well as dosage amount, which can be adjusted for, e.g., parenteral (applied by routes other than the digestive tract for systemic or local effects) applications. For instance, administration of a bispecific antibody or composition thereof is typically via injection and often intravenous, intramuscular, intratumoral, or a combination thereof.

An engineered antibody or composition thereof may be administered by infusion or by local injection, e.g. by infusion at a rate of about 10 mg/h to about 200 mg/h, about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m²/day, about 4 mg/m²/day to about 6 mg/m²/day, about 4.5 mg/m²/day to about 5.5 mg/m²/day. Administration (e.g., by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. A bispecific antibody or composition thereof can also be administered as part of a combination therapy, in which at least one of an immunotherapy, a cancer chemotherapy or a radiation therapy is administered to the subject.

Routes of Administration

In practicing the methods, routes of administration (path by which the engineered antibody or composition thereof is brought into an individual or a subject) may vary. An engineered antibody or composition thereof can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

In some embodiments, an engineered antibody described herein is formulated for parenteral administration. In some cases, the engineered antibody is formulated for intravenous, subcutaneous, intramuscular, intra-arterial, intracranial, intracerebral, intracerebroventricular or intrathecal administration. In some instances, the engineered antibody is administered to a subject as an injection. In other instances, the engineered antibody is administered to a subject as an infusion.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the individual as well as the target disease or condition and the stage thereof in the individual.

Antibody-Cell Complex

In some embodiments, disclosed herein further include an antibody-cell complex. In some embodiments, an antibody-cell complex has an engineered antibody wherein the engineered antibody has a first antigen binding region that binds to a guide antigen on a cell, and a second antigen binding region that binds to an effector antigen on the cell, wherein the cell is characterized by a density ratio of about 4:1 guide antigen to effector antigen. In some embodiments, an antibody-cell complex has an engineered antibody wherein the engineered antibody has a first antigen binding region that binds to a guide antigen on a cell, and a second antigen binding region that binds to an effector antigen on the cell, wherein the cell has about 15,000 or more copies of the guide antigen expressed on the cell surface. In some instances, the cell characterized by a density ratio of about 5:1 guide antigen to effector antigen. In some instances, the cell characterized by a density ratio of about 10:1 guide antigen to effector antigen. In some instances, the cell has about 15,000 or more copies of the guide antigen, expressed on the surface of the cell. In some cases, the cell has about 20,000 or more copies of the guide antigen, expressed on the surface of the cell.

In some embodiments, the disclosure provides an antibody-cell complex including an engineered antibody wherein the engineered antibody has a first antigen binding region that binds to a guide antigen on a cell, and a second antigen binding region that binds to an effector antigen on the cell, wherein the cell is characterized by a density ratio of about 4:1 guide antigen to effector antigen.

In some embodiments, in the complex the cell is characterized by a density ratio of about 5:1 guide antigen to effector antigen.

In some embodiments, in the complex the cell is characterized by a density ratio of about 10:1 guide antigen to effector antigen.

In some embodiments, in the complex the cell has about 15,000 or more copies of the guide antigen, expressed on the surface of the cell.

In some embodiments, in the complex the cell has about 20,000 or more copies of the guide antigen, expressed on the surface of the cell.

In some embodiments, the disclosure provides an antibody-cell complex including an engineered antibody wherein the engineered antibody has a first antigen binding region that binds to a guide antigen on a cell, and a second antigen binding region that binds to an effector antigen on the cell, wherein the cell has about 15,000 or more copies of the guide antigen expressed on the cell surface.

In some embodiments, in the complex the cancer cell has about 20,000 or more copies of the guide antigen, expressed on the surface of the cell.

In some embodiments, in the complex the cell is further characterized by a density ratio of about 4:1 guide antigen to effector antigen.

In some embodiments, in the complex the cell is further characterized by a density ratio of about 5:1 guide antigen to effector antigen.

In some embodiments, in the complex the cell is further characterized by a density ratio of about 10:1 guide antigen to effector antigen.

In some instances, the effector antigen is a tumor antigen. In some cases, the effector antigen is a tumor-associated antigen. In other cases, the effector antigen is a tumor-specific antigen. In some cases, the effector antigen is LRP6.

In some embodiments, the second antigen binding region has a heavy chain variable region having three complementarity determining regions (CDRs), wherein the CDRs from the heavy chain variable region are selected from Tables 3 and 4. In some instances, the second antigen binding region has a light chain variable region having three complementarity determining regions (CDRs), wherein the CDRs from the light chain variable region are selected from Tables 3 and 4. In some cases, the second antigen binding region has a heavy chain variable region having three complementarity determining regions (CDRs) and a light chain variable region having three complementarity determining regions (CDRs), wherein the CDRs from the heavy chain variable region and the CDRs from light chain variable region are selected from Tables 3 and 4. In some cases, the second antigen binding region has a heavy chain variable region having at least 80%, 85%, 90%, 95%, or 99% sequence identity to a heavy chain variable sequence selected from Tables 3 and 4. In some cases, the second antigen binding region has a light chain variable region having at least 80%, 85%, 90%, 95%, or 99% sequence identity to a light chain variable sequence selected from Tables 3 and 4. In some cases, the second antigen binding region has a heavy chain variable region having at least 80%, 85%, 90%, 95%, or 99% sequence identity to a heavy chain variable sequence selected from Tables 3 and 4 and a light chain variable region having at least 80%, 85%, 90%, 95%, or 99% sequence identity to a light chain variable sequence selected from Tables 3 and 4. In some cases, the second antigen binding region has a heavy chain variable region having a sequence selected from Tables 3 and 4 and a light chain variable region having a sequence selected from Tables 3 and 4.

In some embodiments, the guide antigen is a cell type-selective cell surface antigen. In some embodiments, the guide antigen is a tumor-associated antigen. In some embodiments, the guide antigen is a tumor specific antigen.

In some embodiments, the first antigen binding region has a heavy chain variable region having three complementarity determining regions (CDRs), wherein the CDRs from the heavy chain variable region are selected from Table 5. In some instances, the first antigen binding region has a light chain variable region having three complementarity determining regions (CDRs), wherein the CDRs from the light chain variable region are selected from Table 5. In some instances, the first antigen binding region has a heavy chain variable region having three complementarity determining regions (CDRs) and a light chain variable region having three complementarity determining regions (CDRs), wherein the CDRs from the heavy chain variable region and the CDRs from light chain variable region are selected from Table 5. In some instances, the first antigen binding region has a heavy chain variable region having at least 80%, 85%, 90%, 95%, or 99% sequence identity to a heavy chain variable sequence selected from Table 5. In some instances, the first antigen binding region has a light chain variable region having at least 80%, 85%, 90%, 95%, or 99% sequence identity to a light chain variable sequence selected from Table 5. In some instances, the first antigen binding region has a heavy chain variable region having at least 80%, 85%, 90%, 95%, or 99% sequence identity to a heavy chain variable sequence selected from Table 5 and a light chain variable region having at least 80%, 85%, 90%, 95%, or 99% sequence identity to a light chain variable sequence selected from Table 5.

Method of Making Bispecific Antibodies

Example methods of making an antibody according to the present disclosure are presented below.

Antibodies can be prepared using a wide variety of techniques known in the art including the use of hybridoma, recombinant, and phage display technologies, or a combination thereof. For example, antibody may be made and isolated using methods of phage display. The antibody may also be isolated from sera of an animal host immunized with an immunogenic composition having an antigen (e.g. an effector antigen or a guide antigen), which encompasses whole proteins and a fragment thereof. Exemplary antibodies include an isolated antibody capable of specifically binding to the antigen or a fragment thereof.

The antigen that coats the wells for phage display panning or the immunogenic composition used to elicit the antibody of the present disclosure may can include an aggregate of one or more antigens. The method may involve exposing antigens to an aggregating condition so as to form an aggregate. Thus the methods of production described above may further include a step of forming an aggregate of the isolated antigens. Examples of the aggregating conditions include heating, addition of an excipient that facilitates aggregation, and the like.

Antigens used to coat the wells for phage panning or to elicit antibodies of the present disclosure may be conjugated to another molecule. For example, the antigen can be conjugated to a second molecule such as a peptide, polypeptide, lipid, carbohydrate and the like that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.).

A particular embodiment of an antigen conjugated to a second molecule is where the second molecule is an immunomodulator "Immunomodulator" is a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid.

Phage Display

Phage display is used for the high-throughput screening of protein interactions. Phages may be utilized to display antigen-binding domains expressed from a repertoire or combinatorial antibody library (e.g., human or murine). Phage expressing an antigen binding domain that binds the protease of interest can be selected or identified with the protease of interest, e.g., using labeled effector or guide antigen, or a fragment thereof bound or captured to a solid surface or bead. Phage used in these methods are typically filamentous phage including fd and M13 binding domains expressed from phage with Fab, Fv (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 2000, 21:371; Nagy et al. Nat. Med. 2002, 8:801; Huie et al., *Proc. Natl. Acad. Sci. USA* 2001, 98:2682; Lui et al., *J. Mol. Biol.* 2002, 315:1063, each of which is incorporated herein by reference. Several publications (e.g., Marks et al., *Bio/Technology* 1992, 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes et al., *Nat. Biotechnol.* 2000, 18:1287; Wilson et al., *Proc. Natl. Acad. Sci. USA* 2001, 98:3750; or Irving et al., *J. Immunol. Methods* 2001, 248:31). Cell surface libraries may be screened for antibodies (Boder et al., *Proc. Natl. Acad. Sci. USA* 2000, 97:10701; Daugherty et al., *J. Immunol. Methods* 2000, 243:211). Such procedures provide alternatives to traditional hybridoma techniques for the isolation and subsequent cloning of monoclonal antibodies. See the Examples section below.

In phage display methods, functional antibody domains are displayed on the surface of phage particles which carry the polynucleotide sequences encoding them. For example, DNA sequences encoding heavy chain variable ($V_H$) and light chain variable ($V_L$) regions are amplified or otherwise isolated from animal cDNA libraries (e.g., human or murine cDNA libraries of lymphoid tissues) or synthetic cDNA libraries. The DNA encoding the $V_H$ and $V_L$ regions may be joined together by an scFv linker by PCR and cloned into a phagemid vector (e.g., p CANTAB 6 or pComb 3 HSS). The vector is electroporated in E. coli and the E. coli is infected with helper phage. The $V_H$ or $V_L$ regions are usually recombinantly fused to either the phage gene III or gene VIII. Phage expressing an antigen binding domain that binds to an antigen of interest can be selected or identified with antigen, e.g., using labeled antigen or antigen bound or captured to a solid surface or bead.

As described in the references listed above, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art.

Immunization and Antibody Production

The method of eliciting antibodies in a host animal involves administering an effective amount of an antigen of interest (e.g. an effector or guide antigen) or a fragment thereof as antigens described above to the host animal (i.e., a suitable mammal such as a mouse, rabbit or guinea pig, or a suitable avian, such as a chicken) to elicit production of an antibody that specifically binds to the antigen or a fragment thereof. Methods of immunizing animal, including the adjuvants used, booster schedules, sites of injection, suitable animals, etc. are well understood in the art. Next, a population of antibody producing cells is generated. In one embodiment, the population of cells is produced using hybridoma methods that well known to one of skill in the art (see, e.g., Harlow Antibodies: A Laboratory Manual, First Edition (1988) Cold Spring Harbor, N.Y.). Cells are fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT). In alternative embodiments, populations of cells expressing monoclonal antibodies may be made using phage display methods.

Antibodies, including antigen binding fragments of antibodies, may also be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library can be constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Phage Panning and Screening

Once the population of antibody-producing cells or phages is produced, the antibodies are screened using one or a combination of a variety of assays. In general, these assays are functional assays, and may be grouped as follows: assays that detect an antibody's binding affinity or specificity, and assays that detect the ability of an antibody to initialize or inhibit a process.

For example, the antigen is coupled to beads or wells or other solid support and incubated with phage displaying the antibody of interest. After washings, bound phage is then recovered by inoculation of log phase E. coli cells. The cells are grown and expanded with helper phage. Steps are repeated for the amplification of tightly bound phages. The phage-infected E. coli colonies after several round of enrichment are harvested and Fab antibodies are purified from the periplasmic fractions. The purified antibodies are then analyzed in accordance with methods known in the art. Certain exemplary examples are detailed below.

The population of antibody isolated from phage-infected cells or hybridomas is further analyzed and/or screened for binding to a single antigen (i.e., antigens that are not mixed with other antigens of the plurality of antigens) of the plurality of antigens in vitro or in situ (e.g. on cells). Immunospecific binding may be carried out according to methods routine and known in the art. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. See, e.g., Ausubel et al, eds, 1994, Current Protocols in Molecular Biology, Vol. 1, John Wiley & Sons, Inc., New York, which is incorporated by reference herein in its entirety.

Antibodies of the present disclosure may also be screened in vivo. The method involves administering an antibody to an animal model for a disease or condition and determining the effect of the antibody on the disease or condition of the model animal. In vivo assays in some embodiments of the present disclosure include controls, where suitable controls include a sample in the absence of the antibody. Generally, a plurality of assay mixtures is run in parallel with different antibody concentrations to obtain a differential response to the various concentrations. Typically, one of these concentrations serves as a negative control, i.e., at zero concentration or below the level of detection.

Methods of Screening

A screening method provided by the present disclosure may involve the use of a phage library to screen for an antibody that specifically binds to an antigen of interest or a fragment thereof. The method may be executed according to the phage display method described above.

Briefly, an antigen of interest or a fragment thereof may be immobilized on an ELISA plate or on beads through a covalent or non-covalent interaction, such as hydrophobic adsorption, biotin-avidin interaction, and $Ni^{2+}$-6×His interaction. The phage library is then incubated with the immobilized antigen/protease, washed, and recovered. During panning and selection, the bound phage is recovered and amplified in E. coli. Multiple successive selection rounds ensure a selection of a phage displaying a polypeptide that acts as an antibody specific for the antigen of interest or a fragment thereof. The stringency of the washes increases over a number of rounds (e.g. three). Many techniques well known in the art may be employed to increase the specificity of the recovered phage. Examples include increased wash times, increased detergent concentrations, increased salt concentrations, and inclusion of known macromolecular inhibitors (e.g., small peptidic substrates, BPTI, Ecotin, and/or previously identified antibody inhibitors). Identification of inhibitory antibodies may include ELISAs and inhibition assays. Details on the assays to be performed in the method for selecting and isolating an antibody that is specific to the antigen of interest are discussed above.

Also contemplated by the present disclosure is a library of nucleic acid constructs encoding the candidate antibodies described herein. The library encodes a plurality of candidate antibodies that may have one or more polypeptide regions in common (e.g. a heavy chain CDR3) and at least one other polypeptide region that varies among the population.

Methods of Engineering Antibodies

Any of the antibodies described herein may also be in the form of an antibody fragment. Antibody fragments can include a portion of an intact full length antibody and can include an antigen binding or variable region of the intact antibody. Examples of antibody fragments include Fab; Fab; F(ab')2; Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; VHH containing antibodies; and other polypeptides formed from antibody fragments.

Methods of making antibody fragments are known in the art (see for example, Harlow and Lane, Antibodies: A Laboratory Manual, Cold Spring Harbor Laboratory, N Y, 1988, incorporated herein by reference). Antibody fragments can be prepared by proteolytic hydrolysis of the antibody or by expression in cells encoding the fragment. Antibody fragments can be obtained by, e.g. pepsin or papain digestion of whole antibodies conventional methods. For example, antibody fragments can be produced by enzymatic cleavage of antibodies with pepsin to provide a 5 S fragment denoted F(ab')2. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments can include an association of $V_H$ and $V_L$ chains. This association may be noncovalent or the variable chains can be linked by an intermolecular disulfide bond or cross-linked by chemicals such as glutaraldehyde. Preferably, the Fv fragments can include $V_H$ and $V_L$ chains connected by a peptide linker. These single-chain antigen binding proteins (sFv) are prepared by constructing a structural gene having DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

A single chain Fv ("scFv") polypeptide is a covalently linked $V_H$::$V_L$ heterodimer which may be expressed from a nucleic acid including $V_H$- and $V_L$-encoding sequences either joined directly or joined by a peptide-encoding linker (Huston, et al. (1988) Proc. Nat. Acad. Sci. USA, 85: 5879-5883). A number of structures are available for converting the light and heavy polypeptide chains from an antibody V region into an scFv molecule which will fold into a three dimensional structure substantially similar to the structure of an antigen-binding site.

Recombinant design methods may be used to develop suitable chemical structures (linkers) for converting two heavy and light polypeptide chains from an antibody variable region into a scFv molecule which will fold into a three-dimensional structure that is substantially similar to native antibody structure.

Design criteria include determination of the appropriate length to span the distance between the C-terminal of one chain and the N-terminal of the other, wherein the linker is generally formed from small hydrophilic amino acid residues that do not tend to coil or form secondary structures.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker having a minimum number of residues consistent with the need for molecule stability. A pair of sites defines a "gap" to be linked. Linkers connecting the C-terminus of one domain to the N-terminus of the next generally can include hydrophilic amino acids which assume an unstructured configuration in physiological solutions and may be free of residues having large side groups which might interfere with proper folding of the $V_H$ and $V_L$ chains. Thus, suitable linkers generally can include polypeptide chains of alternating sets of glycine and serine residues, and may include glutamic acid and lysine residues inserted to enhance solubility. One particular linker has the amino acid sequence (Gly$_4$Ser)$_3$. Another particularly preferred linker has the amino acid sequence having 2 or 3 repeats of [(Ser)$_4$Gly], such as [(Ser)$_4$Gly]$_3$, and the like. Nucleotide sequences encoding such linker moieties can be readily provided using various oligonucleotide synthesis techniques known in the art (see, e.g., Sambrook, supra.).

"Variants of peptide sequences" means that the peptides may be modified, for example by addition, deletion and/or substitution of one or more of the amino acid residues. Other modification may can include derivatives such as esters, sugars, etc.

Variants of the peptide fragments according to the disclosures can include, within the same variant, or fragments thereof or among different variants, or fragments thereof, at least one substitution as described elsewhere in the present disclosure.

Humanized and Non-Humanized Antibodies

The disclosures contemplate human and humanized forms of non-human (e.g. murine) antibodies. Such humanized antibodies are chimeric immunoglobulins, immunoglobulin chains or fragments thereof (such as Fv, Fab, Fab', F(ab')2 or other antigen-binding subsequences of antibodies) that contain a minimal sequence derived from non-human immunoglobulin, such as the epitope recognizing sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es), such as a sequence(s) recognizing the epitope(s) described herein, is a preferred embodiment of the present disclosure.

In some instances, Fv framework residues of the human immunoglobulin are replaced by corresponding non-human residues. Furthermore, humanized antibodies can include residues that are found neither in the recipient antibody nor in the imported CDR or framework sequences. These modifications are made to further refine and optimize antibody performance. In general, humanized antibodies will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

In some embodiments, an engineered antibody of the disclosure is generated by the method that includes a) selecting a cell expressing a plurality of guide antigens and effector antigens on the cell surface; b) determining a density ratio of the plurality of guide antigens and effector antigens; and c) preparing an engineered antibody having a first antigen binding region that binds to the guide antigen and a second antigen binding region that binds to the effector antigen on the cell if the density ratio of the guide antigen to effector antigen is at least 4:1.

In some embodiments, in the method the density ratio of the guide antigen to effector antigen is at least 5:1.

In some embodiments, in the method the density ratio of the guide antigen to effector antigen is at least 10:1.

In some embodiments, in the method the cell expresses at least 15,000 or more copies of the guide antigen on the cell surface.

In some embodiments, in the method the cell expresses at least 20,000 or more copies of the guide antigen on the cell surface.

In some embodiments, an engineered antibody of the disclosure is generated by the method that includes a) selecting a cell expressing a plurality of guide antigens and effector antigens on the cell surface; b) determining a copy number of the guide antigen expressed on the cell surface; and c) preparing an engineered antibody having a first antigen binding region that binds to the guide antigen and a second antigen binding region that binds to the effector antigen on the cell if the cell expresses at least 15,000 copies of the guide antigen.

In some embodiments, in the method the cell expresses at least 20,000 or more copies of the guide antigen on the cell surface.

In some embodiments, in the method the method further includes determining a density ratio of guide antigens to effector antigens.

In some embodiments, in the method the density ratio of the guide antigen to effector antigen is at least 4:1.

In some embodiments, in the method the density ratio of the guide antigen to effector antigen is at least 5:1.

In some embodiments, in the method the density ratio of the guide antigen to effector antigen is at least 10:1.

In some embodiments, the disclosure provides an engineered antibody produced by the process of: a) selecting a cell expressing a plurality of guide antigens and effector antigens on the cell surface; b) determining a density ratio of the plurality of guide antigens and effector antigens; and c) preparing an engineered antibody having a first antigen binding region that binds to the guide antigen and a second antigen binding region that binds to the effector antigen on the cell if the density ratio of the guide antigen to effector antigen is at least 4:1.

In some embodiments, the density ratio of the guide antigen to effector antigen is at least 5:1.

In some embodiments, the density ratio of the guide antigen to effector antigen is at least 10:1.

In some embodiments, the cell expresses at least 15,000 or more copies of the guide antigen on the cell surface.

In some embodiments, the cell expresses at least 20,000 or more copies of the guide antigen on the cell surface.

In some embodiments, the disclosure provides an engineered antibody produced by the process of: a) selecting a cell expressing a plurality of guide antigens and effector antigens on the cell surface; b) determining a copy number of the guide antigen expressed on the cell surface; and c) preparing an engineered antibody having a first antigen binding region that binds to the guide antigen and a second antigen binding region that binds to the effector antigen on the cell if the cell expresses at least 15,000 copies of the guide antigen.

In some embodiments, the cell expresses at least 20,000 or more copies of the guide antigen on the cell surface.

In some embodiments, the process further includes determining a density ratio of guide antigens to effector antigens.

In some embodiments, the density ratio of the guide antigen to effector antigen is at least 4:1.

In some embodiments, the density ratio of the guide antigen to effector antigen is at least 5:1.

In some embodiments, the density ratio of the guide antigen to effector antigen is at least 10:1.

Pharmaceutical Formulations

Also provided by the present disclosure are pharmaceutical compositions that include any of bispecific antibodies described herein, or any of the conjugates or derivatives thereof, and a pharmaceutically acceptable excipient, e.g. pharmaceutically acceptable carrier.

Pharmaceutical compositions of the present disclosure containing a bispecific antibody or conjugate or derivative of the present disclosure as an active ingredient may contain pharmaceutically acceptable excipients or additives depending on the route of administration.

Formulation of the pharmaceutical compositions of the present disclosure will vary according to the route of administration selected (e.g., solution, emulsion). An appropriate composition having the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

Therapeutic formulations of bispecific antibodies of the present disclosure can be prepared for storage by mixing the antibody having the desired degree of purity with optional pharmaceutically acceptable carriers, excipients or stabilizers. Acceptable carriers, excipients, or stabilizers are nontoxic to recipients at the dosages and concentrations employed, and include buffers such as phosphate, citrate, and other organic acids; antioxidants including ascorbic acid and methionine; preservatives; polypeptides; proteins; hydrophilic polymers; amino acids; any types of carbohydrates; salt-forming counter-ions; metal complexes; and/or non-ionic surfactants.

In some embodiments, pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent.

Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate {i.e., break down into the individual entities of drug and counterion) in an aqueous environment. Preferably, the counterion is a pharmaceutically acceptable counterion.

Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the antibody. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

The formulation herein may also contain more than one active compound (e.g., a second active agent in addition to the bispecific antibody or conjugate thereof) as necessary for the particular indication being treated (e.g., cancer), and which may be selected to complementary activities that do not adversely affect each other. Such molecules are suitably present in combination in amounts that are effective for the purpose intended.

Engineered antibodies of the present disclosure may be lyophilized for storage and reconstituted in a suitable carrier prior to use. This technique has been shown to be effective with conventional immunoglobulins. Any suitable lyophilization and reconstitution techniques can be employed. Lyophilization and reconstitution can lead to varying degrees of antibody activity loss and that use levels may have to be adjusted to compensate.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) having one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include engineered antibodies and reagents for use with the engineered antibody as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

While various embodiments and aspects of the disclosures herewith are shown and described herein, it will be obvious to those skilled in the art that such embodiments and aspects are provided by way of example only. Numerous variations, changes, and substitutions will now occur to those skilled in the art without departing from the disclosures provided herewith. It should be understood that various alternatives to the embodiments of the disclosures described herein may be employed in practicing various embodiments of the present disclosures.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

EXAMPLES

Cell signaling pathways are critical for maintaining homeostasis and regulating cell growth and survival. Normal and disease cells often use overlapping pathways, creating a roadblock to therapeutic targeting. Selective sensitivity of disease cells to pathway modulation allows certain pathways to be targeted for treatment. Nonetheless, toxicity to normal cells restricts the therapeutic window. It remains a fundamental challenge to achieve cell-type selective modulation of signaling pathways that are commonly utilized by disease and normal cells. Cell signaling pathways are often shared between normal and diseased cells. How to achieve cell type-specific or -selective, potent inhibition of signaling pathways can be an important challenge with implications for therapeutic development.

Disclosed herewith includes a generally applicable approach to achieve cell-type selective or specific signaling pathway modulation by bispecific antibody. For the purpose of illustrating some embodiments of the disclosures, the Wnt/β-catenin pathway was employed as a model system to demonstrate specificity and potency, and studied other variables such as receptor copy number on cell surface and antibody-induced receptor internalization. In this illustrative and non-limiting example, anti-LRP6 human mAbs was generated and it was used to generate bsAbs in which the anti-LRP6 mAb was joined with a guide antibody targeting a tumor-associated antigen, creating a guide/effector bispecific system. To broaden applicability and investigate the impact of receptor copy number per cell on affinity, specificity and functionality of bsAbs, several tumor associated cell surface antigens were tested. The authors of the present application have previously identified and characterized human scFv antibodies that target the intercellular adhesion molecule 1 (ICAM-1), ephrin type-A receptor 2 (EphA2), and activated leukocyte cell adhesion molecule (ALCAM) (Conrad, Ha, Liu2007). These tumor-associated antigens are overexpressed in multiple cancers (Veitonmaki, Weidle, Tandon). In the illustrative example provided in the present disclosures, when expressed at an above threshold level on the tumor cell surface, antibodies targeting those guide antigens serve as a cell-type selector as well as potency enhancer, resulting in potent and selective inhibition of the Wnt/β-catenin signaling in tumor cells.

The Wnt/β-catenin signaling plays crucial roles in embryonic development and disease pathogenesis. Aberrant activation of Wnt signaling has been observed in many types of cancer and plays a role in development of cancer stem-like cells. In the canonical Wnt/β-catenin signaling cascade, Wnt ligand binding leads to assembly of a co-receptor complex composed of the 7-transmembrane receptor Frizzled (Fzd) and the low-density lipoprotein receptor-related proteins 5 or 6 (LRP5/6), followed by phosphorylation of LRP5/6. The phosphorylated LRP5/6 sequestrates GSK-3β/Axin complex to the plasma membrane to inhibit β-catenin degradation, allowing stabilized β-catenin to translocate into the nucleus, which then binds to the T-cell factor/lymphoid enhancer factor (TCF/LEF) transcription factors, and induces the expression of various Wnt target genes including cyclin D1 and the proto-oncogene c-Myc.

The extracellular region of LRP6 has four domains, namely E1 to E4, each including a conserved YWTD β-propeller and EGF-like motif. The ligand-binding sites are separately located on the E1-E2 domain for Wnt1, Wnt2, or Wnt9 and E3-E4 domain for Wnt3 or Wnt3a. In addition to Wnt ligands, Norrin or R-spondins (RSPO1 to 4) have been shown to upregulate Wnt/β-catenin signaling by preventing turnover of LRP6. LRP6 has been considered to be a promising target for therapy development against Wnt-dependent cancers, but it is also expressed on normal cells, raising concerns of low targeting specificity that may restrict the therapeutic window.

Materials and Methods

Cell Lines

Human embryonic kidney (HEK) 293 and 293A cell lines, lung cancer cell line A549, colon cancer cell lines HCT116 and HT29, prostate cancer cell line PC3 were obtained from American Type Culture Collection (ATCC). Cells were maintained in DMEM or McCoy's 5A (colon cancer cell lines) supplemented with 10% FBS (Fisher Scientific), 100

µg/ml penicillin/streptomycin (Axenia BioLogix) at 37° C. in a humidified atmosphere containing 5% $CO_2$.

Plasmids

Full-length human LRP6, ICAM-1, or EphA2 cDNA cloned into pCMV-Entry (Origene) were used for subcloning or transient transfection. pFUSE-hIgG1-Fc2 (InvivoGen) was used for Fc-fusion constructs of truncated LRP6E1E2 and LRP6E3E4 domains. For bispecific tandem scFv-Fc constructs, pFUSE-hIgG1-Fc2 vector was modified by inserting a $(G_4S)_5$ linker between two scFv fusions. IgG-Abvec plasmids (Ig-γ and Ig-λ) were kindly provided by Dr. Patrick Wilson at University of Chicago. β-catenin-responsive luciferase reporter SuperTopFlash (STF) and pRL-SV40 *Renilla* luciferase constructs (Addgene) were used for STF reporter assays. To provide Wnt ligands in STF reporter assays, pcDNA-Wnt1 or -Wnt3a expression plasmid (Addgene) was utilized for transient transfections.

Generation of Anti-LRP6 scFv Antibodies

Phage antibody display library was constructed from pooled mRNAs from PBMCs and lymph nodes (Nam-Kyung Lee and Bin Liu, unpublished observations) and used for selection on recombinant extracellular domains of LRP6. Methods for phage antibody display library construction are known in the art (Sheets). Recombinant LRP6E1E2 or LRP6E3E4 Fc-fusion was purified from HEK293A transfectants and used for selection rounds. Briefly, LRP6E1E2 or LRP6E3E4 Fc was coated on SPHERO™ Polystyrene Magnetic Particles (Spherotech) by overnight incubation at 4° C. To allow phage antibody binding in every rounds, magnetic beads coated with each Fc fusion were incubated with phages depleted with uncoated beads for 1 hr. Beads were then washed with PBS/0.1% Tween20 and PBS five times each, and bound phages were recovered and propagated as described previously (Connell, Liu 2000). After the third round of panning, monoclonal phage binders were screened by flow cytometry using full-length LRP6-transfected HEK293 cells. To detect phage binders, biotin-labeled anti-fd phage antibody (Sigma Aldrich) and streptavidin-R-PE (Invitrogen) were used as described (Ha). To test the anti-Wnt signaling activity of phages by STF luciferase reporter assays, candidate phage clones were individually amplified and purified as previously described (Ruan, Zhu2010, An 2008, Liu2004).

Recombinant Antibody Expression and Purification

To construct bispecific tandem scFv-Fc fusions, a nucleotide cassette consisting of restriction enzyme sites and a linker [AgeI-SalI-(Gly4Ser)$_5$-NcoI-NotI] was inserted into pFUSE-hIgG1-Fc2 to create the pFUSE-T-scFv-Fc vector. AgeI and SalI or NcoI and NotI restriction enzyme sites were used for the cloning of guide scFv antibodies or anti-LRP6 scFv antibodies, respectively. To produce monospecific scFv-Fc fusions, scFv genes were cloned into unmodified pFUSE-hIgG1-Fc2 plasmid. For IgG production, heavy and light chain variable fragments of antibodies were amplified by PCR and subcloned into Ig-γ and -λ expression vectors, respectively, as described previously (Smith 2009). To construct IgG-scFv bispecific antibodies, Ig-λ, Abvec was modified with a (Gly4Ser)$_3$ linker and restriction enzyme sites for cloning a guide scFv to the C-terminus of the light chain constant region. Anti-LRP6 IgG was used as a backbone, and the guide scFv H3 was inserted into the modified Ig-λ Abvec to form VL-CL-(Gly4Ser)$_3$-scFv, similarly as described (Orcutt). To produce all constructs described above, plasmid DNA was mixed with polyethylenimine in Opti-MEM (Life Technologies) and added to HEK293A cells for 24 hrs. After changing media to serum-free DMEM containing Nutridoma-SP (Roche), the cells were cultured for 6-8 days. Supernatants containing secreted antibodies were collected and purified on protein A agarose (Pierce®/Thermo Scientific) following the manufacturer's instructions. All purified antibodies were analyzed on SDS-PAGE gradient gels (4-20%) and stained with PageBlue™ Protein Staining Solution (Thermo Scientific).

SuperTopFlash (STF) Luciferase Reporter Gene Assays

HEK293 or A549 cells prepared into a 24-well culture plate were transfected with 200 ng/well of STF luciferase reporter and 20 ng/well of pRL-SV40 mixed with 1.5 µl/well TransIT-2020 (Mirus Bio), with or without plasmids encoding Wnt1 and/or Wnt3a gene. For simultaneous expression of ICAM-1 or EphA2 in HEK293 cells, varying amounts of ICAM-1 or EphA2 plasmid DNA were transfected into cells. Following 6 hrs (HEK293) or 24 hrs (A549) post transfection, cells were treated with testing agents (purified phages or antibodies) diluted in growth media and further incubated for an additional 16 hrs. Firefly luciferase (FL) and Renila luciferase (RL) activities were separately measured using Dual-Luciferase Reporter Assay System (Promega) and each FL value was normalized with corresponding RL value. Normalized data were expressed as a percentage relative to control experiments treated without antibodies. To evaluate EphA2-targeted bispecific antibodies, HEK293-EphA2 cell model that stably expresses high levels of EphA2 was generated by lentiviral transduction and STF reporter assays were performed as described above. For RSPO1-mediated reporter activity stimulation, 100 ng/ml of recombinant human RSPO1 (R&D Systems) was additionally treated within the culture medium and STF report assays were performed as described above.

Antigen Copy Number Quantification

Cells were harvested by trypsinization, washed and resuspended in FACS buffer (PBS, 1% FBS, pH 7.4). To detect each guide or effector antigen, the cells were incubated with each antibody fluorophore-labeled by Alexa Fluor® 647 Monoclonal Antibody Labeling Kit (Molecular Probes) for 1 hr. After washing with PBS, the cells were analyzed by BD Accuri C6 flow cytometer (BD Biosciences). MFI (Median Fluorescence Intensity) values were converted into Molecules of Equivalent Soluble Fluorochrome (MESF) using Quantum™ Alexa Fluor® 647 MESF (Bang's Laboratory) according to manufacturer's recommendations. To convert MESF into Antibody Binding Capacity (ABC), we measured effective Fluorophore/Protein (F/P) ratio of each Alexa Fluor® 647-conjugated target-specific IgG using Simply Cellular® anti-Human IgG (Bang's Laboratory) according to manufacturer's instructions.

LRP6 Occupancy Quantification

Receptor occupancy of effector antigen LRP6 was determined after pre-treatment of mono- or bi-specific scFv-Fc constructs to tested cells. Varying concentrations of each antibody was incubated with A549 cells for 16 hrs as described in STF reporter assays. The cells incubated with antibodies were washed twice with chilled PBS and blocked with PBS supplemented with 1% BSA. Alexa Fluor® 647-conjugated E34N19 IgG was incubated with the cells for 1 hr on ice and unoccupied LRP6 levels were detected by flow cytometry. MFI values measured from each experimental group were normalized against the maximum MFI signal in a control group with no-antibody treatment.

Apparent $K_D$ Determination

The apparent antibody binding affinity was measured on target cells by FACS as described (An, Zhu). Briefly, $3\times10^5$ cells were incubated with varying concentrations of antibodies in final 1 ml of FACS buffer. Following overnight incubation at 4° C., the cells were washed with ice-cold PBS and then resuspended in 100 µl FACS buffer containing Alexa Fluor® 647-labeled goat anti-human IgG. After 1 hr incubation, cells were washed and analyzed by FACS as described above. The apparent $K_D$ was determined by a curve fit method using MFI values as described (Benedict, An, Zhu).

Immunofluorescence Microscopy Study

Cells were seeded at $1.5\times10^4$/well on Labteck 8-well culture chamber slides (Thermo Fisher Scientific). To evaluate antibody-target colocalization, cells were pre-incubated with each antibody for 1 hr in growth media. Then the cells were fixed with 4% PFA (paraformaldehyde) and permeabilized in PBS supplemented with 1% FBS/0.2% Triton-X100. FITC-labeled goat anti-human IgG was used to detect pre-incubated antibodies and Alexa Fluor 647®-labeled anti-LRP6 IgGs generated by Monoclonal Antibody Labeling Kit (Invitrogen) were used for LRP6 staining. To validate nucluear β-catenin translocation, each antibody in DMEM/10% FBS supplemented with 20% Wnt3a conditioned medium (Wnt3a-CM) was incubated for 24 hrs into chamber wells. Mouse anti-β-catenin primary antibody (Cell Signaling Technology) was used for β-catenin detection and the cells were treated with Alexa Fluor® 647-labeled rabbit anti-mouse secondary IgG (Jackson ImmunoResearch). All cells were counterstained using Hoechst33342 (Thermo Scientific) and then imaged on FluoView® FV10i laser confocal microscope (Olympus) with an Olympus 60X phase contrast water-immersion objective.

Cell Proliferation Assays

Cells were seeded at $1.0\times10^3$/well on 96-well cell culture plates. After overnight culturing, varying concentrations of each antibody were diluted in DMEM/0.5% FBS/5% Wnt3a-CM for A549 cells. Cell viability was determined using a Calcein-AM cell viability assay kit (Biotium Inc.) at 4 days post-treatment.

Immunoblotting

Whole cell lysates or cell-membrane fractions were prepared using RIPA buffer (50 mM Tris, pH 7.5, 150 mM NaCl, 0.1% SDS, 0.5% sodium deoxycholate, 1% NP-40) supplemented with protease/phosphatase inhibitors (Cell Signaling Technology). For cytosolic protein extraction, cells were resuspended in hypotonic buffer (10 mM Tris-HCl, 10 mM KCl, protease inhibitors, pH 7.5) and lysed by three freeze-thaw cycles. Equal amount of protein were loaded onto a SDS-PAGE gradient gel (4-20%), separated, and transferred to PVDF membrane (Millipore). Target proteins were probed with appropriate primary antibodies followed by incubation with secondary antibodies conjugated with Horseradish Peroxidase (HRP). Chemiluminescence signals were generated using ECL reagents (Millipore) and detected by c-DiGiT Blot Scanner (LI-COR). The blot image was analyzed using ImageJ (Schneider) to determine band intensity.

Cell Migration and Invasion Assays

For wound-healing migration assays, cells were seeded in 96-well plates and allowed to reach confluence. Growth media was changed to serum-free media containing 10 µg/ml mitomycin C (Sigma Aldrich) and cells were incubated for 2 hrs. A scratch into each well was made on a uniform layer of cells using a sterile micropipette tip. After washing the cells using PBS, varying concentrations of antibodies diluted in DMEM/20% Wnt3a-CM were treated to the cells. The cells were incubated for up to 48 hrs and stained with 2 µM Calcein-AM (Sigma Aldrich), and the plate was scanned by CellInsight™ NXT HCS platform (Thermo Scientific) at the indicated time points. Wound areas were measured using ImageJ software and IC50 values were generated based on the relative wound area data against a control group. Alternatively, cells were assessed in transwell invasion assays with CultureCoat 24-well high BME insert (Trevigen). Cells resuspended in serum-free media with different concentrations of antibodies were added into the upper compartment of a transwell insert, and the culture medium containing 20% Wnt3a-CM was used as a chemoattractant and placed in the lower compartment. After 24 hrs incubation, the cells were fixed with 4% PFA and stained with 0.1% crystal violet (Sigma Aldrich) in PBS. The invaded cell number in each transwell was counted in 5 fields all over the membrane.

Self-Renewal Sphere-Forming Assays

For analysis of sphere formation, second-generation spheres were thoroughly trypsinized and sieved through a cell strainer with 40-µm nylon mesh (FisherBrand) to prepare a single-cell suspension. Cells were suspended in serum-free media (SFM) composed of DMEM/F12 (Gibco), 20 ng/ml EGF, 10 ng/ml bFGF, 10 ng/ml IGF, 2% B27 supplement (Gibco), and 10% Wnt3a-CM, and 200 cells per well were seeded in ultra-low attachment 24-well culture plate (Corning). Various conditions of antibodies were added and the cells were fed twice a week by 100 µl SFM. After 14 days incubation, 63 fields in each well were scanned and merged using BIOREVO microscope (BZ-9000; Keyence) to display the whole well image. The number or size of tumor spheres (>100 µM) was counted or measured from the images. To determine total number of viable sphere-forming cells, spheres were collected by centrifugation and dissociated into single-cell suspension by trypsinization. Cells were washed twice with PBS and stained with 2 µM Calcein-AM for 1 hr, then analyzed by flow cytometry.

Example 1—Identification of Anti-LRP6 scFvs

Figure 1A:
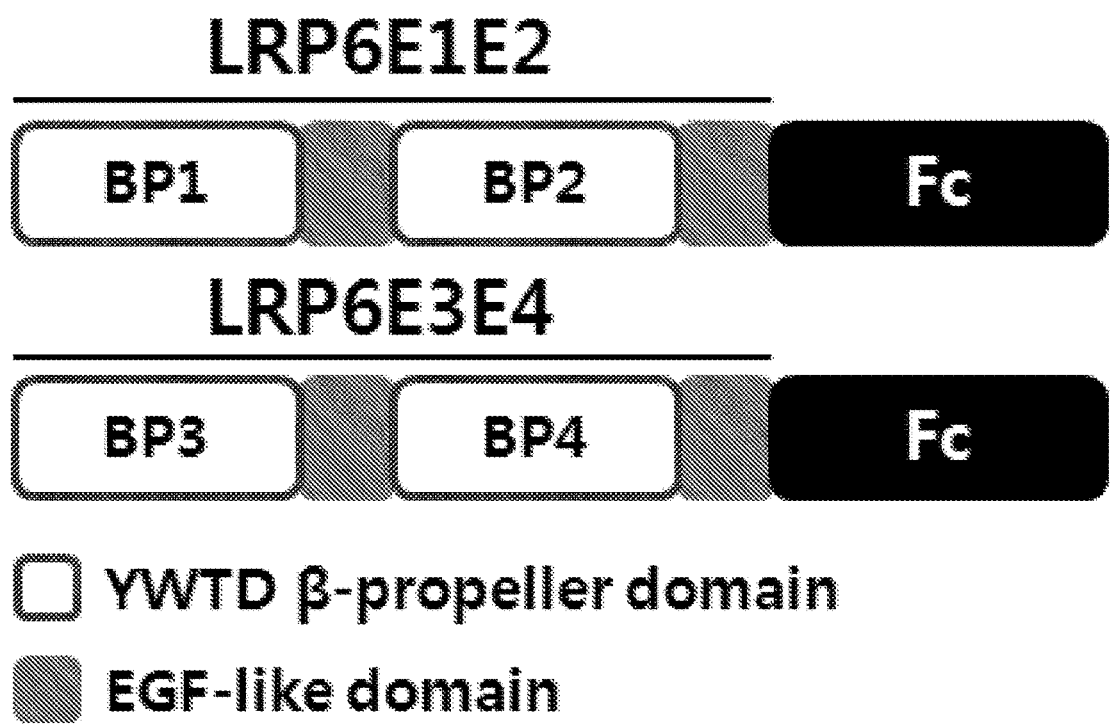
FIGS. 1A-1D depict the results illustrating identification and anti-Wnt signaling activity validation of scFv antibodies specific to LRP6 sub-domains.
Figure 1B:
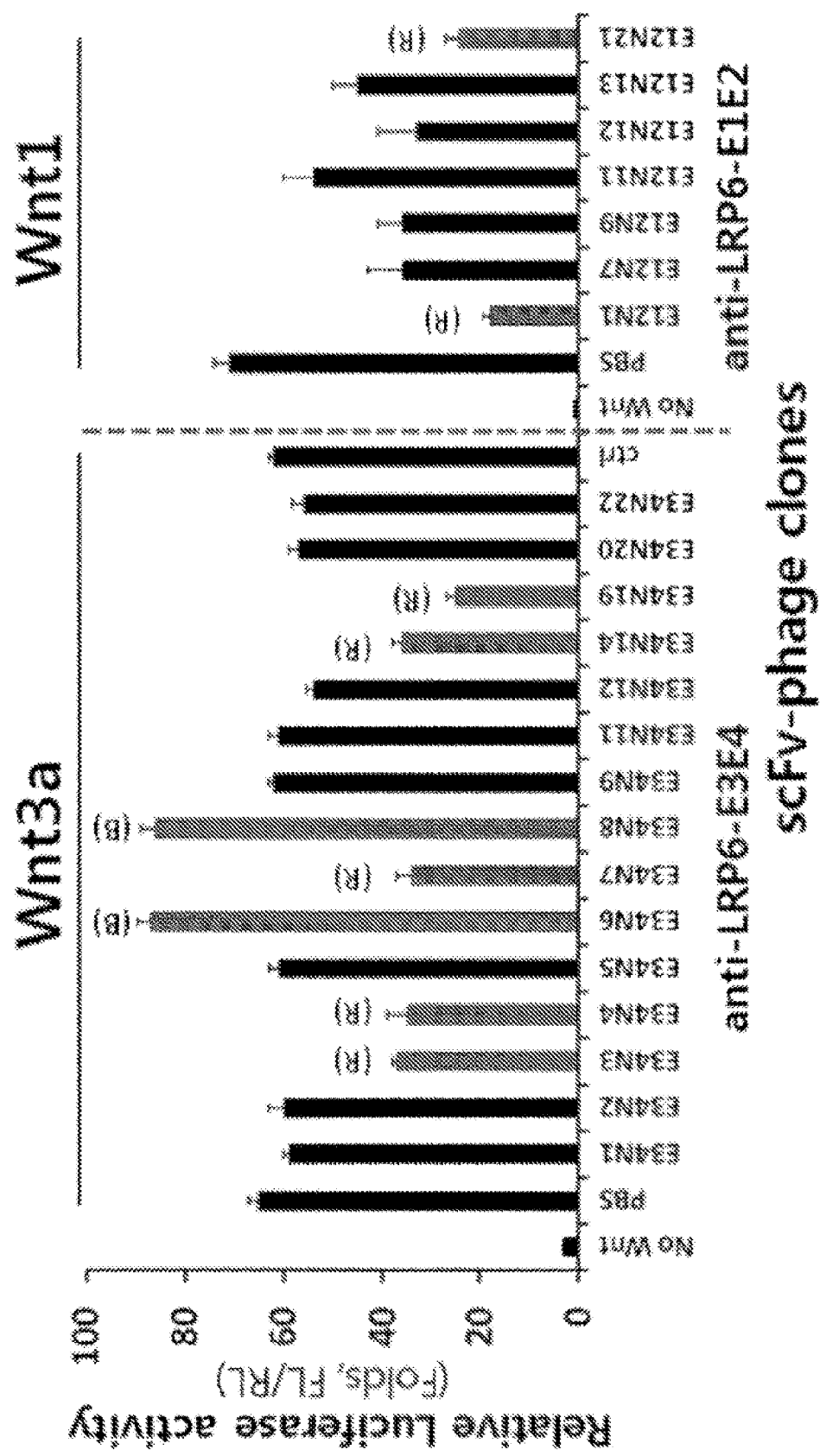
Figure 1C:
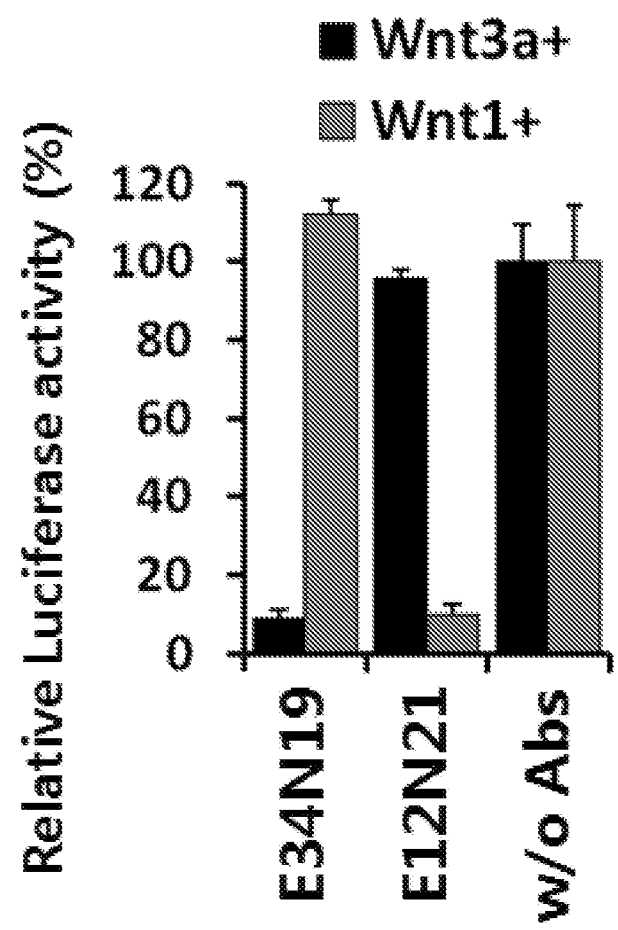
Figure 1D:
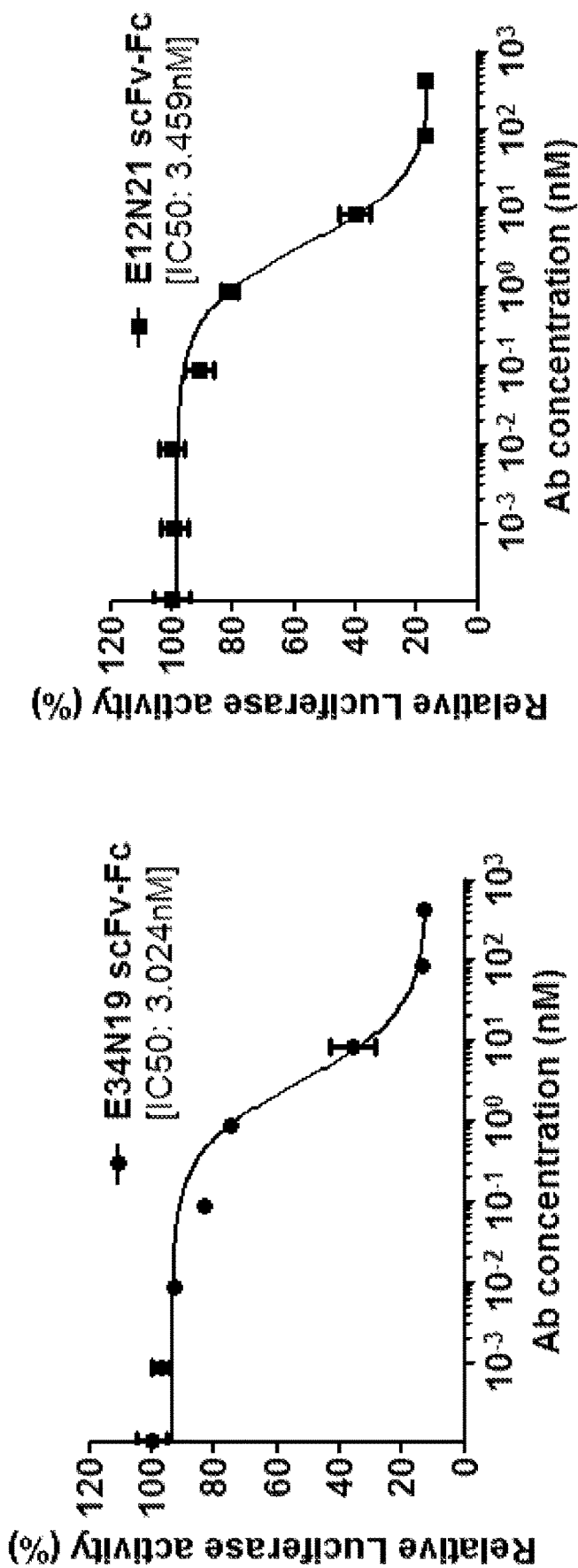

To inhibit Wnt/β-catenin signaling induced by Wnt ligand binding to LRP6, human scFvs binding to the E1E2 and E3E4 domains of LRP6 were generated by phage antibody display using recombinant LRP6E1E2-Fc and LRP6E3E4-Fc fusions as the bait (FIG. 1A). Selection outputs were screened first against recombinant LRP6E1E2- and LRP6E3E4-Fc molecules by ELISA and then HEK293 cells transfected with full-length human LRP6 by FACS (FIG. 7A). Specific binders and studied their abilities to regulate Wnt-induced β-catenin signaling were identified using purified phage. Various agonist and antagonist activities were observed with some showing potent inhibition of the β-catenin-responsive luciferase SuperTopFlash (STF) reporter activity (FIG. 1B). Soluble recombinant scFv-Fc fusions derived from phage showed similar activities. For example, the E12N21 scFv against E1E2 and the E34N19 scFv against E3E4 domains of LRP6 were produced as scFv-Fc fusions and showed strong inhibition of Wnt1 and Wnt3a-induced STF reporter activity, respectively (FIG. 1C). Apparent binding affinities of E34N19 and E12N21 scFv-Fc molecules on HEK293 cells that express LRP6 were measured. The apparent $K_D$ values were estimated to be 1.4 nM and 5.2 nM for the E34N19 and E12N21 scFv-Fc, respectively (FIGS. 7B and 7C). To determine their potency on Wnt-induced β-catenin signaling, HEK293 cells were transfected with plasmids encoding Wnt ligands (Wnt3a or Wnt1) and incubated with varying concentrations of scFv-Fc (E34N19 for Wnt3a or E12N21 for Wnt1). As shown in FIG. 1D, the scFv-Fcs were potent in inhibiting β-catenin signaling with IC50 values of approximately 3.0 nM (for E34N19 scFv-Fc) and 3.5 nM (for E12N21 scFv-Fc). Thus the generation of anti-LRP6 human monoclonal antibodies with low nanomolar apparent binding affinities and their potent inhibition of LRP6E1E2/Wnt1- and LRP6E3E4/Wnt3a-mediated Wnt/β-catenin signaling were confirmed.

Example 2—Construction of Bispecific Antibodies Targeting LRP6 (the Effector) and a Tumor Cell Surface Antigen (the Guide)

Figure 2A:
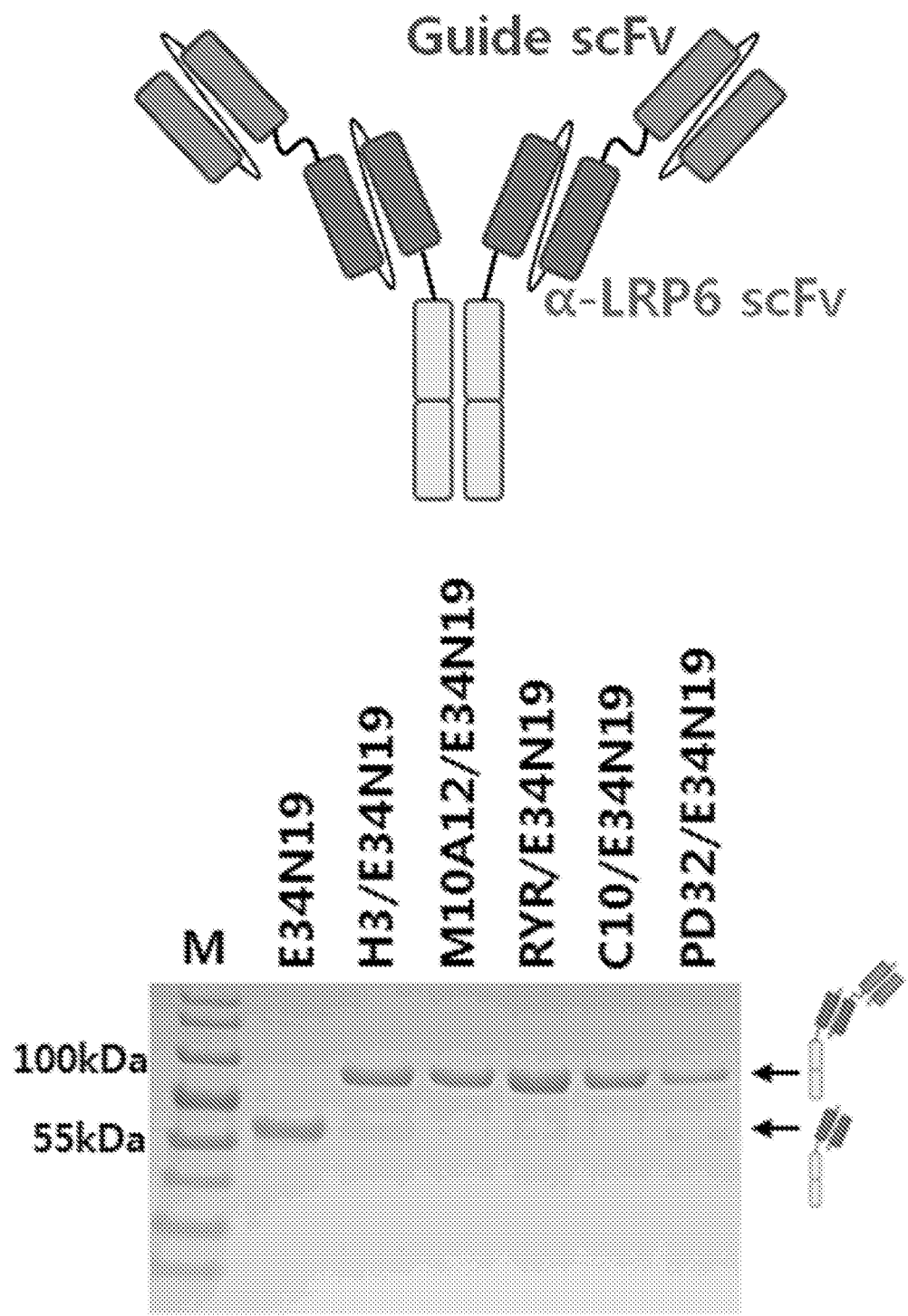
FIGS. 2A-2D depict the results illustrating that a guide antibody confers potent anti-Wnt signaling activity on bispecific anti-LRP6 antibodies.
Figure 2B:
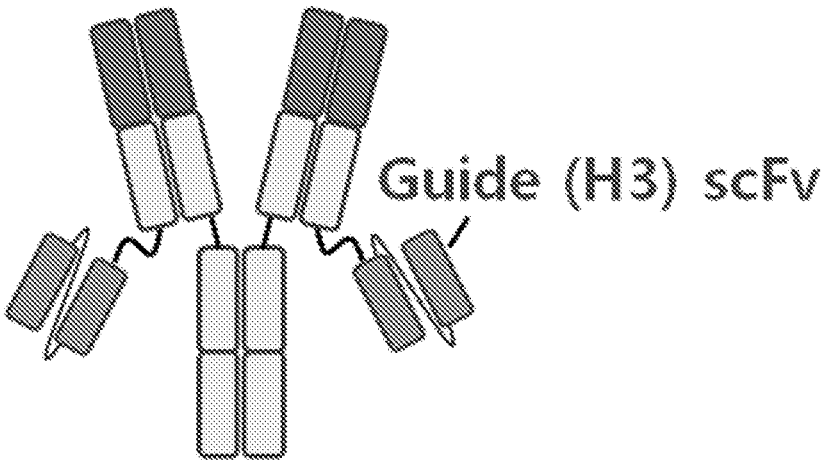
Figure 2B:
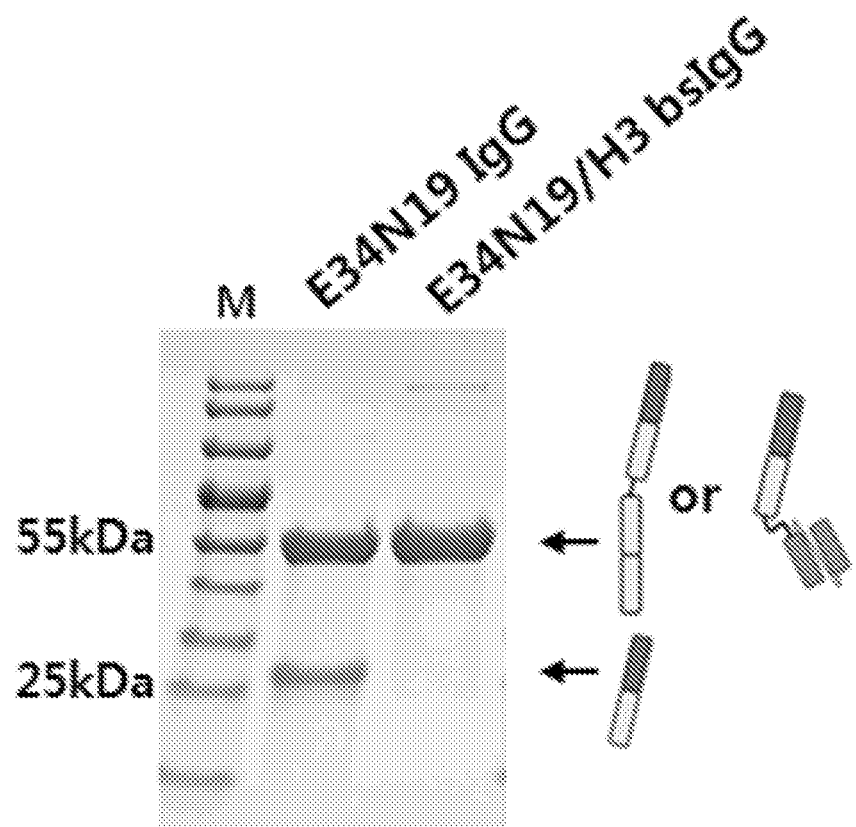

Bispecific tandem scFv-Fcs (termed TaFv-Fc) composed of the anti-LRP6 E34N19 scFv and each of the following anti-guide scFvs: M10A12 (anti-ICAM-1), RYR (anti-EphA2), H3 (anti-ALCAM), and PD32 (anti-ALCAM with a reduced affinity compared to H3) were designed (FIG. 2A). The TaFv-Fcs showed the expected molecular weight of about 90 kDa under reducing conditions (FIG. 2A). To account for potential format differences, we also generated a bispecific IgG-scFv (bsIgG) (Orcutt) by fusing anti-ALCAM H3 scFv to the light chain C-terminus of the anti-LRP6 E34N19 IgG (FIG. 2B). Binding of bispecific H3/E34N19 TaFv-Fc or E34N19/H3 bsIgG to HEK293 cells, which express a low level of LRP6 but a high level of ALCAM (Table 1) was tested. The bispecific H3/E34N19 TaFv-Fc and E34N19/H3 bsIgG showed strong binding to HEK293 cells, whereas the monospecific E34N19 scFv-Fc or IgG binds weakly due to the low level of LRP6 expression on the cell surface (FIG. 7D). The monospecific anti-ALCAM H3 IgG binds strongly to HEK293, consistent with high level of ALCAM expression on those cells (FIG. 7D). All of the designed bispecific antibodies in this manner were tested on cells expressing high levels of the appropriate tumor-associated guide antigen and confirmed for their expected pattern and level of binding (similar to the monospecific guide antibody) (FIG. 7E), indicating that the guide antibody component is functional in all the bispecific constructs.

Figure 2C:
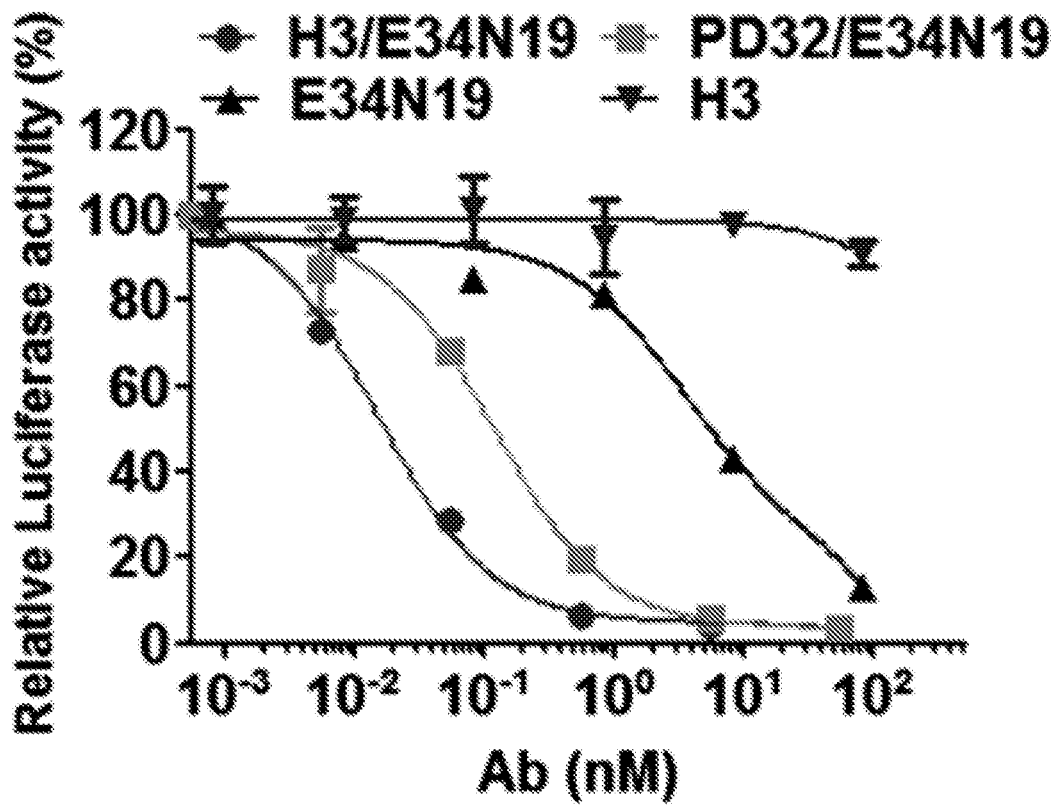
Figure 2D:
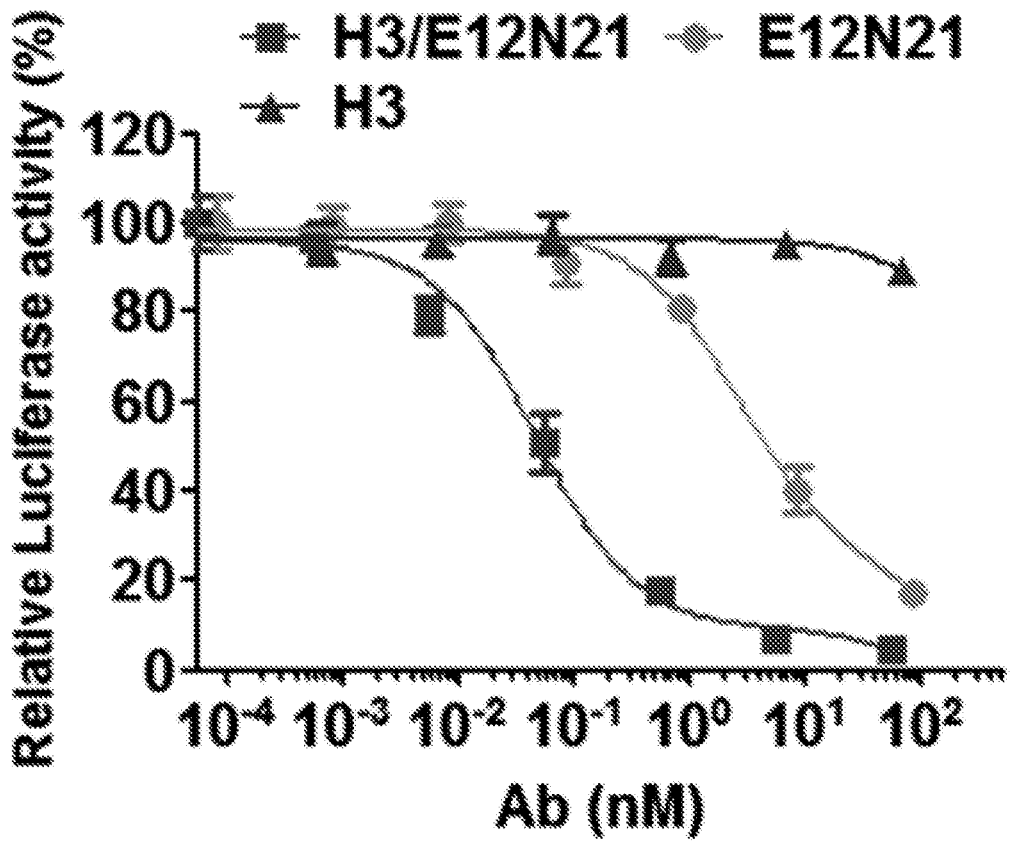

Example 3—Bispecific Anti-LRP6/Anti-Tumor Antibodies Greatly Enhance the Potency of Wnt-Signaling Inhibition Next STF reporter inhibition assays were performed to determine if the bispecific antibody incorporating a guide antibody component is capable of more potent inhibition of Wnt signaling than its monospecific counterpart. Both bispecific TaFv-Fcs targeting LRP6 and ALCAM (H3/E34N19 and PD32/E34N19) showed significantly more potent STF reporter inhibition compared to that of monospecific E34N19 scFv-Fc with IC50 being 15.14 pM for H3/E34N19 and 118.8 pM for PD32/E34N19 respectively, compared to 3.43 nM for the monospecific E34N19 (FIG. 2C). The more potent inhibition by H3/E34N19 compared to PD32/E34N19, both of which binds to ALCAM, may be due to the higher affinity binding of the guide antibody H3 compared to PD32 (apparent $K_D$ on cell being 7.34 pM for H3 and 387.5 pM for PD32). To investigate this effect, the apparent $K_D$ of the bispecific H3/E34N19 and PD32/E34N19 on HEK293 cells were measured. It was found that the apparent $K_D$ of H3/E34N19 is about 20-fold lower than that of PD32/E34N19 (FIGS. 8A and 8B), consistent with the affinity differential seen in the corresponding mAbs. Since both the H3 and the PD32 guide antibodies bind to the same cell surface target (ALCAM), this may suggest that the potency of Wnt signaling blockade by the bispecific is at least partially determined by the affinity of the guide antibody. The E34N19/H3 bsIgG, a different form of the bispecific, also showed a profound STF reporter inhibitory effect compared to the monospecific E34N19 IgG, suggesting that the observed potency enhancement applies across different bispecific platforms (FIG. 8C). To broaden applicability of the bispecific-based potency enhancement, H3/E12N21 TaFv-Fc composed of the H3 scFv (anti-ALCAM) and the anti-LRP6E1E2 E12N21 scFv (Wnt1 blocker) was created. H3/E12N21 was 50 times more potent in inhibiting Wnt1-induced reporter activity than the monoclonal E12N21 (IC50 of 46.16 pM vs 2.63 nM) (FIG. 2D), suggesting that the observed potency enhancement is not unique to the E34N19 antibody but rather generally applicable.

Figure 3A:
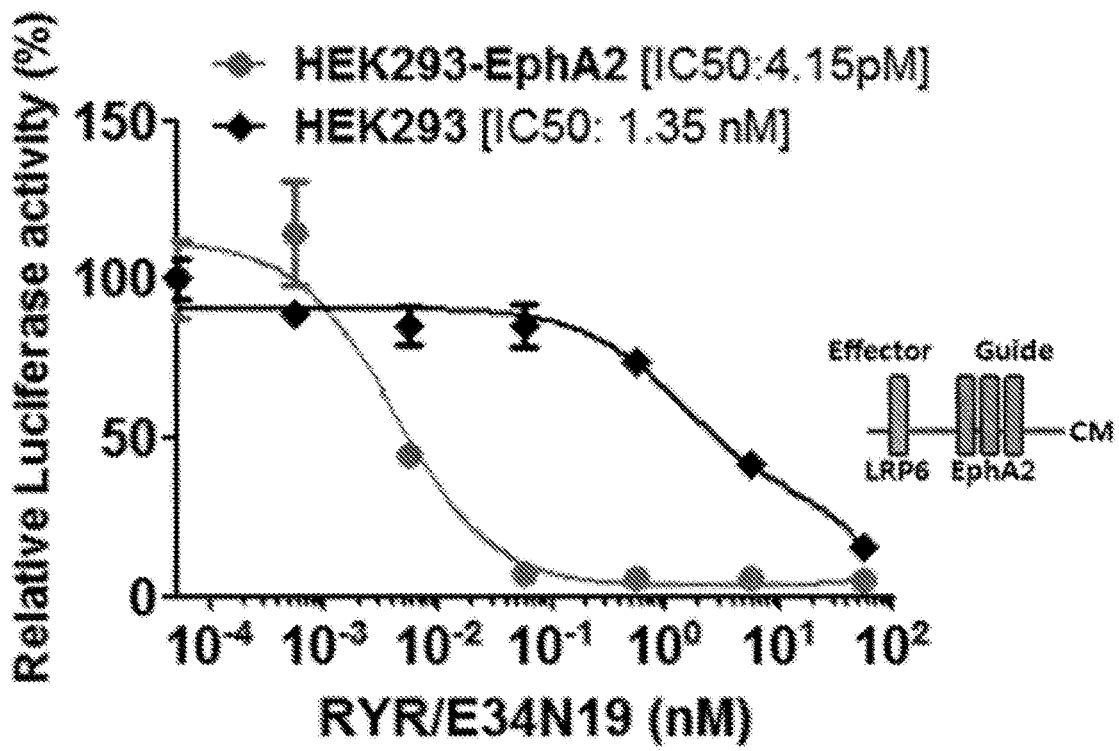
FIGS. 3A-3F depict the results illustrating that anti-LRP6 bsAbs potently suppress Wnt/β-catenin reporter activity in a guide antigen-selective manner.
Figure 3B:
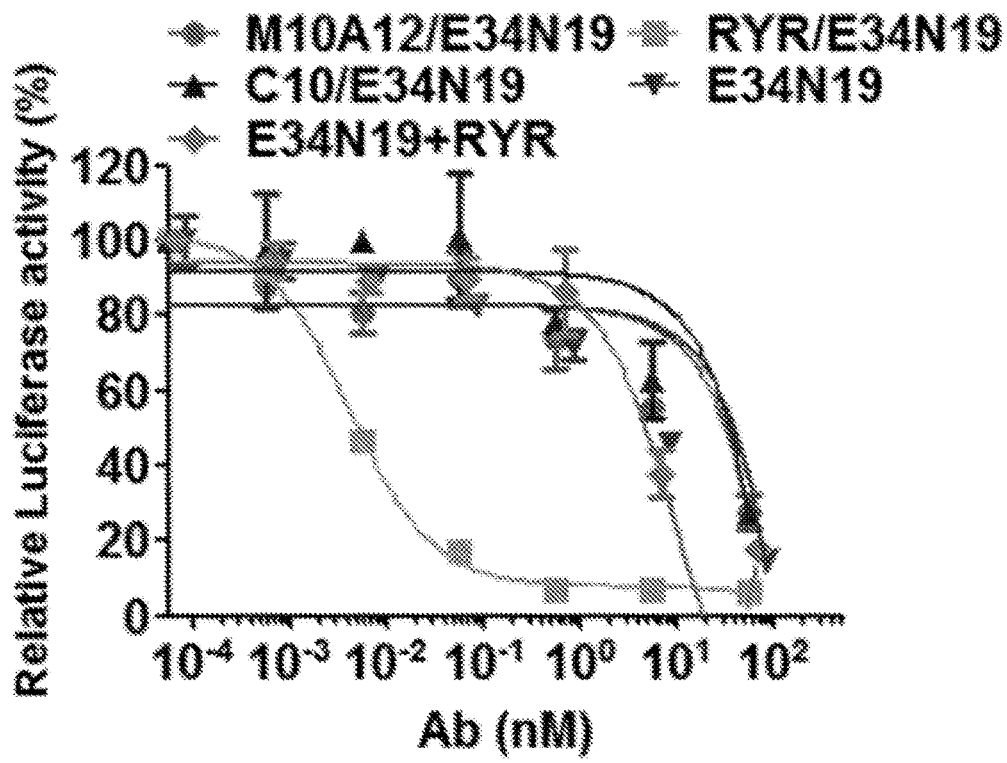
Figure 3C:
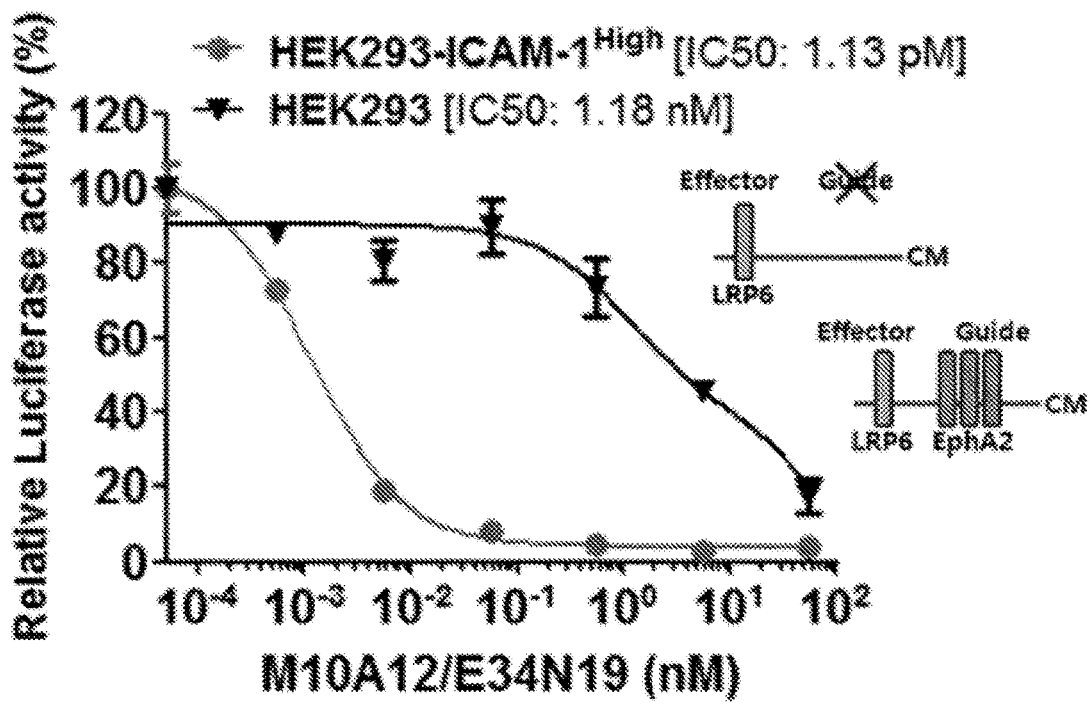
Figure 3D:
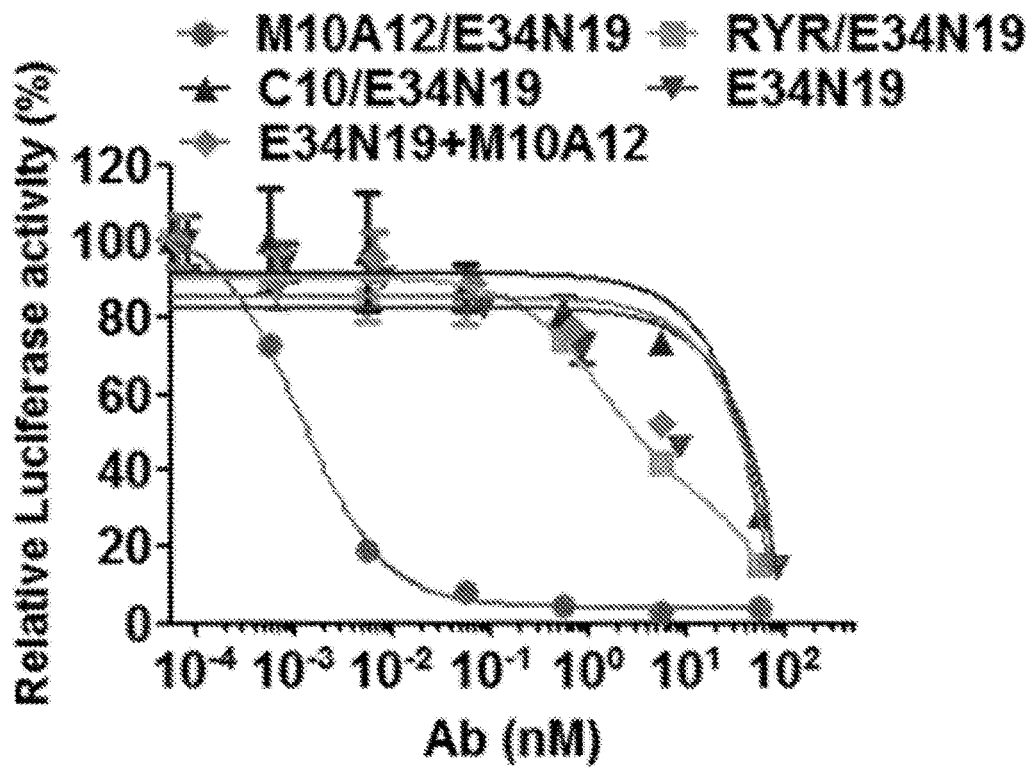

Example 4—Cell Type-Selective Wnt Signaling Pathway Inhibition by Bispecific Antibodies The guide antigen not only provides enhanced potency but more importantly cell type specificity of the signaling pathway inhibition. HEK293 cells express very low levels of ICAM-1 and EphA2 are considered to be ICAM-1 negative/EphA2 negative. An EphA2-expressing HEK293 cell line (named HEK293-EphA2) was generated by lentiviral transduction and used it to evaluate mono- or bi-specific antibodies in Wnt signaling blockade. As shown in FIG. 3A, inhibition of Wnt3a-induced signaling by the anti-EphA2/LRP6E3E4 (RYR/E34N19) bispecific is much more (325-fold) potent in the guide antigen expressing HEK293-EphA2 than the parental HEK293 cells (IC50 is about 4.15 pM for HEK293-EphA2 vs. 1.35 nM for HEK293). The guide antigen dependence was further studied on HEK293 cells using control bispecific and monospecific antibodies. As shown in FIG. 3B, the potent inhibitory effect is only seen for the bispecific (RYR/E34N19) that targets both the guide and the effector antigens, but not for (1) the anti-effector mAb E34N19; (2) a simple mixture of mAbs that target the guide and the effector (RYR+E34N19); (3) a control bispecific that does not bind to the guide antigen, i.e., C10/E34N19 with C10 being a non-binding antibody, and M10A12/E34N19 with M10A12 binding to ICAM-1 that is not expressed by HEK293. To broaden applicability, cell-type specificity was studied using a second guide antigen ICAM-1. HEK293 cells were transfected with ICAM-1 expressing plasmid to create guide antigen-positive cells. As shown in FIG. 3C, the bispecific M10A12/E34N19 potently inhibits Wnt signaling in HEK293-ICAM-1 but not HEK293 cells (IC50 values 1.13 pM vs. 1.18 nM, a 1,044-fold differential). Control bispecific and monospecific antibodies were also studied (FIG. 3D). The striking potency enhancement is considered to be dependent on the bispecific that binds to both the guide and the effector antigens, and is not observed for (1) the monospecific anti-effector antibody, (2) the simple mix of the monospecific anti-guide and anti-effector antibodies, or (3) control bispecific that does not bind to the guide antigen (C10/E34N19 and EphA2/E34N19, neither of which binds to the guide antigen ICAM-1 or the HEK293-ICAM-1 expressing cells).

Figure 3E:
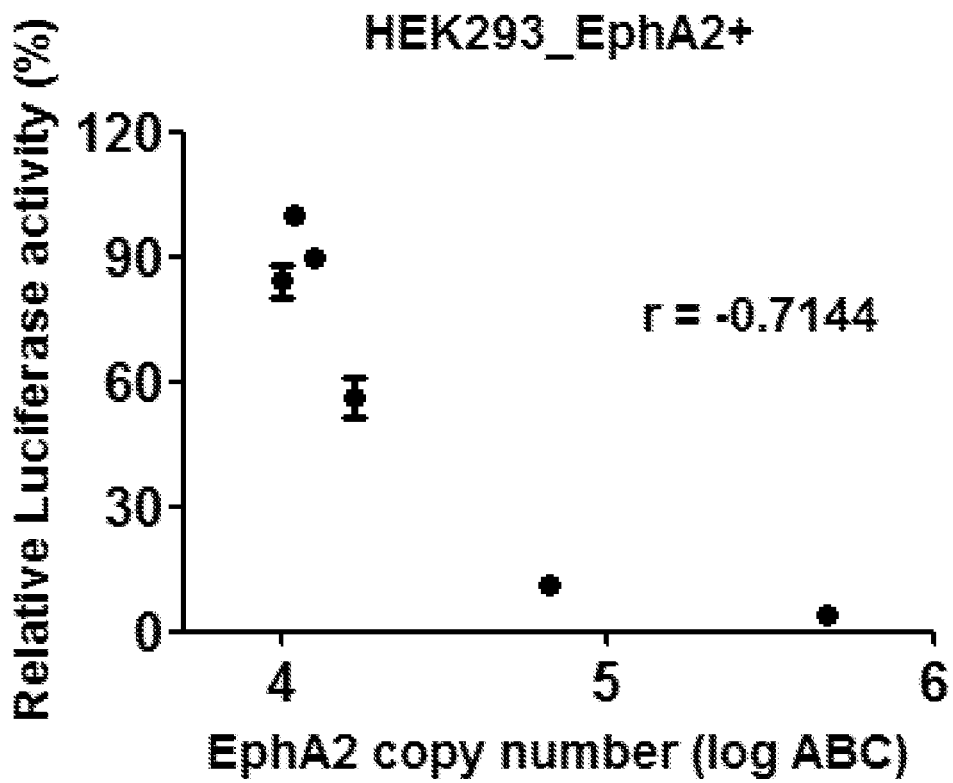
Figure 3F:
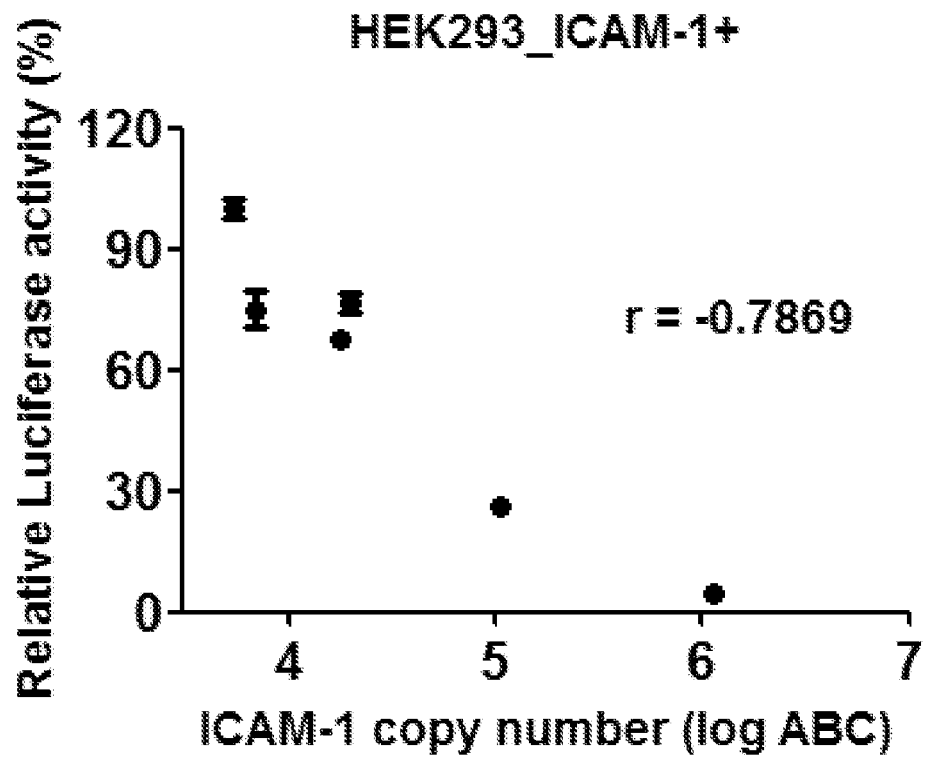

Example 5—the Guide Antigen Expression Level Impacts the Potency of the Bispecific-Mediated Cell Type-Specific Wnt Signaling Inhibition Next it was sought to determine if the cell surface expression level of the guide antigen impacts the potency of the bispecific. As stated above, HEK293 cells express very low levels of ICAM-1 and EphA2, creating an opportunity to investigate the issue using HEK293 cells expressing varying levels of the guide antigen (ICAM-1 or EphA2). First, cell surface antigen copy number was measured using a FACS-based quantification method that determines the antibody binding capacity (ABC, operationally defined "antigen density") from median fluorescence intensity (MFI) (Table 1). STF reporter Wnt signaling inhibition assays were performed and IC50 values were determined for the M10A12/E34N19 bispecific on HEK293 cells expressing varying cell surface copies of ICAM-1: 484,486 (IC50=1.13 pM), 205,962 (IC50=3.76 pM), 30,702 (IC50=16.89 pM) and 10,016 (parent HEK293, IC50=1.18 nM) (Table 2). (For comparison, the EC50 value for the monospecific E34N19 is 3.02 nM as shown previously in FIG. 1D) These data show that in some embodiments a threshold level of expression (about 15,000-20,000 copy/cell of the guide antigen (ICAM-1)) may be required for the bispecific to exert a synergistic potent enhancement of reporter inhibition. Above the threshold, the potency increases (IC50 value decreases) as the copy number of the guide antigen ICAM-1 increases. The dependence on the guide antigen expression level was also shown in another assay where a given concentration of the bispecific was incubated with HEK293 cells expressing varying amounts of the guide antigen ALCAM or EphA2 (cell surface copy number measurement is shown in Table 2). Pearson's correlation coefficient analysis showed increased potency of reporter inhibition as the cell surface copy number of the guide antigen increases (FIGS. 3E and 3F). The ratio of the guide to effector antigen density is also shown in Table 2. Based on the three guide antigens that were studied in this example, a guide to effector ratio >5-10 can generally be preferred to achieve two to three orders of magnitude of potency enhancement in at least some embodiments.

As readily apparent to a person having ordinary skill in the art, a ratio between a guide antigen and an effector antigen that is capable of resulting in a desired level of effectiveness of bispecific antibody may vary depending on multiple factors, e. g. types of the antigens, a type(s) of target cells and the environment surrounding the target cell(s). The preferred ratio would be able to be determined in view of the guidance provided in this disclosure as well as techniques available in the field. Accordingly, any ratios between a guide antigen and an effector antigen that is sufficient to lead to a desired potency of bispecific antibody in modulating a signaling pathway are within the scope of the present disclosure.

The impact of the guide antigen density on the apparent $K_D$ of the bispecific was also evaluated (Table 2). For the ALCAM-guided bispecific, increasing guide antigen density concurs with increasing potency. For the ICAM-1-guided bispecific, apparent $K_D$ values decrease with increasing guide antigen density, but the changes are about 10-fold, not enough to account for the 1,000-fold enhancement in potency. Similar results were seen for the EphA2-guided bispecific. Other mechanisms beyond avidity-driven apparent $K_D$ improvement may account for the bispecific phenomenon that we have observed. It was hypothesized that the observed potency enhancement of the bispecific may be the result of a more effective occupation of the effector antigen due to its ability to engage the guide antigen on the same cell, a physical basis of the "neighborhood" effect. To test this hypothesis, LRP6 occupancy was investigated by the bispecific and monospecific on HEK293 cells. Interestingly, about 80% of the surface LRP6 was occupied by the bispecific H3/E34N19 even at a low concentration (0.5 nM) (FIG. 8D). At the same concentration, only about 10% of LRP6 was occupied by the monospecific E34N19. The concentration required to achieve 50% occupancy of the effector LRP6 is about 50 pM for the bispecific but 20 nM for the monospecific, a difference of greater than 400-fold (FIG. 8D).

Taken together, the data show that a bispecific antibody incorporating a guide antigen-targeting component can significantly enhance potency and specificity of Wnt pathway inhibition. This phenomenon is likely mediated by bispecific-induced higher occupancy of the effector antigen. For a given level of effector antigen expression, the overall inhibition potency is affected by (1) the guide antigen density or the guide/effector ratio (preferably >10:1 in some embodiments), and (2) the affinity of the anti-guide antibody. In some embodiments, these two conditions may need to be met together in order to provide substantial enhancement of potency on bispecific antibodies. In some occasions the apparent binding affinity of the bispecific to the target cell increases as the guide antigen density increases; however the concurrent increase may be insufficient to explain the huge IC50 change seen for the bispecific. For the three guide antigens studied, only the ALCAM-based bispecific showed concurrent improvement between the apparent $K_D$ and IC50. For the ICAM-1-guided bispecific, the apparent $K_D$ improvement is modest (about 10-fold), while the IC50 value decreases by over 1,000-fold compared to the monoclonal anti-effector antibody. Similarly, the dramatic increase in potency for the EphA2-guided bispecific cannot be explained by the moderate improvement in apparent binding affinity. This phenomenon may be resolved by the notion that the guide antigen density dramatically impacts the occupancy of the effector antigen by the bispecific. When the ratio of the guide to effector antigen density is greater than 10 to 1, binding of the bispecific resulted in almost complete occupation of the effector antigen at concentrations well below the apparent $K_D$ of the bispecific. The guide antigen seems to provide a local or community effect where the effector antigen is fully and persistently occupied even when the guide antigen itself is only partially occupied. This community effect is only seen when the guide and effector antigens are present in cis on the same target cell, and is unique to the bispecific but not a mix of the monospecific antibodies (i.e., oligoclonal antibodies). This result further highlights the criticality of the bispecific's configuration of the present disclosure that is necessary to exhibit the significant improvement on the properties of bispecific that is unachievable with simple mixt of monospecific antibodies.

Example 6—Internalizing Guide Antibody Inhibits Multi-Ligand Wnt Signaling Via Cell Surface Removal of LRP6 (Effector)

Figure 4A:
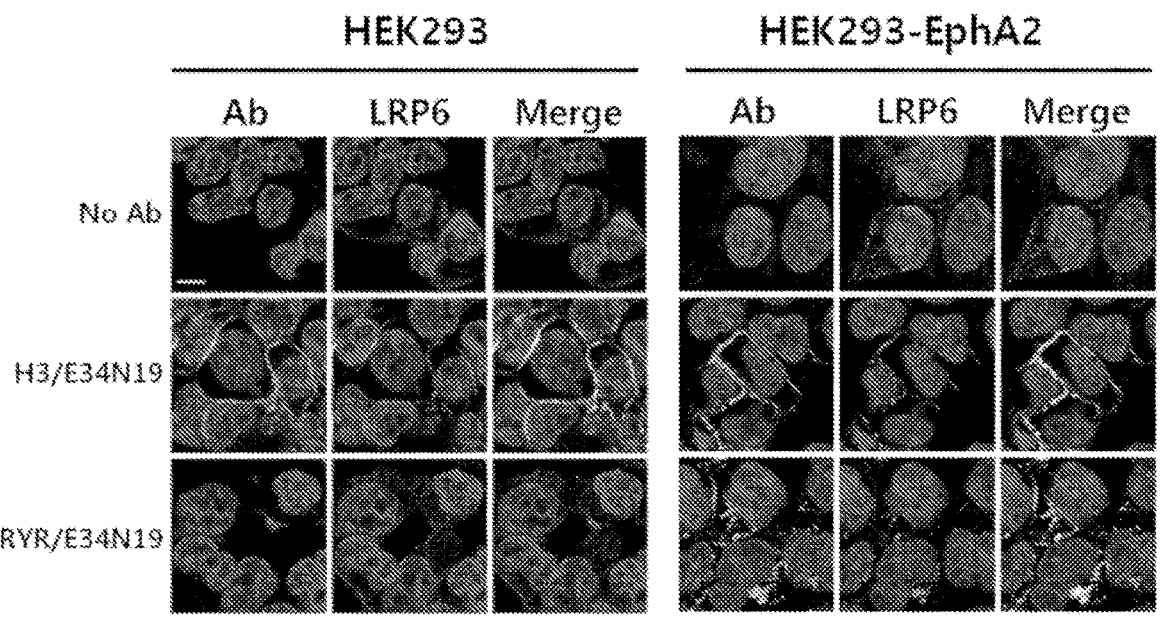
FIGS. 4A-4C depict the results illustrating that LRP6 turnover by RYR/E34N19 inhibits Wnt1-mediated β-catenin signaling.
Figure 4B:
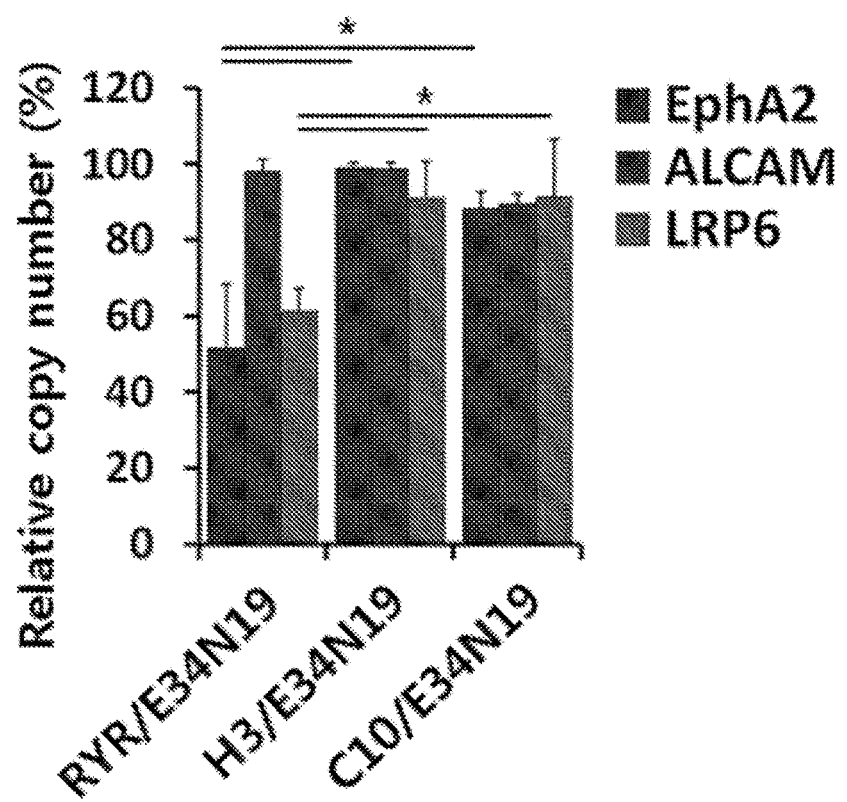

Internalizing antibodies can cause receptor depletion from the cell surface thereby preventing ligand binding and signaling. The anti-EphA2 scFv (RYR) used in this example rapidly internalizes via macropinocytosis and efficiently removed EphA2 from the cell surface. Internalization of the bispecific RYR/E34N19 was studied on the EphA2-overexpressing HEK293-EphA2 cell line. RYR/E34N19 is internalized rapidly and specifically by HEK293-EphA2 cells, and it drags the effector antigen LRP6 together with the guide antigen EphA2 into the cells (FIG. 4A). In contrast, the H3/E34N19 bispecific, with H3 being a slowly internalizing antibody binding to the guide antigen ALCAM expressed by HEK293, is detected mainly on the cell surface with LRP6 (FIG. 4A). To evaluate quantitatively this target-specific internalization event induced by RYR/E34N19, the surface expression level of effector and guide antigens were investigated after incubating HEK293-EphA2 cells with bispecific antibodies. As shown in FIG. 4B, incubation of RYR/E34N19 efficiently reduced the cell surface copy numbers of both EphA2 (the guide) and LRP6 (the effector). No surface depletion was observed for control bispecific antibodies that either binds to a slowly internalizing guide antigen (H3/E34N19) or does not bind to any guide antigen expressed by the target cell (C10/E34N19) (FIG. 4B).

Figure 4C:
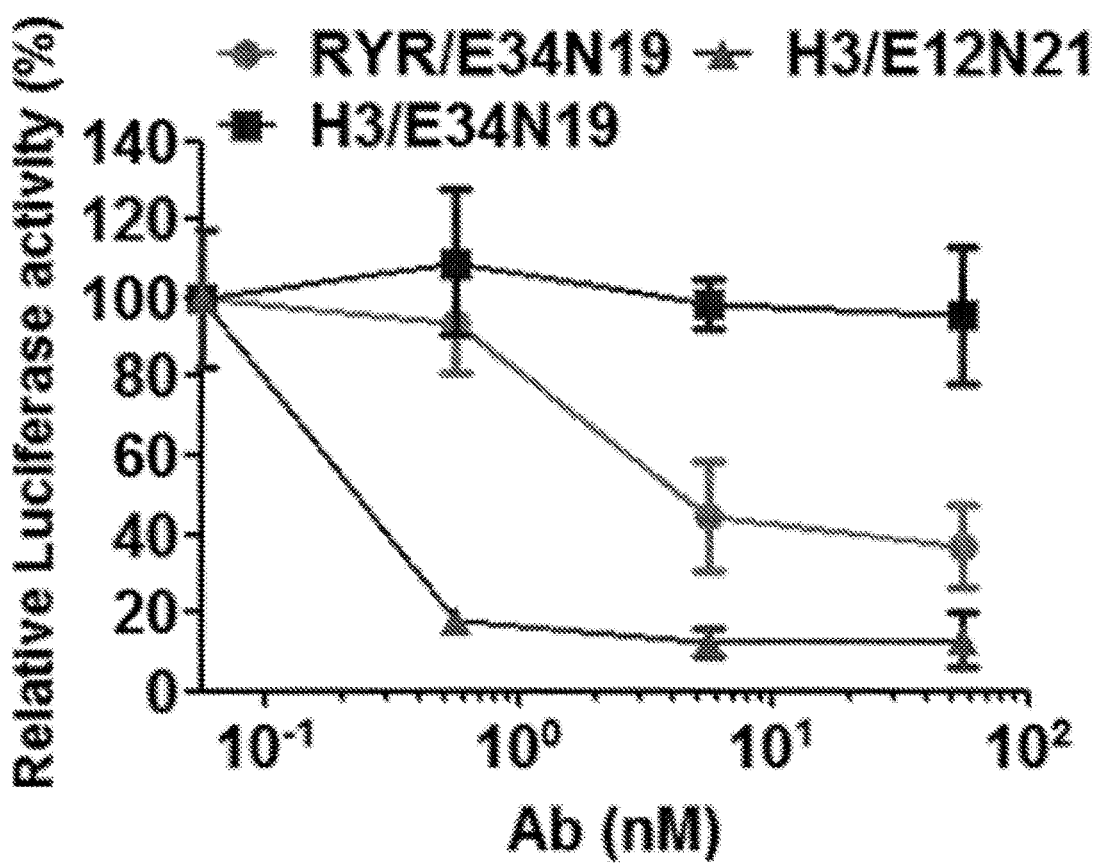

Surface removal of the effector antigen may result in blocking of multi-ligand actions. The next investigation was performed to test whether inhibition of Wnt1-mediated signaling through LRP6 internalization would be induced by the bispecific that binds to Wnt3a binding site on LRP6 (E3E4) and the internalizing guide EphA2. On Wnt1-transfected HEK293-EphA2 cells, H3/E12N21 but not H3/E34N19 potently inhibited STF reporter activity (FIG. 4C). This is consistent with the notion that 12/−21 but not E34N19 blocks Wnt-1-mediated signaling. H3 binds to ALCAM that is hardly internalizing and does not result in LRP6 surface removal (shown above in FIG. 4B). In contrast, the bispecific RYR/E34N19 showed significant inhibitory effect on Wnt-1-induced signaling, even though it binds to the E3E4 but not the E1E2 domain and does not directly interfere with Wnt1 binding to LRP6. This suggests that the RYR/E34N19 bispecific removed the effector antigen LRP6 from the cell surface and in so doing blocked Wnt signaling initiated by a ligand binding to a different region of the effector LRP6.

Example 7—Application of the Bispecific Design to Wnt Inhibition in Tumor Cells

Going beyond the HEK293 model system, an experiment was performed to determine if the principle of the bispecific guide/effector design is applicable to tumor cells. First, the A549 lung cancer cell line that expresses the effector LRP6 (7,341 copy/cell, Table 1) and the guide ALCAM (874,813 copy/cell, Table 1) was tested. Cell binding data for bispecific (H3/E34N19 and H3/E12N21) and monospecific (E34N19, E12N21, and H3) antibodies are shown in FIG. 9A. As shown in Supplemental FIGS. 9B and 9C, the bispecific H3/E34N19 and H3/E12N21 showed greater potency (>100-fold) in inhibiting the Wnt3a- or Wnt1-induced STF reporter activities, respectively, compared to that of the monospecific E34N19 or E12N21 scFv-Fc. Receptor occupancy for the effector LRP6 by bispecific and monospecific antibodies was also investigated under the same condition as that of the STF reporter assay. Similar to what was found in the HEK293 occupancy study (FIG. 8D), it was found that about 85% of the surface LRP6 was occupied by the bispecific H3/E34N19 even at concentrations as low as 0.1 nM (FIG. 9D). However, the monospecific E34N19 only occupies about 50% at 100-fold higher concentration (10 nM), and the control H3 IgG showed no significant effect (FIG. 9D).

To expand the observation beyond reporter assays, next it was tested if bispecific antibodies can affect cell function in a cell-type selective manner. The effect of the bispecific H3/E34N19 and the monospecific E34N19 on nuclear β-catenin levels in A549 cells was investigated. Immunofluorescence staining results showed that H3/E34N19 treatment significantly reduced β-catenin in the nuclei, and the effect is more potent than the monospecific E34N19 (FIG. 5A).

Since canonical Wnt signaling plays an important role in enhancing self-renewal capacity of cancer stem-like cells (Holland), antigen-specific effects of bispecific antibodies on Wnt-dependent self-renewal of ALCAM$^{high}$ cells (A549 and HEK293) was also investigated using tumor-sphere formation assay. Wnt3a-conditioned media (Wnt3a-CM) augmented sphere-forming capacity of A549 and HEK293 cells (FIG. 5B and FIG. 10A, respectively). The bispecific H3/E34N19 showed a stronger inhibitory effect on both A549 and HEK293 sphere growth induced by Wnt3a compared to the monospecific E34N19 (FIG. 5B and FIG. 10A).

Besides A549 (and HEK293), the bispecific-mediated cell-type selective effect on Wnt signaling was further studied on colon cancer cell lines HCT116 and HT29 that express the effector antigen LRP6 and different levels of the guide antigen ALCAM (708,341 copy/cell for HCT116, and 20,227 copy/cell for HT29, see Table 1). As shown in FIG. 10B, the bispecific H3/E34N19 specifically reduced the sphere-forming ability of the ALCAM$^{high}$ HCT116 but not the ALCAM$^{low}$ HT29 cells, suggesting that the guide antigen (ALCAM) plays an important role in potent and specific Wnt signaling inhibition.

In addition to sphere formation, scratch wound-healing migration assay was conducted to determine functional effects of the bispecific. A549 cells were treated with the bispecific E34N19/H3 bsIgG and the monospecific E34N19 IgG. A tankyrase inhibitor XAV939 (Huang) was used as a positive control. The Wnt3a-induced A549 cell migration was more potently inhibited preferentially by the bispecific compared to the monospecific (IC50=0.57 nM for the bispecific E34N19/H3, compared to IC50=3.53 nM for the monospecific E34N19) (FIG. 5C and FIG. 11).

Invasion assay was performed using the PC3 prostate cancer cell line that expresses a high level of both the EphA2 and ALCAM guide antigens. Both the H3/E34N19 and RYR/E34N19 effectively inhibited invasion of PC3 cells at low concentrations (11 nM) (FIG. 5D).

The bispecific effect on Wnt3a-dependent cell proliferation was also studied using A549 and HCT116 tumor cells that overexpress the guide antigen ALCAM. Tested at the same concentration (10 μg/ml), the bispecific H3/E34N19 is more potent compared to the monospecific E34N19 (FIG. 12A for A549 and S6B for HCT116). H3/E34N19 suppressed LRP6 phosphorylation and cytosolic β-catenin accumulation in A549 cells, and downregulated c-Myc protein, a target gene of β-catenin/TCF complex (FIG. 12C).

Taken together, these results show that bispecific antibodies inhibit Wnt signaling in tumor cells, affecting β-catenin activity, sphere formation/clonogenic activity, migration/invasion, and proliferation of cancer cells in vitro, and the effect is specific to cells expressing the guide antigen.

Example 7—Anti-LRP6 bsAbs Efficiently Inhibit Additional β-Catenin Activation Induced by RSPO1

It has been shown that RSPO1 stimulates Wnt/β-catenin signaling by preventing DKK1/Kremen- or RNF43/ZNRF3-mediated turnover of LRP6 on the cell surface. To determine whether anti-LRP6 bsAbs can antagonize RSPO1-stimulated Wnt signaling, HEK293 cells transiently expressing Wnt3a or Wnt1 ligand were incubated with RSPO1 and anti-LRP6E1E2/ALCAM (H3/E34N19) or anti-LRP6E3E4/ALCAM (H3/E12N21) bsAb, respectively. RSPO1 amplified Wnt3a- or Wnt1-mediated reporter activity (FIG. 6A). However, treatment with H3/E34N19 or H3/E12N21 led to potent inhibition of the reporter response induced by Wnt3a/RSPO1 or Wnt1/RSPO1, respectively (FIG. 6A). The IC50 value for the ALCAM-guided bispecific H3/E34N19 was 327 pM (FIG. 13A) but greater than 100 nM for the control bispecific C10/E34N19. Guide antigen-dependence of the bispecific effect was accessed on RSPO1-induced Wnt signaling, using the HEK293-EphA2 line that overexpress the guide antigen EphA2 (the parental HEK293 line expresses EphA2 poorly). Under the condition that supports Wnt3a and RSPO1 signaling, the anti-EphA2/LRP6 bispecific (RYR/E34N19) showed a potent reporter inhibition in HEK293-EphA2 cells (IC50=9.0 pM, FIG. 6B), over five thousand-fold greater than that in parent HEK293 cells (IC50=~50 nM, FIG. 13A). Moreover, on HEK293-EphA2 cells, RYR/E34N19 (9.0 pM) is 120-fold greater in potency than H3/E34N19 (IC50 9.0 pM vs. 1.1 nM as shown in FIG. 6B), due to difference in guide antigen density (5,244,589 for EphA2 vs. 268,022 for ALCAM, Table 1). EphA2 is also rapidly internalizing, which may have further enhanced potency of the EphA2-guided bispecific compared to the slowly/non-internalizing ALCAM-guided one.

Going beyond the reporter assay on the HEK293 cell-based models and extending the finding to tumor cells, the bispecific phenomenon was further studied on the A549 cancer cell line. As shown in FIG. 6C, the Wnt3a/RSPO1-induced STF reporter activity was inhibited following treatment with the ALCAM-guided bispecific H3/E34N19 but not the control bispecific C10/E34N19 or the monospecific E34N19. Western blot analysis also showed that the levels of phosphorylated LRP6 and cytosolic β-catenin enhanced by RSPO1 were reduced significantly following H3/E34N19 treatment compared to controls (C10/E34N19 or E34N19 treatment) (FIG. 13B).

To extend the finding to other tumor cells and to evaluate the impact of guide antigen internalization, in vitro invasion assay of prostate cancer PC3 cells that express similar levels of the slowly/non-internalizing guide antigen ALCAM and the rapidly-internalizing guide antigen EphA2 were studied (see Table 1 for antigen density). As shown in FIG. 6D, both the ALCAM-guided bispecific H3/E34N19 and the EphA2-guided bispecific RYR/E34N19 inhibited PC3 cell invasion. Interestingly, the EphA2-guided RYR/E34N19 that is internalizing showed a more potent inhibition than the ALCAM-guided H3/E34N19 that is slowly/non-internalizing, suggesting that cell surface removal of LRP6 is an important parameter in reducing RSPO1-stimulated Wnt signaling. These results suggest that bispecific anti-LRP6 antibodies can inhibit the RSPO1-mediated Wnt signaling amplification and downstream events such as tumor cell invasion, with the guide antigen providing cell type specificity and potency enhancement. Internalizing anti-guide antibody is more efficient in removing the effector antigen from the cell surface, resulting in greater potency compared to a non-internalizing bispecific.

At least the above examples demonstrate that the guide antigen density impacts the behavior of the bispecific in two ways: (1) The apparent binding affinity of the bispecfiic to the target cell increases as the guide antigen density increases. The concurrent increase, however, was insufficient to explain the huge IC50 change seen for the bispecific. For the three guide antigens studied, only the ALCAM-based bispecific showed concurrent improvement between the apparent $K_D$ and IC50. For the ICAM-1-guided bispecific, the apparent $K_D$ improvement was modest (about 10-fold), while the IC50 value decreaseseds by over 1,000-fold compared to the monoclonal anti-effector antibody. Similarly, the dramatic increase in potency for the EphA2-guided bispecific cannot be explained by the moderate improvement in apparent binding affinity. (2) The guide antigen density dramatically impacts the occupancy of the effector antigen by the bispecific. When the ratio of the guide to effector antigen density is greater than 10 to 1, binding of the bispecific resulted in almost complete occupation of the effector antigen at concentrations well below the apparent $K_D$ of the bispecific. The guide antigen seems to provide a local or community effect where the effector antigen is fully and persistently occupied even when the guide antigen itself is only partially occupied. This community effect is only seen when the guide and effector antigens are present in cis on the same target cell, and is unique to the bispecific but not a mix of the monoclonal antibodies (i.e., oligoclonal antibodies).

In the example, the tested bispecific antibodies that are in accordance with a guide-effector system of the present disclosure have the guide and effector antigens co-presented on the same target cell. When a set of conditions is met, i.e., guide to effector ratio and threshold level of guide expression, the bispecific antibodies can achieve a striking synergistic effect on the effector antigen-mediated signaling, due to efficient and persistent effector antigen occupation by the bispecific. In the examples, two different bispecific formats, tandem scFv-Fc and IgG-scFv, were tested and found that the bispecific phenomenon was observed for both, suggesting that the guide/effector design of the present disclosure is not format-bound and should be applicable to other forms of bispecific.

As demonstrated in the above examples, a guide/effector bispecific design of the present disclosure enables cell-type selective signaling pathway modulation, and should facilitate development of new therapies that more selectively and potently inhibit signaling pathways critical for, e.g. tumorigenesis. The above examples were focused on Wnt signaling pathway as a model system, but the approach can be generally applicable to any signaling pathway. The approach in accordance with the present disclosure allows modular development of bispecific antibody with the goal of achieving maximum effect on a target cell, e.g. tumor but minimum effect on normal cells. The above examples chose ALCAM, ICAM-1 and EphA2 as model guide antigens to illustrate the principle. The threshold effect on each guide antigen suggests that there is no need for absolute specificity as the system can tolerate some level of normal tissue expression of the guide antigen. Depending on the nature of the effector antigen and the specific disease application, other tumor-specific or cell type-selective cell surface molecules can be used as guide antigens. The present disclosure therefore provides a novel finding regarding the relationship between the cell surface guide antigen density and the potency and specificity of the bispecific.

Example 8—Tables

Table 1 depicts summary of antigen densities expressed on each cell line.

|  | Antigen density (Mean ABC ± SD, n ≥ 2) | | | |
| --- | --- | --- | --- | --- |
|  | ICAM1 | EphA2 | ALCAM | LRP6 |
| HEK293-EphA2 | 10,186 ± 2,310 | 5,244,589 ± 432,186 | 268,022 ± 77,453 | 8,491 ± 210 |
| HEK293 | 8,005 ± 76 | 12,026 ± 7,278 | 285,933 ± 23,044 | 7,746 ± 2,616 |

-continued

|  | Antigen density (Mean ABC ± SD, n ≥ 2) | | | |
| --- | --- | --- | --- | --- |
|  | ICAM1 | EphA2 | ALCAM | LRP6 |
| A549 | 7,223 ± 510 | 30,902 ± 1,774 | 874,813 ± 40,631 | 7,341 ± 1,078 |
| PC3 | 117,123 ± 3,982 | 1,243,814 ± 407,118 | 891,442 ± 248,550 | 6,479 ± 1,077 |
| HCT116 | 8,534 ± 780 | 214,109 ± 19,430 | 708,341 ± 94,425 | 6,382 ± 1,787 |
| HT29 | 3,752 ± 72 | 63,147 ± 863 | 20,227 ± 779 | 6,444 ± 335 |

Table 2 depicts summary of guide antigen density and guide/effector ratio on the cell models, and apparent $K_D$ and anti-Wnt signaling activity (IC50) of each guided bsAb.

| Guide antigen | Guided bsAb | Cell model | Guide antigen density (Mean ABC, n ≥ 2) | Guide/ Effector Ratio | Apparent $K_D$ (pM) | IC50 (pM) |
| --- | --- | --- | --- | --- | --- | --- |
| ICAM-1 | M10A12/ E34N19 | HEK293-ICAM-1$^{high}$ | 484,486 | 85.9 | 789 | 1.13 |
|  |  | HEK293-ICAM-1$^{Int}$ | 205,962 | 34.3 | 843 | 3.76 |
|  |  | HEK293-ICAM-1$^{low}$ | 30,702 | 4.4 | 871 | 16.89 |
|  |  | HEK293 | 10,016 | 2.0 | 7,268 | 1,183 |
| ALCAM | H3/ E34N19 | HEK293 | 285,933 | 36.9 | 28 | 15.14 |
|  |  | HEK293-ALCAM$^{Int}$ | 93,254 | 12.5 | 45.2 | 67.85 |
|  |  | HEK293-ALCAM$^{low}$ | 49,353 | 6.6 | 136 | 141.1 |
|  | PD32/ E34N19 | HEK293 | 285,933 | 36.9 | 578 | 118.8 |
| EphA2 | RYR/ E34N19 | HEK293-EphA2 | 5,244,589 | 617.7 | 787 | 4.15 |
|  |  | HEK293-EphA2#8 | 1,922,502 | 250.6 | 1,123 | 8.36 |
|  |  | HEK293-EphA2$^{high}$ | 1,434,711 | 254.3 | 1,554 | 6.55 |
|  |  | HEK293-EphA2$^{Int}$ | 614,989 | 102.3 | 4,734 | 12.7 |
|  |  | HEK293-EphA2$^{low}$ | 100,309 | 14.4 | 18,090 | 24.45 |
|  |  | HEK293 | 5,797 | 0.8 | 15,960 | 1,346 |

In Tables 3-5, shaded regions represent CDR1 (underlined with a single line), CDR2 (undeirned with a double line) and CDR3 (underlined with a dotted line), respectively. Table 3 depicts peptide sequences of scFv fragments that bind to E1E2 domain of LRP6.

| Name | VH | Linker | VL | SEQ ID NO. |
| --- | --- | --- | --- | --- |
| E12N21 | QVQLQESGGGLVKPGGSLRLSCA ASGFTFSSYWMSWVRQAPGKGLE WVANIKQDGSEKYYVDSVKGRFT ISRDNSKNTLYLQMNSLRAEDTAI YYCAKTMTASAWLGGGRDSWGQ GTLVTVSS (SEQ ID NO: 1) | GGGG SGGG GSGG GGS (SEQ ID NO: 2) | QSVLTQDPAVSVALGQTVRIT CQGDSLRTLSTNWYQQKSGQ APVLVIYGNSNRPSGVPDRFS GSSSGNTASLTITGAQAEDEA DYYCQSYDNSVRGSRVFGTG TKLTVL (SEQ ID NO: 3) | 4 |
| E12N21I | QVQLQESGGGLVKPGGSLRLSCA ASGFTFSSYWMSWVRQAPGKGLE WVANIKQDGSEKYYVDSVKGRFT ISRDNSKNTLYLQMNSLRAEDTAI YYCAKTMTASAWLGGGRDSWGQ GTLVTVSS (SEQ ID NO: 5) | GGGG SGGG GSGG GGS | QSVLTQDPAVSVALGQTVRIT CQGDSLRTLSTNWYQQKSGQ APVLVIYGNSNRPSGVPDRFS GSSSGNTASLTITGAQAEDEA DYYCQSYDNSVRGSRVFGTG TKLTIL (SEQ ID NO: 6) | 7 |
| E12N7 | QVQLQQSGGGLVQPGGSLRLSCE VSGFTFSRYWMTWVRQAPGKGL EGVSYISSSSSYTNYADSVKGRFTI SRDNAKNSLYLQMNSLRAEDTAV YYCARDIGRVQYFFDYWGQGTLV TVSS (SEQ ID NO: 8) | GGGG SGGG GSGG GGS | SQSVLTQPPSVSGAPGQTVTIS CTGSNSDIGAGYDVHWYQQL PGTAPKLLIYGNHQRPSGVPD RFSGSRSGTSASLAITGVQAE DEADYYCQSYGNSVRGSRVF GTGTKLTVL (SEQ ID NO: 9) | 10 |

-continued

| Name | VH | Linker | VL | SEQ ID NO. |
|---|---|---|---|---|
| E12N12 | QVNLRESGGGLVQPGGSLRLSCA ASG<u>FTFSDYGMS</u>WVRQAPGKGLE WVSG<u>ISGSGGS</u>TYYADSVKGRFTI SRDNSKNTLYLQMNSLRAEDTAV YYCA<u>KDQFNWNYAYYYGMDVW</u> GQGTTVTVSS (SEQ ID NO: 11) | GGGG SGGG GSGG GGS | QSALTQDPAVSVALGQTVRIT CQGD<u>SLRNSYA</u>NWYQQKPG QAPLLVIY<u>GKN</u>IRPSGIPDRFS GSKSGDTASLTITGAQAEDEA DYYC<u>NSRDSSGNGMF</u>GGG T KLTVL (SEQ ID NO: 12) | 13 |
| E12N12EQV | EVQLVESGGGLVQPGGSLRLSCA ASG<u>FTFSDYGMS</u>WVRQAPGKGLE WVSG<u>ISGSGGS</u>TYYADSVKGRFTI SRDNSKNTLYLQMNSLRAEDTAV YYCA<u>KDQFNWNYAYYYGMDVW</u> GQGTTVTVSS (SEQ ID NO: 14) | GGGG SGGG GSGG GGS | QSALTQDPAVSVALGQTVRIT CQGD<u>SLRNSYA</u>NWYQQKPG QAPLLVIY<u>GKN</u>IRPSGIPDRFS GSKSGDTASLTITGAQAEDEA DYYC<u>NSRDSSGNGMF</u>GGG T KLTVL (SEQ ID NO: 15) | 16 |
| E12N13 | QVQLVESGGGVVQPGRSLRLSCA ASG<u>FTFSSYAMS</u>WVRQAPGKGLE WVSA<u>ISGSGGS</u>TYYADSVKGRFTI SRDNSKNTLYLQMNSLRAEDTAV YYCA<u>KAPRLYYYYMDVW</u>GKGT TVTVSS (SEQ ID NO: 17) | GGGG SGGG GSGG GGS | QSVLTQPPSVSGAPGQRVTIS CTGS<u>SSNIGAGYD</u>VHWYQQL PGTAPKLLIY<u>GSD</u>SRPAGVPD RFSGSKSGTSASLAITGLQAE DEADYYC<u>GTWDSSLSVVVFG</u> GGTKLTVL (SEQ ID NO: 18) | 19 |
| E12N1 | QVQLVESGAEVKKPGASVKVSCK ASG<u>YTFTSYSMN</u>WVRQAPGQGLE WMGW<u>INPNGGDP</u>RYAQKFQGRV TLTSDSSISTAYMELSRLSDDTA VYYCA<u>SPKLTGDPATFDLW</u>GRST LVTVPS (SEQ ID NO: 20) | GGGG SGGG GSGG GGS | QSVLTQPPSLSVSPGQTASITC SGD<u>NLEDKY</u>ANWYQQKPGQ SPVLVIY<u>RDT</u>KRPSGIPERFSG SRSGTSASLAITGVQAEDEAD YYC<u>QSYDNSVRGS</u>RVFGTGT KVTVL (SEQ ID NO: 21) | 22 |
| E12N11 | QVQLVESGGGLVKPGGSLRLSCA ASG<u>FTFSSYSMN</u>WVRQAPGKGLE WVSS<u>ISSSSSYI</u>YYADSVKGRFTIS RDNSKNTLHLQMNSLRAEDTAVY YCA<u>KDPVFKSPSIAGLLDYW</u>GQG TLV TVSS (SEQ ID NO: 23) | GGGG SGGG GSGG GGS | SYVLTQDPAVSVALGQTVRIT CQGD<u>SLRNSYA</u>NWYQQKPG QAPVLVIY<u>AKT</u>NRPSGIPDRF SGSSSGNTASLTITGAQAEDE ADYYC<u>QSYDNSLRGS</u>RVFG T GTKLTVL (SEQ ID NO: 24) | 25 |
| E12N11R | QVQLVESGGGLVKPGGSLRLSCA ASG<u>FTFSSYSMN</u>WVRQAPGKGLE WVSSISSSSSYIYYADSVKGRFTIS RDNSKNTLHLQMNSLRAEDTAVY YRA<u>KDPVFKSPSIAGLLDYW</u>GQG TLV TVSS (SEQ ID NO: 26) | GGGG SGGG GSGG GGS | SYVLTQDPAVSVALGQTVRIT CQGD<u>SLRNSYA</u>NWYQQKPG QAPVLVIY<u>AKT</u>NRPSGIPDRF SGSSSGNTASLTITGAQAEDE ADYYC<u>QSYDNSLRGS</u>RVFG T GTKLTVL (SEQ ID NO: 27) | 28 |
| E12N35 | QVQLVQSGAEVKKPGASVKVSCK ASG<u>YTFTSYYMH</u>WVRQAPGQGL EWMGI<u>INPSGGST</u>SYAQKFQGRVT MTRDTSTSTVYMELSSLRSEDTAV YYCARA<u>KPPGIAVAGLFYW</u>GQGT LVTVSS (SEQ ID NO: 29) | GGGG SGGG GSGG GGS | SELTQDPAVSVALGQTVRITC QGD<u>SLRSYYA</u>SWYQQKPGQ APVLVIY<u>GKN</u>NRPSGIPDRFS GSSSGNTASLTITGAQAEDEA DYYC<u>NSRDSSGNYV</u>VFGGGT KLTVL (SEQ ID NO: 30) | 31 |

-continued

| Name | VH | Linker | VL | SEQ ID NO. |
|---|---|---|---|---|
| E12N39 | QVQLVQSGAEVKKPGASVKVSCK ASG<u>GYTFTSYYMH</u>WVRQAPGQGL EWMGI<u>INPSGGST</u>SYPQKFQGRVT MTRDTSTNTVYMELSSLRSEDTA<br><br>VYYCAR<u>AKPPGIAVAGLLY</u>WGQG<br><br>TLVTVSS (SEQ ID NO: 32) | GGGG SGGG GSGG GGS | SELTHDPAVSVALGQTVRITC QGD<u>SLRSYYA</u>SWYQQKPGQ APVLVIY<u>GKNN</u>RPSGIPDRFS GSSSGNTASLTITGAQAEDEA<br><br>DYYC<u>NSRDSSGNYV</u>VFGGGT<br><br>KLTVL (SEQ ID NO: 33) | 34 |
| E12N45 | QVQLVQSGGGLVQPGGSLRLSCA ASG<u>GFTFSSYAM</u>SWVRQAPGKGLE WVSG<u>ISGSGGST</u>YYADSVKGRFTI SRDNSKDTLYLQMTSLRAEDTAV<br><br>YYCAR<u>YSSGWPRAEYFQH</u>WGQG<br><br>TLVTVSS (SEQ ID NO: 35) | GGGG SGGG GSGG GGS | SELTQDPAVSVALGQPVRITC QGD<u>SLRSYYA</u>SWYQQKPGQ APVLVIY<u>GKNN</u>RPSGIPDRFS GSSSGDTASLTITGAQAEDEA<br><br>DYYC<u>NSRDSSGNRHSNYV</u>FG<br><br>IGTKVTVL (SEQ ID NO: 36) | 37 |
| E12N45T | QVQLVQSGGGLVQPGGSLRLSCA ASG<u>GFTFSSYAM</u>SWVRQAPGKGLE WVSG<u>ISGSGGST</u>YYADSVKGRFTI SRDNSKDTLYLQMTSLRAEDTAV<br><br>YYCAR<u>YSSGWPRAEYFQH</u>WGQG<br><br>TLVTVSS (SEQ ID NO: 38) | GGGG SGGG GSGG GGS | SELTQDPAVSVALGQPVRITC QGD<u>SLRSYYA</u>SWYQQKPGQ APVLVIY<u>GKNN</u>RPSGIPDRFS GSSSGDTASLTITGAQAEDEA<br><br>DYYC<u>NSRDSSGNRHSNYV</u>FG<br><br>TGTKVTVL (SEQ ID NO: 39) | 40 |

Table 4 depicts peptide sequences of scFv fragments that bind to E3E4 domain of LRP6.

| Name | VH | Linker | VL | SEQ ID NO. |
|---|---|---|---|---|
| E34N19 | QVNLRESGGGLVQPGGSLRLSCA ASG<u>GFTFSSYAM</u>SWVRQAPGKGLE WVSA<u>ISGSGGST</u>YYADSVKGRFTI SRDNSKNTLYLQMNSLRAEDTAV<br><br>YYCAK<u>VRGHGGNSGWVDY</u>WGQ<br><br>GTLVTVSS (SEQ ID NO: 41) | GGGG SGGG GSGG GGS | QSVLTQDPAVSVALGQTVKIT CQGD<u>SLRTYYT</u>SWYQQRPGQ APILVLY<u>ANTH</u>RPSSIPDRFSG SSSGTTASLTITGAQAEDEAD<br><br>YYC<u>NSRDSSGNYL</u>FGGGTKL<br><br>TVL (SEQ ID NO: 42) | 43 |
| E34N19E QV | EVQLVESGGGLVQPGGSLRLSCA ASG<u>GFTFSSYAM</u>SWVRQAPGKGLE WVSA<u>ISGSGGST</u>YYADSVKGRFTI SRDNSKNTLYLQMNSLRAEDTAV<br><br>YYCAK<u>VRGHGGNSGWVDY</u>WGQ<br><br>GTLVTVSS (SEQ ID NO: 44) | GGGG SGGG GSGG GGS | QSVLTQDPAVSVALGQTVKIT CQGD<u>SLRTYYT</u>SWYQQRPGQ APILVLY<u>ANTH</u>RPSSIPDRFSG SSSGTTASLTITGAQAEDEAD<br><br>YYC<u>NSRDSSGNYL</u>FGGGTKL<br><br>TVL (SEQ ID NO: 45) | 46 |
| E34N1 | QVQLVESGGGLVQPGGSLRLSCA ASG<u>GFTFSSYAM</u>SWVRQAPGKGLE WVST<u>MSVSGAST</u>YYADSVKGRFT ISRDNSKNTLYLQMNSLRAEDTA<br><br>VYYCAK<u>GEYYYDSSGYYD</u>WGQG<br><br>TLVTVSS (SEQ ID NO: 47) | GGGG SGGG GSGG GGS | SELTQDPAVSVALGQTVRITC QGD<u>SLRSYYA</u>SWYQQKPGQ APVLVIY<u>GKNN</u>RPSGIPDRFS GSSSGNTASLTITGAQAEDEA<br><br>DYYC<u>NSRDSSGTVV</u>FGGGTK<br><br>LTVL (SEQ ID NO: 48) | 49 |

-continued

| Name | VH | Linker | VL | SEQ ID NO. |
|---|---|---|---|---|
| E34N2 | QVQLVESGGGLIQPGGSLRLSCAA SGFTVSSNFMTWVRQAPGKGLEW SVSIYGGNTYYADSVKGRFTISR DNSKNTLYLQMNSLRAEDTAVYY CARGRYSYVDYWGQGTLVTVSS (SEQ ID NO: 50) | GGGG SGGG GSGG GGS | QSALTQPASVSGSPGQSITISC TGTSSDVGGYNYVSWYQQH PGKAPKLMIYEVSNRPSGVSN RFSGSKSGNTASLTISGLQAE DEADYYCSSYAGNYSWIFGG GTKVTVL (SEQ ID NO: 51) | 52 |
| E34N3 | QVQLQESGGGVVQPGGSLRLSCA ASGFTFSSYGMHWVRQAPGKGLE WVAVISYDGSNKYYADSVKGRFT ISRDNSKNTLYLQMNSLRAEDTA VYYCARDYTPEGWDYWGQGTLV TVSS (SEQ ID NO: 53) | GGGG SGGG GSGG GGS | SELTQDPAVSVALGQTVRITC QGDSLKSYYASWYQQKPQ APVLVIYGKNNRPSGIPDRFS GSSSGNTASLTITGAQAEDEA DYYCNSRDSSGNHLVFGGGT KLTVL (SEQ ID NO: 54) | 55 |
| E34N4 | QVQLVQSGGGLVQPGGSLRLSCA ASGFTFSSYAMSWVRQAPGKGLE WVANIKQDGSEKYYVDSVKGRFT ISRDSSKNTLYLQMNTLRAEDTAV YYCARGYYDVDYWGQGTLVTVS S (SEQ ID NO: 56) | GGGG SGGG GSGG GGS | DVVMTQSPSSLSASVGDRVTI TCQASQDISNYLNWYQQKPG KAPKLLIYAASSLQSGVPSRF SGSGSGTDFTLTISSLQPEDFA TYYCQQSYSTPPTFGQGTKVE IK (SEQ ID NO: 57) | 58 |
| E34N5 | QVQLLQSAGGVVQPGRSLRLSCA ASGFTFSSYGMHWVRQAPGKGLE WVAVISYDGSNKYYADSVKGRFT ISRDNSKNTLYLQMNSLRAEDTA VYYCAKGEDYPYMDVWGQGTTV TVSS (SEQ ID NO: 59) | GGGG SGGG GSGG GGS | QSVLTQPPSVSGAPGQRVTIS CTGSSSNVGAGFDVHWYQQL PGTAPKLLIYGDNNRPSGVPD RFSGSRSGTSASLAITGLQAE DEADYYCQSYDSSLSGSVFG GGTKVTVL (SEQ ID NO: 60) | 61 |
| E34N6 | QVQLLQSGGGLVQPGGSLRLSCA ASGFTFSTYAMSWVRQAPGKGLE WVSTIGPSGSSTYYAYADSVKGRF TISRDNYKNMLYLQMNSLRAEDT AVYYCAKEGPNSGYFDFDYWGQ GTLVTVSS (SEQ ID NO: 62) | GGGG SGGG GSGG GGS | EIVLTQSPSSLSASVGDRVTIT CRASQSISTYLNWYQQKPGK APKVLIYAASSLQSGVPSRISG SGSGTDFTLTISSLQPEDFATY YCQQSYSIPLTFGGGTKLEIK (SEQ ID NO: 63) | 64 |
| E34N7 | QVQLVESGGGVVQPGRSLRLSCA ASGFTFSSYAMSWVRQAPGKGLE WVSAISGSGGSTYYADSVKGRFTI SRDNSKNTLYLQMNSLRAEDTAV YYCAKASSSYPIAARRYYYGMDV WGQGTTVTVSS (SEQ ID NO: 65) | GGGG SGGG GSGG GGS | QSVLTQPASVSGSPGQSITISC TGTNSDVGGYNFVSWYQQY PGKAPKLIIFDVSDRPSRVSNR FSGSKSGNTASLTISGLQAED EADYYCSSYAGNNNVVFGG GTKLTVL (SEQ ID NO: 66) | 67 |
| E34N8 | QVQLVQSGAEVKKPGSSVKVSCK GSGYTFSGYYIHWVRQAPGQGLE WMGWINPNSGNTGYAQKFQDRV TITADKSTSTAYMELSSLRSEDTAV YYCARTYYDFWSGYPFDYWGQG TLVTVSS (SEQ ID NO: 68) | GGGG SGGG GSGG GGS | DVVMTQSPSTLSASVGDRVTI TCRASQTIGSWLAWYQQTPG RAPKLLIYKASSLESGVPSRFS GSESGTDFTLTISSLQPDDFAT YYCQQYNSYPRTFGQGTK LE IK (SEQ ID NO: 69) | 70 |

| Name | VH | Linker | VL | SEQ ID NO. |
|---|---|---|---|---|
| E34N9 | QVQLQESGGGLVQPGGSLRLSCA ASGFTFSSYAMSWVRQAPGKGLE WVSTISGSGGSTYYADSVKGRFTIS RDNSKNTLYLQMNSLRAEDTAVY YCAKDGSYSYGYVDYWGQGTL VTVSS (SEQ ID NO: 71) | GGGG SGGG GSGG GGS | SELTQDPAMSVALGQTVNITC QGDSLRRYFPSWYQQKPGQA PVLVLYGRNTRPSGIPDRFSGS NSGNSASLTITGAQAEDEADY YCHSRGSSGTHLRVFGGGTKL TVL (SEQ ID NO: 72) | 73 |
| E34N11 | QVQLQESGGGLVQPGGSLRLSCA ASGFTFSSYAMSWVRQAPGKGLE WVSSISSGSTYISYADSVKGRFTIS RDNAKNSLYLQMNSLRVDDTAVY YCAAAGGASNWYFDLWGRGTLV TVSS (SEQ ID NO: 74) | GGGG SGGG GSGG GGS | SELTQDPAVSVALGQTVRITC QGDSLRTFDASWYQQKPGQA PVVVIYGENNRPSGIPDRFSGS SSGNSASLTITGAQAEDEADY YCSSRDSRGNHLALFGGGTKL TVL (SEQ ID NO: 75) | 76 |
| E34N12 | QVQLQESGGGMVQPGGSLRLSCA ASGFTFSSYAMSWVRQAPGKGLE WVSAISGSGGSTYYADSVKGRFTI SRDNSKNTLYLQMNSLRAEDTAV YYCAKARAKIAARAQGFDYWGQ GTLVTVSS (SEQ ID NO: 77) | GGGG SGGG GSGG GGS | QSVLTQPPSVSAAPGQKVTIS CSGSSSNIGNNYVSWYQQLPG TAPKLLIYDNNKRPSGIPDRFS GSKSGNTASLTISGLQAEDEA DYYCSSYTTSSTLVFGGGTKV TVL (SEQ ID NO: 78) | 79 |
| E34N13 | QVQLVESGGGVVQPGRSLRLSCA ASGFTFSSYGMHWVRQAPGKGLE WVAVISYDGSNKYYADSVKGRFTI SRDNSKNTLYLQMNSLRAEDTAV YYCASKRGEYSSGWYGPDYWGQ GTLVTVSS (SEQ ID NO: 80) | GGGG SGGG GSGG GGS | SYVLTQPPSVSGAPGQRVTISC TGSSSNIGAGYDVHWYQQLP GTAPKLLIYGNSNRPSGVPDR FSGSKSGTSASLAITGLQAEDE ADYYCQSYDSSLSGVVFGGG TKVTVL (SEQ ID NO: 81) | 82 |
| E34N14 | QVQLVESGGGLVQPGGSLRLSCA ASGFSFSNYAMDWVRQAPGKGLE WVSAISGSGGRTYYADSVKGRFTI SRDNSKNTLYLQMNSLRAEDTAV YYCAKDRVPGTPPAEYFQHWGQG TLVTVSS (SEQ ID NO: 83) | GGGG SGGG GSGG GGS | SELTQDPAVSVALGQTVRITC QGDSLKSYYASWYQQKPGQA PVLVIYGENSRPSGIPDRFSGS SSGNTASLTITGAQAEDEADY YCHSRDSSGTHLRVFGGGTK VTVL (SEQ ID NO: 84) | 85 |
| E34N14M | QMQLVESGGGLVQPGGSLRLSCA ASGFSFSNYAMDWVRQAPGKGLE WVSAISGSGGRTYYADSVKGRFTI SRDNSKNTLYLQMNSLRAEDTAV YYCAKDRVPGTPPAEYFQHWGQG TLVTVSS (SEQ ID NO: 86) | GGGG SGGG GSGG GGS | SELTQDPAVSVALGQTVRITC QGDSLKSYYASWYQQKPGQA PVLVIYGENSRPSGIPDRFSGS SSGNTASLTITGAQAEDEADY YCHSRDSSGTHLRVFGGGTK VTVL (SEQ ID NO: 87) | 88 |
| E34N15 | QVQLVESGGGLVQPGGSLRLSCA ASGFTFSSSAMNWVRQAPGKGLE WVSAITGGGGTTYYADSVKGRFTI SRDNSKNTLYLQMDSLSTADAAL YYCAKPPVGGILHAFDIWGQGTM VTVSS (SEQ ID NO: 89) | GGGG SGGG GSGG GGS | DVVMTQSPSSLSASVGDRVTI TCRASQGIRNDLGWYQQKPG RAPKLLIHPASTLQSGVPSRFS ASGFGTDFTLTITSLQPEDSAT YYCLQDYNSFTFGPGTKLVTV L (SEQ ID NO: 90) | 91 |

| Name | VH | Linker | VL | SEQ ID NO. |
|---|---|---|---|---|
| E34N20 | QVQLQESGGGVVQPGRSLRLSCA ASGFIFNKYGMHWVRQAPGKGLE WVSVISGSGGSTYYADSVKGRFTI SRDNSKNTLFLQMNSLRDDDTAV YYCAKRGDGYNSGWYSFDYWGQ GTLVTVSS (SEQ ID NO: 92) | GGGG SGGG GSGG GGS | QSVLTQPPSVSGAPGQRVTISC TGSSSNIGAGYDVHWYQQLP GTAPKLLIYGNSNRPSGVPDR FSGSKSGTSASLAITGLQAEDE ADYYCQSYDSSLSVVVFGGG TKVTVL (SEQ ID NO: 93) | 94 |
| E34N22 | QVQLVQSGGGLVQPGGSLRLSCA ASGFTFSSYGMHWVRQAPGKGLE WVAVISYDGSNKYYADSVKGRFTI SRDNSKNTLYLQMNSLRAEDTAV YYCARGSLWRAFDIWGQGTMVT VSS (SEQ ID NO: 95) | GGGG SGGG GSGG GGS | QSVLTQPPSVSGAPGQRVTISC TGSSSNIGAGYDVHWYQQLP GTAPKLLIYADSNRPSGVPDR FSGSRSGTSASLAITGLLAEDE ADYFCQSYDSSLSSVVFGGGT KVTVL (SEQ ID NO: 96) | 97 |
| E34N26C | QVQLQESGGGVVRPGGSLRLSCA ASGFTFDDYGMSWVRQAPGKGLE WVSSISGSGGSTYYADSVKGRFTIS RDNSKNTLYLQMNSLRSDDTAVY YCARGARGNYVSNWFDPWGQGT LVTVSS (SEQ ID NO: 98) | GGGG SGGG GSGG GGS | QSALTQPASVSGSPGQSITISC TGTSSDVGGYKYVSWYQQHP GKAPKLMIYEVSQRPSGVPDR FSGSKSDNTASLTVSGLRAED EADYYCSSYAGSNNWVFGGG TKVTVL (SEQ ID NO: 99) | 100 |
| E34N26R | QVQLQESGGGVVRPGGSLRLSCA ASGFTFDDYGMSWVRQAPGKGLE WVSSISGSGGSTYYADSVKGRFTIS RDNSKNTLYLQMNSLRSDDTAVY YCARGARGNYVSNWFDPWGQGT LVTVSS (SEQ ID NO: 101) | GGGG SGGG GSGG GGS | QSALTQPASVSGSPGQSITISC TGTSSDVGGYKYVSWYQQHP GKAPKLMIYEVSQRPSGVPDR FSGSKSDNTASLTVSGLRAED EADYYRSSYAGSNNWVFGGG TKVTVL (SEQ ID NO: 102) | 103 |

Table 5 depicts peptide sequences of scFv fragments that bind to various non-limiting exemplary guide antigens

| Name | VH | Linker | VL | SEQ ID NO. |
|---|---|---|---|---|
| H3 | QVQLVESGGGLVQPGGSLRLSCA ASGFTFSSYAMSWVRQAPGKGLE WVSAISGSGGSTYYADSVKGRFTI SRDNSKDTLYLQMNSLRAEDTAV YYCASRSLLDYWGQGTLVTVSS (SEQ ID NO: 104) | GGGG SGGG GSGG GGS | NFMLTQNPAVSVALGQTVRI TCQGDSLRSYYASWYQQKPG QAPLLVIYGKNNRPSGIPDRF SGSSSGNTASLTITGAQAEDE ADYYCNSRDSSGNPVFGGGT KVTVL (SEQ ID NO: 105) | 106 |
| 58541 (H3 variant1) | QVQLVESGGGLVQPGGSLRLSCA ASGFTFSSYAMWVRQAPGKGLE WVSAISGSGGSTYYADSVKGRFTI SRDNSKDTLYLQMNSLRAEDTAV YYCASRSLLDYWGQGTLVTVSS (SEQ ID NO: 107) | GGGG SGGG GSGG GGS | NFMLTQPAVSVALGQTVRI TCQGDSLRSYYASWYQQKPG QAPLLVIYGKNNRPSGIPDRF SGSSSGNTASLTITGAQAEDE ADYYCNSRDSSGNPVFGGGT KVTVL (SEQ ID NO: 108) | 109 |

| Name | VH | Linker | VL | SEQ ID NO. |
|---|---|---|---|---|
| 58541.1 H3 variant2) | QVQLVESGGGLVQPGGSLRLSCA ASGFTFSSYAMSWVRQAPGKGLE WVSAISGSGGSTYYADSVKGRFTI SRDNSKDTLYLQMNSLRAEDTAV YYCASRSLLDYWGQGTLVTVSS (SEQ ID NO: 110) | GGGG SGGG GSGG GGS | NFMLTQPAVSVALGQTVRI TCQGDSLRSYYASWYQQKPG QAPLLVIYGKNNRPSGIPDRF SGSSSGNTASLTITGAQAEDE ADYYCNSRDSSGNPVFGGGT KVTVL (SEQ ID NO: 111) | 112 |
| PD32 | QVQLQESGGGLVQPGGSLRLSCA ASGFTFSSYALSWVRQAPGKGLE WVSAISGSGGSTYYAGSVKGRFTI SRDNSKNTLYLQMNSLRAEDTAV YYCAKGLIASHWGQGTLVTVSS SEQ ID NO: 113) | GGGG SGGG GSGG GGS | SELTQDPAVSVALGQTVRITC QGDSLRSYYASWYQQKPGQ APVLVIYGKNNRPSGIPDRFS GSSSGNTASLTITGAQAEDEA DYYCNSRDSSGIHLVFGGGT KLTVL (SEQ ID NO: 114) | 115 |
| M10A12 | QVQLVESGGGVVQPGRSLRLSCT ASGFTFSSYGMHWVRQAPGKGLE WVAVISYDGSNKYYADSVKGRFT ISRDNSKNTLYLQMNSLRAEDTA VYYCARGGRYSSNWFSYYYYGMDV WGQGTTVTVSS(SEQ ID NO: 116) | GGGG SGGG GSGG GGS | SELTQDPAVSVALGQTVRITC QGDSLRSYYASWYQQKPGQ APLLVIYGENNRPSGIPDRFSG SSSGNTAFLTISRVEAGDEAD YYCQVWDSSSDHPGVVFGG GTKVTVL (SEQ ID NO: 117) | 118 |
| RYR | QVQLQESGGGLVQPGGSLRLSCA ASGFTFSSYSMNWVRQAPGKGLE WVSYISSSSSTIYYADSVKGRFTIS RDNAKNSLYLQMNSLRAEDTAVY YCARYRLPDFWSGYPNYGMDVW GQGTTVTVSS (SEQ ID NO: 119) | GGGG SGGG GSGG GGS | QSVLTQPPSVSGAPGQRVTIS CTGSSSNIGAGYDVHWYQQL PGTAPKLLIYGNSNRPSGVPD RFSGSKSGTSASLAITGLQAE DEADYYCQSYDSSLSGHVVF GGGTKLTVL (SEQ ID NO: 120) | 121 |

Figure 15A:
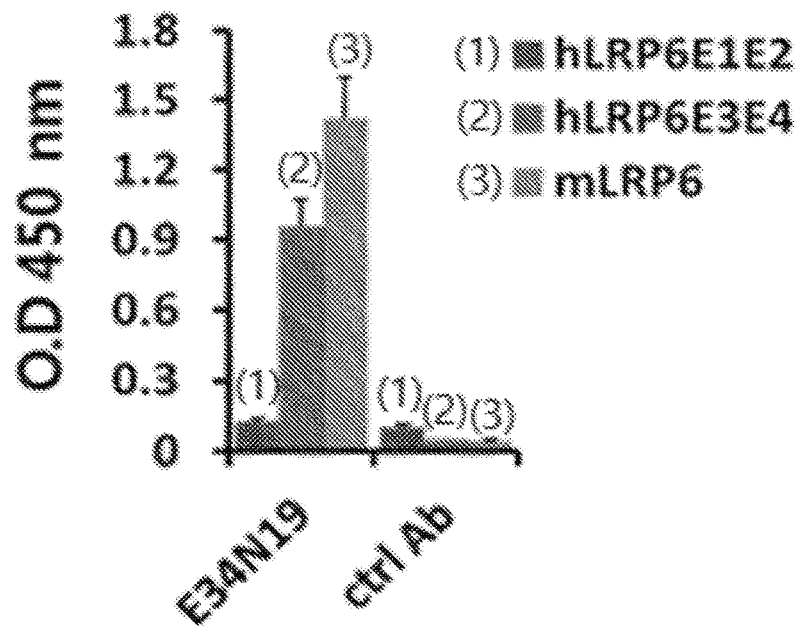
Figure 15B:
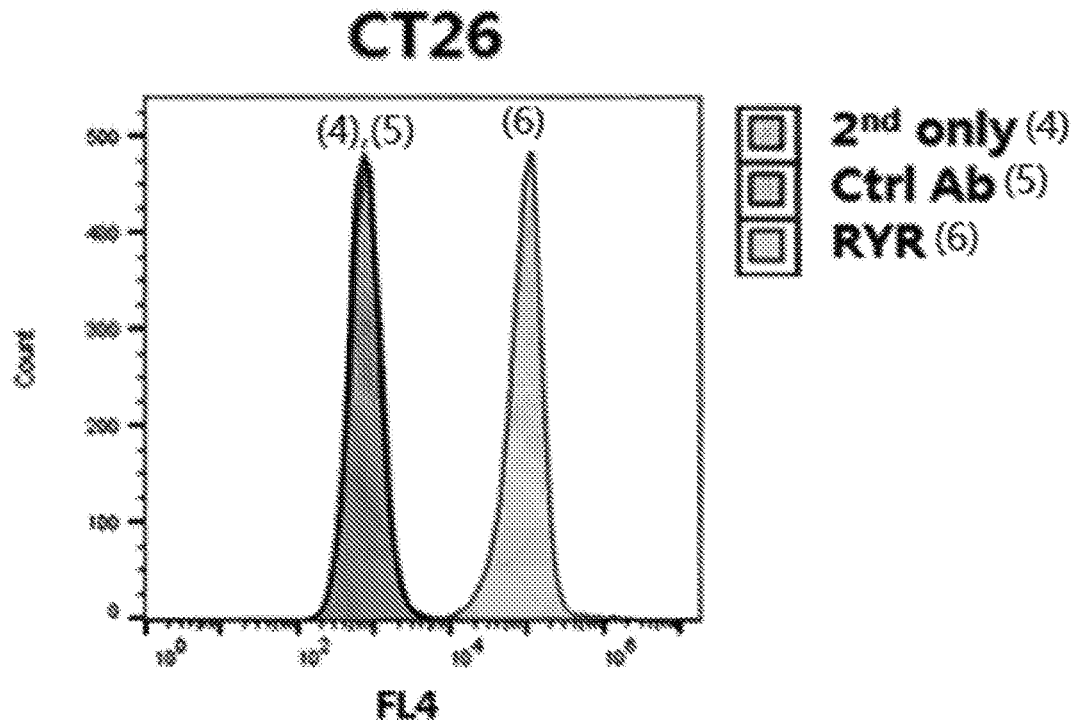
Figure 15C:
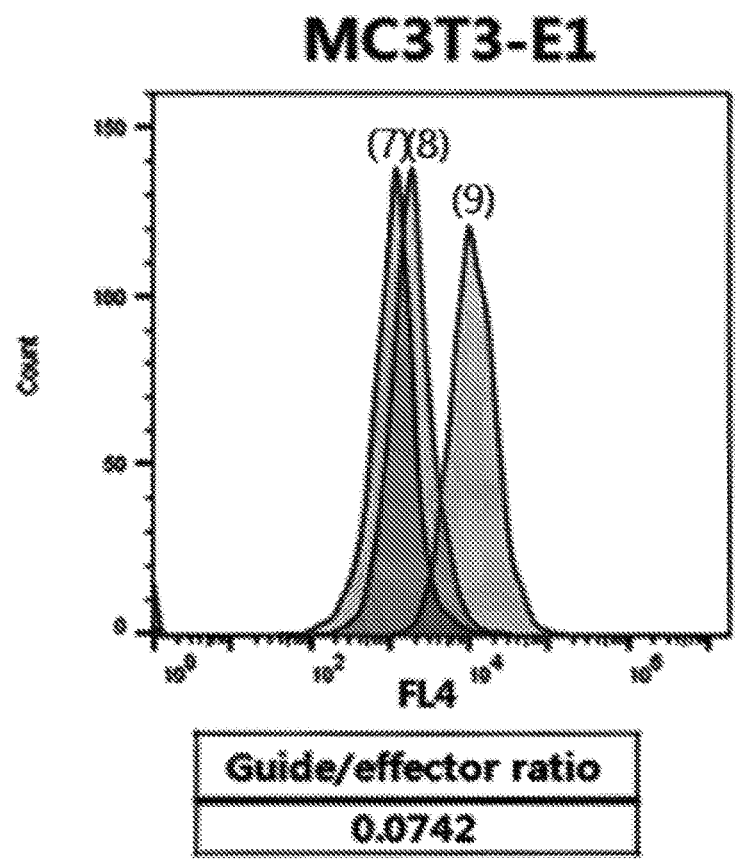
Figure 15D:
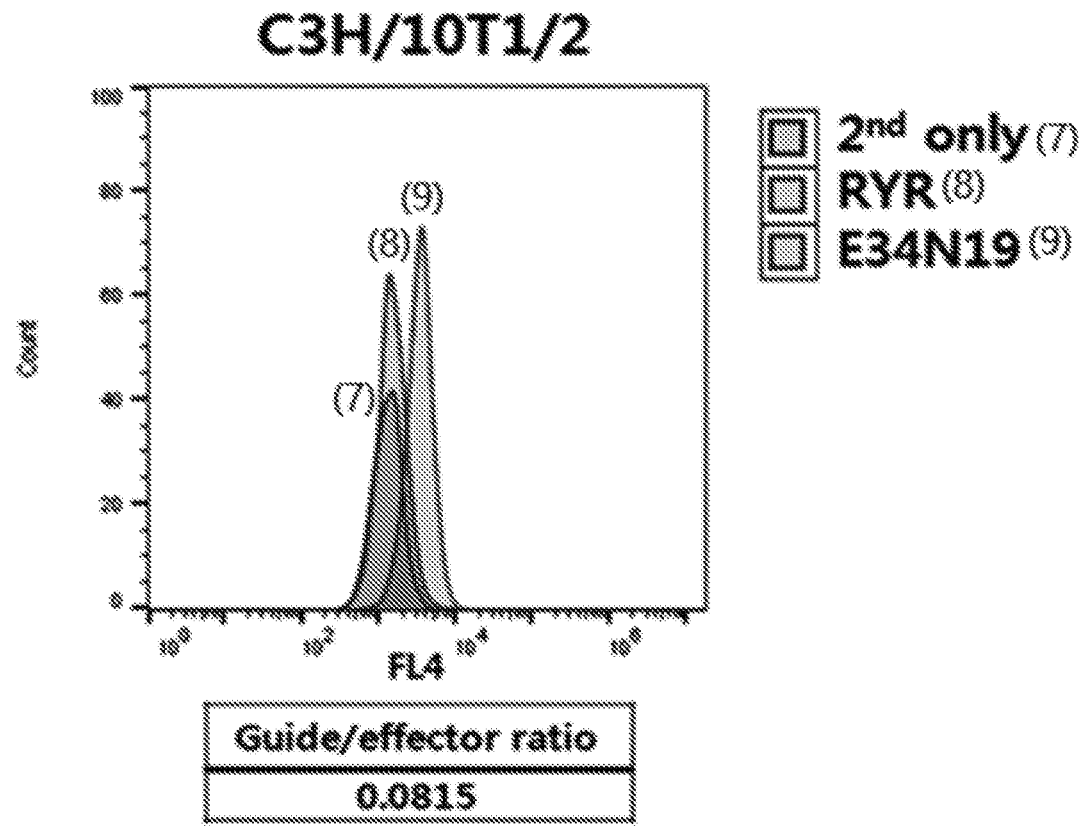
Figure 15E:
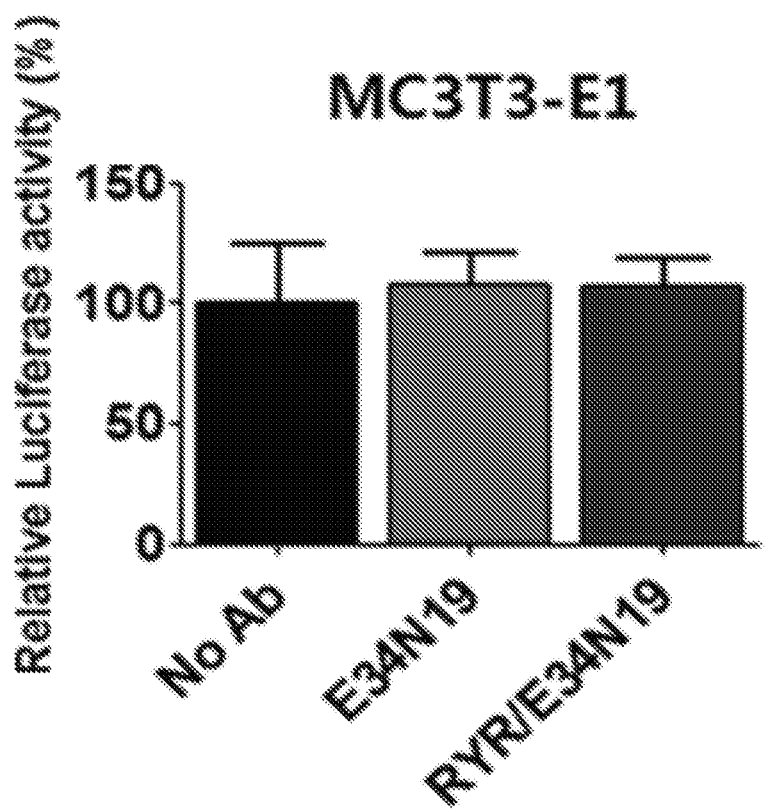
Figure 15F:
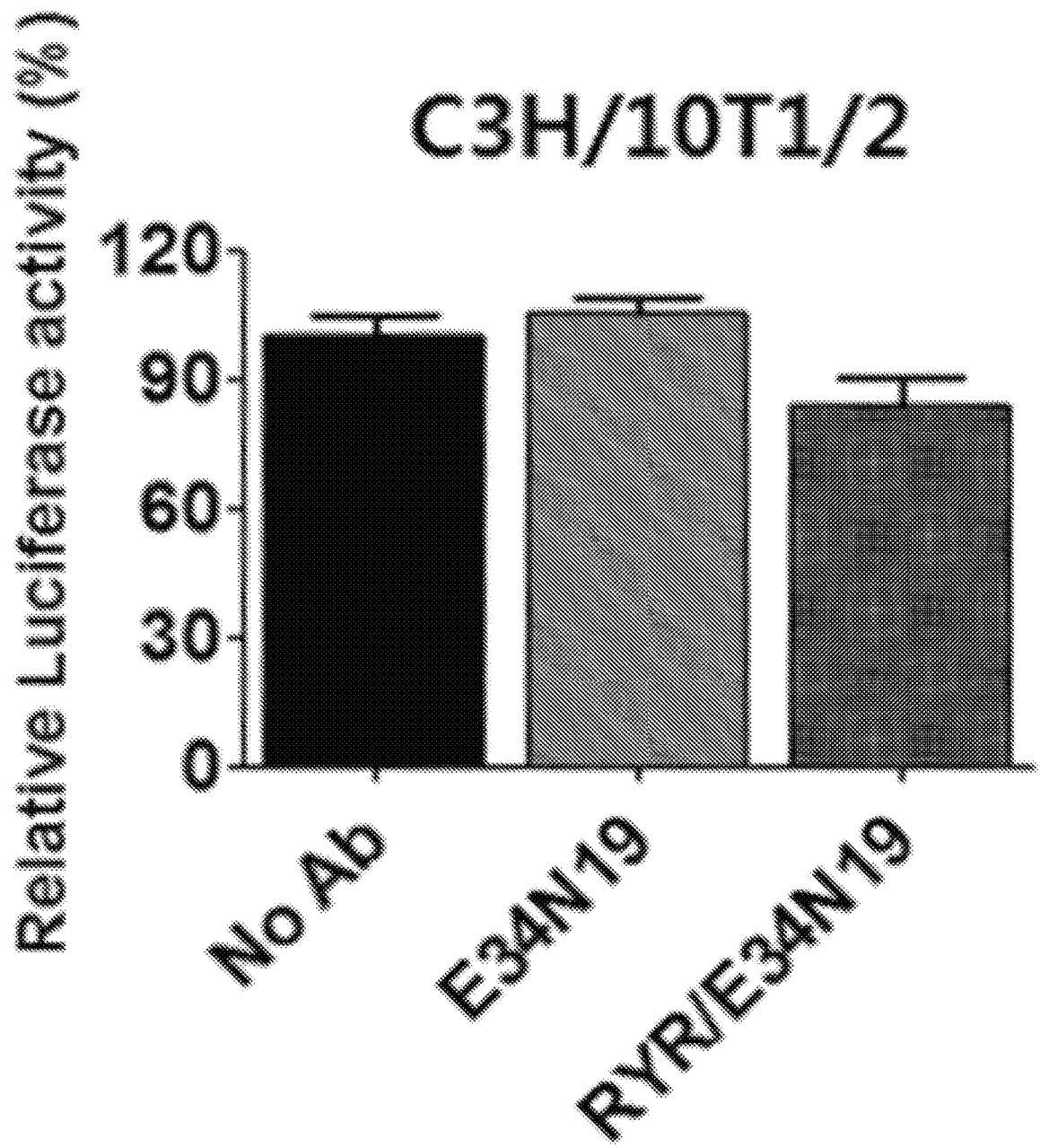
Figure 16A:
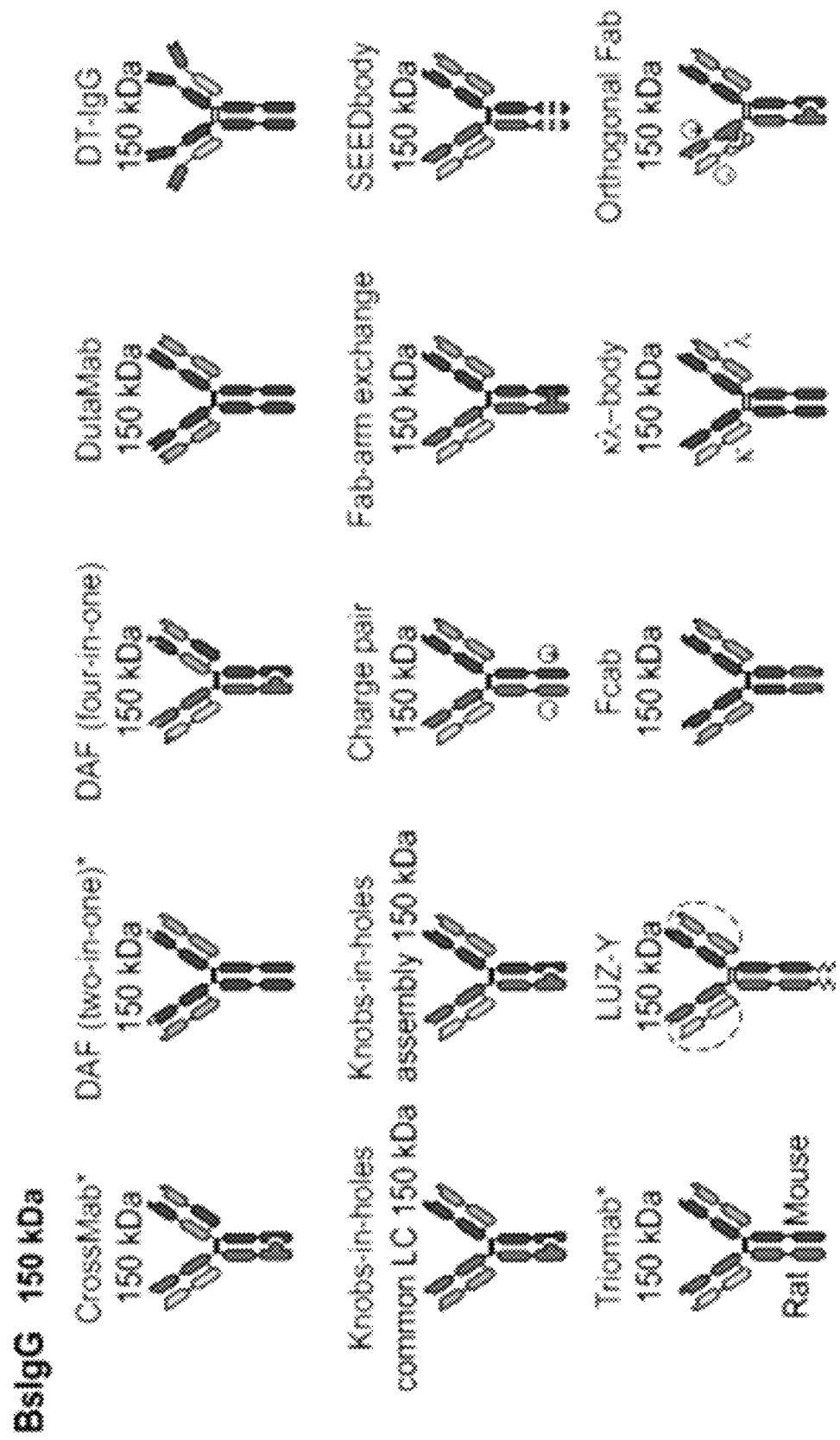
Figure 16B:
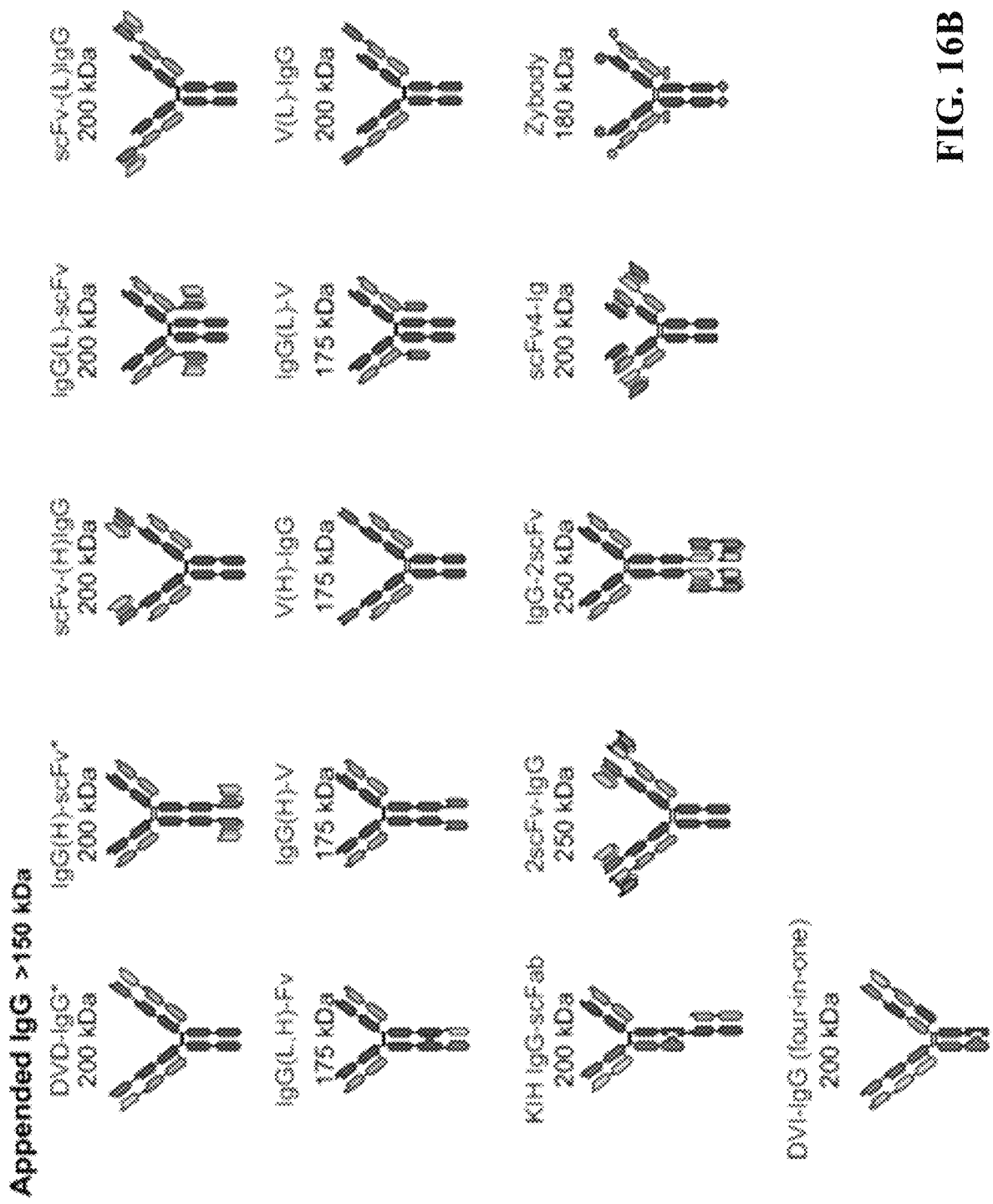
Figure 16D:
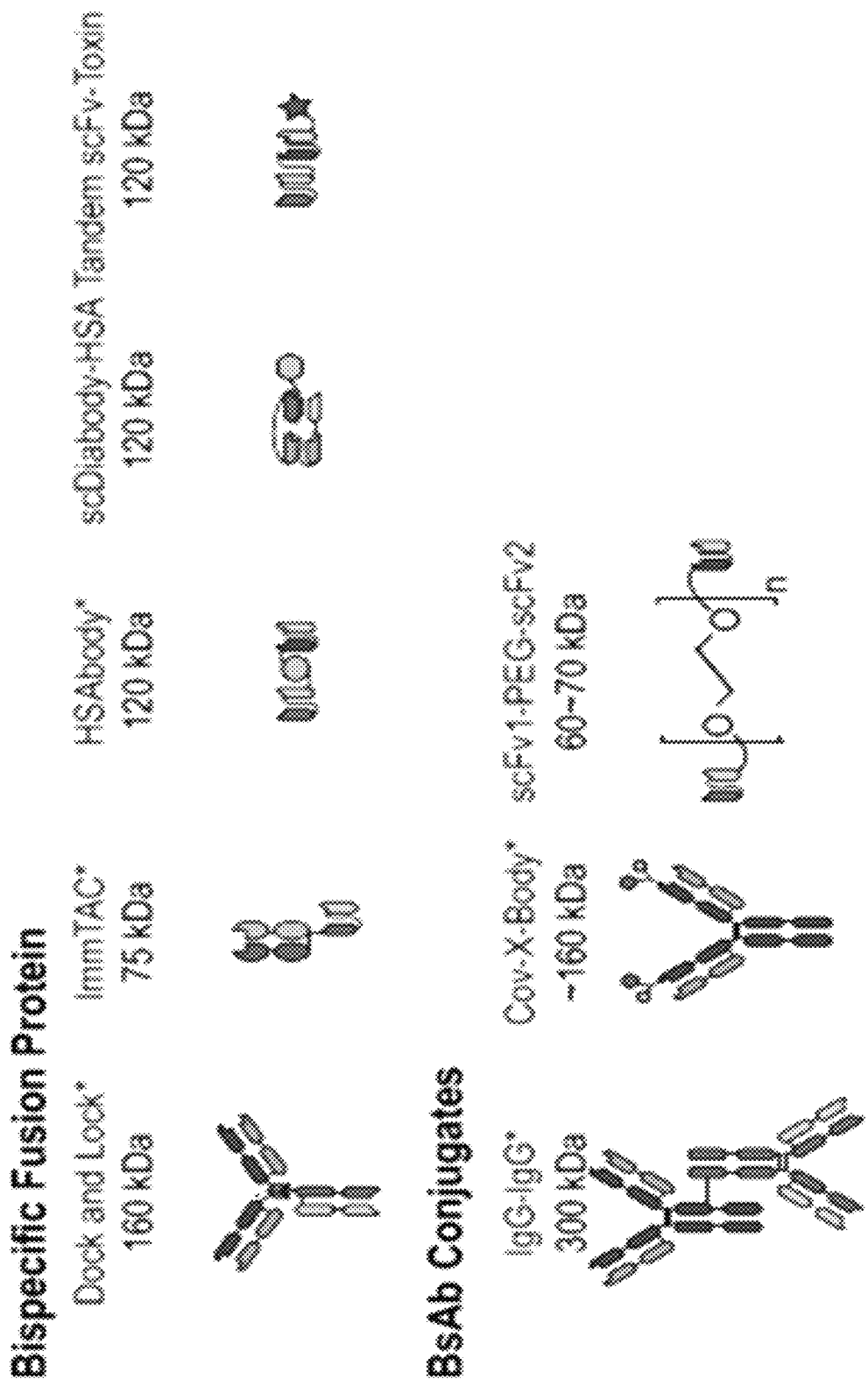

Example 9—the Bispecific does not Affect Wnt Signaling in Normal Cells that Express No or a Low Level of the Guide Antigen To expand the study on cell type selectivity and functional specificity, we next investigated the effect of the bispecific on two normal cell lines MC3T3-E1 (a mouse preosteoblast line) and C3H/10T1/2 (a mouse mesenchymal stem cell line), which are commonly used in study of osteoblast differentiation controlled by Wnt signaling. We first showed that our anti-effector (E3E4N19 against LRP6E3E4) and anti-guide (RYR against EphA2) antibodies bind to both murine and human targets (FIGS. 15A and 15B). We next determined that both MC3T3-E1 and C3H/10T1/2 cells express a low level of the guide antigen EphA2 and has a low guide to effector ratio (FIGS. 15C and 15D). We then performed the STF reporter assay and found that the EphA2-guided RYR/E34N19 did not affect wnt signaling in both cell lines (FIGS. 15E and 15F), demonstrating that the bispecific is cell type selective and does not inhibit wnt signaling in normal cells that express no or a low level of the guide antigen.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An engineered protein comprising an antigen binding region that binds to a guide antigen and an antigen binding region that binds to an effector antigen; wherein the guide antigen and the effector antigen are expressed on the surface of a cell; wherein the antigen density of the guide antigen is at least four-fold higher than the antigen density of the effector antigen; wherein the guide antigen is ICAM-1, EphA2, or ALCAM, and the effector antigen is LRP6; and wherein
   (a) the antigen binding region that binds the guide antigen ICAM-1 comprises all six complementarity determining regions (CDRs) of SEQ ID NO: 118,
   (b) the antigen binding region that binds the guide antigen EphA2 comprises all six CDRs of SEQ ID NO: 121,
   (c) the antigen binding region that binds the guide antigen ALCAM comprises all six CDRs of SEQ ID NO: 106, SEQ ID NO: 109, SEQ ID NO: 112, or SEQ ID NO: 115: and
   (d) the antigen binding region that binds the effector antigen LRP6 comprises all six CDRs of SEQ ID NO: 4 or SEQ ID NO: 43.

2. The engineered protein of claim 1, wherein at least one of the antigen binding regions comprises a single chain variable fragment (scFv).

3. The engineered protein of claim 1, wherein the engineered protein is a bispecific antibody.

4. The engineered protein of claim 1, wherein the antigen binding region that binds the guide antigen ICAM-1 comprises a heavy chain variable region (VH) and a light chain variable region (VL) of SEQ ID NO: 116 and SEQ ID NO: 117, respectively.

5. The engineered protein of claim 1, wherein the antigen binding region that binds the guide antigen EphA2 comprises a VH region and a VL region of SEQ ID NO: 119 and SEQ ID NO: 120, respectively.

6. The engineered protein of claim 1, wherein the antigen binding region that binds the guide antigen ALCAM comprises:
   (a) a VH region and a VL region of SEQ ID NO: 104 and SEQ ID NO: 105, respectively;
   (b) a VH region and a VL region of SEQ ID NO: 107 and SEQ ID NO: 108, respectively;
   (c) a VH region and a VL region of SEQ ID NO: 110 and SEQ ID NO: 111, respectively; or
   (d) a VH region and a VL region of SEQ ID NO: 113 and SEQ ID NO: 114, respectively.

7. The engineered protein of claim 1, wherein the level of occupancy of the effector antigen is higher for the engineered protein compared to the level of occupancy using an antibody monospecific for the effector antigen when equivalent molar amounts of the engineered protein or the antibody monospecific for the effector antigen are administered to the cell.

8. The engineered protein of claim 1, wherein binding of the engineered protein to the cell results in modulation of a signaling pathway.

9. The engineered protein of claim 1, wherein binding of the engineered protein to the cell results in downregulation of a signaling pathway.

10. The engineered protein of claim 1, wherein the effector antigen is LRP6 and the signaling pathway is Wnt signaling pathway.

11. The engineered protein of claim 1, wherein an IC50 value of the engineered protein is decreased at least 100-fold compared to an IC50 value of an antibody monospecific to the effector antigen.

12. The engineered protein of claim 1, wherein the antigen binding region that binds the effector antigen LRP6 comprises:
   (a) a VH region and a VL region of SEQ ID NO: 1 and SEQ ID NO: 3, respectively; or
   (b) a VH region and a VL region of SEQ ID NO: 41 and SEQ ID NO: 42, respectively.

13. The engineered protein of claim 1, wherein:
   (a) the antigen binding region that binds to the guide antigen comprises the sequence of SEQ ID NO: 106, SEQ ID NO: 109, SEQ ID NO: 112, SEQ ID NO: 115, SEQ ID NO: 118, or SEQ ID NO: 121; and
   (b) the antigen binding region that binds to the effector antigen comprises the sequence of SEQ ID NO: 4 or SEQ ID NO: 43.

14. A method of modulating a signaling pathway in a cell comprising administering to the cell the engineered protein of claim 1.

15. The method of claim 14, wherein the signaling pathway is the Wnt signaling pathway of the cell.

16. A method of treating a disease or condition associated with a dysregulation of a signaling pathway in a cell in a subject in need thereof comprising administering to the subject a therapeutically effective amount of the engineered protein of claim 1.

17. A method of generating an engineered protein comprising:
   a) selecting a cell expressing a plurality of guide antigens and effector antigens on the cell surface;
   b) determining a density ratio of a plurality of the guide antigens and the effector antigens; and
   c) preparing the engineered protein comprising a first antigen binding region that binds to the guide antigen and a second antigen binding region that binds to the effector antigen on the cell, wherein the guide antigen is ICAM-1, EphA2, or ALCAM and the effector antigen is LRP6;
   wherein the antigen density of the guide antigen is at least four-fold higher than the antigen density of the effector antigen; and
   wherein the cell expresses at least 15,000 or more copies of the guide antigen on the cell surface.

* * * * *

SEQUENCE LISTING

<160> NUMBER OF SEQ ID NOS: 121

<210> SEQ ID NO 1
<211> LENGTH: 123
<212> TYPE: PRT
<213> ORGANISM: Artificial Sequence
<220> FEATURE:
<223> OTHER INFORMATION: Synthetic sequence-E12N21 VH

```
<400> SEQUENCE: 1

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Thr Met Thr Ala Ser Ala Trp Leu Gly Gly Gly Arg Asp Ser
            100                 105                 110

Trp Gly Gln Gly Thr Leu Val Thr Val Ser Ser
        115                 120

<210> SEQ ID NO 2
<211> LENGTH: 15
<212> TYPE: PRT
<213> ORGANISM: Artificial Sequence
<220> FEATURE:
<223> OTHER INFORMATION: Synthetic sequence-E12N21 Linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 109
<212> TYPE: PRT
<213> ORGANISM: Artificial Sequence
<220> FEATURE:
<223> OTHER INFORMATION: Synthetic sequence-E12N21 VL

<400> SEQUENCE: 3

Gln Ser Val Leu Thr Gln Asp Pro Ala Val Ser Val Ala Leu Gly Gln
1               5                   10                  15

Thr Val Arg Ile Thr Cys Gln Gly Asp Ser Leu Arg Thr Leu Ser Thr
            20                  25                  30

Asn Trp Tyr Gln Gln Lys Ser Gly Gln Ala Pro Val Leu Val Ile Tyr
        35                  40                  45

Gly Asn Ser Asn Arg Pro Ser Gly Val Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Tyr Asp Asn Ser Val Arg Gly
                85                  90                  95

Ser Arg Val Phe Gly Thr Gly Thr Lys Leu Thr Val Leu
            100                 105

<210> SEQ ID NO 4
<211> LENGTH: 247
<212> TYPE: PRT
<213> ORGANISM: Artificial Sequence
<220> FEATURE:
<223> OTHER INFORMATION: Synthetic sequence - E12N21

<400> SEQUENCE: 4
```

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Thr Met Thr Ala Ser Ala Trp Leu Gly Gly Gly Arg Asp Ser
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gln Ser Val Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Thr Leu Ser Thr Asn Trp Tyr Gln Gln Lys
                165                 170                 175

Ser Gly Gln Ala Pro Val Leu Val Ile Tyr Gly Asn Ser Asn Arg Pro
            180                 185                 190

Ser Gly Val Pro Asp Arg Phe Ser Gly Ser Ser Ser Gly Asn Thr Ala
        195                 200                 205

Ser Leu Thr Ile Thr Gly Ala Gln Ala Glu Asp Glu Ala Asp Tyr Tyr
    210                 215                 220

Cys Gln Ser Tyr Asp Asn Ser Val Arg Gly Ser Arg Val Phe Gly Thr
225                 230                 235                 240

Gly Thr Lys Leu Thr Val Leu
                245

<210> SEQ ID NO 5
<211> LENGTH: 123
<212> TYPE: PRT
<213> ORGANISM: Artificial Sequence
<220> FEATURE:
<223> OTHER INFORMATION: Synthetic sequence - E12N21I VH

<400> SEQUENCE: 5

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Thr Met Thr Ala Ser Ala Trp Leu Gly Gly Gly Arg Asp Ser
            100                 105                 110

Trp Gly Gln Gly Thr Leu Val Thr Val Ser Ser
        115                 120

<210> SEQ ID NO 6
<211> LENGTH: 109
<212> TYPE: PRT
<213> ORGANISM: Artificial Sequence
<220> FEATURE:
<223> OTHER INFORMATION: Synthetic sequence - E12N21I VL

<400> SEQUENCE: 6

Gln Ser Val Leu Thr Gln Asp Pro Ala Val Ser Val Ala Leu Gly Gln
1               5                   10                  15

Thr Val Arg Ile Thr Cys Gln Gly Asp Ser Leu Arg Thr Leu Ser Thr
            20                  25                  30

Asn Trp Tyr Gln Gln Lys Ser Gly Gln Ala Pro Val Leu Val Ile Tyr
        35                  40                  45

Gly Asn Ser Asn Arg Pro Ser Gly Val Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Tyr Asp Asn Ser Val Arg Gly
                85                  90                  95

Ser Arg Val Phe Gly Thr Gly Thr Lys Leu Thr Ile Leu
            100                 105

<210> SEQ ID NO 7
<211> LENGTH: 247
<212> TYPE: PRT
<213> ORGANISM: Artificial Sequence
<220> FEATURE:
<223> OTHER INFORMATION: Synthetic sequence - E12N21I

<400> SEQUENCE: 7

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Thr Met Thr Ala Ser Ala Trp Leu Gly Gly Gly Arg Asp Ser
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gln Ser Val Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Thr Leu Ser Thr Asn Trp Tyr Gln Gln Lys
                165                 170                 175

Ser Gly Gln Ala Pro Val Leu Val Ile Tyr Gly Asn Ser Asn Arg Pro

```
            180                 185                 190
Ser Gly Val Pro Asp Arg Phe Ser Gly Ser Ser Gly Asn Thr Ala
        195                 200                 205
Ser Leu Thr Ile Thr Gly Ala Gln Ala Glu Asp Glu Ala Asp Tyr Tyr
        210                 215                 220
Cys Gln Ser Tyr Asp Asn Ser Val Arg Gly Ser Arg Val Phe Gly Thr
225                 230                 235                 240
Gly Thr Lys Leu Thr Ile Leu
                245

<210> SEQ ID NO 8
<211> LENGTH: 120
<212> TYPE: PRT
<213> ORGANISM: Artificial Sequence
<220> FEATURE:
<223> OTHER INFORMATION: Synthetic sequence - E12N7 VH

<400> SEQUENCE: 8

Gln Val Gln Leu Gln Gln Ser Gly Gly Gly Leu Val Gln Pro Gly Gly
1               5                   10                  15
Ser Leu Arg Leu Ser Cys Glu Val Ser Gly Phe Thr Phe Ser Arg Tyr
            20                  25                  30
Trp Met Thr Trp Val Arg Gln Ala Pro Gly Lys Gly Leu Glu Gly Val
        35                  40                  45
Ser Tyr Ile Ser Ser Ser Ser Tyr Thr Asn Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Ile Gly Arg Val Gln Tyr Phe Phe Asp Tyr Trp Gly Gln
            100                 105                 110
Gly Thr Leu Val Thr Val Ser Ser
        115                 120

<210> SEQ ID NO 9
<211> LENGTH: 113
<212> TYPE: PRT
<213> ORGANISM: Artificial Sequence
<220> FEATURE:
<223> OTHER INFORMATION: Synthetic sequence - E12N7 VL

<400> SEQUENCE: 9

Ser Gln Ser Val Leu Thr Gln Pro Pro Ser Val Ser Gly Ala Pro Gly
1               5                   10                  15
Gln Thr Val Thr Ile Ser Cys Thr Gly Ser Asn Ser Asp Ile Gly Ala
            20                  25                  30
Gly Tyr Asp Val His Trp Tyr Gln Gln Leu Pro Gly Thr Ala Pro Lys
        35                  40                  45
Leu Leu Ile Tyr Gly Asn His Gln Arg Pro Ser Gly Val Pro Asp Arg
    50                  55                  60
Phe Ser Gly Ser Arg Ser Gly Thr Ser Ala Ser Leu Ala Ile Thr Gly
65                  70                  75                  80
Val Gln Ala Glu Asp Glu Ala Asp Tyr Tyr Cys Gln Ser Tyr Gly Asn
                85                  90                  95
Ser Val Arg Gly Ser Arg Val Phe Gly Thr Gly Thr Lys Leu Thr Val
            100                 105                 110
```

Leu

<210> SEQ ID NO 10
<211> LENGTH: 248
<212> TYPE: PRT
<213> ORGANISM: Artificial Sequence
<220> FEATURE:
<223> OTHER INFORMATION: Synthetic sequence - E12N7

<400> SEQUENCE: 10

Gln Val Gln Leu Gln Gln Ser Gly Gly Gly Leu Val Gln Pro Gly Gly
1               5                   10                  15

Ser Leu Arg Leu Ser Cys Glu Val Ser Gly Phe Thr Phe Ser Arg Tyr
            20                  25                  30

Trp Met Thr Trp Val Arg Gln Ala Pro Gly Lys Gly Leu Glu Gly Val
        35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Arg Val Gln Tyr Phe Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Gln Ser Val Leu Thr Gln Pro Pro
    130                 135                 140

Ser Val Ser Gly Ala Pro Gly Gln Thr Val Thr Ile Ser Cys Thr Gly
145                 150                 155                 160

Ser Asn Ser Asp Ile Gly Ala Gly Tyr Asp Val His Trp Tyr Gln Gln
                165                 170                 175

Leu Pro Gly Thr Ala Pro Lys Leu Leu Ile Tyr Gly Asn His Gln Arg
            180                 185                 190

Pro Ser Gly Val Pro Asp Arg Phe Ser Gly Ser Arg Ser Gly Thr Ser
        195                 200                 205

Ala Ser Leu Ala Ile Thr Gly Val Gln Ala Glu Asp Glu Ala Asp Tyr
    210                 215                 220

Tyr Cys Gln Ser Tyr Gly Asn Ser Val Arg Gly Ser Arg Val Phe Gly
225                 230                 235                 240

Thr Gly Thr Lys Leu Thr Val Leu
                245

<210> SEQ ID NO 11
<211> LENGTH: 124
<212> TYPE: PRT
<213> ORGANISM: Artificial Sequence
<220> FEATURE:
<223> OTHER INFORMATION: Synthetic sequence - E12N12 VH

<400> SEQUENCE: 11

Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gln Phe Asn Trp Asn Tyr Ala Tyr Tyr Gly Met Asp
                100                 105                110

Val Trp Gly Gln Gly Thr Thr Val Thr Val Ser Ser
            115                 120

<210> SEQ ID NO 12
<211> LENGTH: 107
<212> TYPE: PRT
<213> ORGANISM: Artificial Sequence
<220> FEATURE:
<223> OTHER INFORMATION: Synthetic sequence - E12N12 VL

<400> SEQUENCE: 12

Gln Ser Ala Leu Thr Gln Asp Pro Ala Val Ser Val Ala Leu Gly Gln
  1               5                  10                  15

Thr Val Arg Ile Thr Cys Gln Gly Asp Ser Leu Arg Asn Ser Tyr Ala
                 20                  25                  30

Asn Trp Tyr Gln Gln Lys Pro Gly Gln Ala Pro Leu Leu Val Ile Tyr
                 35                  40                  45

Gly Lys Asn Ile Arg Pro Ser Gly Ile Pro Asp Arg Phe Ser Gly Ser
            50                  55                  60

Lys Ser Gly Asp Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Gly
                 85                  90                  95

Met Phe Gly Gly Gly Thr Lys Leu Thr Val Leu
                100                 105

<210> SEQ ID NO 13
<211> LENGTH: 246
<212> TYPE: PRT
<213> ORGANISM: Artificial Sequence
<220> FEATURE:
<223> OTHER INFORMATION: Synthetic sequence - E12N12

<400> SEQUENCE: 13

Gln Val Asn Leu Arg Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Gly Met Ser Trp Val Arg Gln Ala Pro Gly Lys Gly Leu Glu Trp Val
                 35                  40                  45

Ser Gly Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gln Phe Asn Trp Asn Tyr Ala Tyr Tyr Gly Met Asp
                100                 105                110

Val Trp Gly Gln Gly Thr Thr Val Thr Val Ser Ser Gly Gly Gly Gly
            115                 120                 125

```
Ser Gly Gly Gly Gly Ser Gly Gly Gly Ser Gln Ser Ala Leu Thr
            130                 135                 140

Gln Asp Pro Ala Val Ser Val Ala Leu Gly Gln Thr Val Arg Ile Thr
145                 150                 155                 160

Cys Gln Gly Asp Ser Leu Arg Asn Ser Tyr Ala Asn Trp Tyr Gln Gln
                165                 170                 175

Lys Pro Gly Gln Ala Pro Leu Leu Val Ile Tyr Gly Lys Asn Ile Arg
            180                 185                 190

Pro Ser Gly Ile Pro Asp Arg Phe Ser Gly Ser Lys Ser Gly Asp Thr
        195                 200                 205

Ala Ser Leu Thr Ile Thr Gly Ala Gln Ala Glu Asp Glu Ala Asp Tyr
    210                 215                 220

Tyr Cys Asn Ser Arg Asp Ser Ser Gly Asn Gly Met Phe Gly Gly Gly
225                 230                 235                 240

Thr Lys Leu Thr Val Leu
                245

<210> SEQ ID NO 14
<211> LENGTH: 124
<212> TYPE: PRT
<213> ORGANISM: Artificial Sequence
<220> FEATURE:
<223> OTHER INFORMATION: Synthetic sequence - E12N12EQV VH

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Phe Asn Trp Asn Tyr Ala Tyr Tyr Gly Met Asp
            100                 105                 110

Val Trp Gly Gln Gly Thr Thr Val Thr Val Ser Ser
        115                 120

<210> SEQ ID NO 15
<211> LENGTH: 107
<212> TYPE: PRT
<213> ORGANISM: Artificial Sequence
<220> FEATURE:
<223> OTHER INFORMATION: Synthetic sequence - E12N12EQV VL

<400> SEQUENCE: 15

Gln Ser Ala Leu Thr Gln Asp Pro Ala Val Ser Val Ala Leu Gly Gln
1               5                   10                  15

Thr Val Arg Ile Thr Cys Gln Gly Asp Ser Leu Arg Asn Ser Tyr Ala
            20                  25                  30

Asn Trp Tyr Gln Gln Lys Pro Gly Gln Ala Pro Leu Leu Val Ile Tyr
        35                  40                  45

Gly Lys Asn Ile Arg Pro Ser Gly Ile Pro Asp Arg Phe Ser Gly Ser
```

```
            50                  55                  60
Lys Ser Gly Asp Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Gly
                 85                  90                  95

Met Phe Gly Gly Gly Thr Lys Leu Thr Val Leu
            100                 105
```

<210> SEQ ID NO 16
<211> LENGTH: 246
<212> TYPE: PRT
<213> ORGANISM: Artificial Sequence
<220> FEATURE:
<223> OTHER INFORMATION: Synthetic sequence - E12N12EQV

<400> SEQUENCE: 16

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Gly Met Ser Trp Val Arg Gln Ala Pro Gly Lys Gly Leu Glu Trp Val
         35                  40                  45

Ser Gly Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gln Phe Asn Trp Asn Tyr Ala Tyr Tyr Gly Met Asp
            100                 105                 110

Val Trp Gly Gln Gly Thr Thr Val Thr Val Ser Ser Gly Gly Gly Gly
            115                 120                 125

Ser Gly Gly Gly Gly Ser Gly Gly Gly Ser Gln Ser Ala Leu Thr
            130                 135                 140

Gln Asp Pro Ala Val Ser Val Ala Leu Gly Gln Thr Val Arg Ile Thr
145                 150                 155                 160

Cys Gln Gly Asp Ser Leu Arg Asn Ser Tyr Ala Asn Trp Tyr Gln Gln
                165                 170                 175

Lys Pro Gly Gln Ala Pro Leu Leu Val Ile Tyr Gly Lys Asn Ile Arg
            180                 185                 190

Pro Ser Gly Ile Pro Asp Arg Phe Ser Gly Ser Lys Ser Gly Asp Thr
            195                 200                 205

Ala Ser Leu Thr Ile Thr Gly Ala Gln Ala Glu Asp Glu Ala Asp Tyr
        210                 215                 220

Tyr Cys Asn Ser Arg Asp Ser Ser Gly Asn Gly Met Phe Gly Gly
225                 230                 235                 240

Thr Lys Leu Thr Val Leu
            245
```

<210> SEQ ID NO 17
<211> LENGTH: 121
<212> TYPE: PRT
<213> ORGANISM: Artificial Sequence
<220> FEATURE:
<223> OTHER INFORMATION: Synthetic sequence - E12N13 VH

<400> SEQUENCE: 17

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Arg Leu Tyr Tyr Tyr Tyr Met Asp Val Trp Gly
            100                 105                 110

Lys Gly Thr Thr Val Thr Val Ser Ser
            115                 120

<210> SEQ ID NO 18
<211> LENGTH: 111
<212> TYPE: PRT
<213> ORGANISM: Artificial Sequence
<220> FEATURE:
<223> OTHER INFORMATION: Synthetic sequence - E12N13 VL

<400> SEQUENCE: 18

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Ser Asp Ser Arg Pro Ala Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gly Thr Trp Asp Ser Ser
                85                  90                  95

Leu Ser Val Val Val Phe Gly Gly Gly Thr Lys Leu Thr Val Leu
            100                 105                 110

<210> SEQ ID NO 19
<211> LENGTH: 247
<212> TYPE: PRT
<213> ORGANISM: Artificial Sequence
<220> FEATURE:
<223> OTHER INFORMATION: Synthetic sequence - E12N13

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ala Pro Arg Leu Tyr Tyr Tyr Tyr Met Asp Val Trp Gly
            100                 105                 110

Lys Gly Thr Thr Val Thr Val Ser Ser Gly Gly Gly Ser Gly Gly
        115                 120                 125

Gly Gly Ser Gly Gly Gly Ser Gln Ser Val Leu Thr Gln Pro Pro
130                 135                 140

Ser Val Ser Gly Ala Pro Gly Gln Arg Val Thr Ile Ser Cys Thr Gly
145                 150                 155                 160

Ser Ser Ser Asn Ile Gly Ala Gly Tyr Asp Val His Trp Tyr Gln Gln
                165                 170                 175

Leu Pro Gly Thr Ala Pro Lys Leu Leu Ile Tyr Gly Ser Asp Ser Arg
            180                 185                 190

Pro Ala Gly Val Pro Asp Arg Phe Ser Gly Ser Lys Ser Gly Thr Ser
        195                 200                 205

Ala Ser Leu Ala Ile Thr Gly Leu Gln Ala Glu Asp Glu Ala Asp Tyr
    210                 215                 220

Tyr Cys Gly Thr Trp Asp Ser Ser Leu Ser Val Val Phe Gly Gly
225                 230                 235                 240

Gly Thr Lys Leu Thr Val Leu
                245

<210> SEQ ID NO 20
<211> LENGTH: 121
<212> TYPE: PRT
<213> ORGANISM: Artificial Sequence
<220> FEATURE:
<223> OTHER INFORMATION: Synthetic sequence - E12N1 VH

<400> SEQUENCE: 20

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met Asn Trp Val Arg Gln Ala Pro Gly Gln Gly Leu Glu Trp Met
        35                  40                  45

Gly Trp Ile Asn Pro Asn Gly Asp Pro Arg Tyr Ala Gln Lys Phe
    50                  55                  60

Gln Gly Arg Val Thr Leu Thr Ser Asp Ser Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Pro Lys Leu Thr Gly Asp Pro Ala Thr Phe Asp Leu Trp Gly
            100                 105                 110

Arg Ser Thr Leu Val Thr Val Pro Ser
        115                 120

<210> SEQ ID NO 21
<211> LENGTH: 109
<212> TYPE: PRT
<213> ORGANISM: Artificial Sequence
<220> FEATURE:
<223> OTHER INFORMATION: Synthetic sequence - E12N1 VL

<400> SEQUENCE: 21

Gln Ser Val Leu Thr Gln Pro Pro Ser Leu Ser Val Ser Pro Gly Gln
```

```
1               5                   10                  15
Thr Ala Ser Ile Thr Cys Ser Gly Asp Asn Leu Glu Asp Lys Tyr Ala
                20                  25                  30

Asn Trp Tyr Gln Gln Lys Pro Gly Gln Ser Pro Val Leu Val Ile Tyr
                35                  40                  45

Arg Asp Thr Lys Arg Pro Ser Gly Ile Pro Glu Arg Phe Ser Gly Ser
 50                  55                  60

Arg Ser Gly Thr Ser Ala Ser Leu Ala Ile Thr Gly Val Gln Ala Glu
 65                  70                  75                  80

Asp Glu Ala Asp Tyr Tyr Cys Gln Ser Tyr Asp Asn Ser Val Arg Gly
                85                  90                  95

Ser Arg Val Phe Gly Thr Gly Thr Lys Val Thr Val Leu
                100                 105

<210> SEQ ID NO 22
<211> LENGTH: 245
<212> TYPE: PRT
<213> ORGANISM: Artificial Sequence
<220> FEATURE:
<223> OTHER INFORMATION: Synthetic sequence - E12N1

<400> SEQUENCE: 22

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ser Met Asn Trp Val Arg Gln Ala Pro Gly Gln Gly Leu Glu Trp Met
                35                  40                  45

Gly Trp Ile Asn Pro Asn Gly Gly Asp Pro Arg Tyr Ala Gln Lys Phe
 50                  55                  60

Gln Gly Arg Val Thr Leu Thr Ser Asp Ser Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Ser Pro Lys Leu Thr Gly Asp Pro Ala Thr Phe Asp Leu Trp Gly
                100                 105                 110

Arg Ser Thr Leu Val Thr Val Pro Ser Gly Gly Gly Ser Gly Gly
                115                 120                 125

Gly Gly Ser Gly Gly Gly Ser Gln Ser Val Leu Thr Gln Pro Pro
                130                 135                 140

Ser Leu Ser Val Ser Pro Gly Gln Thr Ala Ser Ile Thr Cys Ser Gly
145                 150                 155                 160

Asp Asn Leu Glu Asp Lys Tyr Ala Asn Trp Tyr Gln Gln Lys Pro Gly
                165                 170                 175

Gln Ser Pro Val Leu Val Ile Tyr Arg Asp Thr Lys Arg Pro Ser Gly
                180                 185                 190

Ile Pro Glu Arg Phe Ser Gly Ser Arg Ser Gly Thr Ser Ala Ser Leu
                195                 200                 205

Ala Ile Thr Gly Val Gln Ala Glu Asp Glu Ala Asp Tyr Tyr Cys Gln
                210                 215                 220

Ser Tyr Asp Asn Ser Val Arg Gly Ser Arg Val Phe Gly Thr Gly Thr
225                 230                 235                 240

Lys Val Thr Val Leu
                245
```

```
<210> SEQ ID NO 23
<211> LENGTH: 124
<212> TYPE: PRT
<213> ORGANISM: Artificial Sequence
<220> FEATURE:
<223> OTHER INFORMATION: Synthetic sequence - E12N11 VH

<400> SEQUENCE: 23

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Lys Asp Pro Val Phe Lys Ser Pro Ser Ile Ala Gly Leu Leu Asp
            100                 105                 110

Tyr Trp Gly Gln Gly Thr Leu Val Thr Val Ser Ser
        115                 120

<210> SEQ ID NO 24
<211> LENGTH: 109
<212> TYPE: PRT
<213> ORGANISM: Artificial Sequence
<220> FEATURE:
<223> OTHER INFORMATION: Synthetic sequence - E12N11 VL

<400> SEQUENCE: 24

Ser Tyr Val Leu Thr Gln Asp Pro Ala Val Ser Val Ala Leu Gly Gln
1               5                   10                  15

Thr Val Arg Ile Thr Cys Gln Gly Asp Ser Leu Arg Asn Ser Tyr Ala
            20                  25                  30

Asn Trp Tyr Gln Gln Lys Pro Gly Gln Ala Pro Val Leu Val Ile Tyr
        35                  40                  45

Ala Lys Thr Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Tyr Asp Asn Ser Leu Arg Gly
                85                  90                  95

Ser Arg Val Phe Gly Thr Gly Thr Lys Leu Thr Val Leu
            100                 105

<210> SEQ ID NO 25
<211> LENGTH: 248
<212> TYPE: PRT
<213> ORGANISM: Artificial Sequence
<220> FEATURE:
<223> OTHER INFORMATION: Synthetic sequence - E12N11

<400> SEQUENCE: 25

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

Ser Met Asn Trp Val Arg Gln Ala Pro Gly Lys Gly Leu Glu Trp Val
         35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ser Lys Asn Thr Leu His
 65                  70                  75                  80

Leu Gln Met Asn Ser Leu Arg Ala Glu Asp Thr Ala Val Tyr Tyr Cys
                 85                  90                  95

Ala Lys Asp Pro Val Phe Lys Ser Pro Ser Ile Ala Gly Leu Leu Asp
                100                 105                 110

Tyr Trp Gly Gln Gly Thr Leu Val Thr Val Ser Gly Gly Gly
            115                 120                 125

Ser Gly Gly Gly Gly Ser Gly Gly Gly Ser Ser Tyr Val Leu Thr
        130                 135                 140

Gln Asp Pro Ala Val Ser Val Ala Leu Gly Gln Thr Val Arg Ile Thr
145                 150                 155                 160

Cys Gln Gly Asp Ser Leu Arg Asn Ser Tyr Ala Asn Trp Tyr Gln Gln
                165                 170                 175

Lys Pro Gly Gln Ala Pro Val Leu Val Ile Tyr Ala Lys Thr Asn Arg
            180                 185                 190

Pro Ser Gly Ile Pro Asp Arg Phe Ser Gly Ser Ser Gly Asn Thr
            195                 200                 205

Ala Ser Leu Thr Ile Thr Gly Ala Gln Ala Glu Asp Glu Ala Asp Tyr
210                 215                 220

Tyr Cys Gln Ser Tyr Asp Asn Ser Leu Arg Gly Ser Arg Val Phe Gly
225                 230                 235                 240

Thr Gly Thr Lys Leu Thr Val Leu
                245

<210> SEQ ID NO 26
<211> LENGTH: 124
<212> TYPE: PRT
<213> ORGANISM: Artificial Sequence
<220> FEATURE:
<223> OTHER INFORMATION: Synthetic sequence - E12N11R VH

<400> SEQUENCE: 26

Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
         35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ser Lys Asn Thr Leu His
 65                  70                  75                  80

Leu Gln Met Asn Ser Leu Arg Ala Glu Asp Thr Ala Val Tyr Tyr Arg
                 85                  90                  95

Ala Lys Asp Pro Val Phe Lys Ser Pro Ser Ile Ala Gly Leu Leu Asp
                100                 105                 110

Tyr Trp Gly Gln Gly Thr Leu Val Thr Val Ser Ser
            115                 120

<210> SEQ ID NO 27

```
<211> LENGTH: 109
<212> TYPE: PRT
<213> ORGANISM: Artificial Sequence
<220> FEATURE:
<223> OTHER INFORMATION: Synthetic sequence - E12N11R VL

<400> SEQUENCE: 27

Ser Tyr Val Leu Thr Gln Asp Pro Ala Val Ser Val Ala Leu Gly Gln
1               5                   10                  15

Thr Val Arg Ile Thr Cys Gln Gly Asp Ser Leu Arg Asn Ser Tyr Ala
            20                  25                  30

Asn Trp Tyr Gln Gln Lys Pro Gly Gln Ala Pro Val Leu Val Ile Tyr
        35                  40                  45

Ala Lys Thr Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Tyr Asp Asn Ser Leu Arg Gly
                85                  90                  95

Ser Arg Val Phe Gly Thr Gly Thr Lys Leu Thr Val Leu
            100                 105

<210> SEQ ID NO 28
<211> LENGTH: 248
<212> TYPE: PRT
<213> ORGANISM: Artificial Sequence
<220> FEATURE:
<223> OTHER INFORMATION: Synthetic sequence - E12N11R

<400> SEQUENCE: 28

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Arg
                85                  90                  95

Ala Lys Asp Pro Val Phe Lys Ser Pro Ser Ile Ala Gly Leu Leu Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Ser Tyr Val Leu Thr
130                 135                 140

Gln Asp Pro Ala Val Ser Val Ala Leu Gly Gln Thr Val Arg Ile Thr
145                 150                 155                 160

Cys Gln Gly Asp Ser Leu Arg Asn Ser Tyr Ala Asn Trp Tyr Gln Gln
                165                 170                 175

Lys Pro Gly Gln Ala Pro Val Leu Val Ile Tyr Ala Lys Thr Asn Arg
            180                 185                 190

Pro Ser Gly Ile Pro Asp Arg Phe Ser Gly Ser Ser Ser Gly Asn Thr
        195                 200                 205

Ala Ser Leu Thr Ile Thr Gly Ala Gln Ala Glu Asp Glu Ala Asp Tyr
```

Tyr Cys Gln Ser Tyr Asp Asn Ser Leu Arg Gly Ser Arg Val Phe Gly
225                 230                 235                 240

Thr Gly Thr Lys Leu Thr Val Leu
                245

<210> SEQ ID NO 29
<211> LENGTH: 122
<212> TYPE: PRT
<213> ORGANISM: Artificial Sequence
<220> FEATURE:
<223> OTHER INFORMATION: Synthetic sequence - E12N35 VH

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Lys Pro Pro Gly Ile Ala Val Ala Gly Leu Phe Tyr Trp
            100                 105                 110

Gly Gln Gly Thr Leu Val Thr Val Ser Ser
        115                 120

<210> SEQ ID NO 30
<211> LENGTH: 107
<212> TYPE: PRT
<213> ORGANISM: Artificial Sequence
<220> FEATURE:
<223> OTHER INFORMATION: Synthetic sequence - E12N35 VL

<400> SEQUENCE: 30

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
                20                  25                  30

Trp Tyr Gln Gln Lys Pro Gly Gln Ala Pro Val Leu Val Ile Tyr Gly
            35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn Tyr Val
                85                  90                  95

Val Phe Gly Gly Gly Thr Lys Leu Thr Val Leu
            100                 105

<210> SEQ ID NO 31
<211> LENGTH: 244
<212> TYPE: PRT
<213> ORGANISM: Artificial Sequence
<220> FEATURE:

<223> OTHER INFORMATION: Synthetic sequence - E12N35

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Lys Pro Pro Gly Ile Ala Val Ala Gly Leu Phe Tyr Trp
            100                 105                 110

Gly Gln Gly Thr Leu Val Thr Val Ser Ser Gly Gly Gly Ser Gly
            115                 120                 125

Gly Gly Gly Ser Gly Gly Gly Ser Ser Glu Leu Thr Gln Asp Pro
        130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Asn Thr Ala Ser Leu
        195                 200                 205

Thr Ile Thr Gly Ala Gln Ala Glu Asp Glu Ala Asp Tyr Tyr Cys Asn
    210                 215                 220

Ser Arg Asp Ser Ser Gly Asn Tyr Val Val Phe Gly Gly Gly Thr Lys
225                 230                 235                 240

Leu Thr Val Leu
```

<210> SEQ ID NO 32
<211> LENGTH: 122
<212> TYPE: PRT
<213> ORGANISM: Artificial Sequence
<220> FEATURE:
<223> OTHER INFORMATION: Synthetic sequence - E12N39 VH

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Pro Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Ala Lys Pro Pro Gly Ile Ala Val Ala Gly Leu Leu Tyr Trp
            100                 105                 110

Gly Gln Gly Thr Leu Val Thr Val Ser Ser
        115                 120
```

<210> SEQ ID NO 33
<211> LENGTH: 107
<212> TYPE: PRT
<213> ORGANISM: Artificial Sequence
<220> FEATURE:
<223> OTHER INFORMATION: Synthetic sequence - E12N39 VL

<400> SEQUENCE: 33

```
Ser Glu Leu Thr His Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn Tyr Val
                85                  90                  95

Val Phe Gly Gly Gly Thr Lys Leu Thr Val Leu
            100                 105
```

<210> SEQ ID NO 34
<211> LENGTH: 244
<212> TYPE: PRT
<213> ORGANISM: Artificial Sequence
<220> FEATURE:
<223> OTHER INFORMATION: Synthetic construct - E12N39

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Pro Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Ala Lys Pro Pro Gly Ile Ala Val Ala Gly Leu Leu Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Ser Glu Leu Thr His Asp Pro
    130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175
```

```
Gln Ala Pro Val Leu Val Ile Tyr Gly Lys Asn Asn Arg Pro Ser Gly
            180                 185                 190

Ile Pro Asp Arg Phe Ser Gly Ser Ser Gly Asn Thr Ala Ser Leu
            195                 200                 205

Thr Ile Thr Gly Ala Gln Ala Glu Asp Glu Ala Asp Tyr Tyr Cys Asn
        210                 215                 220

Ser Arg Asp Ser Ser Gly Asn Tyr Val Val Phe Gly Gly Gly Thr Lys
225                 230                 235                 240

Leu Thr Val Leu

<210> SEQ ID NO 35
<211> LENGTH: 122
<212> TYPE: PRT
<213> ORGANISM: Artificial Sequence
<220> FEATURE:
<223> OTHER INFORMATION: Synthetic sequence - E12N45 VH

<400> SEQUENCE: 35

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Thr Ser Leu Arg Ala Glu Asp Thr Ala Val Tyr Tyr Cys
                85                  90                  95

Ala Arg Tyr Ser Ser Gly Trp Pro Arg Ala Glu Tyr Phe Gln His Trp
            100                 105                 110

Gly Gln Gly Thr Leu Val Thr Val Ser Ser
            115                 120

<210> SEQ ID NO 36
<211> LENGTH: 110
<212> TYPE: PRT
<213> ORGANISM: Artificial Sequence
<220> FEATURE:
<223> OTHER INFORMATION: Synthetic sequence - E12N45 VL

<400> SEQUENCE: 36

Ser Glu Leu Thr Gln Asp Pro Ala Val Ser Val Ala Leu Gly Gln Pro
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asp Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn Arg His
                85                  90                  95

Ser Asn Tyr Val Phe Gly Ile Gly Thr Lys Val Thr Val Leu
            100                 105                 110
```

<210> SEQ ID NO 37
<211> LENGTH: 247
<212> TYPE: PRT
<213> ORGANISM: Artificial Sequence
<220> FEATURE:
<223> OTHER INFORMATION: Synthetic sequence - E12N45

<400> SEQUENCE: 37

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Thr Ser Leu Arg Ala Glu Asp Thr Ala Val Tyr Tyr Cys
                85                  90                  95

Ala Arg Tyr Ser Ser Gly Trp Pro Arg Ala Glu Tyr Phe Gln His Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Ser Glu Leu Thr Gln Asp Pro
    130                 135                 140

Ala Val Ser Val Ala Leu Gly Gln Pro Val Arg Ile Thr Cys Gln Gly
145                 150                 155                 160

Asp Ser Leu Arg Ser Tyr Tyr Ala Ser Trp Tyr Gln Gln Lys Pro Gly
            165                 170                 175

Gln Ala Pro Val Leu Val Ile Tyr Gly Lys Asn Asn Arg Pro Ser Gly
        180                 185                 190

Ile Pro Asp Arg Phe Ser Gly Ser Ser Ser Gly Asp Thr Ala Ser Leu
    195                 200                 205

Thr Ile Thr Gly Ala Gln Ala Glu Asp Glu Ala Asp Tyr Tyr Cys Asn
210                 215                 220

Ser Arg Asp Ser Ser Gly Asn Arg His Ser Asn Tyr Val Phe Gly Ile
225                 230                 235                 240

Gly Thr Lys Val Thr Val Leu
                245
```

<210> SEQ ID NO 38
<211> LENGTH: 122
<212> TYPE: PRT
<213> ORGANISM: Artificial Sequence
<220> FEATURE:
<223> OTHER INFORMATION: Synthetic sequence - E12N45T VH

<400> SEQUENCE: 38

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
```

```
                    50                  55                  60
Lys Gly Arg Phe Thr Ile Ser Arg Asp Asn Ser Lys Asp Thr Leu Tyr
 65                  70                  75                  80

Leu Gln Met Thr Ser Leu Arg Ala Glu Asp Thr Ala Val Tyr Tyr Cys
                    85                  90                  95

Ala Arg Tyr Ser Ser Gly Trp Pro Arg Ala Glu Tyr Phe Gln His Trp
                   100                 105                 110

Gly Gln Gly Thr Leu Val Thr Val Ser Ser
               115                 120

<210> SEQ ID NO 39
<211> LENGTH: 110
<212> TYPE: PRT
<213> ORGANISM: Artificial Sequence
<220> FEATURE:
<223> OTHER INFORMATION: Synthetic sequence - E12N45T VL

<400> SEQUENCE: 39

Ser Glu Leu Thr Gln Asp Pro Ala Val Ser Val Ala Leu Gly Gln Pro
 1               5                  10                  15

Val Arg Ile Thr Cys Gln Gly Asp Ser Leu Arg Ser Tyr Tyr Ala Ser
                    20                  25                  30

Trp Tyr Gln Gln Lys Pro Gly Gln Ala Pro Val Leu Val Ile Tyr Gly
                35                  40                  45

Lys Asn Asn Arg Pro Ser Gly Ile Pro Asp Arg Phe Ser Gly Ser Ser
 50                  55                  60

Ser Gly Asp Thr Ala Ser Leu Thr Ile Thr Gly Ala Gln Ala Glu Asp
 65                  70                  75                  80

Glu Ala Asp Tyr Tyr Cys Asn Ser Arg Asp Ser Ser Gly Asn Arg His
                    85                  90                  95

Ser Asn Tyr Val Phe Gly Thr Gly Thr Lys Val Thr Val Leu
                   100                 105                 110

<210> SEQ ID NO 40
<211> LENGTH: 247
<212> TYPE: PRT
<213> ORGANISM: Artificial Sequence
<220> FEATURE:
<223> OTHER INFORMATION: Synthetic sequence - E12N45T

<400> SEQUENCE: 40

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                    20                  25                  30

Ala Met Ser Trp Val Arg Gln Ala Pro Gly Lys Gly Leu Glu Trp Val
                35                  40                  45

Ser Gly Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asp Thr Leu Tyr
 65                  70                  75                  80

Leu Gln Met Thr Ser Leu Arg Ala Glu Asp Thr Ala Val Tyr Tyr Cys
                    85                  90                  95

Ala Arg Tyr Ser Ser Gly Trp Pro Arg Ala Glu Tyr Phe Gln His Trp
                   100                 105                 110

Gly Gln Gly Thr Leu Val Thr Val Ser Ser Gly Gly Gly Gly Ser Gly
               115                 120                 125
```

Gly Gly Gly Ser Gly Gly Gly Ser Ser Glu Leu Thr Gln Asp Pro
            130                 135                 140

Ala Val Ser Val Ala Leu Gly Gln Pro Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Gly Asp Thr Ala Ser Leu
        195                 200                 205

Thr Ile Thr Gly Ala Gln Ala Glu Asp Glu Ala Asp Tyr Tyr Cys Asn
210                 215                 220

Ser Arg Asp Ser Ser Gly Asn Arg His Ser Asn Tyr Val Phe Gly Thr
225                 230                 235                 240

Gly Thr Lys Val Thr Val Leu
            245

<210> SEQ ID NO 41
<211> LENGTH: 122
<212> TYPE: PRT
<213> ORGANISM: Artificial Sequence
<220> FEATURE:
<223> OTHER INFORMATION: Synthetic sequence - E34N19 VH

<400> SEQUENCE: 41

Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Gly His Gly Gly Asn Ser Gly Trp Val Asp Tyr Trp
            100                 105                 110

Gly Gln Gly Thr Leu Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: Synthetic construct - E34N19 VL

<400> SEQUENCE: 42

Gln Ser Val Leu Thr Gln Asp Pro Ala Val Ser Val Ala Leu Gly Gln
1               5                   10                  15

Thr Val Lys Ile Thr Cys Gln Gly Asp Ser Leu Arg Tyr Tyr Thr
            20                  25                  30

Ser Trp Tyr Gln Gln Arg Pro Gly Gln Ala Pro Ile Leu Val Leu Tyr
        35                  40                  45

Ala Asn Thr His Arg Pro Ser Ser Ile Pro Asp Arg Phe Ser Gly Ser
    50                  55                  60

```
Ser Ser Gly Thr Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Tyr
                85                  90                  95

Leu Phe Gly Gly Gly Thr Lys Leu Thr Val Leu
            100                 105
```

<210> SEQ ID NO 43
<211> LENGTH: 244
<212> TYPE: PRT
<213> ORGANISM: Artificial Sequence
<220> FEATURE:
<223> OTHER INFORMATION: Synthetic sequence - E34N19

<400> SEQUENCE: 43

```
Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Gly His Gly Gly Asn Ser Gly Trp Val Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gln Ser Val Leu Thr Gln Asp
    130                 135                 140

Pro Ala Val Ser Val Ala Leu Gly Gln Thr Val Lys Ile Thr Cys Gln
145                 150                 155                 160

Gly Asp Ser Leu Arg Thr Tyr Tyr Thr Ser Trp Tyr Gln Gln Arg Pro
                165                 170                 175

Gly Gln Ala Pro Ile Leu Val Leu Tyr Ala Asn Thr His Arg Pro Ser
            180                 185                 190

Ser Ile Pro Asp Arg Phe Ser Gly Ser Ser Ser Gly Thr Thr Ala Ser
        195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Asn Tyr Leu Phe Gly Gly Gly Thr Lys
225                 230                 235                 240

Leu Thr Val Leu
```

<210> SEQ ID NO 44
<211> LENGTH: 122
<212> TYPE: PRT
<213> ORGANISM: Artificial Sequence
<220> FEATURE:
<223> OTHER INFORMATION: Synthetic sequence - E34N19EQV VH

<400> SEQUENCE: 44

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Gly His Gly Gly Asn Ser Gly Trp Val Asp Tyr Trp
            100                 105                 110

Gly Gln Gly Thr Leu Val Thr Val Ser Ser
            115                 120

<210> SEQ ID NO 45
<211> LENGTH: 107
<212> TYPE: PRT
<213> ORGANISM: Artificial Sequence
<220> FEATURE:
<223> OTHER INFORMATION: Synthetic sequence - E34N19EQV VL

<400> SEQUENCE: 45

Gln Ser Val Leu Thr Gln Asp Pro Ala Val Ser Val Ala Leu Gly Gln
1               5                   10                  15

Thr Val Lys Ile Thr Cys Gln Gly Asp Ser Leu Arg Thr Tyr Tyr Thr
            20                  25                  30

Ser Trp Tyr Gln Gln Arg Pro Gly Gln Ala Pro Ile Leu Val Leu Tyr
            35                  40                  45

Ala Asn Thr His Arg Pro Ser Ser Ile Pro Asp Arg Phe Ser Gly Ser
        50                  55                  60

Ser Ser Gly Thr Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Tyr
                85                  90                  95

Leu Phe Gly Gly Gly Thr Lys Leu Thr Val Leu
            100                 105

<210> SEQ ID NO 46
<211> LENGTH: 244
<212> TYPE: PRT
<213> ORGANISM: Artificial Sequence
<220> FEATURE:
<223> OTHER INFORMATION: Synthetic sequence - E34N19EQV

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Lys Val Arg Gly His Gly Gly Asn Ser Gly Trp Val Asp Tyr Trp
                    100                 105                 110

Gly Gln Gly Thr Leu Val Thr Val Ser Ser Gly Gly Gly Ser Gly
            115                 120                 125

Gly Gly Gly Ser Gly Gly Gly Ser Gln Ser Val Leu Thr Gln Asp
        130                 135                 140

Pro Ala Val Ser Val Ala Leu Gly Gln Thr Val Lys Ile Thr Cys Gln
145                 150                 155                 160

Gly Asp Ser Leu Arg Thr Tyr Tyr Thr Ser Trp Tyr Gln Gln Arg Pro
                165                 170                 175

Gly Gln Ala Pro Ile Leu Val Leu Tyr Ala Asn Thr His Arg Pro Ser
                180                 185                 190

Ser Ile Pro Asp Arg Phe Ser Gly Ser Ser Ser Gly Thr Thr Ala Ser
                195                 200                 205

Leu Thr Ile Thr Gly Ala Gln Ala Glu Asp Glu Ala Asp Tyr Tyr Cys
            210                 215                 220

Asn Ser Arg Asp Ser Ser Gly Asn Tyr Leu Phe Gly Gly Gly Thr Lys
225                 230                 235                 240

Leu Thr Val Leu

<210> SEQ ID NO 47
<211> LENGTH: 121
<212> TYPE: PRT
<213> ORGANISM: Artificial Sequence
<220> FEATURE:
<223> OTHER INFORMATION: Synthetic sequence - E34N1 VH

<400> SEQUENCE: 47

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Thr Met Ser Val Ser Gly Ala Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Tyr Tyr Tyr Asp Ser Ser Gly Tyr Tyr Asp Trp Gly
                100                 105                 110

Gln Gly Thr Leu Val Thr Val Ser Ser
            115                 120

<210> SEQ ID NO 48
<211> LENGTH: 106
<212> TYPE: PRT
<213> ORGANISM: Artificial Sequence
<220> FEATURE:
<223> OTHER INFORMATION: Synthetic sequence - E34N1 VL

<400> SEQUENCE: 48

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
```

```
                    20                  25                  30

Trp Tyr Gln Gln Lys Pro Gly Gln Ala Pro Val Leu Val Ile Tyr Gly
            35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Thr Val Val
                85                  90                  95

Phe Gly Gly Gly Thr Lys Leu Thr Val Leu
            100                 105

<210> SEQ ID NO 49
<211> LENGTH: 242
<212> TYPE: PRT
<213> ORGANISM: Artificial Sequence
<220> FEATURE:
<223> OTHER INFORMATION: Synthetic sequence - E34N1

<400> SEQUENCE: 49

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Met Ser Val Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Tyr Tyr Asp Ser Ser Gly Tyr Tyr Asp Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Thr Val Val Phe Gly Gly Gly Thr Lys Leu Thr
225                 230                 235                 240

Val Leu

<210> SEQ ID NO 50
<211> LENGTH: 116
<212> TYPE: PRT
<213> ORGANISM: Artificial Sequence
```

<220> FEATURE:
<223> OTHER INFORMATION: Synthetic sequence - E34N2 VH

<400> SEQUENCE: 50

```
Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Phe Met Thr Trp Val Arg Gln Ala Pro Gly Lys Gly Leu Glu Trp Val
        35                  40                  45

Ser Val Ile Tyr Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Ser Tyr Val Asp Tyr Trp Gly Gln Gly Thr Leu Val
            100                 105                 110

Thr Val Ser Ser
        115
```

<210> SEQ ID NO 51
<211> LENGTH: 110
<212> TYPE: PRT
<213> ORGANISM: Artificial Sequence
<220> FEATURE:
<223> OTHER INFORMATION: Synthetic sequence - E34N2 VL

<400> SEQUENCE: 51

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Asn
                85                  90                  95

Tyr Ser Trp Ile Phe Gly Gly Gly Thr Lys Val Thr Val Leu
            100                 105                 110
```

<210> SEQ ID NO 52
<211> LENGTH: 241
<212> TYPE: PRT
<213> ORGANISM: Artificial Sequence
<220> FEATURE:
<223> OTHER INFORMATION: Synthetic sequence - E34N2

<400> SEQUENCE: 52

```
Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Phe Met Thr Trp Val Arg Gln Ala Pro Gly Lys Gly Leu Glu Trp Val
        35                  40                  45
```

```
Ser Val Ile Tyr Gly Gly Asn Thr Tyr Tyr Ala Asp Ser Val Lys
    50              55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Arg Gly Arg Tyr Ser Tyr Val Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Ala Leu Thr Gln Pro Ala Ser Val Ser Gly Ser
130                 135                 140

Pro Gly Gln Ser Ile Thr Ile Ser Cys Thr Gly Thr Ser Ser Asp Val
145                 150                 155                 160

Gly Gly Tyr Asn Tyr Val Ser Trp Tyr Gln Gln His Pro Gly Lys Ala
                165                 170                 175

Pro Lys Leu Met Ile Tyr Glu Val Ser Asn Arg Pro Ser Gly Val Ser
            180                 185                 190

Asn Arg Phe Ser Gly Ser Lys Ser Gly Asn Thr Ala Ser Leu Thr Ile
        195                 200                 205

Ser Gly Leu Gln Ala Glu Asp Glu Ala Asp Tyr Tyr Cys Ser Ser Tyr
210                 215                 220

Ala Gly Asn Tyr Ser Trp Ile Phe Gly Gly Gly Thr Lys Val Thr Val
225                 230                 235                 240

Leu

<210> SEQ ID NO 53
<211> LENGTH: 118
<212> TYPE: PRT
<213> ORGANISM: Artificial Sequence
<220> FEATURE:
<223> OTHER INFORMATION: Synthetic sequence - E34N3 VH

<400> SEQUENCE: 53

Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Thr Pro Glu Gly Trp Asp Tyr Trp Gly Gln Gly Thr
            100                 105                 110

Leu Val Thr Val Ser Ser
        115

<210> SEQ ID NO 54
<211> LENGTH: 107
<212> TYPE: PRT
<213> ORGANISM: Artificial Sequence
<220> FEATURE:
<223> OTHER INFORMATION: Synthetic sequence - E34N3 VL
```

<400> SEQUENCE: 54

Ser Glu Leu Thr Gln Asp Pro Ala Val Ser Val Ala Leu Gly Gln Thr
1               5                   10                  15

Val Arg Ile Thr Cys Gln Gly Asp Ser Leu Lys Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Leu
                85                  90                  95

Val Phe Gly Gly Gly Thr Lys Leu Thr Val Leu
            100                 105

<210> SEQ ID NO 55
<211> LENGTH: 240
<212> TYPE: PRT
<213> ORGANISM: Artificial Sequence
<220> FEATURE:
<223> OTHER INFORMATION: Synthetic sequence - E34N3

<400> SEQUENCE: 55

Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Thr Pro Glu Gly Trp Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Ser Glu Leu Thr Gln Asp Pro Ala Val Ser Val
        130                 135                 140

Ala Leu Gly Gln Thr Val Arg Ile Thr Cys Gln Gly Asp Ser Leu Lys
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
    210                 215                 220

Ser Gly Asn His Leu Val Phe Gly Gly Gly Thr Lys Leu Thr Val Leu
225                 230                 235                 240

<210> SEQ ID NO 56
<211> LENGTH: 116
<212> TYPE: PRT
<213> ORGANISM: Artificial Sequence
<220> FEATURE:
<223> OTHER INFORMATION: Synthetic sequence - E34N4 VH

<400> SEQUENCE: 56

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Gly Tyr Tyr Asp Val Asp Tyr Trp Gly Gln Gly Thr Leu Val
            100                 105                 110

Thr Val Ser Ser
            115
```

<210> SEQ ID NO 57
<211> LENGTH: 107
<212> TYPE: PRT
<213> ORGANISM: Artificial Sequence
<220> FEATURE:
<223> OTHER INFORMATION: Synthetic sequence - E34N4 VL

<400> SEQUENCE: 57

```
Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105
```

<210> SEQ ID NO 58
<211> LENGTH: 238
<212> TYPE: PRT
<213> ORGANISM: Artificial Sequence
<220> FEATURE:
<223> OTHER INFORMATION: Synthetic sequence - E34N4

<400> SEQUENCE: 58

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
Ala Met Ser Trp Val Arg Gln Ala Pro Gly Lys Gly Leu Glu Trp Val
                35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Gly Tyr Tyr Asp Val Asp Tyr Trp Gly Gln Gly Thr Leu Val
            100                 105                 110

Thr Val Ser Ser Gly Gly Gly Ser Gly Gly Gly Ser Gly Gly
            115                 120                 125

Gly Gly Ser Asp Val Val Met Thr Gln Ser Pro Ser Ser Leu Ser Ala
        130                 135                 140

Ser Val Gly Asp Arg Val Thr Ile Thr Cys Gln Ala Ser Gln Asp Ile
145                 150                 155                 160

Ser Asn Tyr Leu Asn Trp Tyr Gln Gln Lys Pro Gly Lys Ala Pro Lys
                165                 170                 175

Leu Leu Ile Tyr Ala Ala Ser Ser Leu Gln Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Gln Gln Ser Tyr Ser
    210                 215                 220

Thr Pro Pro Thr Phe Gly Gln Gly Thr Lys Val Glu Ile Lys
225                 230                 235

<210> SEQ ID NO 59
<211> LENGTH: 118
<212> TYPE: PRT
<213> ORGANISM: Artificial Sequence
<220> FEATURE:
<223> OTHER INFORMATION: Synthetic sequence - E34N5 VH

<400> SEQUENCE: 59

Gln Val Gln Leu Leu Gln Ser Ala Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Asp Tyr Pro Tyr Met Asp Val Trp Gly Gln Gly Thr
            100                 105                 110

Thr Val Thr Val Ser Ser
        115

<210> SEQ ID NO 60
<211> LENGTH: 111
<212> TYPE: PRT
```

```
<213> ORGANISM: Artificial Sequence
<220> FEATURE:
<223> OTHER INFORMATION: Synthetic sequence - E34N5 VL

<400> SEQUENCE: 60

Gln Ser Val Leu Thr Gln Pro Pro Ser Val Gly Ala Pro Gly Gln
1               5                   10                  15

Arg Val Thr Ile Ser Cys Thr Gly Ser Ser Asn Val Gly Ala Gly
                20                  25                  30

Phe Asp Val His Trp Tyr Gln Gln Leu Pro Gly Thr Ala Pro Lys Leu
            35                  40                  45

Leu Ile Tyr Gly Asp Asn Asn Arg Pro Ser Gly Val Pro Asp Arg Phe
50                      55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Val Thr Val Leu
                100                 105                 110

<210> SEQ ID NO 61
<211> LENGTH: 244
<212> TYPE: PRT
<213> ORGANISM: Artificial Sequence
<220> FEATURE:
<223> OTHER INFORMATION: Synthetic sequence - E34N5

<400> SEQUENCE: 61

Gln Val Gln Leu Leu Gln Ser Ala Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Asp Tyr Pro Tyr Met Asp Val Trp Gly Gln Gly Thr
            100                 105                 110

Thr Val Thr Val Ser Ser Gly Gly Gly Gly Ser Gly Gly Gly Gly Ser
            115                 120                 125

Gly Gly Gly Gly Ser Gln Ser Val Leu Thr Gln Pro Pro Ser Val Ser
130                 135                 140

Gly Ala Pro Gly Gln Arg Val Thr Ile Ser Cys Thr Gly Ser Ser Ser
145                 150                 155                 160

Asn Val Gly Ala Gly Phe Asp Val His Trp Tyr Gln Gln Leu Pro Gly
                165                 170                 175

Thr Ala Pro Lys Leu Leu Ile Tyr Gly Asp Asn Asn Arg Pro Ser Gly
            180                 185                 190

Val Pro Asp Arg Phe Ser Gly Ser Arg Ser Gly Thr Ser Ala Ser Leu
        195                 200                 205

Ala Ile Thr Gly Leu Gln Ala Glu Asp Glu Ala Asp Tyr Tyr Cys Gln
    210                 215                 220
```

-continued

Ser Tyr Asp Ser Ser Leu Ser Gly Ser Val Phe Gly Gly Gly Thr Lys
225                 230                 235                 240

Val Thr Val Leu

<210> SEQ ID NO 62
<211> LENGTH: 123
<212> TYPE: PRT
<213> ORGANISM: Artificial Sequence
<220> FEATURE:
<223> OTHER INFORMATION: Synthetic sequence - E34N6 VH

<400> SEQUENCE: 62

Gln Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Ile Gly Pro Ser Gly Ser Thr Tyr Tyr Ala Tyr Ala Asp
    50                  55                  60

Ser Val Lys Gly Arg Phe Thr Ile Ser Arg Asp Asn Tyr Lys Asn Met
65                  70                  75                  80

Leu Tyr Leu Gln Met Asn Ser Leu Arg Ala Glu Asp Thr Ala Val Tyr
                85                  90                  95

Tyr Cys Ala Lys Glu Gly Pro Asn Ser Gly Tyr Phe Asp Phe Asp Tyr
            100                 105                 110

Trp Gly Gln Gly Thr Leu Val Thr Val Ser Ser
        115                 120

<210> SEQ ID NO 63
<211> LENGTH: 107
<212> TYPE: PRT
<213> ORGANISM: Artificial Sequence
<220> FEATURE:
<223> OTHER INFORMATION: Synthetic sequence - E34N6 VL

<400> SEQUENCE: 63

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Ile Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gly Gly Thr Lys Leu Glu Ile Lys
            100                 105

<210> SEQ ID NO 64
<211> LENGTH: 245
<212> TYPE: PRT
<213> ORGANISM: Artificial Sequence
<220> FEATURE:
<223> OTHER INFORMATION: Synthetic sequence - E34N6

<400> SEQUENCE: 64

Gln Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Ile Gly Pro Ser Gly Ser Thr Tyr Tyr Ala Tyr Ala Asp
    50                  55                  60

Ser Val Lys Gly Arg Phe Thr Ile Ser Arg Asp Asn Tyr Lys Asn Met
65                  70                  75                  80

Leu Tyr Leu Gln Met Asn Ser Leu Arg Ala Glu Asp Thr Ala Val Tyr
                85                  90                  95

Tyr Cys Ala Lys Glu Gly Pro Asn Ser Gly Tyr Phe Asp Phe Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Ile Val Leu Thr Gln
            130                 135                 140

Ser Pro Ser Ser Leu Ser Ala Ser Val Gly Asp Arg Val Thr Ile Thr
145                 150                 155                 160

Cys Arg Ala Ser Gln Ser Ile Ser Thr Tyr Leu Asn Trp Tyr Gln Gln
            165                 170                 175

Lys Pro Gly Lys Ala Pro Lys Val Leu Ile Tyr Ala Ala Ser Ser Leu
            180                 185                 190

Gln Ser Gly Val Pro Ser Arg Ile Ser Gly Ser Gly Ser Gly Thr Asp
            195                 200                 205

Phe Thr Leu Thr Ile Ser Ser Leu Gln Pro Glu Asp Phe Ala Thr Tyr
        210                 215                 220

Tyr Cys Gln Gln Ser Tyr Ser Ile Pro Leu Thr Phe Gly Gly Gly Thr
225                 230                 235                 240

Lys Leu Glu Ile Lys
                245

<210> SEQ ID NO 65
<211> LENGTH: 128
<212> TYPE: PRT
<213> ORGANISM: Artificial Sequence
<220> FEATURE:
<223> OTHER INFORMATION: Synthetic sequence - E34N7 VH

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ser Ser Ser Tyr Pro Ile Ala Ala Arg Arg Tyr Tyr Tyr
            100                 105                 110

Tyr Gly Met Asp Val Trp Gly Gln Gly Thr Thr Val Thr Val Ser Ser
            115                 120                 125

<210> SEQ ID NO 66
<211> LENGTH: 110
<212> TYPE: PRT
<213> ORGANISM: Artificial Sequence
<220> FEATURE:
<223> OTHER INFORMATION: Synthetic sequence - E34N7 VL

<400> SEQUENCE: 66

Gln Ser Val Leu Thr Gln Pro Ala Ser Val Ser Gly Ser Pro Gly Gln
1               5                   10                  15

Ser Ile Thr Ile Ser Cys Thr Gly Thr Asn Ser Asp Val Gly Gly Tyr
            20                  25                  30

Asn Phe Val Ser Trp Tyr Gln Gln Tyr Pro Gly Lys Ala Pro Lys Leu
        35                  40                  45

Ile Ile Phe Asp Val Ser Asp Arg Pro Ser Arg Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Asn
                85                  90                  95

Asn Asn Val Val Phe Gly Gly Gly Thr Lys Leu Thr Val Leu
            100                 105                 110

<210> SEQ ID NO 67
<211> LENGTH: 253
<212> TYPE: PRT
<213> ORGANISM: Artificial Sequence
<220> FEATURE:
<223> OTHER INFORMATION: Synthetic sequence - E34N7

<400> SEQUENCE: 67

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ser Ser Ser Tyr Pro Ile Ala Ala Arg Arg Tyr Tyr Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Ser Gly Gly Gly Gly Ser Gln
        130                 135                 140

Ser Val Leu Thr Gln Pro Ala Ser Val Ser Gly Ser Pro Gly Gln Ser
145                 150                 155                 160

Ile Thr Ile Ser Cys Thr Gly Thr Asn Ser Asp Val Gly Gly Tyr Asn
                165                 170                 175

Phe Val Ser Trp Tyr Gln Gln Tyr Pro Gly Lys Ala Pro Lys Leu Ile

```
                180             185             190
Ile Phe Asp Val Ser Asp Arg Pro Ser Arg Val Ser Asn Arg Phe Ser
                    195                 200                 205

Gly Ser Lys Ser Gly Asn Thr Ala Ser Leu Thr Ile Ser Gly Leu Gln
            210                 215                 220

Ala Glu Asp Glu Ala Asp Tyr Tyr Cys Ser Ser Tyr Ala Gly Asn Asn
225                 230                 235                 240

Asn Val Val Phe Gly Gly Gly Thr Lys Leu Thr Val Leu
                245                 250

<210> SEQ ID NO 68
<211> LENGTH: 122
<212> TYPE: PRT
<213> ORGANISM: Artificial Sequence
<220> FEATURE:
<223> OTHER INFORMATION: Synthetic sequence - E34N8 VH

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Ser Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Tyr Tyr Asp Phe Trp Ser Gly Tyr Pro Phe Asp Tyr Trp
            100                 105                 110

Gly Gln Gly Thr Leu Val Thr Val Ser Ser
        115                 120

<210> SEQ ID NO 69
<211> LENGTH: 107
<212> TYPE: PRT
<213> ORGANISM: Artificial Sequence
<220> FEATURE:
<223> OTHER INFORMATION: Synthetic sequence - E34N8 VL

<400> SEQUENCE: 69

Asp Val Val Met Thr Gln Ser Pro Ser Thr Leu Ser Ala Ser Val Gly
1               5                   10                  15

Asp Arg Val Thr Ile Thr Cys Arg Ala Ser Gln Thr Ile Gly Ser Trp
            20                  25                  30

Leu Ala Trp Tyr Gln Gln Thr Pro Gly Arg Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Arg
                85                  90                  95

Thr Phe Gly Gln Gly Thr Lys Leu Glu Ile Lys
            100                 105
```

<210> SEQ ID NO 70
<211> LENGTH: 244
<212> TYPE: PRT
<213> ORGANISM: Artificial Sequence
<220> FEATURE:
<223> OTHER INFORMATION: Synthetic sequence - E34N8

<400> SEQUENCE: 70

```
Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Ser Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Tyr Tyr Asp Phe Trp Ser Gly Tyr Pro Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Val Val Met Thr Gln Ser
    130                 135                 140

Pro Ser Thr Leu Ser Ala Ser Val Gly Asp Arg Val Thr Ile Thr Cys
145                 150                 155                 160

Arg Ala Ser Gln Thr Ile Gly Ser Trp Leu Ala Trp Tyr Gln Gln Thr
                165                 170                 175

Pro Gly Arg Ala Pro Lys Leu Leu Ile Tyr Lys Ala Ser Ser Leu Glu
            180                 185                 190

Ser Gly Val Pro Ser Arg Phe Ser Gly Ser Glu Ser Gly Thr Asp Phe
        195                 200                 205

Thr Leu Thr Ile Ser Ser Leu Gln Pro Asp Asp Phe Ala Thr Tyr Tyr
    210                 215                 220

Cys Gln Gln Tyr Asn Ser Tyr Pro Arg Thr Phe Gly Gln Gly Thr Lys
225                 230                 235                 240

Leu Glu Ile Lys
```

<210> SEQ ID NO 71
<211> LENGTH: 121
<212> TYPE: PRT
<213> ORGANISM: Artificial Sequence
<220> FEATURE:
<223> OTHER INFORMATION: Synthetic sequence - E34N9 VH

<400> SEQUENCE: 71

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Ser Gly Tyr Ser Tyr Gly Tyr Val Asp Tyr Trp Gly
            100                 105                 110

Gln Gly Thr Leu Val Thr Val Ser Ser
        115                 120
```

```
<210> SEQ ID NO 72
<211> LENGTH: 108
<212> TYPE: PRT
<213> ORGANISM: Artificial Sequence
<220> FEATURE:
<223> OTHER INFORMATION: Synthetic sequence - E34N9 VL

<400> SEQUENCE: 72

Ser Glu Leu Thr Gln Asp Pro Ala Met Ser Val Ala Leu Gly Gln Thr
 1               5                  10                  15

Val Asn Ile Thr Cys Gln Gly Asp Ser Leu Arg Arg Tyr Phe Pro Ser
                 20                  25                  30

Trp Tyr Gln Gln Lys Pro Gly Gln Ala Pro Val Leu Val Leu Tyr Gly
             35                  40                  45

Arg Asn Thr Arg Pro Ser Gly Ile Pro Asp Arg Phe Ser Gly Ser Asn
 50                  55                  60

Ser Gly Asn Ser Ala Ser Leu Thr Ile Thr Gly Ala Gln Ala Glu Asp
 65                  70                  75                  80

Glu Ala Asp Tyr Tyr Cys His Ser Arg Gly Ser Ser Gly Thr His Leu
                 85                  90                  95

Arg Val Phe Gly Gly Gly Thr Lys Leu Thr Val Leu
            100                 105
```

```
<210> SEQ ID NO 73
<211> LENGTH: 244
<212> TYPE: PRT
<213> ORGANISM: Artificial Sequence
<220> FEATURE:
<223> OTHER INFORMATION: Synthetic sequence - E34N9

<400> SEQUENCE: 73

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Thr Ile Ser Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Ser Gly Tyr Ser Tyr Gly Tyr Val Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Ser Glu Leu Thr Gln Asp Pro Ala
        130                 135                 140
```

```
Met Ser Val Ala Leu Gly Gln Thr Val Asn Ile Thr Cys Gln Gly Asp
145                 150                 155                 160

Ser Leu Arg Arg Tyr Phe Pro Ser Trp Tyr Gln Gln Lys Pro Gly Gln
                165                 170                 175

Ala Pro Val Leu Val Leu Tyr Gly Arg Asn Thr Arg Pro Ser Gly Ile
            180                 185                 190

Pro Asp Arg Phe Ser Gly Ser Asn Ser Gly Asn Ser Ala Ser Leu Thr
        195                 200                 205

Ile Thr Gly Ala Gln Ala Glu Asp Glu Ala Asp Tyr Tyr Cys His Ser
    210                 215                 220

Arg Gly Ser Ser Gly Thr His Leu Arg Val Phe Gly Gly Gly Thr Lys
225                 230                 235                 240

Leu Thr Val Leu

<210> SEQ ID NO 74
<211> LENGTH: 120
<212> TYPE: PRT
<213> ORGANISM: Artificial Sequence
<220> FEATURE:
<223> OTHER INFORMATION: Synthetic sequence - E34N11 VH

<400> SEQUENCE: 74

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Gly Ser Thr Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Asp Asp Thr Ala Val Tyr Tyr Cys
                85                  90                  95

Ala Ala Ala Gly Gly Ala Ser Asn Trp Tyr Phe Asp Leu Trp Gly Arg
            100                 105                 110

Gly Thr Leu Val Thr Val Ser Ser
        115                 120

<210> SEQ ID NO 75
<211> LENGTH: 108
<212> TYPE: PRT
<213> ORGANISM: Artificial Sequence
<220> FEATURE:
<223> OTHER INFORMATION: Synthetic sequence - E34N11 VL

<400> SEQUENCE: 75

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Phe Asp Ala Ser
            20                  25                  30

Trp Tyr Gln Gln Lys Pro Gly Gln Ala Pro Val Val Ile Tyr Gly
        35                  40                  45

Glu Asn Asn Arg Pro Ser Gly Ile Pro Asp Arg Phe Ser Gly Ser Ser
    50                  55                  60

Ser Gly Asn Ser Ala Ser Leu Thr Ile Thr Gly Ala Gln Ala Glu Asp
65                  70                  75                  80
```

Glu Ala Asp Tyr Tyr Cys Ser Ser Arg Asp Ser Arg Gly Asn His Leu
                85                  90                  95

Ala Leu Phe Gly Gly Thr Lys Leu Thr Val Leu
            100                 105

<210> SEQ ID NO 76
<211> LENGTH: 243
<212> TYPE: PRT
<213> ORGANISM: Artificial Sequence
<220> FEATURE:
<223> OTHER INFORMATION: Synthetic sequence - E34N11

<400> SEQUENCE: 76

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Gly Ser Thr Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Asp Asp Thr Ala Val Tyr Tyr Cys
                85                  90                  95

Ala Ala Ala Gly Gly Ala Ser Asn Trp Tyr Phe Asp Leu Trp Gly Arg
            100                 105                 110

Gly Thr Leu Val Thr Val Ser Gly Gly Gly Ser Gly Gly Gly
            115                 120                 125

Gly Ser Gly Gly Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Phe Asp Ala Ser Trp Tyr Gln Gln Lys Pro Gly Gln Ala
                165                 170                 175

Pro Val Val Val Ile Tyr Gly Glu Asn Asn Arg Pro Ser Gly Ile Pro
            180                 185                 190

Asp Arg Phe Ser Gly Ser Ser Gly Asn Ser Ala Ser Leu Thr Ile
        195                 200                 205

Thr Gly Ala Gln Ala Glu Asp Glu Ala Asp Tyr Tyr Cys Ser Ser Arg
    210                 215                 220

Asp Ser Arg Gly Asn His Leu Ala Leu Phe Gly Gly Thr Lys Leu
225                 230                 235                 240

Thr Val Leu

<210> SEQ ID NO 77
<211> LENGTH: 124
<212> TYPE: PRT
<213> ORGANISM: Artificial Sequence
<220> FEATURE:
<223> OTHER INFORMATION: Synthetic sequence - E34N12 VH

<400> SEQUENCE: 77

Gln Val Gln Leu Gln Glu Ser Gly Gly Gly Met Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Ala Lys Ile Ala Ala Arg Ala Gln Gly Phe Asp Tyr
                100                 105                 110

Trp Gly Gln Gly Thr Leu Val Thr Val Ser Ser Ser
        115                 120

<210> SEQ ID NO 78
<211> LENGTH: 109
<212> TYPE: PRT
<213> ORGANISM: Artificial Sequence
<220> FEATURE:
<223> OTHER INFORMATION: Synthetic sequence - E34N12 VL

<400> SEQUENCE: 78

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Tyr Thr Thr Ser Ser
                85                  90                  95

Thr Leu Val Phe Gly Gly Gly Thr Lys Val Thr Val Leu
            100                 105

<210> SEQ ID NO 79
<211> LENGTH: 248
<212> TYPE: PRT
<213> ORGANISM: Artificial Sequence
<220> FEATURE:
<223> OTHER INFORMATION: Synthetic sequence - E34N12

<400> SEQUENCE: 79

Gln Val Gln Leu Gln Glu Ser Gly Gly Gly Met Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Ala Lys Ile Ala Ala Arg Ala Gln Gly Phe Asp Tyr

```
                100                 105                 110
Trp Gly Gln Gly Thr Leu Val Thr Val Ser Ser Gly Gly Gly
            115                 120                 125

Ser Gly Gly Gly Ser Gly Gly Gly Ser Gln Ser Val Leu Thr
        130                 135                 140

Gln Pro Pro Ser Val Ser Ala Ala Pro Gly Gln Lys Val Thr Ile Ser
145                 150                 155                 160

Cys Ser Gly Ser Ser Ser Asn Ile Gly Asn Asn Tyr Val Ser Trp Tyr
                165                 170                 175

Gln Gln Leu Pro Gly Thr Ala Pro Lys Leu Leu Ile Tyr Asp Asn Asn
            180                 185                 190

Lys Arg Pro Ser Gly Ile Pro Asp Arg Phe Ser Gly Ser Lys Ser Gly
                195                 200                 205

Asn Thr Ala Ser Leu Thr Ile Ser Gly Leu Gln Ala Glu Asp Glu Ala
            210                 215                 220

Asp Tyr Tyr Cys Ser Ser Tyr Thr Thr Ser Ser Thr Leu Val Phe Gly
225                 230                 235                 240

Gly Gly Thr Lys Val Thr Val Leu
                245

<210> SEQ ID NO 80
<211> LENGTH: 123
<212> TYPE: PRT
<213> ORGANISM: Artificial Sequence
<220> FEATURE:
<223> OTHER INFORMATION: Synthetic sequence - E34N13 VH

<400> SEQUENCE: 80

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Lys Arg Gly Glu Tyr Ser Ser Gly Trp Tyr Gly Pro Asp Tyr
            100                 105                 110

Trp Gly Gln Gly Thr Leu Val Thr Val Ser Ser
        115                 120

<210> SEQ ID NO 81
<211> LENGTH: 111
<212> TYPE: PRT
<213> ORGANISM: Artificial Sequence
<220> FEATURE:
<223> OTHER INFORMATION: Synthetic sequence - E34N13 VL

<400> SEQUENCE: 81

Ser Tyr Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Val Thr Val Leu
            100                 105                 110

<210> SEQ ID NO 82
<211> LENGTH: 249
<212> TYPE: PRT
<213> ORGANISM: Artificial Sequence
<220> FEATURE:
<223> OTHER INFORMATION: Synthetic sequence - E34N13

<400> SEQUENCE: 82

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Lys Arg Gly Glu Tyr Ser Ser Gly Trp Tyr Gly Pro Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Ser Tyr Val Leu Thr Gln
            130                 135                 140

Pro Pro Ser Val Ser Gly Ala Pro Gly Gln Arg Val Thr Ile Ser Cys
145                 150                 155                 160

Thr Gly Ser Ser Ser Asn Ile Gly Ala Gly Tyr Asp Val His Trp Tyr
                165                 170                 175

Gln Gln Leu Pro Gly Thr Ala Pro Lys Leu Leu Ile Tyr Gly Asn Ser
            180                 185                 190

Asn Arg Pro Ser Gly Val Pro Asp Arg Phe Ser Gly Ser Lys Ser Gly
            195                 200                 205

Thr Ser Ala Ser Leu Ala Ile Thr Gly Leu Gln Ala Glu Asp Glu Ala
            210                 215                 220

Asp Tyr Tyr Cys Gln Ser Tyr Asp Ser Ser Leu Ser Gly Val Val Phe
225                 230                 235                 240

Gly Gly Gly Thr Lys Val Thr Val Leu
                245

<210> SEQ ID NO 83
<211> LENGTH: 123
<212> TYPE: PRT
<213> ORGANISM: Artificial Sequence
<220> FEATURE:

<223> OTHER INFORMATION: Synthetic sequence - E34N14 VH

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asn Tyr
            20                  25                  30

Ala Met Asp Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Pro Gly Thr Pro Pro Ala Glu Tyr Phe Gln His
            100                 105                 110

Trp Gly Gln Gly Thr Leu Val Thr Val Ser Ser
        115                 120

<210> SEQ ID NO 84
<211> LENGTH: 108
<212> TYPE: PRT
<213> ORGANISM: Artificial Sequence
<220> FEATURE:
<223> OTHER INFORMATION: Synthetic sequence - E34N14 VL

<400> SEQUENCE: 84

Ser Glu Leu Thr Gln Asp Pro Ala Val Ser Val Ala Leu Gly Gln Thr
1               5                   10                  15

Val Arg Ile Thr Cys Gln Gly Asp Ser Leu Lys Ser Tyr Tyr Ala Ser
            20                  25                  30

Trp Tyr Gln Gln Lys Pro Gly Gln Ala Pro Val Leu Val Ile Tyr Gly
        35                  40                  45

Glu Asn Ser Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys His Ser Arg Asp Ser Ser Gly Thr His Leu
                85                  90                  95

Arg Val Phe Gly Gly Gly Thr Lys Val Thr Val Leu
            100                 105

<210> SEQ ID NO 85
<211> LENGTH: 246
<212> TYPE: PRT
<213> ORGANISM: Artificial Sequence
<220> FEATURE:
<223> OTHER INFORMATION: Synthetic sequence - E34N14

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asn Tyr
            20                  25                  30

Ala Met Asp Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Asp Arg Val Pro Gly Thr Pro Pro Ala Glu Tyr Phe Gln His
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Ser Glu Leu Thr Gln Asp
        130                 135                 140

Pro Ala Val Ser Val Ala Leu Gly Gln Thr Val Arg Ile Thr Cys Gln
145                 150                 155                 160

Gly Asp Ser Leu Lys Ser Tyr Tyr Ala Ser Trp Tyr Gln Gln Lys Pro
                165                 170                 175

Gly Gln Ala Pro Val Leu Val Ile Tyr Gly Glu Asn Ser Arg Pro Ser
                180                 185                 190

Gly Ile Pro Asp Arg Phe Ser Gly Ser Ser Gly Asn Thr Ala Ser
            195                 200                 205

Leu Thr Ile Thr Gly Ala Gln Ala Glu Asp Glu Ala Asp Tyr Tyr Cys
    210                 215                 220

His Ser Arg Asp Ser Ser Gly Thr His Leu Arg Val Phe Gly Gly
225                 230                 235                 240

Thr Lys Val Thr Val Leu
                245

<210> SEQ ID NO 86
<211> LENGTH: 123
<212> TYPE: PRT
<213> ORGANISM: Artificial Sequence
<220> FEATURE:
<223> OTHER INFORMATION: Synthetic sequence - E34N14M VH

<400> SEQUENCE: 86

Gln Met Gln Leu Val Glu Ser Gly Gly Leu Val Gln Pro Gly Gly
 1               5                  10                  15

Ser Leu Arg Leu Ser Cys Ala Ala Ser Gly Phe Ser Phe Ser Asn Tyr
                 20                  25                  30

Ala Met Asp Trp Val Arg Gln Ala Pro Gly Lys Gly Leu Glu Trp Val
             35                  40                  45

Ser Ala Ile Ser Gly Ser Gly Gly Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Asp Arg Val Pro Gly Thr Pro Pro Ala Glu Tyr Phe Gln His
                100                 105                 110

Trp Gly Gln Gly Thr Leu Val Thr Val Ser Ser
            115                 120

<210> SEQ ID NO 87
<211> LENGTH: 108
<212> TYPE: PRT
<213> ORGANISM: Artificial Sequence
<220> FEATURE:
<223> OTHER INFORMATION: Synthetic sequence - E34N14M VL
```

<400> SEQUENCE: 87

```
Ser Glu Leu Thr Gln Asp Pro Ala Val Ser Val Ala Leu Gly Gln Thr
1               5                   10                  15

Val Arg Ile Thr Cys Gln Gly Asp Ser Leu Lys Ser Tyr Tyr Ala Ser
            20                  25                  30

Trp Tyr Gln Gln Lys Pro Gly Gln Ala Pro Val Leu Val Ile Tyr Gly
        35                  40                  45

Glu Asn Ser Arg Pro Ser Gly Ile Pro Asp Arg Phe Ser Gly Ser Ser
50                  55                  60

Ser Gly Asn Thr Ala Ser Leu Thr Ile Thr Gly Ala Gln Ala Glu Asp
65                  70                  75                  80

Glu Ala Asp Tyr Tyr Cys His Ser Arg Asp Ser Ser Gly Thr His Leu
                85                  90                  95

Arg Val Phe Gly Gly Gly Thr Lys Val Thr Val Leu
            100                 105
```

<210> SEQ ID NO 88
<211> LENGTH: 246
<212> TYPE: PRT
<213> ORGANISM: Artificial Sequence
<220> FEATURE:
<223> OTHER INFORMATION: Synthetic sequence - E34N14M

<400> SEQUENCE: 88

```
Gln Met Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asn Tyr
            20                  25                  30

Ala Met Asp Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Pro Gly Thr Pro Pro Ala Glu Tyr Phe Gln His
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Ser Glu Leu Thr Gln Asp
    130                 135                 140

Pro Ala Val Ser Val Ala Leu Gly Gln Thr Val Arg Ile Thr Cys Gln
145                 150                 155                 160

Gly Asp Ser Leu Lys Ser Tyr Tyr Ala Ser Trp Tyr Gln Gln Lys Pro
                165                 170                 175

Gly Gln Ala Pro Val Leu Val Ile Tyr Gly Glu Asn Ser Arg Pro Ser
            180                 185                 190

Gly Ile Pro Asp Arg Phe Ser Gly Ser Ser Ser Gly Asn Thr Ala Ser
        195                 200                 205

Leu Thr Ile Thr Gly Ala Gln Ala Glu Asp Glu Ala Asp Tyr Tyr Cys
    210                 215                 220

His Ser Arg Asp Ser Ser Gly Thr His Leu Arg Val Phe Gly Gly Gly
225                 230                 235                 240
```

```
Thr Lys Val Thr Val Leu
            245

<210> SEQ ID NO 89
<211> LENGTH: 121
<212> TYPE: PRT
<213> ORGANISM: Artificial Sequence
<220> FEATURE:
<223> OTHER INFORMATION: Synthetic sequence - E34N15 VH

<400> SEQUENCE: 89

Gln Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Ser
            20                  25                  30

Ala Met Asn Trp Val Arg Gln Ala Pro Gly Lys Gly Leu Glu Trp Val
        35                  40                  45

Ser Ala Ile Thr Gly Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Ser Thr Ala Asp Ala Ala Leu Tyr Tyr Cys
                85                  90                  95

Ala Lys Pro Pro Val Gly Gly Ile Leu His Ala Phe Asp Ile Trp Gly
            100                 105                 110

Gln Gly Thr Met Val Thr Val Ser Ser
        115                 120

<210> SEQ ID NO 90
<211> LENGTH: 107
<212> TYPE: PRT
<213> ORGANISM: Artificial Sequence
<220> FEATURE:
<223> OTHER INFORMATION: Synthetic sequence - E34N15 VL

<400> SEQUENCE: 90

Asp Val Val Met Thr Gln Ser Pro Ser Ser Leu Ser Ala Ser Val Gly
1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Arg Ala Pro Lys Leu Leu Ile
        35                  40                  45

His Pro Ala Ser Thr Leu Gln Ser Gly Val Pro Ser Arg Phe Ser Ala
    50                  55                  60

Ser Gly Phe Gly Thr Asp Phe Thr Leu Thr Ile Thr Ser Leu Gln Pro
65                  70                  75                  80

Glu Asp Ser Ala Thr Tyr Tyr Cys Leu Gln Asp Tyr Asn Ser Phe Thr
                85                  90                  95

Phe Gly Pro Gly Thr Lys Leu Val Thr Val Leu
            100                 105

<210> SEQ ID NO 91
<211> LENGTH: 243
<212> TYPE: PRT
<213> ORGANISM: Artificial Sequence
<220> FEATURE:
<223> OTHER INFORMATION: Synthetic sequence - E34N15

<400> SEQUENCE: 91

Gln Val Gln Leu Val Glu Ser Gly Gly Gly Leu Val Gln Pro Gly Gly
```

```
                1               5                  10                  15
Ser Leu Arg Leu Ser Cys Ala Ala Ser Gly Phe Thr Phe Ser Ser
            20                  25                  30

Ala Met Asn Trp Val Arg Gln Ala Pro Gly Lys Gly Leu Glu Trp Val
            35                  40                  45

Ser Ala Ile Thr Gly Gly Gly Thr Thr Tyr Tyr Ala Asp Ser Val
        50              55                  60

Lys Gly Arg Phe Thr Ile Ser Arg Asp Asn Ser Lys Asn Thr Leu Tyr
65                  70                  75                  80

Leu Gln Met Asp Ser Leu Ser Thr Ala Asp Ala Leu Tyr Tyr Cys
                85                  90                  95

Ala Lys Pro Pro Val Gly Gly Ile Leu His Ala Phe Asp Ile Trp Gly
                100                 105                 110

Gln Gly Thr Met Val Thr Val Ser Ser Gly Gly Gly Ser Gly Gly
            115                 120                 125

Gly Gly Ser Gly Gly Gly Ser Asp Val Val Met Thr Gln Ser Pro
        130                 135                 140

Ser Ser Leu Ser Ala Ser Val Gly Asp Arg Val Thr Ile Thr Cys Arg
145                 150                 155                 160

Ala Ser Gln Gly Ile Arg Asn Asp Leu Gly Trp Tyr Gln Gln Lys Pro
                165                 170                 175

Gly Arg Ala Pro Lys Leu Leu Ile His Pro Ala Ser Thr Leu Gln Ser
                180                 185                 190

Gly Val Pro Ser Arg Phe Ser Ala Ser Gly Phe Gly Thr Asp Phe Thr
                195                 200                 205

Leu Thr Ile Thr Ser Leu Gln Pro Glu Asp Ser Ala Thr Tyr Tyr Cys
            210                 215                 220

Leu Gln Asp Tyr Asn Ser Phe Thr Phe Gly Pro Gly Thr Lys Leu Val
225                 230                 235                 240

Thr Val Leu

<210> SEQ ID NO 92
<211> LENGTH: 123
<212> TYPE: PRT
<213> ORGANISM: Artificial Sequence
<220> FEATURE:
<223> OTHER INFORMATION: Synthetic sequence - E34N20 VH

<400> SEQUENCE: 92

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Ile Phe Asn Lys Tyr
            20                  25                  30

Gly Met His Trp Val Arg Gln Ala Pro Gly Lys Gly Leu Glu Trp Val
            35                  40                  45

Ser Val Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Asp Asp Thr Ala Val Tyr Tyr Cys
                85                  90                  95

Ala Lys Arg Gly Asp Gly Tyr Asn Ser Gly Trp Tyr Ser Phe Asp Tyr
                100                 105                 110

Trp Gly Gln Gly Thr Leu Val Thr Val Ser Ser
            115                 120
```

<210> SEQ ID NO 93
<211> LENGTH: 111
<212> TYPE: PRT
<213> ORGANISM: Artificial Sequence
<220> FEATURE:
<223> OTHER INFORMATION: Synthetic sequence - E34N20 VL

<400> SEQUENCE: 93

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Val Val Val Phe Gly Gly Gly Thr Lys Val Thr Val Leu
            100                 105                 110
```

<210> SEQ ID NO 94
<211> LENGTH: 249
<212> TYPE: PRT
<213> ORGANISM: Artificial Sequence
<220> FEATURE:
<223> OTHER INFORMATION: Synthetic sequence - E34N20

<400> SEQUENCE: 94

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Ile Phe Asn Lys Tyr
            20                  25                  30

Gly Met His Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Asp Asp Thr Ala Val Tyr Tyr Cys
                85                  90                  95

Ala Lys Arg Gly Asp Gly Tyr Asn Ser Gly Trp Tyr Ser Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gln Ser Val Leu Thr Gln
    130                 135                 140

Pro Pro Ser Val Ser Gly Ala Pro Gly Gln Arg Val Thr Ile Ser Cys
145                 150                 155                 160

Thr Gly Ser Ser Asn Ile Gly Ala Gly Tyr Asp Val His Trp Tyr
                165                 170                 175

Gln Gln Leu Pro Gly Thr Ala Pro Lys Leu Leu Ile Tyr Gly Asn Ser
            180                 185                 190

Asn Arg Pro Ser Gly Val Pro Asp Arg Phe Ser Gly Ser Lys Ser Gly
```

195                 200                 205

Thr Ser Ala Ser Leu Ala Ile Thr Gly Leu Gln Ala Glu Asp Glu Ala
    210                 215                 220

Asp Tyr Tyr Cys Gln Ser Tyr Asp Ser Ser Leu Ser Val Val Val Phe
225                 230                 235                 240

Gly Gly Gly Thr Lys Val Thr Val Leu
            245

<210> SEQ ID NO 95
<211> LENGTH: 118
<212> TYPE: PRT
<213> ORGANISM: Artificial Sequence
<220> FEATURE:
<223> OTHER INFORMATION: Synthetic sequence - E34N22 VH

<400> SEQUENCE: 95

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Trp Arg Ala Phe Asp Ile Trp Gly Gln Gly Thr
            100                 105                 110

Met Val Thr Val Ser Ser
        115

<210> SEQ ID NO 96
<211> LENGTH: 111
<212> TYPE: PRT
<213> ORGANISM: Artificial Sequence
<220> FEATURE:
<223> OTHER INFORMATION: Synthetic sequence - E34N22 VL

<400> SEQUENCE: 96

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asp Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Leu Ala Glu Asp Glu Ala Asp Tyr Phe Cys Gln Ser Tyr Asp Ser Ser
                85                  90                  95

Leu Ser Ser Val Val Phe Gly Gly Gly Thr Lys Val Thr Val Leu
            100                 105                 110

<210> SEQ ID NO 97
<211> LENGTH: 244

```
<212> TYPE: PRT
<213> ORGANISM: Artificial Sequence
<220> FEATURE:
<223> OTHER INFORMATION: Synthetic sequence - E34N22

<400> SEQUENCE: 97
```

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Trp Arg Ala Phe Asp Ile Trp Gly Gln Gly Thr
            100                 105                 110

Met Val Thr Val Ser Ser Gly Gly Gly Ser Gly Gly Gly Gly Gly Ser
        115                 120                 125

Gly Gly Gly Gly Ser Gln Ser Val Leu Thr Gln Pro Pro Ser Val Ser
130                 135                 140

Gly Ala Pro Gly Gln Arg Val Thr Ile Ser Cys Thr Gly Ser Ser Ser
145                 150                 155                 160

Asn Ile Gly Ala Gly Tyr Asp Val His Trp Tyr Gln Gln Leu Pro Gly
                165                 170                 175

Thr Ala Pro Lys Leu Leu Ile Tyr Ala Asp Ser Asn Arg Pro Ser Gly
            180                 185                 190

Val Pro Asp Arg Phe Ser Gly Ser Arg Ser Gly Thr Ser Ala Ser Leu
        195                 200                 205

Ala Ile Thr Gly Leu Leu Ala Glu Asp Glu Ala Asp Tyr Phe Cys Gln
    210                 215                 220

Ser Tyr Asp Ser Ser Leu Ser Ser Val Val Phe Gly Gly Gly Thr Lys
225                 230                 235                 240

Val Thr Val Leu

```
<210> SEQ ID NO 98
<211> LENGTH: 122
<212> TYPE: PRT
<213> ORGANISM: Artificial Sequence
<220> FEATURE:
<223> OTHER INFORMATION: Synthetic sequence - E34N26C VH

<400> SEQUENCE: 98
```

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                    85                  90                  95

Ala Arg Gly Ala Arg Gly Asn Tyr Val Ser Asn Trp Phe Asp Pro Trp
                100                 105                 110

Gly Gln Gly Thr Leu Val Thr Val Ser Ser
            115                 120

<210> SEQ ID NO 99
<211> LENGTH: 110
<212> TYPE: PRT
<213> ORGANISM: Artificial Sequence
<220> FEATURE:
<223> OTHER INFORMATION: Synthetic sequence - E34N26C VL

<400> SEQUENCE: 99

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Lys Tyr Val Ser Trp Tyr Gln Gln His Pro Gly Lys Ala Pro Lys Leu
            35                  40                  45

Met Ile Tyr Glu Val Ser Gln Arg Pro Ser Gly Val Pro Asp Arg Phe
50                  55                  60

Ser Gly Ser Lys Ser Asp Asn Thr Ala Ser Leu Thr Val Ser Gly Leu
65                  70                  75                  80

Arg Ala Glu Asp Glu Ala Asp Tyr Tyr Cys Ser Ser Tyr Ala Gly Ser
                85                  90                  95

Asn Asn Trp Val Phe Gly Gly Gly Thr Lys Val Thr Val Leu
                100                 105                 110

<210> SEQ ID NO 100
<211> LENGTH: 247
<212> TYPE: PRT
<213> ORGANISM: Artificial Sequence
<220> FEATURE:
<223> OTHER INFORMATION: Synthetic sequence - E34N26C

<400> SEQUENCE: 100

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Ser Ile Ser Gly Ser Gly Gly Ser Thr Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Gly Ala Arg Gly Asn Tyr Val Ser Asn Trp Phe Asp Pro Trp
                100                 105                 110

Gly Gln Gly Thr Leu Val Thr Val Ser Ser Gly Gly Gly Gly Ser Gly
            115                 120                 125

Gly Gly Ser Gly Gly Gly Gly Ser Gln Ser Ala Leu Thr Gln Pro
        130                 135                 140

Ala Ser Val Ser Gly Ser Pro Gly Gln Ser Ile Thr Ile Ser Cys Thr
145                 150                 155                 160

```
Gly Thr Ser Ser Asp Val Gly Tyr Lys Tyr Val Ser Trp Tyr Gln
            165                 170                 175

Gln His Pro Gly Lys Ala Pro Lys Leu Met Ile Tyr Glu Val Ser Gln
            180                 185                 190

Arg Pro Ser Gly Val Pro Asp Arg Phe Ser Gly Ser Lys Ser Asp Asn
            195                 200                 205

Thr Ala Ser Leu Thr Val Ser Gly Leu Arg Ala Glu Asp Glu Ala Asp
            210                 215                 220

Tyr Tyr Cys Ser Ser Tyr Ala Gly Ser Asn Asn Trp Val Phe Gly Gly
225                 230                 235                 240

Gly Thr Lys Val Thr Val Leu
                245

<210> SEQ ID NO 101
<211> LENGTH: 122
<212> TYPE: PRT
<213> ORGANISM: Artificial Sequence
<220> FEATURE:
<223> OTHER INFORMATION: Synthetic sequence - E34N26R VH

<400> SEQUENCE: 101

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Gly Ala Arg Gly Asn Tyr Val Ser Asn Trp Phe Asp Pro Trp
            100                 105                 110

Gly Gln Gly Thr Leu Val Thr Val Ser Ser
        115                 120

<210> SEQ ID NO 102
<211> LENGTH: 110
<212> TYPE: PRT
<213> ORGANISM: Artificial Sequence
<220> FEATURE:
<223> OTHER INFORMATION: Synthetic sequence - E34N26R VL

<400> SEQUENCE: 102

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu
        35                  40                  45

Met Ile Tyr Glu Val Ser Gln Arg Pro Ser Gly Val Pro Asp Arg Phe
    50                  55                  60

Ser Gly Ser Lys Ser Asp Asn Thr Ala Ser Leu Thr Val Ser Gly Leu
65                  70                  75                  80

Arg Ala Glu Asp Glu Ala Asp Tyr Tyr Arg Ser Ser Tyr Ala Gly Ser
```

```
                    85                  90                  95
Asn Asn Trp Val Phe Gly Gly Gly Thr Lys Val Thr Val Leu
                100                 105                 110

<210> SEQ ID NO 103
<211> LENGTH: 247
<212> TYPE: PRT
<213> ORGANISM: Artificial Sequence
<220> FEATURE:
<223> OTHER INFORMATION: Synthetic sequence - E34N26R

<400> SEQUENCE: 103

Gln Val Gln Leu Gln Glu Ser Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Ser Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Gly Ala Arg Gly Asn Tyr Val Ser Asn Trp Phe Asp Pro Trp
                100                 105                 110

Gly Gln Gly Thr Leu Val Thr Val Ser Ser Gly Gly Gly Gly Ser Gly
            115                 120                 125

Gly Gly Ser Gly Gly Gly Ser Gln Ser Ala Leu Thr Gln Pro
        130                 135                 140

Ala Ser Val Ser Gly Ser Pro Gly Gln Ser Ile Thr Ile Ser Cys Thr
145                 150                 155                 160

Gly Thr Ser Ser Asp Val Gly Gly Tyr Lys Tyr Val Ser Trp Tyr Gln
                165                 170                 175

Gln His Pro Gly Lys Ala Pro Lys Leu Met Ile Tyr Glu Val Ser Gln
                180                 185                 190

Arg Pro Ser Gly Val Pro Asp Arg Phe Ser Gly Ser Lys Ser Asp Asn
            195                 200                 205

Thr Ala Ser Leu Thr Val Ser Gly Leu Arg Ala Glu Asp Glu Ala Asp
        210                 215                 220

Tyr Tyr Arg Ser Ser Tyr Ala Gly Ser Asn Asn Trp Val Phe Gly Gly
225                 230                 235                 240

Gly Thr Lys Val Thr Val Leu
                245

<210> SEQ ID NO 104
<211> LENGTH: 115
<212> TYPE: PRT
<213> ORGANISM: Artificial Sequence
<220> FEATURE:
<223> OTHER INFORMATION: Synthetic sequence - H3 VH

<400> SEQUENCE: 104

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30
```

```
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser
        115

<210> SEQ ID NO 105
<211> LENGTH: 107
<212> TYPE: PRT
<213> ORGANISM: Artificial Sequence
<220> FEATURE:
<223> OTHER INFORMATION: Synthetic sequence - H3 VL

<400> SEQUENCE: 105

Asn Phe Met Leu Thr Gln Asn Pro Ala Val Ser Val Ala Leu Gly Gln
 1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Ile Tyr
            35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Pro
                85                  90                  95

Val Phe Gly Gly Gly Thr Lys Val Thr Val Leu
            100                 105

<210> SEQ ID NO 106
<211> LENGTH: 237
<212> TYPE: PRT
<213> ORGANISM: Artificial Sequence
<220> FEATURE:
<223> OTHER INFORMATION: Synthetic sequence - H3

<400> SEQUENCE: 106

Gln Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110
```

```
Val Ser Ser Gly Gly Gly Ser Gly Gly Gly Ser Gly Gly Gly
        115                 120                 125
Gly Ser Asn Phe Met Leu Thr Gln Asn Pro Ala Val Ser Val Ala Leu
130                 135                 140
Gly Gln Thr Val Arg Ile Thr Cys Gln Gly Asp Ser Leu Arg Ser Tyr
145                 150                 155                 160
Tyr Ala Ser Trp Tyr Gln Gln Lys Pro Gly Gln Ala Pro Leu Leu Val
                165                 170                 175
Ile Tyr Gly Lys Asn Asn Arg Pro Ser Gly Ile Pro Asp Arg Phe Ser
                180                 185                 190
Gly Ser Ser Gly Asn Thr Ala Ser Leu Thr Ile Thr Gly Ala Gln
                195                 200                 205
Ala Glu Asp Glu Ala Asp Tyr Tyr Cys Asn Ser Arg Asp Ser Ser Gly
210                 215                 220
Asn Pro Val Phe Gly Gly Gly Thr Lys Val Thr Val Leu
225                 230                 235
```

```
<210> SEQ ID NO 107
<211> LENGTH: 115
<212> TYPE: PRT
<213> ORGANISM: Artificial Sequence
<220> FEATURE:
<223> OTHER INFORMATION: Synthetic sequence - 58541 (H3 variant1) VH

<400> SEQUENCE: 107

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Gly Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
50                  55                  60
Lys Gly Arg Phe Thr Ile Ser Arg Asp Asn Ser Lys Asp Thr Leu Tyr
65                  70                  75                  80
Leu Gln Met Asn Ser Leu Arg Ala Glu Asp Thr Ala Val Tyr Tyr Cys
                85                  90                  95
Ala Ser Arg Ser Leu Leu Asp Tyr Trp Gly Gln Gly Thr Leu Val Thr
            100                 105                 110
Val Ser Ser
        115
```

```
<210> SEQ ID NO 108
<211> LENGTH: 107
<212> TYPE: PRT
<213> ORGANISM: Artificial Sequence
<220> FEATURE:
<223> OTHER INFORMATION: Synthetic sequence - 58541 (H3 variant1) VL

<400> SEQUENCE: 108

Asn Phe Met Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
                20                  25                  30
Ser Trp Tyr Gln Gln Lys Pro Gly Gln Ala Pro Leu Leu Val Ile Tyr
            35                  40                  45
Gly Lys Asn Asn Arg Pro Ser Gly Ile Pro Asp Arg Phe Ser Gly Ser
```

```
                    50                  55                  60
Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Pro
                 85                  90                  95

Val Phe Gly Gly Gly Thr Lys Val Thr Val Leu
            100                 105

<210> SEQ ID NO 109
<211> LENGTH: 237
<212> TYPE: PRT
<213> ORGANISM: Artificial Sequence
<220> FEATURE:
<223> OTHER INFORMATION: Synthetic sequence - 58541 (H3 variant1)

<400> SEQUENCE: 109

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Gly Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Tyr Cys
                 85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
    210                 215                 220

Asn Pro Val Phe Gly Gly Gly Thr Lys Val Thr Val Leu
225                 230                 235

<210> SEQ ID NO 110
<211> LENGTH: 115
<212> TYPE: PRT
<213> ORGANISM: Artificial Sequence
<220> FEATURE:
<223> OTHER INFORMATION: Synthetic sequence - 58541.1 (H3 variant2) VH

<400> SEQUENCE: 110

Gln Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser
        115

<210> SEQ ID NO 111
<211> LENGTH: 107
<212> TYPE: PRT
<213> ORGANISM: Artificial Sequence
<220> FEATURE:
<223> OTHER INFORMATION: Synthetic sequence - 58541.1 (H3 variant2) VL

<400> SEQUENCE: 111

Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

Val Phe Gly Gly Gly Thr Lys Val Thr Val Leu
            100                 105

<210> SEQ ID NO 112
<211> LENGTH: 237
<212> TYPE: PRT
<213> ORGANISM: Artificial Sequence
<220> FEATURE:
<223> OTHER INFORMATION: Synthetic sequence - 58541.1 (H3 variant2)

<400> SEQUENCE: 112

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95
```

```
Ala Ser Arg Ser Leu Leu Asp Tyr Trp Gly Gln Gly Thr Leu Val Thr
            100                 105                 110

Val Ser Ser Gly Gly Gly Ser Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
    210                 215                 220

Asn Pro Val Phe Gly Gly Gly Thr Lys Val Thr Val Leu
225                 230                 235

<210> SEQ ID NO 113
<211> LENGTH: 115
<212> TYPE: PRT
<213> ORGANISM: Artificial Sequence
<220> FEATURE:
<223> OTHER INFORMATION: Synthetic sequence - PD32 VH

<400> SEQUENCE: 113

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Ile Ala Ser His Trp Gly Gln Gly Thr Leu Val Thr
            100                 105                 110

Val Ser Ser
        115

<210> SEQ ID NO 114
<211> LENGTH: 107
<212> TYPE: PRT
<213> ORGANISM: Artificial Sequence
<220> FEATURE:
<223> OTHER INFORMATION: Synthetic sequence - PD32 VL

<400> SEQUENCE: 114

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
```

```
                35                  40                  45
Lys Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Arg Asp Ser Ser Gly Ile His Leu
                 85                  90                  95

Val Phe Gly Gly Gly Thr Lys Leu Thr Val Leu
            100                 105

<210> SEQ ID NO 115
<211> LENGTH: 237
<212> TYPE: PRT
<213> ORGANISM: Artificial Sequence
<220> FEATURE:
<223> OTHER INFORMATION: Synthetic sequence - PD32

<400> SEQUENCE: 115

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Leu Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Gly Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Leu Ile Ala Ser His Trp Gly Gln Gly Thr Leu Val Thr
            100                 105                 110

Val Ser Ser Gly Gly Gly Gly Ser Gly Gly Gly Gly Ser Gly Gly Gly
            115                 120                 125

Gly Ser Ser Glu Leu Thr Gln Asp Pro Ala Val Ser Val Ala Leu Gly
130                 135                 140

Gln Thr Val Arg Ile Thr Cys Gln Gly Asp Ser Leu Arg Ser Tyr Tyr
145                 150                 155                 160

Ala Ser Trp Tyr Gln Gln Lys Pro Gly Gln Ala Pro Val Leu Val Ile
                165                 170                 175

Tyr Gly Lys Asn Asn Arg Pro Ser Gly Ile Pro Asp Arg Phe Ser Gly
            180                 185                 190

Ser Ser Ser Gly Asn Thr Ala Ser Leu Thr Ile Thr Gly Ala Gln Ala
        195                 200                 205

Glu Asp Glu Ala Asp Tyr Tyr Cys Asn Ser Arg Asp Ser Ser Gly Ile
210                 215                 220

His Leu Val Phe Gly Gly Gly Thr Lys Leu Thr Val Leu
225                 230                 235

<210> SEQ ID NO 116
<211> LENGTH: 127
<212> TYPE: PRT
<213> ORGANISM: Artificial Sequence
<220> FEATURE:
<223> OTHER INFORMATION: Synthetic sequence - M10A12 VH

<400> SEQUENCE: 116
```

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Tyr Ser Ser Asn Trp Phe Ser Tyr Tyr Tyr Tyr
            100                 105                 110

Gly Met Asp Val Trp Gly Gln Gly Thr Thr Val Thr Val Ser Ser
            115                 120                 125

<210> SEQ ID NO 117
<211> LENGTH: 109
<212> TYPE: PRT
<213> ORGANISM: Artificial Sequence
<220> FEATURE:
<223> OTHER INFORMATION: Synthetic sequence - M10A12 VL

<400> SEQUENCE: 117

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Leu Leu Val Ile Tyr Gly
            35                  40                  45

Glu Asn Asn Arg Pro Ser Gly Ile Pro Asp Arg Phe Ser Gly Ser Ser
        50                  55                  60

Ser Gly Asn Thr Ala Phe Leu Thr Ile Ser Arg Val Glu Ala Gly Asp
65                  70                  75                  80

Glu Ala Asp Tyr Tyr Cys Gln Val Trp Asp Ser Ser Ser Asp His Pro
                85                  90                  95

Gly Val Val Phe Gly Gly Gly Thr Lys Val Thr Val Leu
            100                 105

<210> SEQ ID NO 118
<211> LENGTH: 251
<212> TYPE: PRT
<213> ORGANISM: Artificial Sequence
<220> FEATURE:
<223> OTHER INFORMATION: Synthetic sequence - M10A12

<400> SEQUENCE: 118

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Gly Gly Arg Tyr Ser Ser Asn Trp Phe Ser Tyr Tyr Tyr Tyr
               100                 105                 110

Gly Met Asp Val Trp Gly Gln Gly Thr Thr Val Thr Val Ser Ser Gly
        115                 120                 125

Gly Gly Gly Ser Gly Gly Gly Ser Gly Gly Gly Gly Ser Ser Glu
    130                 135                 140

Leu Thr Gln Asp Pro Ala Val Ser Val Ala Leu Gly Gln Thr Val Arg
145                 150                 155                 160

Ile Thr Cys Gln Gly Asp Ser Leu Arg Ser Tyr Tyr Ala Ser Trp Tyr
                165                 170                 175

Gln Gln Lys Pro Gly Gln Ala Pro Leu Leu Val Ile Tyr Gly Glu Asn
            180                 185                 190

Asn Arg Pro Ser Gly Ile Pro Asp Arg Phe Ser Gly Ser Ser Ser Gly
        195                 200                 205

Asn Thr Ala Phe Leu Thr Ile Ser Arg Val Glu Ala Gly Asp Glu Ala
    210                 215                 220

Asp Tyr Tyr Cys Gln Val Trp Asp Ser Ser Ser Asp His Pro Gly Val
225                 230                 235                 240

Val Phe Gly Gly Gly Thr Lys Val Thr Val Leu
                245                 250

<210> SEQ ID NO 119
<211> LENGTH: 126
<212> TYPE: PRT
<213> ORGANISM: Artificial Sequence
<220> FEATURE:
<223> OTHER INFORMATION: Synthetic sequence - RYR VH

<400> SEQUENCE: 119

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Leu Pro Asp Phe Trp Ser Gly Tyr Pro Asn Tyr Gly
               100                 105                 110

Met Asp Val Trp Gly Gln Gly Thr Thr Val Thr Val Ser Ser
        115                 120                 125

<210> SEQ ID NO 120
<211> LENGTH: 112
<212> TYPE: PRT
<213> ORGANISM: Artificial Sequence
<220> FEATURE:
<223> OTHER INFORMATION: Synthetic sequence - RYR VL

<400> SEQUENCE: 120

Gln Ser Val Leu Thr Gln Pro Pro Ser Val Ser Gly Ala Pro Gly Gln
```

```
            1               5                  10                  15
          Arg Val Thr Ile Ser Cys Thr Gly Ser Ser Asn Ile Gly Ala Gly
                           20                  25                  30

Tyr Asp Val His Trp Tyr Gln Gln Leu Pro Gly Thr Ala Pro Lys Leu
                       35                  40                  45

Leu Ile Tyr Gly Asn Ser Asn Arg Pro Ser Gly Val Pro Asp Arg Phe
                   50                  55                  60

Ser Gly Ser Lys Ser Gly Thr Ser Ala Ser Leu Ala Ile Thr Gly Leu
          65                  70                  75                  80

Gln Ala Glu Asp Glu Ala Asp Tyr Tyr Cys Gln Ser Tyr Asp Ser Ser
                           85                  90                  95

Leu Ser Gly His Val Val Phe Gly Gly Gly Thr Lys Leu Thr Val Leu
                       100                 105                 110

<210> SEQ ID NO 121
<211> LENGTH: 253
<212> TYPE: PRT
<213> ORGANISM: Artificial Sequence
<220> FEATURE:
<223> OTHER INFORMATION: Synthetic sequence - RYR

<400> SEQUENCE: 121

Gln Val Gln Leu Gln Glu Ser Gly Gly Gly Leu Val Gln Pro Gly Gly
          1               5                  10                  15

Ser Leu Arg Leu Ser Cys Ala Ala Ser Gly Phe Thr Phe Ser Ser Tyr
                           20                  25                  30

Ser Met Asn Trp Val Arg Gln Ala Pro Gly Lys Gly Leu Glu Trp Val
                       35                  40                  45

Ser Tyr Ile Ser Ser Ser Ser Ser Thr Ile Tyr Tyr Ala Asp Ser Val
                   50                  55                  60

Lys Gly Arg Phe Thr Ile Ser Arg Asp Asn Ala Lys Asn Ser Leu Tyr
          65                  70                  75                  80

Leu Gln Met Asn Ser Leu Arg Ala Glu Asp Thr Ala Val Tyr Tyr Cys
                           85                  90                  95

Ala Arg Tyr Arg Leu Pro Asp Phe Trp Ser Gly Tyr Pro Asn Tyr Gly
                       100                 105                 110

Met Asp Val Trp Gly Gln Gly Thr Thr Val Thr Val Ser Ser Gly Gly
                       115                 120                 125

Gly Gly Ser Gly Gly Gly Gly Ser Gly Gly Gly Gly Ser Gln Ser Val
                   130                 135                 140

Leu Thr Gln Pro Pro Ser Val Ser Gly Ala Pro Gly Gln Arg Val Thr
          145                 150                 155                 160

Ile Ser Cys Thr Gly Ser Ser Ser Asn Ile Gly Ala Gly Tyr Asp Val
                           165                 170                 175

His Trp Tyr Gln Gln Leu Pro Gly Thr Ala Pro Lys Leu Leu Ile Tyr
                       180                 185                 190

Gly Asn Ser Asn Arg Pro Ser Gly Val Pro Asp Arg Phe Ser Gly Ser
                   195                 200                 205

Lys Ser Gly Thr Ser Ala Ser Leu Ala Ile Thr Gly Leu Gln Ala Glu
          210                 215                 220

Asp Glu Ala Asp Tyr Tyr Cys Gln Ser Tyr Asp Ser Ser Leu Ser Gly
          225                 230                 235                 240

His Val Val Phe Gly Gly Gly Thr Lys Leu Thr Val Leu
                       245                 250
```